US012618839B2

(12) United States Patent
LaBaer et al.

(10) Patent No.: US 12,618,839 B2
(45) Date of Patent: May 5, 2026

(54) ANTIBODIES FOR DETECTING EPSTEIN BARR VIRUS-POSITIVE GASTRIC CANCER

(71) Applicant: Arizona Board of Regents on behalf of Arizona State University, Scottsdale, AZ (US)

(72) Inventors: Joshua LaBaer, Chandler, AZ (US); Lusheng Song, Tempe, AZ (US); Ji Qiu, Chandler, AZ (US); Yunro Chung, Chandler, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 1011 days.

(21) Appl. No.: 17/771,595

(22) PCT Filed: Oct. 23, 2020

(86) PCT No.: PCT/US2020/057010
§ 371 (c)(1),
(2) Date: Apr. 25, 2022

(87) PCT Pub. No.: WO2021/081296
PCT Pub. Date: Apr. 29, 2021

(65) Prior Publication Data
US 2022/0373548 A1 Nov. 24, 2022

Related U.S. Application Data

(60) Provisional application No. 62/925,584, filed on Oct. 24, 2019.

(51) Int. Cl.
*G01N 33/569* (2006.01)
*A61P 35/00* (2006.01)
*G01N 33/574* (2006.01)

(52) U.S. Cl.
CPC ........ *G01N 33/56994* (2013.01); *A61P 35/00* (2018.01); *G01N 33/57446* (2013.01); *G01N 2333/05* (2013.01); *G01N 2474/10* (2021.08)

(58) Field of Classification Search
CPC ....... G01N 33/56994; G01N 33/57446; G01N 2333/05; G01N 2474/10; A61P 35/00; A61P 43/00
See application file for complete search history.

(56) References Cited

U.S. PATENT DOCUMENTS

| | | | |
|---|---|---|---|
| 6,696,262 B2 | 2/2004 | Harkonen | |
| 7,939,269 B2 | 5/2011 | Egawa et al. | |
| 2002/0051790 A1 | 5/2002 | Cripps et al. | |
| 2002/0192642 A1 | 12/2002 | Lo et al. | |
| 2004/0180331 A1 | 9/2004 | Vervoort MBHJ et al. | |
| 2006/0216763 A1 | 9/2006 | Clancy et al. | |
| 2015/0329865 A1 | 11/2015 | Lee et al. | |
| 2017/0146534 A1 | 5/2017 | Lerner et al. | |
| 2018/0318418 A1 | 11/2018 | Rosato et al. | |

FOREIGN PATENT DOCUMENTS

| | | |
|---|---|---|
| CN | 106706921 A | 5/2017 |
| WO | 1999045155 A2 | 9/1999 |
| WO | 2010004251 A1 | 1/2010 |
| WO | 2012072516 A1 | 6/2012 |
| WO | 2012139068 A2 | 10/2012 |
| WO | 2012167112 A2 | 12/2012 |
| WO | 2018081459 A1 | 5/2018 |
| WO | 2018201099 A1 | 11/2018 |

OTHER PUBLICATIONS

Hu C, Yuan L, Cheng X. Current status of early gastric cancer screening research. Cancer Biol Med. Jan. 2, 2024;21(3):218-22. (Year: 2024).*
Zhang R, Strong MJ, Baddoo M, Lin Z, Wang YP, Flemington EK, Liu YZ. Interaction of Epstein-Barr virus genes with human gastric carcinoma transcriptome. Oncotarget. Jun. 13, 2017;8(24):38399-38412. (Year: 2017).*
Naseem M, Barzi A, Brezden-Masley C, Puccini A, Berger MD, Tokunaga R, Battaglin F, Soni S, McSkane M, et. al. Outlooks on Epstein-Barr virus associated gastric cancer. Cancer Treat Rev. May 2018;66:15-22. Epub Mar. 31, 2018. (Year: 2018).*
Anderson et al., "Multiplexed detection of antibodies using programmable bead arrays," Protein Microarray for Disease Analysis. Humana Press, 2011: 227-238.
Blaser, M. J., Perez-Perez, G. I., Kleanthous, H., Cover, T. L., Peek, R. M., Chyou, P. H., . . . & Nomura, A. (1995). Infection with *Helicobacter pylori* strains possessing cagA is associated with an increased risk of developing adenocarcinoma of the stomach. Cancer research, 55(10), 2111-2115.
Cao et al., "Fluctuations of Epstein-Barr Virus Serological Anitbodies and Risk for Nasopharyngeal Carcinoma: A Prospective Screening Study with a 20-Year Follow-Up," PLoS One, Apr. 22, 2011. vol. 6, Iss. 4, pp. 1-10. entire document.

(Continued)

*Primary Examiner* — Rachel B Gill
(74) *Attorney, Agent, or Firm* — Quarles & Brady LLP

(57) ABSTRACT

Provided herein are methods, compositions, kits, and systems for detecting Epstein Barr virus infection (EBV) in gastric cancer (GC) patients. In particular, provided herein are methods, composition, kits, and systems for diagnosing and treating EBV-positive gastric cancer (EBV⁺ GC) in a biological sample of an individual based on the presence and level of antibodies against particular Epstein Barr virus proteins. EBV⁺ GC is a distinct subtype of gastric cancer and is associated with unique molecular profiles. Also provided herein are methods for providing more personalized therapy for each of these distinct cancer subtypes and methods for determining an Epstein Barr virus-positive gastric cancer antibody signature, and kits comprising components and protocols for performing the methods of this disclosure.

20 Claims, 9 Drawing Sheets
Specification includes a Sequence Listing.

(56) References Cited

OTHER PUBLICATIONS

Coghill et al., "Identification of a Novel, EBV-Based Anitbody Risk Stratification Signature for Early Dectection of Nasopharyngeal Carcinoma in Taiwan," Clinical Cancer Research, Mar. 15, 2018, vol. 24, Iss. 6, pp. 1305-1314. entire document.

International Search Report and Written Opinion for corresponding PCT/US2020/057010, mailed Jan. 7, 2021.

Lu et al., "Genome-Wide Transcription Program and Expression of the Rta Responsive Gene of Epstein-Barr Virus," Virology, Feb. 20, 2006, vol. 345, Iss. 2, pp. 358-372. entire document.

Shibayama, K., Kamachi, K., Nagata, N., Yagi, T., Nada, T., Doi, Y., . . . & Arakawa, Y. (2003). A novel apoptosis-inducing protein from *Helicobacter pylori*. Molecular microbiology, 47(2), 443-451.

Traylen et al., "Identification of Epstein-Barr Virus Replication Proteins in Burkitts's Lymphoma Cells," Pathogens, Oct. 30, 2015, vol. 4, pp. 739-751.

Zheng et al., "Comparison of Humoral Immune Responses to Epstein-Barr Virus and Kaposi's Sarcoma-Assoicated Herpesvirus Using a Viral Proteome Microarray," The Journal of Infectious Diseases, Oct. 11, 2011, vol. 204, Iss. 11, pp. 1683-1691. entire document.

* cited by examiner

A.

B.

Discovery (n=28 *vs* 34)

Validation (n=24 *vs* 65)

SEQUENCE LISTING

<160> NUMBER OF SEQ ID NOS: 151

<210> SEQ ID NO 1
<211> LENGTH: 576
<212> TYPE: DNA
<213> ORGANISM: Artificial Sequence
<220> FEATURE:
<223> OTHER INFORMATION: Synthetic

<400> SEQUENCE: 1

```
atggcctatt caacaaggga gatactgtta gccctgtgta tacgggacag tcgtgtgcat        60
ggaaatggta ccctgcatcc tgtgttggag ctagcagcaa gagaaacacc tctccgcctt       120
tcgccagagg acactgtagt tctgcgttat catgtgttgc ttgaggagat aattgaacga       180
aattcagaga catttacaga aacttggaac agatttataa cacacaccga acatgtggac       240
ctggatttta actcagtatt tttagagata tttcaccgtg gagacccaag ccttgggcgc       300
gcgttggcct ggatggcctg gtgcatgcat gcctgcagga cattgtgttg taaccagtct       360
```
actccttact atgttgtgga cctgtcagtt cgtgggatgt tagaagccag cgaaggcctg      420
gatggttgga ttcatcaaca gggcggctgg tctacattaa ttgaagacaa cattcctgga      480
tccagaaggt ttagctggac tttgtttctc gctggactga cttttgagtct gttagttata      540 tgtagttatt tatttatctc cagaggaaga cactaa                               576

<210> SEQ ID NO 2
<211> LENGTH: 191
<212> TYPE: PRT
<213> ORGANISM: Artificial Sequence
<220> FEATURE:
<223> OTHER INFORMATION: Synthetic

<400> SEQUENCE: 2

Met Ala Tyr Ser Thr Arg Glu Ile Leu Leu Ala Leu Cys Ile Arg Asp
1               5                   10                  15

Ser Arg Val His Gly Asn Gly Thr Leu His Pro Val Leu Glu Leu Ala
            20                  25                  30

Ala Arg Glu Thr Pro Leu Arg Leu Ser Pro Glu Asp Thr Val Val Leu
        35                  40                  45

Arg Tyr His Val Leu Leu Glu Glu Ile Ile Glu Arg Asn Ser Glu Thr
    50                  55                  60

Phe Thr Glu Thr Trp Asn Arg Phe Ile Thr His Thr Glu His Val Asp
65                  70                  75                  80

Leu Asp Phe Asn Ser Val Phe Leu Glu Ile Phe His Arg Gly Asp Pro
                85                  90                  95

Ser Leu Gly Arg Ala Leu Ala Trp Met Ala Trp Cys Met His Ala Cys
            100                 105                 110

Arg Thr Leu Cys Cys Asn Gln Ser Thr Pro Tyr Tyr Val Val Asp Leu
        115                 120                 125

Ser Val Arg Gly Met Leu Glu Ala Ser Glu Gly Leu Asp Gly Trp Ile
    130                 135                 140

His Gln Gln Gly Gly Trp Ser Thr Leu Ile Glu Asp Asn Ile Pro Gly
145                 150                 155                 160

Ser Arg Arg Phe Ser Trp Thr Leu Phe Leu Ala Gly Leu Thr Leu Ser
                165                 170                 175

Leu Leu Val Ile Cys Ser Tyr Leu Phe Ile Ser Arg Gly Arg His
            180                 185                 190

<210> SEQ ID NO 3
<211> LENGTH: 5964
<212> TYPE: DNA
<213> ORGANISM: Artificial Sequence
<220> FEATURE:
<223> OTHER INFORMATION: Synthetic

<400> SEQUENCE: 3
gggcgaatta attccggtta ttttccacca tattgccgtc ttttggcaat gtgagggccc       60
ggaaacctgg ccctgtcttc ttgacgagca ttcctagggg tctttcccct ctcgccaaag      120
gaatgcaagg tctgttgaat gtcgtgaagg aagcagttcc tctggaagct tcttgaagac      180
aaacaacgtc tgtagcgacc ctttgcaggc agcggaaccc cccacctggc gacaggtgcc      240
tctgcggcca aaagccacgt gtataagata cacctgcaaa ggcggcacaa ccccagtgcc      300
acgttgtgag ttggatagtt gtggaaagag tcaaatggct cacctcaagc gtattcaaca      360
aggggctgaa ggatgcccag aaggtacccc attgtatggg atctgatctg gggcctcggt      420
gcacatgctt tacatgtgtt tagtcgaggt taaaaaacgt ctaggcccc cgaaccacgg      480

-continued

```
ggacgtggtt ttcctttgaa aaacacgatg ataatatgga tcggatccga attcgagctc     540
cgtcatcaac aagtttgtac aaaaaagctg aacgagaaac gtaaaatgat ataaatatca     600
atatattaaa ttagattttg cataaaaaac agactacata atactgtaaa acacaacata     660
tccagtcact atggcggccg cattaggcac cccaggcttt acactttatg cttccggctc     720
gtataatgtg tggattttga gttaggatcc gtcgagattt tcaggagcta aggaagctaa     780
aatggagaaa aaaatcactg gatataccac cgttgatata tcccaatggc atcgtaaaga     840
acattttgag gcatttcagt cagttgctca atgtacctat aaccagaccg ttcagctgga     900
tattacggcc tttttaaaga ccgtaaagaa aaataagcac aagttttatc cggcctttat     960
tcacattctt gcccgcctga tgaatgctca tccggaattc cgtatggcaa tgaaagacgg    1020
tgagctggtg atatgggata gtgttcaccc ttgttacacc gttttccatg agcaaactga    1080
aacgttttca tcgctctgga gtgaatacca cgacgatttc cggcagtttc tacacatata    1140
ttcgcaagat gtggcgtgtt acggtgaaaa cctggcctat ttccctaaag ggtttattga    1200
gaatatgttt ttcgtctcag ccaatccctg ggtgagtttc accagttttg atttaaacgt    1260
ggccaatatg gacaacttct tcgcccccgt tttcaccatg ggcaaatatt atacgcaagg    1320
cgacaaggtg ctgatgccgc tggcgattca ggttcatcat gccgtctgtg atggcttcca    1380
tgtcggcaga atgcttaatg aattacaaca gtactgcgat gagtggcagg gcggggcgta    1440
aagatctgga tccggcttac taaaagccag ataacagtat gcgtatttgc gcgctgattt    1500
ttgcggtata agaatatata ctgatatgta tacccgaagt atgtcaaaaa gaggtgtgct    1560
atgaagcagc gtattacagt gacagttgac agcgacagct atcagttgct caaggcatat    1620
atgatgtcaa tatctccggt ctggtaagca caaccatgca gaatgaagcc cgtcgtctgc    1680
gtgccgaacg ctggaaagcg gaaaatcagg aagggatggc tgaggtcgcc cggtttattg    1740
aaatgaacgg ctcttttgct gacgagaaca gggactggtg aaatgcagtt taaggtttac    1800
acctataaaa gagagagccg ttatcgtctg tttgtggatg tacagagtga tattattgac    1860
acgcccgggc gacggatggt gatccccctg gccagtgcac gtctgctgtc agataaagtc    1920
tcccgtgaac tttacccggt ggtgcatatc ggggatgaaa gctggcgcat gatgaccacc    1980
gatatggcca gtgtgccggt ctccgttatc ggggaagaag tggctgatct cagccaccgc    2040
gaaaatgaca tcaaaaacgc cattaacctg atgttctggg aatataaat gtcaggctcc    2100 cttatacaca gccagtctgc aggtcgacca tagtgactgg atatgttgtg ttttacagta    2160
ttatgtagtc tgttttttat gcaaaatcta atttaatata ttgatattta tatcatttta    2220
cgtttctcgt tcagctttct tgtacaaagt ggttgatgac aagcttgcgg ccgcactcga    2280
gcctatacta ggttattgga aaattaaggg ccttgtgcaa cccactcgac ttcttttgga    2340
atatcttgaa gaaaaatatg aagagcattt gtatgagcgc gatgaaggtg ataaatggcg    2400
aaacaaaaag tttgaattgg gtttggagtt tcccaatctt ccttattata ttgatggtga    2460
tgttaaatta acacagtcta tggccatcat acgttatata gctgacaagc acaacatgtt    2520
gggtggttgt ccaaaagagc gtgcagagat ttcaatgctt gaaggagcgg ttttggatat    2580
tagatacggt gtttcgagaa ttgcatatag taaagacttt gaaactctca agttgatttt    2640
tcttagcaag ctacctgaaa tgctgaaaat gttcgaagat cgtttatgtc ataaaacata    2700
tttaaatggt gatcatgtaa cccatcctga cttcatgttg tatgacgctc ttgatgttgt    2760
tttatacatg gacccaatgt gcctggatgc gttcccaaaa ttagtttgtt ttaaaaaacg    2820
```

-continued

```
tattgaagct atcccacaaa ttgataagta cttgaaatcc agcaagtata tagcatggcc   2880
tttgcagggc tggcaagcca cgtttggtgg tggcgaccat cctccaaaat cggatctggt   2940
tccgcgttga agatctgact gaaaaaaaaa aaaaaaaaa aaaaaaaaa agtttaaaca     3000 ctagtccgct gagcaataac tagcataacc ccttgggggcc tctaaacggg tcttgagggg   3060
ttttttgctg aaaggaggaa ctatatccgg gcttcctcgc tcactgactc gctgcgctcg   3120
gtcgttcggc tgcggcgagc ggtatcagct cactcaaagg cggtaatacg gttatccaca   3180
gaatcagggg ataacgcagg aaagaacatg tgagcaaaag gccagcaaaa ggccaggaac   3240
cgtaaaaagg ccgcgttgct ggcgtttttc cataggctcc gcccccctga cgagcatcac   3300
aaaaatcgac gctcaagtca gaggtggcga aacccgacag gactataaag ataccaggcg   3360
tttccccctg gaagctccct cgtgcgctct cctgttccga ccctgccgct taccggatac   3420
ctgtccgcct ttctcccttc gggaagcgtg cgctttctc atagctcacg ctgtaggtat    3480
ctcagttcgg tgtaggtcgt tcgctccaag ctgggctgtg tgcacgaacc ccccgttcag   3540
cccgaccgct gcgccttatc cggtaactat cgtcttgagt ccaacccggt aagacacgac   3600
ttatcgccac tggcagcagc cactggtaac aggattagca gagcgaggta tgtaggcggt   3660
gctacagagt tcttgaagtg gtggcctaac tacggctaca ctagaaggac agtatttggt   3720
atctgcgctc tgctgaagcc agttaccttc ggaaaaagag ttggtagctc ttgatccggc   3780
aaacaaacca ccgctggtag cggtggtttt tttgtttgca agcagcagat tacgcgcaga   3840
aaaaaaggat ctcaagaaga tcctttgatc ttttctacgg ggtctgacgc tcagtggaac   3900
gaaaactcac gttaagggat tttggtcatg agattatcaa aaaggatctt cacctagatc   3960
cttttaaatt aaaaatgaag ttttaaatca atctaaagta tatatgagta aacttggtct   4020
gacagttacc aatgcttaat cagtgaggca cctatctcag cgatctgtct atttcgttca   4080
tccatagttg cctgactccc cgtcgtgtag ataactacga tacgggaggg cttaccatct   4140
ggccccagtg ctgcaatgat accgcgagac ccacgctcac cggctccaga tttatcagca   4200
ataaaccagc cagccggaag ggccgagcgc agaagtggtc ctgcaacttt atccgcctcc   4260
atccagtcta ttaattgttg ccgggaagct agagtaagta gttcgccagt taatagtttg   4320
cgcaacgttg ttgccattgc tacaggcatc gtggtgtcac gctcgtcgtt tggtatggct   4380
tcattcagct ccggttccca acgatcaagg cgagttacat gatcccccat gttgtgcaaa   4440
aaagcggtta gctccttcgg tcctccgatc gttgtcagaa gtaagttggc cgcagtgtta   4500
tcactcatgg ttatggcagc actgcataat tctcttactg tcatgccatc cgtaagatgc   4560
ttttctgtga ctggtgagta ctcaaccaag tcattctgag aatagtgtat gcggcgaccg   4620
agttgctctt gcccggcgtc aatacgggat aataccgcgc cacatagcag aactttaaaa   4680
gtgctcatca ttggaaaacg ttcttcgggg cgaaaactct caaggatctt accgctgttg   4740
agatccagtt cgatgtaacc cactcgtgca cccaactgat cttcagcatc ttttactttc   4800
accagcgttt ctgggtgagc aaaaacagga aggcaaaatg ccgcaaaaaa gggaataagg   4860
gcgacacgga aatgttgaat actcatactc ttcctttttc aatattattg aagcatttat   4920
cagggttatt gtctcatgag cggatacata tttgaatgta tttagaaaaa taaacaaata   4980
ggggttccgc gcacatttcc ccgaaaagtg ccacctgacg tctaagaaac cattattatc   5040
atgacattaa cctataaaaa taggcgtatc acgaggccct ttcgtctcgc gcgtttcggt   5100
gatgacggtg aaaacctctg acacatgcag ctcccggaga cggtcacagc ttgtctgtaa   5160
gcggatgccg ggagcagaca agcccgtcag ggcgcgtcag cgggtgttgg cgggtgtcgg   5220
```

-continued

```
ggctggctta actatgcggc atcagagcag attgtactga gagtgcacca tatatgcggt    5280
gtgaaatacc gcacagatgc gtaaggagaa aataccgcat caggaaattg taaacgttaa    5340
tattttgtta aaattcgcgt taaatttttg ttaaatcagc tcattttttta accaataggc   5400 cgaaatcggc aaaatccctt ataaatcaaa agaatagacc gagatagggt tgagtgttgt    5460
tccagtttgg aacaagagtc cactattaaa gaacgtggac tccaacgtca aagggcgaaa    5520
aaccgtctat cagggcgatg gcccactacg tgaaccatca ccctaatcaa gttttttggg    5580
gtcgaggtgc cgtaaagcac taaatcggaa ccctaaaggg agcccccgat ttagagcttg    5640
acggggaaag ccggcgaacg tggcgagaaa ggaagggaag aaagcgaaag gagcgggcgc    5700
tagggcgctg gcaagtgtag cggtcacgct gcgcgtaacc accacacccg ccgcgcttaa    5760
tgcgccgcta cagggcgcgt cgcgccattc gccattcagg ctgcgcaact gttgggaagg    5820
gcgatcggtg cgggcctctt cgctattacg ccagctggcg aaagggggat gtgctgcaag    5880
gcgattaagt tgggtaacgc cagggttttc ccagtcacga cgttgtaaaa cgacggccag    5940
tgaattgtaa tacgactcac tata                                          5964
```

<210> SEQ ID NO 4
<211> LENGTH: 909
<212> TYPE: DNA
<213> ORGANISM: Artificial Sequence
<220> FEATURE:
<223> OTHER INFORMATION: Synthetic

<400> SEQUENCE: 4

```
atgtccaagt tgttgtacgt gcgtgatcat gagggctttg cctgcctaac ggtcgaaacc     60
caccgcaacc gctggttcgc ggctcacatt gtcctcacca aggactgcgg gtgtctcaag    120
ctactcaatg agagggactt ggagttttac aagttcctct ttacgttcct ggccatggcc    180
gagaagcttg tgaactttaa cattgatgaa ctggtcacca gcttcgagag ccacgacatt    240
gatcactact acaccgagca gaaggccatg gagaacgtcc acggggagac ttatgctaac    300 atttttaaaca tgctctttga tggggacagg gcggcgatga acgcctacgc agaggccatc    360
atggccgacg aggccctgca agccaagatt tcctggctcc gtgacaaggt ggcggccgcc    420
gtcaccctgc cggagaagat tcttgtgttc ctgctgattg aaggcatctt cttcattagc    480
tccttctaca gcatagccct gctgcgggtc cggggcctaa tgcctggcat ctgcctggcc    540
aataactaca taagtaggga tgagctgctc cacacccgcg ctgcctccct gttatacaat    600
agcatgacag ccaaggctga ccgaccaagg gccacctgga tccaggagct gtttcgcact    660
gcggtggagg tagagactgc cttcatcgag gctcgtggag aggggggttac cttggtggat    720 gtgcgagcca taaagcagtt tctggaggcc acggccgatc gcatcctggg tgacattggt    780
caggctccct tgtatggcac accaccccccc aaggactgcc cgctcaccta catgactagc    840
atcaagcaaa ctaatttctt tgagcaagag agttccgatt acaccatgct ggtggtagat    900
gacctttga                                                            909
```

<210> SEQ ID NO 5
<211> LENGTH: 302
<212> TYPE: PRT
<213> ORGANISM: Artificial Sequence
<220> FEATURE:
<223> OTHER INFORMATION: Synthetic

<400> SEQUENCE: 5

-continued

```
Met Ser Lys Leu Leu Tyr Val Arg Asp His Glu Gly Phe Ala Cys Leu
1               5                   10                  15

Thr Val Glu Thr His Arg Asn Arg Trp Phe Ala Ala His Ile Val Leu
            20                  25                  30

Thr Lys Asp Cys Gly Cys Leu Lys Leu Leu Asn Glu Arg Asp Leu Glu
            35                  40                  45

Phe Tyr Lys Phe Leu Phe Thr Phe Leu Ala Met Ala Glu Lys Leu Val
        50                  55                  60

Asn Phe Asn Ile Asp Glu Leu Val Thr Ser Phe Glu Ser His Asp Ile
65                  70                  75                  80

Asp His Tyr Tyr Thr Glu Gln Lys Ala Met Glu Asn Val His Gly Glu
                85                  90                  95

Thr Tyr Ala Asn Ile Leu Asn Met Leu Phe Asp Gly Asp Arg Ala Ala
            100                 105                 110

Met Asn Ala Tyr Ala Glu Ala Ile Met Ala Asp Glu Ala Leu Gln Ala
            115                 120                 125

Lys Ile Ser Trp Leu Arg Asp Lys Val Ala Ala Ala Val Thr Leu Pro
    130                 135                 140

Glu Lys Ile Leu Val Phe Leu Leu Ile Glu Gly Ile Phe Phe Ile Ser
145                 150                 155                 160

Ser Phe Tyr Ser Ile Ala Leu Leu Arg Val Arg Gly Leu Met Pro Gly
                165                 170                 175

Ile Cys Leu Ala Asn Asn Tyr Ile Ser Arg Asp Glu Leu Leu His Thr
            180                 185                 190

Arg Ala Ala Ser Leu Leu Tyr Asn Ser Met Thr Ala Lys Ala Asp Arg
            195                 200                 205

Pro Arg Ala Thr Trp Ile Gln Glu Leu Phe Arg Thr Ala Val Glu Val
    210                 215                 220

Glu Thr Ala Phe Ile Glu Ala Arg Gly Glu Gly Val Thr Leu Val Asp
225                 230                 235                 240

Val Arg Ala Ile Lys Gln Phe Leu Glu Ala Thr Ala Asp Arg Ile Leu
                245                 250                 255

Gly Asp Ile Gly Gln Ala Pro Leu Tyr Gly Thr Pro Pro Lys Asp
            260                 265                 270

Cys Pro Leu Thr Tyr Met Thr Ser Ile Lys Gln Thr Asn Phe Phe Glu
    275                 280                 285

Gln Glu Ser Ser Asp Tyr Thr Met Leu Val Val Asp Asp Leu
    290                 295                 300
```

<210> SEQ ID NO 6
<211> LENGTH: 2625
<212> TYPE: DNA
<213> ORGANISM: Artificial Sequence
<220> FEATURE:
<223> OTHER INFORMATION: Synthetic

<400> SEQUENCE: 6

```
atgtccgccc ccgtcgtcat caaggccctt gtggcctcaa acactgacat tgcggaggcc          60
atcctcgatg ccatcctctc gcggcctgac gagggcttcc gcctgttttg tttgtgccac         120
aacgcctcgc ccctccacca cgtggcgggt tctctcgtgg aactgcagct tcacctgccc         180
aagaagcggc tgacctcaca gagccgctgc ggcctggttc tgacgctgca cctgccggcg         240
gaggaggcct tccccttcct gcgcggcctc acgccgctca ccgcggaccg tctatccacc         300
tacctagatc gcgcgggggc cctgcgctcg ctcacgcccc tcgtggaact gctcacactg         360
```

```
agcgctaaga aacagccaca gggggatgcc agaggccgcg tggcgtggct gcgtcccaag      420
atcgtgggct gtctgcgccg catctaccgc gttaacatct cggccaggtg gttcattagc      480
acctttggct cccacgaggc ccagttcgtg ctagtcacgg ctgcttacta tttttggggc      540
attccttgta cgattgagac cctggcgcac ctcacggagc tatttacttc cgagtctggt      600
cagagcctgg ccgccgtcac gtccctggcc gagctggggg aggtctttgg ctcctcggca      660
tgggcggagc agaccgaggc ttttgcccac tttgcacacg agaaactgcg gcgggactcg      720
cgagagatcc gcgctgtggc aaggacgata gacgcctaca gggggcgcct tcccctggcc      780
tcggccgatc tcgtgcgcta cgtctatttg gcccacgcac agtgcttcaa cgagggaacc      840
tttaagcgat actctcagtt aacgagcatg ggagaaattg ggtgtctgcc ttcggggggc      900
gtcgtgctcc cctcgctcct ggacaggggc tttgcggagc acatgcgcac ctacttcacc      960
cgggagactt acctggctga gcatgtgcgt gtccagcagc tgaaaatccg catggagccc     1020
ccggccccat acacgtggga ccccgacccc gatgacggac tcatgcgggc ctgggccggg     1080
ctcagtgtgg acgtggcccg ggagctggtg gagctcgcgc gctggcacgc ggatgagggt     1140
cccacatacc cccccacgct tcaagggttt ctatgcttgg ccggccaggc cacctgccgg     1200
ggccagtgga atcccaagga acaattcctc ccacccaccg tccttcgaag ggtgcagcgg     1260
ctaccggtct tcctctgcca ttttgcagac aggcactact ttgtaatgac agccgctgac     1320
cccttctcat cccacctggc ggaggtcgtc tccaccccga ccaactgccg cctcccagac     1380
acgtgtctca ccagggccct ctcctacacc ccagtgtact attcacagaa cagcctgagc     1440
gagcagctct ttgtctcccg gcatgaatac tttaatcccc ggcttccggt ctgcaacctg     1500
gtcttggacc tggatctaaa gatcaagggg gcccctggt cgctggagga aatctatgac      1560
ctgtgccgga ccgtgcggcg tgaggtactg cgcctcatgc gccgcctggg tccagtgtcc     1620
agggcccacc cagtctattt tttcaaatca gcttgtccac ccgccgaccc ggataatatg     1680
gaagatgtgc tcccctttg catatgcacg ggaaaactgg gctttcgcgt catcacccc       1740 ctacctagag gccatgctat tgtgggaaca agcgcagtac aagggtttgt gtctgtgctg     1800
cagaagctca tgggcctaac ggcctgcctg cgccgcatgc gtcacaagat caaagagatt     1860 ggggcccgc ttttttgacag cggcgtgtat cacgccgggc ggtgcatccg gctgccgcat      1920
acctacaagg tggacagggg cggtggtctt agccggcagc tgcgcctctt tgtctgtcat     1980
ccggaagagg aagacaagca cagctatgtt aagaatgccc tcaacattca aaacctctta     2040
catcactcac tgcacgtggg ctggccggcc cccaaaacct tctgctacca catcgcggat     2100
gatgggcgtg actatctaat ccagaggacc cgcgagaccc tgcccccac cgtggagaat       2160 gtctgcgcca tgatagaggg acatctgggc ctggatctcg tcgcctgggt cagctcctgc     2220
atctggccct cgctcatgag caccctggca acagctgtgc cagaagacaa attcccccag     2280
tttctccatg tcacgtttga gcaaaccggg ccaaacttag ttcaggtgtg ccatgcccgg     2340
ggcaggaact ttgcgtgcct gaggcatacc cacagggcca gctccaagaa tgtgagggtg     2400
tttctggtac tctactacac atcacaggcc atcacggtca ccttcatgag tcagtgcttc     2460
gccggtcgct gtgggggccaa tcaaccgacc gcccatttct ccatcagcgt gcccgcctcc     2520
agaatcataa ataggggctga ggccagtcaa gacagcacta catcccagct agcccgtcgt     2580
agagacagac aagatgggttc cttctcagag actctcccga actag                     2625
```

<210> SEQ ID NO 7
<211> LENGTH: 874

-continued

<212> TYPE: PRT
<213> ORGANISM: Artificial Sequence
<220> FEATURE:
<223> OTHER INFORMATION: Synthetic

<400> SEQUENCE: 7

```
Met Ser Ala Pro Val Val Ile Lys Ala Leu Val Ala Ser Asn Thr Asp
1               5                   10                  15

Ile Ala Glu Ala Ile Leu Asp Ala Ile Leu Ser Arg Pro Asp Glu Gly
            20                  25                  30

Phe Arg Leu Phe Cys Leu Cys His Asn Ala Ser Pro Leu His His Val
            35                  40                  45

Ala Gly Ser Leu Val Glu Leu Gln Leu His Leu Pro Lys Lys Arg Leu
        50                  55                  60

Thr Ser Gln Ser Arg Cys Gly Leu Val Leu Thr Leu His Leu Pro Ala
65                  70                  75                  80

Glu Glu Ala Phe Pro Phe Leu Arg Gly Leu Thr Pro Leu Thr Ala Asp
                85                  90                  95

Arg Leu Ser Thr Tyr Leu Asp Arg Ala Gly Ala Leu Arg Ser Leu Thr
            100                 105                 110

Pro Leu Val Glu Leu Leu Thr Leu Ser Ala Lys Lys Gln Pro Gln Gly
            115                 120                 125
```

```
Asp Ala Arg Gly Arg Val Ala Trp Leu Arg Pro Lys Ile Val Gly Cys
    130             135             140

Leu Arg Arg Ile Tyr Arg Val Asn Ile Ser Ala Arg Trp Phe Ile Ser
145             150             155             160

Thr Phe Gly Ser His Glu Ala Gln Phe Val Leu Val Thr Ala Ala Tyr
            165             170             175

Tyr Phe Trp Gly Ile Pro Cys Thr Ile Glu Thr Leu Ala His Leu Thr
            180             185             190

Glu Leu Phe Thr Ser Glu Ser Gly Gln Ser Leu Ala Ala Val Thr Ser
        195             200             205

Leu Ala Glu Leu Gly Glu Val Phe Gly Ser Ser Ala Trp Ala Glu Gln
    210             215             220

Thr Glu Ala Phe Ala His Phe Ala His Glu Lys Leu Arg Arg Asp Ser
225             230             235             240

Arg Glu Ile Arg Ala Val Ala Arg Thr Ile Asp Ala Tyr Arg Gly Arg
            245             250             255

Leu Pro Leu Ala Ser Ala Asp Leu Val Arg Tyr Val Tyr Leu Ala His
            260             265             270

Ala Gln Cys Phe Asn Glu Gly Thr Phe Lys Arg Tyr Ser Gln Leu Thr
        275             280             285

Ser Met Gly Glu Ile Gly Cys Leu Pro Ser Gly Gly Val Val Leu Pro
    290             295             300

Ser Leu Leu Asp Arg Gly Phe Ala Glu His Met Arg Thr Tyr Phe Thr
305             310             315             320

Arg Glu Thr Tyr Leu Ala Glu His Val Arg Val Gln Gln Leu Lys Ile
            325             330             335

Arg Met Glu Pro Pro Ala Pro Tyr Thr Trp Asp Pro Asp Pro Asp Asp
            340             345             350

Gly Leu Met Arg Ala Trp Ala Gly Leu Ser Val Asp Val Ala Arg Glu
        355             360             365

Leu Val Glu Leu Ala Arg Trp His Ala Asp Glu Gly Pro Thr Tyr Pro
    370             375             380

Pro Thr Leu Gln Gly Phe Leu Cys Leu Ala Gly Gln Ala Thr Cys Arg
385             390             395             400

Gly Gln Trp Asn Pro Lys Glu Gln Phe Leu Pro Pro Thr Val Leu Arg
            405             410             415

Arg Val Gln Arg Leu Pro Val Phe Leu Cys His Phe Ala Asp Arg His
            420             425             430

Tyr Phe Val Met Thr Ala Ala Asp Pro Phe Ser Ser His Leu Ala Glu
        435             440             445

Val Val Ser Thr Pro Thr Asn Cys Arg Leu Pro Asp Thr Cys Leu Thr
    450             455             460

Arg Ala Leu Ser Tyr Thr Pro Val Tyr Tyr Ser Gln Asn Ser Leu Ser
465             470             475             480

Glu Gln Leu Phe Val Ser Arg His Glu Tyr Phe Asn Pro Arg Leu Pro
            485             490             495

Val Cys Asn Leu Val Leu Asp Leu Asp Leu Lys Ile Lys Gly Ala Pro
            500             505             510

Trp Ser Leu Glu Glu Ile Tyr Asp Leu Cys Arg Thr Val Arg Arg Glu
        515             520             525

Val Leu Arg Leu Met Arg Arg Leu Gly Pro Val Ser Arg Ala His Pro
    530             535             540

Val Tyr Phe Phe Lys Ser Ala Cys Pro Pro Ala Asp Pro Asp Asn Met
```

-continued

```
545              550              555              560

Glu Asp Val Leu Pro Phe Cys Ile Cys Thr Gly Lys Leu Gly Phe Arg
            565              570              575

Val Ile Thr Pro Leu Pro Arg Gly His Ala Ile Val Gly Thr Ser Ala
            580              585              590

Val Gln Gly Phe Val Ser Val Leu Gln Lys Leu Met Gly Leu Thr Ala
            595              600              605

Cys Leu Arg Arg Met Arg His Lys Ile Lys Glu Ile Gly Ala Pro Leu
            610              615              620

Phe Asp Ser Gly Val Tyr His Ala Gly Arg Cys Ile Arg Leu Pro His
625              630              635              640

Thr Tyr Lys Val Asp Arg Gly Gly Gly Leu Ser Arg Gln Leu Arg Leu
            645              650              655

Phe Val Cys His Pro Glu Glu Glu Asp Lys His Ser Tyr Val Lys Asn
            660              665              670

Ala Leu Asn Ile Gln Asn Leu Leu His His Ser Leu His Val Gly Trp
            675              680              685

Pro Ala Pro Lys Thr Phe Cys Tyr His Ile Ala Asp Asp Gly Arg Asp
            690              695              700

Tyr Leu Ile Gln Arg Thr Arg Glu Thr Leu Pro Pro Thr Val Glu Asn
705              710              715              720

Val Cys Ala Met Ile Glu Gly His Leu Gly Leu Asp Leu Val Ala Trp
            725              730              735

Val Ser Ser Cys Ile Trp Pro Ser Leu Met Ser Thr Leu Ala Thr Ala
            740              745              750

Val Pro Glu Asp Lys Phe Pro Gln Phe Leu His Val Thr Phe Glu Gln
            755              760              765

Thr Gly Pro Asn Leu Val Gln Val Cys His Ala Arg Gly Arg Asn Phe
            770              775              780

Ala Cys Leu Arg His Thr His Arg Ala Ser Ser Lys Asn Val Arg Val
785              790              795              800

Phe Leu Val Leu Tyr Tyr Thr Ser Gln Ala Ile Thr Val Thr Phe Met
            805              810              815

Ser Gln Cys Phe Ala Gly Arg Cys Gly Ala Asn Gln Pro Thr Ala His
            820              825              830

Phe Ser Ile Ser Val Pro Ala Ser Arg Ile Ile Asn Arg Ala Glu Ala
            835              840              845

Ser Gln Asp Ser Thr Thr Ser Gln Leu Ala Arg Arg Arg Asp Arg Gln
850              855              860

Asp Gly Ser Phe Ser Glu Thr Leu Pro Asn
865              870
```

```
<210> SEQ ID NO 8
<211> LENGTH: 837
<212> TYPE: DNA
<213> ORGANISM: Artificial Sequence
<220> FEATURE:
<223> OTHER INFORMATION: Synthetic

<400> SEQUENCE: 8
atggaggcct gtccacacat acgctacgcc ttccagaatg acaagctgtt gctccagcag      60
gctagtgtag ggcggctcac cttggtcaac aagaccacca tcctgctgcg cccgatgaag     120
accacaactg tggacctagg cctctatgcc cgcccacccg agggtcatgg gctcatgctg     180
tggggcagca cctcccgtcc ggtcacgtct catgttggca tcatcgatcc cggctacacg     240
```

```
ggggaactcc ggctaatcct ccagaatcag cggcgctaca actccacgct gcgtccatcg      300
gagctcaaaa tccacctggc tgccttcaga tatgccaccc cccagatgga ggaggacaag      360
ggtcccatca accacccca gtaccccggg gacgtgggcc tggacgtctc tttgccaaag       420
gacctggccc tcttcccca tcagaccgtc tcagtgacac tcaccgtgcc ccccccttct       480
atccctcacc acaggccgac aatctttggc aggtcgggcc tggccatgca gggtattcta     540
gtgaagccct gcaggtggcg ccggggtggg gtggacgtca gcctgaccaa ctttagtgac     600
cagaccgtgt tccttaacaa gtaccggcgc ttctgtcagc ttgtttacct tcacaagcac     660
cacctcacct ccttctacag ccccacagt gacgcgggg tccttggccc cagatctctc      720
tttaggtggg ccagctgcac cttcgaggag gtgccgagcc tggccatggg tgatagtggg    780
ctgagcgagg cgctcgaggg gagacagggg aggggtttg gatcctcggg tcaatga       837
```

```
<210> SEQ ID NO 9
<211> LENGTH: 278
<212> TYPE: PRT
<213> ORGANISM: Artificial Sequence
<220> FEATURE:
<223> OTHER INFORMATION: Synthetic

<400> SEQUENCE: 9

Met Glu Ala Cys Pro His Ile Arg Tyr Ala Phe Gln Asn Asp Lys Leu
1               5                   10                  15

Leu Leu Gln Gln Ala Ser Val Gly Arg Leu Thr Leu Val Asn Lys Thr
                20                  25                  30

Thr Ile Leu Leu Arg Pro Met Lys Thr Thr Thr Val Asp Leu Gly Leu
            35                  40                  45

Tyr Ala Arg Pro Pro Glu Gly His Gly Leu Met Leu Trp Gly Ser Thr
        50                  55                  60

Ser Arg Pro Val Thr Ser His Val Gly Ile Ile Asp Pro Gly Tyr Thr
65                  70                  75                  80

Gly Glu Leu Arg Leu Ile Leu Gln Asn Gln Arg Arg Tyr Asn Ser Thr
                85                  90                  95

Leu Arg Pro Ser Glu Leu Lys Ile His Leu Ala Ala Phe Arg Tyr Ala
            100                 105                 110

Thr Pro Gln Met Glu Glu Asp Lys Gly Pro Ile Asn His Pro Gln Tyr
        115                 120                 125

Pro Gly Asp Val Gly Leu Asp Val Ser Leu Pro Lys Asp Leu Ala Leu
        130                 135                 140

Phe Pro His Gln Thr Val Ser Val Thr Leu Thr Val Pro Pro Pro Ser
145                 150                 155                 160

Ile Pro His His Arg Pro Thr Ile Phe Gly Arg Ser Gly Leu Ala Met
                165                 170                 175

Gln Gly Ile Leu Val Lys Pro Cys Arg Trp Arg Arg Gly Gly Val Asp
            180                 185                 190

Val Ser Leu Thr Asn Phe Ser Asp Gln Thr Val Phe Leu Asn Lys Tyr
            195                 200                 205

Arg Arg Phe Cys Gln Leu Val Tyr Leu His Lys His His Leu Thr Ser
        210                 215                 220

Phe Tyr Ser Pro His Ser Asp Ala Gly Val Leu Gly Pro Arg Ser Leu
225                 230                 235                 240

Phe Arg Trp Ala Ser Cys Thr Phe Glu Glu Val Pro Ser Leu Ala Met
                245                 250                 255
```

-continued

```
Gly Asp Ser Gly Leu Ser Glu Ala Leu Glu Gly Arg Gln Gly Arg Gly
            260                 265                 270

Phe Gly Ser Ser Gly Gln
        275

<210> SEQ ID NO 10
<211> LENGTH: 447
<212> TYPE: DNA
<213> ORGANISM: Artificial Sequence
<220> FEATURE:
<223> OTHER INFORMATION: Synthetic

<400> SEQUENCE: 10
atgtgtccac cagttcgcca gcaccccgcc caggcaccac cagccaagcg tcaggccctg      60
gaaacagttc cacatccaca aaaccggggg aggttaatgt caccaaaggc acgcccccc      120 aaaatgcaac gtcgccccag gccccagtg gccaaaagac ggcggttccc acggtcacct      180
caacaggtgg aaaggccaat tctaccaccg gtggaaagca caccacagga catggagccc      240
ggacaagtac agagcccacc acagattacg gcggtgattc aactacgcca agaccgagat      300
acaatgcgac cacctatcta cctcccagca cttctagcaa actgcggccc cgctggactt      360
ttacgagccc accggttacc acagcccaag ccaccgtgcc agtcccgcca acgtcccagc      420
ccagattctc aaacctctcc atgctag                                         447

<210> SEQ ID NO 11
<211> LENGTH: 148
<212> TYPE: PRT
<213> ORGANISM: Artificial Sequence
<220> FEATURE:
<223> OTHER INFORMATION: Synthetic

<400> SEQUENCE: 11

Met Cys Pro Pro Val Arg Gln His Pro Ala Gln Ala Pro Pro Ala Lys
1               5                   10                  15

Arg Gln Ala Leu Glu Thr Val Pro His Pro Gln Asn Arg Gly Arg Leu
            20                  25                  30

Met Ser Pro Lys Ala Arg Pro Pro Lys Met Gln Arg Arg Pro Arg Pro
        35                  40                  45

Pro Val Ala Lys Arg Arg Arg Phe Pro Arg Ser Pro Gln Gln Val Glu
    50                  55                  60

Arg Pro Ile Leu Pro Pro Val Glu Ser Thr Pro Gln Asp Met Glu Pro
65                  70                  75                  80

Gly Gln Val Gln Ser Pro Pro Gln Ile Thr Ala Val Ile Gln Leu Arg
                85                  90                  95

Gln Asp Arg Asp Thr Met Arg Pro Pro Ile Tyr Leu Pro Ala Leu Leu
            100                 105                 110

Ala Asn Cys Gly Pro Ala Gly Leu Leu Arg Ala His Arg Leu Pro Gln
        115                 120                 125

Pro Lys Pro Pro Cys Gln Ser Arg Gln Arg Pro Ser Pro Asp Ser Gln
    130                 135                 140

Thr Ser Pro Cys
145

<210> SEQ ID NO 12
<211> LENGTH: 672
<212> TYPE: DNA
<213> ORGANISM: Artificial Sequence
<220> FEATURE:
<223> OTHER INFORMATION: Synthetic
```

-continued

```
<400> SEQUENCE: 12
atggtttcat ttaagcaggt gagggtgcca ttgtttaccg ccatcgcact tgttattgtt      60
ctactcctgg catacttttt gccacccagg gtaagaggag gagggcgggt ggcagccgcg     120
gccatcacct gggtacccaa accaaatgta gaggtctggc cggtggatcc tccaccgccg     180
gttaacttta acaagacggc cgagcaggag tatggggaca agaggtaaa actgccacat      240 tggacaccca ccctgcacac atttcaggta ccccaaaact ataccaaagc taactgtaca     300
tactgcaaca ccagagaata cacattttca tataaaggat gctgttttta tttcaccaaa     360
aagaagcaca cctggaatgg gtgtttccaa gcctgtgcag agctatatcc atgcacttat     420
ttttatgggc caacgcccga tattctacct gtggtaacta gaaatctgaa tgccattgag     480
tccctttggg tcggggtgta cagggtggga gaagggaact ggacatcatt agatggggg     540 actttaagg tttatcaaat ttttggctct cattgtacat atgtcagcaa atttagtaca      600
gttccagtct cacaccatga gtgttcattc cttaaaccat gtttatgtgt cagtcaaaga     660
tcaaatagct aa                                                         672
```

```
<210> SEQ ID NO 13
<211> LENGTH: 223
<212> TYPE: PRT
<213> ORGANISM: Artificial Sequence
<220> FEATURE:
<223> OTHER INFORMATION: Synthetic

<400> SEQUENCE: 13

Met Val Ser Phe Lys Gln Val Arg Val Pro Leu Phe Thr Ala Ile Ala
1               5                   10                  15

Leu Val Ile Val Leu Leu Leu Ala Tyr Phe Leu Pro Pro Arg Val Arg
                20                  25                  30

Gly Gly Gly Arg Val Ala Ala Ala Ala Ile Thr Trp Val Pro Lys Pro
            35                  40                  45

Asn Val Glu Val Trp Pro Val Asp Pro Pro Pro Val Asn Phe Asn
        50                  55                  60

Lys Thr Ala Glu Gln Glu Tyr Gly Asp Lys Glu Val Lys Leu Pro His
65                  70                  75                  80

Trp Thr Pro Thr Leu His Thr Phe Gln Val Pro Gln Asn Tyr Thr Lys
                85                  90                  95

Ala Asn Cys Thr Tyr Cys Asn Thr Arg Glu Tyr Thr Phe Ser Tyr Lys
                100                 105                 110

Gly Cys Cys Phe Tyr Phe Thr Lys Lys Lys His Thr Trp Asn Gly Cys
            115                 120                 125

Phe Gln Ala Cys Ala Glu Leu Tyr Pro Cys Thr Tyr Phe Tyr Gly Pro
        130                 135                 140

Thr Pro Asp Ile Leu Pro Val Val Thr Arg Asn Leu Asn Ala Ile Glu
145                 150                 155                 160

Ser Leu Trp Val Gly Val Tyr Arg Val Gly Glu Gly Asn Trp Thr Ser
                165                 170                 175

Leu Asp Gly Gly Thr Phe Lys Val Tyr Gln Ile Phe Gly Ser His Cys
            180                 185                 190

Thr Tyr Val Ser Lys Phe Ser Thr Val Pro Val Ser His His Glu Cys
            195                 200                 205

Ser Phe Leu Lys Pro Cys Leu Cys Val Ser Gln Arg Ser Asn Ser
        210                 215                 220
```

```
<210> SEQ ID NO 14
<211> LENGTH: 933
<212> TYPE: DNA
<213> ORGANISM: Artificial Sequence
<220> FEATURE:
<223> OTHER INFORMATION: Synthetic

<400> SEQUENCE: 14
atggctagta gtaacagagg aaatgcccga ccattaaaat ctttcctcca tgagctttac      60
ctgaaacact atcccgaagt gggggatgtg gtgcatctac tgaacaccat cggggtcgac     120
tgcgacctcc cacctagcca cccactcctg acagcccaga ggggggctgtt cctggcaaga     180 gtcttgcagg ctgtacagca gcacaagctg ctggaagaca ccatcgtccc caagatctta     240
aagaagctgg cttatttctt agagctgcta agctactact cccccaagga tgaacagcgt     300
gacatcgccg aggttcttga ccacctcaag acgaatcggg acctggggct ggacgacaga     360
ctctgggccc tgattaggaa actgcgccaa gacagacacc atgcctctgt aaatgtcctc     420
atgccaggaa gcgactacac agccgtgtcg ctgcagtact acgacggcat ctccataggt     480
atgaggaagg taatcgcgga tgtctgccgc agtggctatg cctccatgcc ctccatgacg     540
gccacgcaca acctctccca ccagctcttg atggcgtccg ggcccagtga ggaaccgtgc     600
gcctggcgcg ggttctttaa ccaggtcctc ctctggactg tggccctctg caagtttcgc     660
agatgcattt actataacta cattcaggga tctatagcca ccatctccca gcttctgcac     720
ctcgagatca aggccctctg cagctggata atatcccagg atggcatgcg cctctttcaa     780
cacagcaggc ctctcctcac cctctgggag agcgtggccg caaatcagga ggtcacggat     840
gccattaccc tgcctgactg cgctgaatac atagacctac taaagcacac aaaacatgtc     900
ttagaaaact gttctgccat gcaatacaaa taa                                  933

<210> SEQ ID NO 15
<211> LENGTH: 310
<212> TYPE: PRT
<213> ORGANISM: Artificial Sequence
<220> FEATURE:
<223> OTHER INFORMATION: Synthetic

<400> SEQUENCE: 15

Met Ala Ser Ser Asn Arg Gly Asn Ala Arg Pro Leu Lys Ser Phe Leu
1               5                   10                  15

His Glu Leu Tyr Leu Lys His Tyr Pro Glu Val Gly Asp Val Val His
                20                  25                  30

Leu Leu Asn Thr Ile Gly Val Asp Cys Asp Leu Pro Pro Ser His Pro
            35                  40                  45

Leu Leu Thr Ala Gln Arg Gly Leu Phe Leu Ala Arg Val Leu Gln Ala
        50                  55                  60

Val Gln Gln His Lys Leu Leu Glu Asp Thr Ile Val Pro Lys Ile Leu
65                  70                  75                  80

Lys Lys Leu Ala Tyr Phe Leu Glu Leu Leu Ser Tyr Tyr Ser Pro Lys
                85                  90                  95

Asp Glu Gln Arg Asp Ile Ala Glu Val Leu Asp His Leu Lys Thr Asn
            100                 105                 110

Arg Asp Leu Gly Leu Asp Asp Arg Leu Trp Ala Leu Ile Arg Lys Leu
        115                 120                 125

Arg Gln Asp Arg His His Ala Ser Val Asn Val Leu Met Pro Gly Ser
    130                 135                 140
```

-continued

```
Asp Tyr Thr Ala Val Ser Leu Gln Tyr Tyr Asp Gly Ile Ser Ile Gly
145                 150                 155                 160

Met Arg Lys Val Ile Ala Asp Val Cys Arg Ser Gly Tyr Ala Ser Met
                165                 170                 175

Pro Ser Met Thr Ala Thr His Asn Leu Ser His Gln Leu Leu Met Ala
                180                 185                 190

Ser Gly Pro Ser Glu Glu Pro Cys Ala Trp Arg Gly Phe Phe Asn Gln
            195                 200                 205

Val Leu Leu Trp Thr Val Ala Leu Cys Lys Phe Arg Arg Cys Ile Tyr
        210                 215                 220

Tyr Asn Tyr Ile Gln Gly Ser Ile Ala Thr Ile Ser Gln Leu Leu His
225                 230                 235                 240

Leu Glu Ile Lys Ala Leu Cys Ser Trp Ile Ile Ser Gln Asp Gly Met
                245                 250                 255

Arg Leu Phe Gln His Ser Arg Pro Leu Leu Thr Leu Trp Glu Ser Val
                260                 265                 270

Ala Ala Asn Gln Glu Val Thr Asp Ala Ile Thr Leu Pro Asp Cys Ala
            275                 280                 285

Glu Tyr Ile Asp Leu Leu Lys His Thr Lys His Val Leu Glu Asn Cys
        290                 295                 300

Ser Ala Met Gln Tyr Lys
305                 310

<210> SEQ ID NO 16
<211> LENGTH: 2430
<212> TYPE: DNA
<213> ORGANISM: Artificial Sequence
<220> FEATURE:
<223> OTHER INFORMATION: Synthetic

<400> SEQUENCE: 16
atggccgagg agccgagggc gccagaggcg ctctcgtcca cgttcatgtt gaacatgacc        60
tcagacgcct ccgtgaggcg tatagtcagg aggataggga ccctggctag gcgccgcgtc       120
caacaactcc cggatatgga gacgttctcc cccgagtttg acccggagct ctcggagccc       180
cccttcctgc cctttcagc ctatgtaatt acgggaacgg cggggggctgg caagagcacc       240 agcgttagct gcctccacca cacgatggac tgcctggtca cgggagccac aaccgtggcc       300
gcacagaacc tctcccagac actccgagcc tactgcccaa ccgtctatag cgcctttggg       360
ttcaagagcc gccacataaa tatgacgcag cgggtcagca gtcatggtcg ctctacggac       420 gccgcctag aggaactcca gcggcgggac ctggccaaat actggccggt actctccgac        480
attgccgccg agttcaggcg aaccaagccc aggggggctct actcgggagt ctctggcccc      540
gcctttgagg tcctgagaga catgcaccag gggcagctat ggaccaccaa tgtgatcgtg       600
gtggacgaag ctggaacgct ttccgtgcac attctaacag ccgtggtctt ttgctactgg       660
ttcttcaacg cctggctgcg tacccactc taccgccggg gccgcattcc ctgcatcgtc        720
tgcgtgggct ctcccaccca gacagacgcc tttcagtcct cctttagcca cgagacccag       780
gtaaacaaga ttcgcgagtg cgacaacatc ctcaccttcc tggtgggcaa ccccagggcc       840
gcgacctacg tggacgtggc ccgcaactgg gccctcttca tcaacaacaa cgcgctgcacc      900 gacgtccagt ttggacacct catgaagacc ctcgagtacg gcctcgagct ctcgccggac       960
atcctggcct acgtcgaccg cttcgtcgtc cccaggcggg ccataatgga ccccgcgcag      1020
tacgtgggct ggacccggct cttcctctcc cacgccgagg tcaagacctt cctcaccacc      1080
```

-continued

```
ctccatgcca cgctcaagac tgccgggcag gggcgtgccg cgcggggaac cggggggagat    1140 gggggcgggg tgaccatgtt tacctgcccg gtggagtgcg aggtcttcct cgatcccctg    1200
gcccagtaca agaccctggt cgggcttccg ggcctcacgg cccacacctg gctccaaaag    1260
aattatgcac gcctcggtaa ctactcgcag ttcgccgacc aagacatggt cccggtgggc    1320
accgagcagg acgaagaacg ggtcaaggtc acctacaatg tcacctacgt caagcacagc    1380
tcggtgtcgg tcaactgcaa gaccaaaaag tccatctgtg gctataccgg caccttcggg    1440
gactttatgg acacgctcga ggcggacagc ttcgtggagg cccacgggca tgagcagccc    1500
gagtatgtct acagcttcct ggcccgactc atctacggag gcatctacgc ttttagccac    1560
ggaggacatt ctctctgtga aaacgggaa tacgtggcgg agcttggtgc tgtgcccctg    1620
cccgggcgta cgtgggatcc ggaggtgact gctgggatgg agctgggcga actgccgctg    1680
gaggttgcct gggatgggga gcggagcccc gccgctgtct tctatgcccg agtactggct    1740
cccccggccg caaattctgc cccccctctgc tccctgttaa acatatataa tgacctcagg    1800
gcctatttca ggcaatgcct ggatgtggcc gtccgctatg gcggaaggga gttcagggac    1860 ctcccccttct gcacatttac caacaacatg ctgattcgcg acaacataga gttcacctca    1920
gacgagcctc tccttcacgg cctcctggac tacgcctcca ccaccgagaa ctacacgctt    1980
ctgggctaca cgcatctcaa cgtcttcttt ggcatccgag aaagcagca gcctcaggac    2040 gctggcagtt cacgcatgcc caggctaatg gtcaaggatg aggcaggctt cgtgtgctgc    2100
ctggaacaca atactaacaa actgtatgag acgatagagg acaagtccct gaacctctgc    2160
agcatccgtg actatggcat tagctcaaag ctggccatga ccatagccaa ggcccagggt    2220
ctgtccctaa acaaagtcgc catctgcttc ggcagccaca gaaacatcaa acccggccat    2280
gtgtatgtgg cgctgtcccg ggcccggcac tctaattgcg tggtcatgga caggaatccc    2340
ctatccgaga tgatcactgg ggaggggaac cccgcgagcg gctacatcgt ggatgcccta    2400
aagaactcac gcgcactact ggtttactga    2430
```

<210> SEQ ID NO 17
<211> LENGTH: 809
<212> TYPE: PRT
<213> ORGANISM: Artificial Sequence
<220> FEATURE:
<223> OTHER INFORMATION: Synthetic
<400> SEQUENCE: 17

```
Met Ala Glu Glu Pro Arg Ala Pro Glu Ala Leu Ser Ser Thr Phe Met
1               5                   10                  15

Leu Asn Met Thr Ser Asp Ala Ser Val Arg Arg Ile Val Arg Arg Ile
            20                  25                  30

Gly Thr Leu Ala Arg Arg Arg Val Gln Gln Leu Pro Asp Met Glu Thr
        35                  40                  45

Phe Ser Pro Glu Phe Asp Pro Glu Leu Ser Glu Pro Pro Phe Leu Pro
    50                  55                  60

Phe Ser Ala Tyr Val Ile Thr Gly Thr Ala Gly Ala Gly Lys Ser Thr
65                  70                  75                  80

Ser Val Ser Cys Leu His His Thr Met Asp Cys Leu Val Thr Gly Ala
                85                  90                  95

Thr Thr Val Ala Ala Gln Asn Leu Ser Gln Thr Leu Arg Ala Tyr Cys
            100                 105                 110

Pro Thr Val Tyr Ser Ala Phe Gly Phe Lys Ser Arg His Ile Asn Met
        115                 120                 125
```

-continued

```
Thr Gln Arg Val Ser Ser His Gly Arg Ser Thr Asp Ala Ala Leu Glu
    130                 135                 140

Glu Leu Gln Arg Arg Asp Leu Ala Lys Tyr Trp Pro Val Leu Ser Asp
145                 150                 155                 160

Ile Ala Ala Glu Phe Arg Arg Thr Lys Pro Arg Gly Leu Tyr Ser Gly
                165                 170                 175

Val Ser Gly Pro Ala Phe Glu Val Leu Arg Asp Met His Gln Gly Gln
                180                 185                 190

Leu Trp Thr Thr Asn Val Ile Val Val Asp Glu Ala Gly Thr Leu Ser
                195                 200                 205

Val His Ile Leu Thr Ala Val Val Phe Cys Tyr Trp Phe Phe Asn Ala
    210                 215                 220

Trp Leu Arg Thr Pro Leu Tyr Arg Arg Gly Arg Ile Pro Cys Ile Val
225                 230                 235                 240

Cys Val Gly Ser Pro Thr Gln Thr Asp Ala Phe Gln Ser Ser Phe Ser
                245                 250                 255

His Glu Thr Gln Val Asn Lys Ile Arg Glu Cys Asp Asn Ile Leu Thr
                260                 265                 270

Phe Leu Val Gly Asn Pro Arg Ala Ala Thr Tyr Val Asp Val Ala Arg
                275                 280                 285

Asn Trp Ala Leu Phe Ile Asn Asn Lys Arg Cys Thr Asp Val Gln Phe
    290                 295                 300

Gly His Leu Met Lys Thr Leu Glu Tyr Gly Leu Glu Leu Ser Pro Asp
305                 310                 315                 320

Ile Leu Ala Tyr Val Asp Arg Phe Val Val Pro Arg Ala Ala Ile Met
                325                 330                 335

Asp Pro Ala Gln Tyr Val Gly Trp Thr Arg Leu Phe Leu Ser His Ala
                340                 345                 350

Glu Val Lys Thr Phe Leu Thr Thr Leu His Ala Thr Leu Lys Thr Ala
                355                 360                 365

Gly Gln Gly Arg Ala Ala Arg Gly Thr Gly Gly Asp Gly Gly Gly Val
    370                 375                 380

Thr Met Phe Thr Cys Pro Val Glu Cys Glu Val Phe Leu Asp Pro Leu
385                 390                 395                 400

Ala Gln Tyr Lys Thr Leu Val Gly Leu Pro Gly Leu Thr Ala His Thr
                405                 410                 415

Trp Leu Gln Lys Asn Tyr Ala Arg Leu Gly Asn Tyr Ser Gln Phe Ala
                420                 425                 430

Asp Gln Asp Met Val Pro Val Gly Thr Glu Gln Asp Glu Glu Arg Val
    435                 440                 445

Lys Val Thr Tyr Asn Val Thr Tyr Val Lys His Ser Ser Val Ser Val
    450                 455                 460

Asn Cys Lys Thr Lys Lys Ser Ile Cys Gly Tyr Thr Gly Thr Phe Gly
465                 470                 475                 480

Asp Phe Met Asp Thr Leu Glu Ala Asp Ser Phe Val Glu Ala His Gly
                485                 490                 495

His Glu Gln Pro Glu Tyr Val Tyr Ser Phe Leu Ala Arg Leu Ile Tyr
                500                 505                 510

Gly Gly Ile Tyr Ala Phe Ser His Gly Gly His Ser Leu Cys Glu Asn
                515                 520                 525

Gly Glu Tyr Val Ala Glu Leu Gly Ala Val Pro Leu Pro Gly Arg Thr
    530                 535                 540
```

```
Trp Asp Pro Glu Val Thr Ala Gly Met Glu Leu Gly Glu Leu Pro Leu
545                 550                 555                 560

Glu Val Ala Trp Asp Gly Glu Arg Ser Pro Ala Ala Val Phe Tyr Ala
                565                 570                 575

Arg Val Leu Ala Pro Pro Ala Ala Asn Ser Ala Pro Leu Cys Ser Leu
                580                 585                 590

Leu Asn Ile Tyr Asn Asp Leu Arg Ala Tyr Phe Arg Gln Cys Leu Asp
            595                 600                 605

Val Ala Val Arg Tyr Gly Gly Arg Glu Phe Arg Asp Leu Pro Phe Cys
            610                 615                 620

Thr Phe Thr Asn Asn Met Leu Ile Arg Asp Asn Ile Glu Phe Thr Ser
625                 630                 635                 640

Asp Glu Pro Leu Leu His Gly Leu Leu Asp Tyr Ala Ser Thr Thr Glu
                645                 650                 655

Asn Tyr Thr Leu Leu Gly Tyr Thr His Leu Asn Val Phe Phe Gly Ile
                660                 665                 670

Arg Gly Lys Gln Gln Pro Gln Asp Ala Gly Ser Ser Arg Met Pro Arg
            675                 680                 685

Leu Met Val Lys Asp Glu Ala Gly Phe Val Cys Cys Leu Glu His Asn
            690                 695                 700

Thr Asn Lys Leu Tyr Glu Thr Ile Glu Asp Lys Ser Leu Asn Leu Cys
705                 710                 715                 720

Ser Ile Arg Asp Tyr Gly Ile Ser Ser Lys Leu Ala Met Thr Ile Ala
                725                 730                 735

Lys Ala Gln Gly Leu Ser Leu Asn Lys Val Ala Ile Cys Phe Gly Ser
                740                 745                 750

His Arg Asn Ile Lys Pro Gly His Val Tyr Val Ala Leu Ser Arg Ala
            755                 760                 765

Arg His Ser Asn Cys Val Val Met Asp Arg Asn Pro Leu Ser Glu Met
        770                 775                 780

Ile Thr Gly Glu Gly Asn Pro Ala Ser Gly Tyr Ile Val Asp Ala Leu
785                 790                 795                 800

Lys Asn Ser Arg Ala Leu Leu Val Tyr
                805
```

<210> SEQ ID NO 18
<211> LENGTH: 2175
<212> TYPE: DNA
<213> ORGANISM: Artificial Sequence
<220> FEATURE:
<223> OTHER INFORMATION: Synthetic

<400> SEQUENCE: 18

```
atgccggatg tttttataggg tccagtcctc ctcagatctc aaacaatgat ggaaacaccc      60
gcggagagcg tcagggcccg ggtcagctcg gttacctttt ataatgtcac ccagaccgca     120
gggcggtggt gggcgatttg ggtcgtgggc atcgtgccca tcaaaaggga ggacgttgag     180
actctgatcg tggtgcaggc ctgccagccg ccgcttggag gctccctgga gccccccgtg     240
gtcaacgcgc cctcgactac cgaactcaac tttttgcgat gggagcggga gctcaggcgc     300
agcggggggc tcattgctat gctcgccgat gccgccgaga aggacctatt tgacctttca     360
tttagaaccc gagaccgcag actcttgtcc gccgccgggg tggaggatga gcagggcctc     420
atcttccagc ctctctttcc agcacaggtg tctgccaaa gctgctcggg ggatgatggg     480
cgggaccaac aacccccacc tggtgatggc ttcgggtccg aggtggaggg ggaacagaca     540
```

-continued

```
tgcccccatg ctcagaggca ctctgagtct cccggacagt tggacgtata catcaggaca    600
ccgcgtgggg atgttttcac ctattccacc gagactcccg acgacccctc tcccgtcccc    660
tttagggaca tcctgcgacc ggtcacttat gaagtagatc tggtgtcgtc cgacggggcc    720
accggccgtg gtggggacgc ccgacggcac cgcgtcagcc tgaaaattct cgagccggct    780
gggggattcg agtcctggct tgtcaactct tggagtatgg ccggggcggg gctctacgcc    840
ttcctccgca gtatctatgc ctcctgctac gccaaccaca gaggcaccaa gcccatcttc    900
tacctcctgg accccgaact ctgcccaggg ggctcagatt ccagcccta tgtcccgggc    960 tttcccttcc tgcccatcca ttatgtggga cgggcgaggc cggccttctg caccgggcg    1020 ccacacagcg agggtctcct gctactggac ctgaacctgg gagtctctgg gacgcccctg    1080
gcagacgccc tcctgggcct cgacgcgcgg tcagggcaac gacgcggctc gctgctccta    1140
caacaaatct ggcccccgac ccgaaaggag attaaccctc gccacgtttg cacgcgggag    1200
ggcggcgagg gagggggga ggacgagacg acggtggttg ggcgcgcgga ggccacagcc    1260
atccttgagg ctgatgccac ttggtggctc tacgaattgg cccgctgcca cctctctgcc    1320
aggggcgccc ctgtgggaac gcctgatggc ggagggcagg cgcgggacgc gcaaacctgg    1380
ctgcgggccc ttcaccgcta tggcacctca gacacgcgac gggcactcgg gggcctctac    1440
accgccgtca cccgggttct cctccacgcg ccgctgacc taggactgac ctgggcttat    1500
gcagacgagt tcatcctggg ctttgtggca acaacctccg cccatccttc agaggagcca    1560
ctagcacagg ctttcctgca aggtgtgaaa gactcggagg atgccagccg gctcgaccgg    1620
gatgttatgg gcggagaggc caccgtggcc cgcagacaca ttcgggtgaa ggctcgacgc    1680
gggcccgcgt gcctactgat ggccatcttt caggggggatc tttacgtggg tggatgtagg    1740
gagcactcgg ggccctttt ggtctggcac gaagccttct cctggaccct ggaccaacta    1800
gcggcgagac ccgaggcaga caaggccccg ccatcccacg accacctgtt gaccctggtc    1860
cgcgacctga cccggagact ggcccctggg cggcgccgaa acaggttttg ggctcttccg    1920
cgagcctggc ttcagcggct gcggagggct gggctgcgcc tctctggaag ccacgtgtgt    1980
ctcctggaca aggatggagc gcgcccggcc ccctgccaga cggccactga gcatggtctc    2040
agccccaccg cctactttcg agagattatg gcctttctgc ttgatgtgat atcggccctc    2100
caccccggct acgccatgcc tatggaaatc actcgagaga cagatttact gatgactgtt    2160
ctcagtttat tctag                                                      2175
```

<210> SEQ ID NO 19
<211> LENGTH: 723
<212> TYPE: PRT
<213> ORGANISM: Artificial Sequence
<220> FEATURE:
<223> OTHER INFORMATION: Synthetic

<400> SEQUENCE: 19

```
Met Pro Asp Val Leu Gly Pro Val Leu Leu Arg Ser Gln Thr Met Met
1               5                   10                  15

Glu Thr Pro Ala Glu Ser Val Arg Ala Arg Val Ser Ser Val Thr Phe
            20                  25                  30

Tyr Asn Val Thr Gln Thr Ala Gly Arg Trp Trp Ala Ile Trp Val Val
        35                  40                  45

Gly Ile Val Pro Ile Lys Arg Glu Asp Val Glu Thr Leu Ile Val Val
    50                  55                  60

Gln Ala Cys Gln Pro Pro Leu Gly Gly Ser Leu Glu Pro Pro Val Val
```

```
65              70              75              80

Asn Ala Pro Ser Thr Thr Glu Leu Asn Phe Leu Arg Trp Glu Arg Glu
                85              90              95

Leu Arg Arg Ser Gly Gly Leu Ile Ala Met Leu Ala Asp Ala Ala Glu
                100             105             110

Lys Asp Leu Phe Asp Leu Ser Phe Arg Thr Arg Asp Arg Arg Leu Leu
            115             120             125

Ser Ala Ala Arg Val Glu Asp Glu Gln Gly Leu Ile Phe Gln Pro Leu
        130             135             140

Phe Pro Ala Gln Val Val Cys Gln Ser Cys Ser Gly Asp Asp Gly Arg
145             150             155             160

Asp Gln Gln Pro Pro Pro Gly Asp Gly Phe Gly Ser Glu Val Glu Gly
                165             170             175

Glu Gln Thr Cys Pro His Ala Gln Arg His Ser Glu Ser Pro Gly Gln
            180             185             190

Leu Asp Val Tyr Ile Arg Thr Pro Arg Gly Asp Val Phe Thr Tyr Ser
            195             200             205

Thr Glu Thr Pro Asp Asp Pro Ser Pro Val Pro Phe Arg Asp Ile Leu
    210             215             220

Arg Pro Val Thr Tyr Glu Val Asp Leu Val Ser Ser Asp Gly Ala Thr
225             230             235             240

Gly Arg Gly Gly Asp Ala Arg Arg His Arg Val Ser Leu Lys Ile Leu
                245             250             255

Glu Pro Ala Gly Gly Phe Glu Ser Trp Leu Val Asn Ser Trp Ser Met
                260             265             270

Ala Gly Gly Gly Leu Tyr Ala Phe Leu Arg Ser Ile Tyr Ala Ser Cys
            275             280             285

Tyr Ala Asn His Arg Gly Thr Lys Pro Ile Phe Tyr Leu Leu Asp Pro
    290             295             300

Glu Leu Cys Pro Gly Gly Ser Asp Phe Gln Pro Tyr Val Pro Gly Phe
305             310             315             320

Pro Phe Leu Pro Ile His Tyr Val Gly Arg Ala Arg Pro Ala Phe Trp
            325             330             335

His Arg Ala Pro His Ser Glu Gly Leu Leu Leu Leu Asp Leu Asn Leu
            340             345             350

Gly Val Ser Gly Thr Pro Leu Ala Asp Ala Leu Leu Gly Leu Asp Ala
    355             360             365

Arg Ser Gly Gln Arg Arg Gly Ser Leu Leu Leu Gln Gln Ile Trp Pro
    370             375             380

Pro Thr Arg Lys Glu Ile Asn Pro Arg His Val Cys Thr Arg Glu Gly
385             390             395             400

Gly Glu Gly Gly Gly Glu Asp Glu Thr Thr Val Val Gly Arg Ala Glu
                405             410             415

Ala Thr Ala Ile Leu Glu Ala Asp Ala Thr Trp Trp Leu Tyr Glu Leu
            420             425             430

Ala Arg Cys His Leu Ser Ala Arg Gly Ala Pro Val Gly Thr Pro Asp
            435             440             445

Gly Gly Gly Gln Ala Arg Asp Ala Gln Thr Trp Leu Arg Ala Leu His
    450             455             460

Arg Tyr Gly Thr Ser Asp Thr Arg Arg Ala Leu Gly Gly Leu Tyr Thr
465             470             475             480

Ala Val Thr Arg Val Leu Leu His Ala Ala Ala Asp Leu Gly Leu Thr
            485             490             495
```

-continued

```
Trp Ala Tyr Ala Asp Glu Phe Ile Leu Gly Phe Val Ala Thr Thr Ser
        500                 505                 510

Ala His Pro Ser Glu Glu Pro Leu Ala Gln Ala Phe Leu Gln Gly Val
        515                 520                 525

Lys Asp Ser Glu Asp Ala Ser Arg Leu Asp Arg Asp Val Met Gly Gly
        530                 535                 540

Glu Ala Thr Val Ala Arg Arg His Ile Arg Val Lys Ala Arg Arg Gly
545                 550                 555                 560

Pro Ala Cys Leu Leu Met Ala Ile Phe Gln Gly Asp Leu Tyr Val Gly
                565                 570                 575

Gly Cys Arg Glu His Ser Gly Pro Phe Leu Val Trp His Glu Ala Phe
                580                 585                 590

Ser Trp Thr Leu Asp Gln Leu Ala Ala Arg Pro Glu Ala Asp Lys Ala
        595                 600                 605

Pro Pro Ser His Asp His Leu Leu Thr Leu Val Arg Asp Leu Thr Arg
        610                 615                 620

Arg Leu Ala Pro Gly Arg Arg Arg Asn Arg Phe Trp Ala Leu Pro Arg
625                 630                 635                 640

Ala Trp Leu Gln Arg Leu Arg Arg Ala Gly Leu Arg Leu Ser Gly Ser
                645                 650                 655

His Val Cys Leu Leu Asp Lys Asp Gly Ala Arg Pro Ala Pro Cys Gln
                660                 665                 670

Thr Ala Thr Glu His Gly Leu Ser Pro Thr Ala Tyr Phe Arg Glu Ile
        675                 680                 685

Met Ala Phe Leu Leu Asp Val Ile Ser Ala Leu His Pro Gly Tyr Ala
        690                 695                 700

Met Pro Met Glu Ile Thr Arg Glu Thr Asp Leu Leu Met Thr Val Leu
705                 710                 715                 720

Ser Leu Phe

<210> SEQ ID NO 20
<211> LENGTH: 1413
<212> TYPE: DNA
<213> ORGANISM: Artificial Sequence
<220> FEATURE:
<223> OTHER INFORMATION: Synthetic

<400> SEQUENCE: 20
atggccgacg tggatgagct cgaggatccc atggaggaga tgacctccta cacgtttgcc      60
cgcttcctcc gcagtccgga gactgaggcc tttgtccgta accttgaccg tccacctcag     120
atgccggcca tgcgctttgt ctatctctat tgcctctgta aacaaataca agagttctct     180
ggtgaaactg gcttctgtga ctttgtctcc tcgttagtcc aagagaatga cagcaaggac     240
ggtccctccc tgaaatccat ttactggggg ctacaggagg ccaccgacga gcagaggact     300
gttctctgct cgtacgtgga gtccatgacc aggggggcagt ctgagaacct gatgtgggac     360
atattgcgaa atggcataat ttcctcttcc aagctgctct ccaccattaa gaatggaccc     420
accaaggtgt ttgagccagc tcccatctcc acaaatcact actttggggg acctgtggcc     480
tttggcctgc ggtgtgagga cacggtcaag gacattgtct gtaagctcat ctgcggggac     540
gcatccgcca accgtcaatt tggctttatg attagtccca cggatggcat ttttggggtg     600
tctctggatc tttgcgtcaa tgtggagtca caggagact ttatactgtt caccgaccgg     660
agctgcattt atgagattaa gtgccgcttc aagtacctct tttccaagtc agaatttgac     720
```

-continued

```
cccatctacc catcctacac tgcgctttac aagaggccat gcaagaggtc atttatcaga      780
tttatcaatt ctatagctcg tcctaccgtg gagtacgtcc cggatgggcg gttgccctcg      840
gagggtgact atctgttgac gcaggatgag gcctggaatc ttaaagatgt ccgtaagcgc      900
aaactgggcc ccggtcatga cctggtggca gacagcctag ctgccaacag gggggtggag      960
tctatgctct acgtaatgac ggacccaagc gaaaatgcgg ggcgcattgg tattaaagac     1020
cgggtcccag tcaacatctt catcaatcca cggcacaact acttctacca ggtgctcctc     1080
caatacaaaa ttgttggaga ctacgtccgc cacagtgggg gtggcaagcc cgggagagac     1140
tgctcacccc gggtgaacat tgtgacggcc ttctttcgaa aacggtcgcc tctagacccg     1200
gcgacctgca cgctcggctc agacctgctt ctggacgcct cggtggagat tcccgtggcg     1260
gtgctggtga cacccgtggt cctgccggac tctgtcatcc gtaagacctt gagcaccgcg     1320
gctggctcct ggaaagcgta cgcagacaat acttttgaca ccgcgccatg ggtgccctct     1380
ggtctctttg ccgacgacga gtcaactcca tag                                  1413
```

```
<210> SEQ ID NO 21
<211> LENGTH: 470
<212> TYPE: PRT
<213> ORGANISM: Artificial Sequence
<220> FEATURE:
<223> OTHER INFORMATION: Synthetic

<400> SEQUENCE: 21

Met Ala Asp Val Asp Glu Leu Glu Asp Pro Met Glu Glu Met Thr Ser
1               5                   10                  15

Tyr Thr Phe Ala Arg Phe Leu Arg Ser Pro Glu Thr Glu Ala Phe Val
            20                  25                  30

Arg Asn Leu Asp Arg Pro Pro Gln Met Pro Ala Met Arg Phe Val Tyr
        35                  40                  45

Leu Tyr Cys Leu Cys Lys Gln Ile Gln Glu Phe Ser Gly Glu Thr Gly
    50                  55                  60

Phe Cys Asp Phe Val Ser Ser Leu Val Gln Glu Asn Asp Ser Lys Asp
65                  70                  75                  80

Gly Pro Ser Leu Lys Ser Ile Tyr Trp Gly Leu Gln Glu Ala Thr Asp
                85                  90                  95

Glu Gln Arg Thr Val Leu Cys Ser Tyr Val Glu Ser Met Thr Arg Gly
            100                 105                 110

Gln Ser Glu Asn Leu Met Trp Asp Ile Leu Arg Asn Gly Ile Ile Ser
        115                 120                 125

Ser Ser Lys Leu Leu Ser Thr Ile Lys Asn Gly Pro Thr Lys Val Phe
    130                 135                 140

Glu Pro Ala Pro Ile Ser Thr Asn His Tyr Phe Gly Gly Pro Val Ala
145                 150                 155                 160

Phe Gly Leu Arg Cys Glu Asp Thr Val Lys Asp Ile Val Cys Lys Leu
                165                 170                 175

Ile Cys Gly Asp Ala Ser Ala Asn Arg Gln Phe Gly Phe Met Ile Ser
            180                 185                 190

Pro Thr Asp Gly Ile Phe Gly Val Ser Leu Asp Leu Cys Val Asn Val
        195                 200                 205

Glu Ser Gln Gly Asp Phe Ile Leu Phe Thr Asp Arg Ser Cys Ile Tyr
    210                 215                 220

Glu Ile Lys Cys Arg Phe Lys Tyr Leu Phe Ser Lys Ser Glu Phe Asp
225                 230                 235                 240
```

-continued

```
Pro Ile Tyr Pro Ser Tyr Thr Ala Leu Tyr Lys Arg Pro Cys Lys Arg
            245                 250                 255

Ser Phe Ile Arg Phe Ile Asn Ser Ile Ala Arg Pro Thr Val Glu Tyr
            260                 265                 270

Val Pro Asp Gly Arg Leu Pro Ser Glu Gly Asp Tyr Leu Leu Thr Gln
            275                 280                 285

Asp Glu Ala Trp Asn Leu Lys Asp Val Arg Lys Arg Lys Leu Gly Pro
        290                 295                 300

Gly His Asp Leu Val Ala Asp Ser Leu Ala Ala Asn Arg Gly Val Glu
305                 310                 315                 320

Ser Met Leu Tyr Val Met Thr Asp Pro Ser Glu Asn Ala Gly Arg Ile
            325                 330                 335

Gly Ile Lys Asp Arg Val Pro Val Asn Ile Phe Ile Asn Pro Arg His
            340                 345                 350

Asn Tyr Phe Tyr Gln Val Leu Leu Gln Tyr Lys Ile Val Gly Asp Tyr
            355                 360                 365

Val Arg His Ser Gly Gly Gly Lys Pro Gly Arg Asp Cys Ser Pro Arg
        370                 375                 380

Val Asn Ile Val Thr Ala Phe Phe Arg Lys Arg Ser Pro Leu Asp Pro
385                 390                 395                 400

Ala Thr Cys Thr Leu Gly Ser Asp Leu Leu Leu Asp Ala Ser Val Glu
            405                 410                 415

Ile Pro Val Ala Val Leu Val Thr Pro Val Val Leu Pro Asp Ser Val
            420                 425                 430

Ile Arg Lys Thr Leu Ser Thr Ala Ala Gly Ser Trp Lys Ala Tyr Ala
            435                 440                 445

Asp Asn Thr Phe Asp Thr Ala Pro Trp Val Pro Ser Gly Leu Phe Ala
        450                 455                 460

Asp Asp Glu Ser Thr Pro
465                 470
```

```
<210> SEQ ID NO 22
<211> LENGTH: 1290
<212> TYPE: DNA
<213> ORGANISM: Artificial Sequence
<220> FEATURE:
<223> OTHER INFORMATION: Synthetic

<400> SEQUENCE: 22
atggatgtga atatggctgc ggagttgagc ccgacgaact cctccagcag tggcgagttg      60
agtgtctccc cagaaccccc tcgagagacc caggcctttt tggggaaggt gactgtcatt     120
gattacttca cctttcagca caaacacctg aaggtgacca acattgatga catgactgag     180
accctctatg taaagctgcc ggagaacatg acgcgctgtg atcacctccc cattacctgc     240
gagtatctgc tggggcgggg gagctacggg gccgtgtatg cacatgcaga taatgccacg     300
gtcaaactct atgactctgt gacggagctg tatcacgagc tcatggtgtg tgacatgatt     360
cagattggga aggccacggc cgaggatggg caggacaagg ccctggtgga ctacctgtcg     420
gcctgcacgt cctgccacgc cctgtttatg ccccagttca gatgcagtct ccaggattat     480
ggccactggc atgatggtag tattgagccc ctggtgcggg ctttcagggg cctcaaagat     540
gccgtttact ttctgaatcg gcactgcggc tcttccatt cggacattag ccccagcaac     600
atcctggtgg atttcacaga caccatgtgg ggcatgggta ggctggtcct gactgattat     660
gggactgctt ccctccacga ccgcaacaag atgctggatg tgcggctaaa gtcttctaag     720
```

-continued

```
ggccggcagc tctatcgcct ctattgccag agggaaccat tttctatagc caaggacacc      780
tataagcccc tctgcctttt gagcaagtgc tacatcttga gggggggctgg gcacatccct      840 gacccctcag cgtgtggccc cgtgggggcg cagacggccc ttcgcctgga tctgcagtcg      900
ctcggctact cgctgctcta tggtatcatg cacctcgctg actccaccca caaaatcccc      960
taccccaacc ctgacatggg atttgaccga tccgacccgc tctactttt  gcaatttgca     1020 gccccaaagg tggtgctgtt ggaggtgctg tcgcagatgt ggaacctgaa cttagacatg     1080
ggcctgacct cgtgtggcga gagtccgtgc gtggatgtca cggcggagca tatgagtcaa     1140
ttcttgcagt ggtgccggag ccttaaaaag aggttcaagg agagctactt cttcaactgt     1200
cgcccacggt ttgagcaccc tcatcttcca ggtctggtag ctgaactctt ggcagacgac     1260
ttctttggtc cagatggccg acgtggatga                                      1290
```

<210> SEQ ID NO 23
<211> LENGTH: 429
<212> TYPE: PRT
<213> ORGANISM: Artificial Sequence
<220> FEATURE:
<223> OTHER INFORMATION: Synthetic

<400> SEQUENCE: 23

```
Met Asp Val Asn Met Ala Ala Glu Leu Ser Pro Thr Asn Ser Ser Ser
1               5                   10                  15

Ser Gly Glu Leu Ser Val Ser Pro Glu Pro Pro Arg Glu Thr Gln Ala
            20                  25                  30

Phe Leu Gly Lys Val Thr Val Ile Asp Tyr Phe Thr Phe Gln His Lys
        35                  40                  45

His Leu Lys Val Thr Asn Ile Asp Asp Met Thr Glu Thr Leu Tyr Val
        50                  55                  60

Lys Leu Pro Glu Asn Met Thr Arg Cys Asp His Leu Pro Ile Thr Cys
65                  70                  75                  80

Glu Tyr Leu Leu Gly Arg Gly Ser Tyr Gly Ala Val Tyr Ala His Ala
                85                  90                  95

Asp Asn Ala Thr Val Lys Leu Tyr Asp Ser Val Thr Glu Leu Tyr His
            100                 105                 110

Glu Leu Met Val Cys Asp Met Ile Gln Ile Gly Lys Ala Thr Ala Glu
        115                 120                 125

Asp Gly Gln Asp Lys Ala Leu Val Asp Tyr Leu Ser Ala Cys Thr Ser
        130                 135                 140

Cys His Ala Leu Phe Met Pro Gln Phe Arg Cys Ser Leu Gln Asp Tyr
145                 150                 155                 160

Gly His Trp His Asp Gly Ser Ile Glu Pro Leu Val Arg Gly Phe Gln
                165                 170                 175

Gly Leu Lys Asp Ala Val Tyr Phe Leu Asn Arg His Cys Gly Leu Phe
            180                 185                 190

His Ser Asp Ile Ser Pro Ser Asn Ile Leu Val Asp Phe Thr Asp Thr
        195                 200                 205

Met Trp Gly Met Gly Arg Leu Val Leu Thr Asp Tyr Gly Thr Ala Ser
        210                 215                 220

Leu His Asp Arg Asn Lys Met Leu Asp Val Arg Leu Lys Ser Ser Lys
225                 230                 235                 240

Gly Arg Gln Leu Tyr Arg Leu Tyr Cys Gln Arg Glu Pro Phe Ser Ile
                245                 250                 255

Ala Lys Asp Thr Tyr Lys Pro Leu Cys Leu Leu Ser Lys Cys Tyr Ile
```

```
               260              265              270

Leu Arg Gly Ala Gly His Ile Pro Asp Pro Ser Ala Cys Gly Pro Val
        275              280              285

Gly Ala Gln Thr Ala Leu Arg Leu Asp Leu Gln Ser Leu Gly Tyr Ser
    290              295              300

Leu Leu Tyr Gly Ile Met His Leu Ala Asp Ser Thr His Lys Ile Pro
305              310              315              320

Tyr Pro Asn Pro Asp Met Gly Phe Asp Arg Ser Asp Pro Leu Tyr Phe
            325              330              335

Leu Gln Phe Ala Ala Pro Lys Val Val Leu Leu Glu Val Leu Ser Gln
            340              345              350

Met Trp Asn Leu Asn Leu Asp Met Gly Leu Thr Ser Cys Gly Glu Ser
        355              360              365

Pro Cys Val Asp Val Thr Ala Glu His Met Ser Gln Phe Leu Gln Trp
    370              375              380

Cys Arg Ser Leu Lys Lys Arg Phe Lys Glu Ser Tyr Phe Phe Asn Cys
385              390              395              400

Arg Pro Arg Phe Glu His Pro His Leu Pro Gly Leu Val Ala Glu Leu
            405              410              415

Leu Ala Asp Asp Phe Phe Gly Pro Asp Gly Arg Arg Gly
            420              425
```

```
<210> SEQ ID NO 24
<211> LENGTH: 678
<212> TYPE: DNA
<213> ORGANISM: Artificial Sequence
<220> FEATURE:
<223> OTHER INFORMATION: Synthetic

<400> SEQUENCE: 24
atgtcagacc aaggccgatt gagcctcccg cggggggagg ggggcacgga tgagcccaat      60
cctcgccacc tgtgctcgta tagtaagctg gagttccatc tcccgttacc tgagagcatg     120
gcctccgtgt ttgcctgctg gggctgtggc gagtaccatg tatgtgatgg atccagcgag     180
tgcaccctga ttgagaccca tgagggagtg gtgtgcgccc ttacaggcaa ctacatgggg     240
ccgcatttcc agccggcgct gaggccctgg actgagatcc gacaagacac acaggaccag     300
cgggacaagt gggagcctga acaagtccag ggcctggtcc agactgtggt caatcacctc     360
tatcactact ttctgaatga gaatgtcatc tccggggtca gcgaggccct ctttgatcag     420 gatgggccc tgaggcctca catcccggcc ctggtttcct ttgtgttccc ttgctgcctg     480
atgctgttta ggggggcctc ctccgagaag gtggtggatg tggtcctcag tctctacatc     540
catgtcatca tctctatttta ctcacaaaag actgtctacg gggccctgtt atttaaatcc     600
accagaaaca agcgctatga tgctgtagcc aaacgcatga gagagctatg gatgtccaca     660
ttgacaacca agtgctga                                                   678
```

```
<210> SEQ ID NO 25
<211> LENGTH: 225
<212> TYPE: PRT
<213> ORGANISM: Artificial Sequence
<220> FEATURE:
<223> OTHER INFORMATION: Synthetic

<400> SEQUENCE: 25

Met Ser Asp Gln Gly Arg Leu Ser Leu Pro Arg Gly Glu Gly Gly Thr
1               5               10              15
```

-continued

```
Asp Glu Pro Asn Pro Arg His Leu Cys Ser Tyr Ser Lys Leu Glu Phe
            20              25                  30

His Leu Pro Leu Pro Glu Ser Met Ala Ser Val Phe Ala Cys Trp Gly
        35              40                  45

Cys Gly Glu Tyr His Val Cys Asp Gly Ser Ser Glu Cys Thr Leu Ile
    50              55                  60

Glu Thr His Glu Gly Val Val Cys Ala Leu Thr Gly Asn Tyr Met Gly
65                  70                  75                  80

Pro His Phe Gln Pro Ala Leu Arg Pro Trp Thr Glu Ile Arg Gln Asp
                85                  90                  95

Thr Gln Asp Gln Arg Asp Lys Trp Glu Pro Glu Gln Val Gln Gly Leu
            100             105                 110

Val Gln Thr Val Val Asn His Leu Tyr His Tyr Phe Leu Asn Glu Asn
            115             120                 125

Val Ile Ser Gly Val Ser Glu Ala Leu Phe Asp Gln Asp Gly Ala Leu
    130             135                 140

Arg Pro His Ile Pro Ala Leu Val Ser Phe Val Phe Pro Cys Cys Leu
145             150                 155                 160

Met Leu Phe Arg Gly Ala Ser Ser Glu Lys Val Val Asp Val Val Leu
            165                 170                 175

Ser Leu Tyr Ile His Val Ile Ile Ser Ile Tyr Ser Gln Lys Thr Val
            180                 185                 190

Tyr Gly Ala Leu Leu Phe Lys Ser Thr Arg Asn Lys Arg Tyr Asp Ala
            195                 200                 205

Val Ala Lys Arg Met Arg Glu Leu Trp Met Ser Thr Leu Thr Thr Lys
    210                 215                 220

Cys
225

<210> SEQ ID NO 26
<211> LENGTH: 1824
<212> TYPE: DNA
<213> ORGANISM: Artificial Sequence
<220> FEATURE:
<223> OTHER INFORMATION: Synthetic

<400> SEQUENCE: 26
atggctggat tccaggaaa ggaggccggc ccgcccggcg gctggcgaaa atgtcaggag      60
gatgagtccc ctgaaaacga aagacacgaa aactttacg ctgagattga tgactttgcc     120
ccctcagttc ttaccccaac cggtagtgac tcaggggcag gtgaggaaga tgacgacggc    180
ctctaccagg tgcccaccca ctggcccccc ttgatggctc cgaccggact gtctggggag    240
agggtgccgt gccggaccca ggctgccgtg acatctaata ctggaaactc tccgggtagc    300
cggcacacat cgtgcccctt taccctgccc aggggagccc agccaccagc acccgcacac    360
caaaagccta ctgcccctac cccgaagccc cgtagccggg agtgtggccc cagcaagacg    420
ccagacccct ctcctggtt ccgcaaaact tcgtgcacaa aggaggtgc ggactccacg      480 agccggagct tcatgtacca gaaaggcttt gaggagggcc tggccggcct tgggctcgat    540
gacaaatctg actgtgagtc tgaggatgag tctaatttcc gcaggccctc ttctcattcc    600
gcgttaaaac aaaagaatgg tggcaagggt aagccttctg gtctcttcga acacctggcc    660
gcccatgggc gcgagtttag taagttatcc aagcatgctg cccagctgaa gcggctaagt    720
gggagtgtga tgaatgttct gaatctggat gatgcccaag acacccgcca ggccaaggct    780
cagaggaagg agagcatgcg ggttccaatt gtgacccacc taacaaatca tgtaccagta    840
```

-continued

```
atcaaacctg cctgttccct attttttggaa ggtgccctg gtgtgggaaa gactactatg      900
ctgaatcatt tgaaggctgt ctttggggac ctgaccattg tagtccctga accgatgcgg      960
tactggactc atgtgtatga aaatgccatt aaggccatgc acaagaatgt gactcgggcg     1020
aggcatggaa gggaagacac gtcggctgag gtttttagcat gccagatgaa atttaccacc     1080
cctttcagag tcttggcctc taggaagcgg agcttgctgg ttaccgagtc tggtgccagg     1140
tcagtcgcgc ccctggattg ttggattttg catgatcgcc atttgctgtc ggcctccgtg     1200
gttttccctc taatgctgct ccggagccag cttctctcct atagtgactt tattcaagtt     1260
ttggccacgt ttaccgcaga cccggggggac accatagtct ggatgaagtt aaacgtggag     1320
gagaacatgc gccgcctgaa gaagcgaggg aggaaacatg agtcaggact ggatgctggc     1380
tacctgaaga gtgtcaacga tgcatatcac gccgtttact gtgcctggct cctaacacag     1440
tattttgccc ccgaggacat tgtgaaggta tgtgccggtc taacaacaat cacgacagta     1500
tgtcatcaaa gccacacccc cataattcga agtggtgtgg ccgagaagct gtataagaac     1560
agcatcttta gtgtacttaa ggaagtcata cagcctttcc gagccgacgc ggtgttgttg     1620
gaagtttgtc ttgcgttcac ccgaacgcta gcctaccttc agtttgtgct tgtggacctc     1680
tcagagtttc aggacgattt acctggatgc tggacggaga tttacatgca ggcattgaag     1740
aatccggcaa tacgatctca gttttttcgat tgggctggtc tgagcaaggt gatctctgat     1800
tttgagaggg gaaatcggga ctag                                             1824
```

<210> SEQ ID NO 27
<211> LENGTH: 607
<212> TYPE: PRT
<213> ORGANISM: Artificial Sequence
<220> FEATURE:
<223> OTHER INFORMATION: Synthetic

<400> SEQUENCE: 27

```
Met Ala Gly Phe Pro Gly Lys Glu Ala Gly Pro Pro Gly Gly Trp Arg
1               5                   10                  15

Lys Cys Gln Glu Asp Glu Ser Pro Glu Asn Glu Arg His Glu Asn Phe
            20                  25                  30

Tyr Ala Glu Ile Asp Asp Phe Ala Pro Ser Val Leu Thr Pro Thr Gly
        35                  40                  45

Ser Asp Ser Gly Ala Gly Glu Glu Asp Asp Asp Gly Leu Tyr Gln Val
    50                  55                  60

Pro Thr His Trp Pro Pro Leu Met Ala Pro Thr Gly Leu Ser Gly Glu
65                  70                  75                  80

Arg Val Pro Cys Arg Thr Gln Ala Ala Val Thr Ser Asn Thr Gly Asn
                85                  90                  95

Ser Pro Gly Ser Arg His Thr Ser Cys Pro Phe Thr Leu Pro Arg Gly
            100                 105                 110

Ala Gln Pro Pro Ala Pro Ala His Gln Lys Pro Thr Ala Pro Thr Pro
        115                 120                 125

Lys Pro Arg Ser Arg Glu Cys Gly Pro Ser Lys Thr Pro Asp Pro Phe
    130                 135                 140

Ser Trp Phe Arg Lys Thr Ser Cys Thr Glu Gly Gly Ala Asp Ser Thr
145                 150                 155                 160

Ser Arg Ser Phe Met Tyr Gln Lys Gly Phe Glu Glu Gly Leu Ala Gly
                165                 170                 175

Leu Gly Leu Asp Asp Lys Ser Asp Cys Glu Ser Glu Asp Glu Ser Asn
```

-continued

```
                180              185               190

Phe Arg Arg Pro Ser Ser His Ser Ala Leu Lys Gln Lys Asn Gly Gly
         195              200               205

Lys Gly Lys Pro Ser Gly Leu Phe Glu His Leu Ala Ala His Gly Arg
         210              215               220

Glu Phe Ser Lys Leu Ser Lys His Ala Ala Gln Leu Lys Arg Leu Ser
225              230              235               240

Gly Ser Val Met Asn Val Leu Asn Leu Asp Asp Ala Gln Asp Thr Arg
             245              250               255

Gln Ala Lys Ala Gln Arg Lys Glu Ser Met Arg Val Pro Ile Val Thr
         260              265               270

His Leu Thr Asn His Val Pro Val Ile Lys Pro Ala Cys Ser Leu Phe
         275              280               285

Leu Glu Gly Ala Pro Gly Val Gly Lys Thr Thr Met Leu Asn His Leu
         290              295               300

Lys Ala Val Phe Gly Asp Leu Thr Ile Val Val Pro Glu Pro Met Arg
305              310              315               320

Tyr Trp Thr His Val Tyr Glu Asn Ala Ile Lys Ala Met His Lys Asn
             325              330               335

Val Thr Arg Ala Arg His Gly Arg Glu Asp Thr Ser Ala Glu Val Leu
         340              345               350

Ala Cys Gln Met Lys Phe Thr Thr Pro Phe Arg Val Leu Ala Ser Arg
         355              360               365

Lys Arg Ser Leu Leu Val Thr Glu Ser Gly Ala Arg Ser Val Ala Pro
         370              375               380

Leu Asp Cys Trp Ile Leu His Asp Arg His Leu Leu Ser Ala Ser Val
385              390              395               400

Val Phe Pro Leu Met Leu Leu Arg Ser Gln Leu Leu Ser Tyr Ser Asp
             405              410               415

Phe Ile Gln Val Leu Ala Thr Phe Thr Ala Asp Pro Gly Asp Thr Ile
             420              425               430

Val Trp Met Lys Leu Asn Val Glu Glu Asn Met Arg Arg Leu Lys Lys
         435              440               445

Arg Gly Arg Lys His Glu Ser Gly Leu Asp Ala Gly Tyr Leu Lys Ser
         450              455               460

Val Asn Asp Ala Tyr His Ala Val Tyr Cys Ala Trp Leu Leu Thr Gln
465              470              475               480

Tyr Phe Ala Pro Glu Asp Ile Val Lys Val Cys Ala Gly Leu Thr Thr
             485              490               495

Ile Thr Thr Val Cys His Gln Ser His Thr Pro Ile Ile Arg Ser Gly
             500              505               510

Val Ala Glu Lys Leu Tyr Lys Asn Ser Ile Phe Ser Val Leu Lys Glu
         515              520               525

Val Ile Gln Pro Phe Arg Ala Asp Ala Val Leu Leu Glu Val Cys Leu
         530              535               540

Ala Phe Thr Arg Thr Leu Ala Tyr Leu Gln Phe Val Leu Val Asp Leu
545              550              555               560

Ser Glu Phe Gln Asp Asp Leu Pro Gly Cys Trp Thr Glu Ile Tyr Met
             565              570               575

Gln Ala Leu Lys Asn Pro Ala Ile Arg Ser Gln Phe Phe Asp Trp Ala
         580              585               590

Gly Leu Ser Lys Val Ile Ser Asp Phe Glu Arg Gly Asn Arg Asp
         595              600               605
```

<210> SEQ ID NO 28
<211> LENGTH: 819
<212> TYPE: DNA
<213> ORGANISM: Artificial Sequence
<220> FEATURE:
<223> OTHER INFORMATION: Synthetic

<400> SEQUENCE: 28
atgttaatgg gactgggggt gcgcgggggat gacgcgcgaa tgacacctgg gattcacggg        60
ctcctcctga agatgctaaa gaactggccg ctttgcgctc tgcgcgagga cgagctcagg       120
tttttgcacc tatccctgac caagctgctg accctaagtg ttaactttta cctgtggcgg       180
gaagccgtga taaatactgg aaaccgcacg aatcgtgtgt tggcacgcaa ggtgccggat       240
gaatactggt acctgcttta ccgggccctg gcccgggtgg gcttcccggc agaggccctg       300
cgccccggta accgctcacg gtctctttgt ctgtttttgc atgaccggcc tgatgtcaca       360
ggggccgtct gtgcatgtgt gtgggcgcag cttggactgc gcaggcgcc ggacctgagc       420 caggtcaccc tggctgacgg aaatctgctc ttcaaccttg gcagtgtcct ccctaaccgc       480
ctggtggtgg gtgtcctcta ctgccttgtc cactgggggtg cagacgagca tgaaacccgg       540
gttcgggcac gccttcgccc cctctttgtg gccttcctct gcctggccgg ctatctgctt       600
ctggaccgtg ccatcctctc ggatgcgcac gactacgagg gcctctggca cgccgtggcc       660
ctgagcatgg cggcctggca cggccttact ccctacccg aaacaagaga cgagaaggag       720
gcaaaacccc cgtgcgatga gtttatttac cttttttgcca atgacccact ccagtgcgag       780
gaactggctc agcttggggc caccggggag gccaggtag                              819

<210> SEQ ID NO 29
<211> LENGTH: 272
<212> TYPE: PRT
<213> ORGANISM: Artificial Sequence
<220> FEATURE:
<223> OTHER INFORMATION: Synthetic

<400> SEQUENCE: 29

Met Leu Met Gly Leu Gly Val Arg Gly Asp Asp Ala Arg Met Thr Pro
1               5                   10                  15

Gly Ile His Gly Leu Leu Leu Lys Met Leu Lys Asn Trp Pro Leu Cys
                20                  25                  30

Ala Leu Arg Glu Asp Glu Leu Arg Phe Leu His Leu Ser Leu Thr Lys
            35                  40                  45

Leu Leu Thr Leu Ser Val Asn Phe Tyr Leu Trp Arg Glu Ala Val Ile
        50                  55                  60

Asn Thr Gly Asn Arg Thr Asn Arg Val Leu Ala Arg Lys Val Pro Asp
65                  70                  75                  80

Glu Tyr Trp Tyr Leu Leu Tyr Arg Ala Leu Ala Arg Val Gly Phe Pro
                85                  90                  95

Ala Glu Ala Leu Arg Pro Gly Asn Arg Ser Arg Ser Leu Cys Leu Phe
            100                 105                 110

Leu His Asp Arg Pro Asp Val Thr Gly Ala Val Cys Ala Cys Val Trp
        115                 120                 125

Ala Gln Leu Gly Leu Arg Arg Ala Pro Asp Leu Ser Gln Val Thr Leu
        130                 135                 140

Ala Asp Gly Asn Leu Leu Phe Asn Leu Gly Ser Val Leu Pro Asn Arg
145                 150                 155                 160

-continued

```
Leu Val Val Gly Val Leu Tyr Cys Leu Val His Trp Gly Ala Asp Glu
            165                 170                 175

His Glu Thr Arg Val Arg Ala Arg Leu Arg Pro Leu Phe Val Ala Phe
        180                 185                 190

Leu Cys Leu Ala Gly Tyr Leu Leu Leu Asp Arg Ala Ile Leu Ser Asp
        195                 200                 205

Ala His Asp Tyr Glu Gly Leu Trp His Ala Val Ala Leu Ser Met Ala
    210                 215                 220

Ala Trp His Gly Leu Thr Pro Leu Pro Glu Thr Arg Asp Glu Lys Glu
225                 230                 235                 240

Ala Lys Pro Pro Cys Asp Glu Phe Ile Tyr Leu Phe Ala Asn Asp Pro
                245                 250                 255

Leu Gln Cys Glu Glu Leu Ala Gln Leu Gly Ala Thr Gly Glu Ala Arg
            260                 265                 270

<210> SEQ ID NO 30
<211> LENGTH: 3387
<212> TYPE: DNA
<213> ORGANISM: Artificial Sequence
<220> FEATURE:
<223> OTHER INFORMATION: Synthetic

<400> SEQUENCE: 30
atgcagggtg cacagactag cgaggataat ctgggcagcc agagccagcc gggtccgtgc     60
ggctacatct acttttaccc cctggccacc taccctctta gggaggtggc cacactgggg    120
accggctacg cgggccacag gtgcctgacg gtgccgctac tttgcggcat caccgtggag    180
ccgggcttca gcatcaatgt caaggctctg cacaggaggc ccgaccccaa ctgcgggctc    240
ctacgcgcta cctcctatca cagggacatc tacgtgttcc acaatgccca tatggttccc    300
cccatctttg aggggccggg tctcgaggcc ctctgtggcg agaccaggga ggtgtttggg    360
tacgacgcct acagcgccct accgagggaa agctccaagc cggggggactt cttccccgaa    420 gggctagatc cctctgccta cctgggggcg gtggcaataa ccgaggcctt caaggagcga    480
ctctacagcg gaaacctggt ggccattcca tcgttaaaac aggaggtagc ggtggggcag    540
tctgcgagcg ttagggtccc gctctacgac aaggaggtgt cccagaggg cgtgcccag     600 ctccgccagt tttacaactc ggacctcagc cgctgcatgc acgaggcgct gtacaccggg    660
ctggcgcagg cgctgcgcgt ccgacgggtg ggcaagctgg tggagctgct ggagaagcag    720
agcctgcagg accaggccaa ggtggccaag gtggccccc tcaaggagtt cccagcctca    780
accatcagtc acccggactc gggagcctta atgattgtgg acagcgcggc atgcgagctg    840
gcggtgagct acgcgcccgc catgctggag gcctcgcacg agaccccggc cagcctcaac    900
tacgactcgt ggcccctgtt tgccgactgt gagggcccag aggcccgtgt ggctgcgtta    960
caccgatata atgccagcct ggcccccac gtgtccacgc agatctttgc caccaattcc   1020
gtcctctacg tctcgggggt ctcgaagtca accggtcagg caaggagag tctctttaac   1080 agtttctaca tgacccacgg cctggggacc ctgcaggagg ggacctggga ccctgccgc   1140 cgacctgct tctcgggctg gggtgggcca gacgtgaccg gaaccaacgg tccgggaaac   1200
tacgctgtgg agcacctggt ctatgcggcc tccttctcgc ccaaccttct tgcccgctat   1260
gcctactacc tgcagttttg ccagggacag aagagctctc tgaccccggt gccggagacg   1320
ggcagctacg tggcgggggc ggccgccagc cccatgtgct cgctctgcga gggcggggcc   1380
ccggccgtgt gcctgaacac gctcttcttt aggctgaggg accgcttccc ccccgtcatg   1440
```

```
tccacgcagc ggagggaccc ctatgtgatc tcggggggcct cgggctccta caacgagacg      1500
gactttttgg gcaactttct caacttcatc gataaggagg acgacgggca gcggccggac      1560
gacgagcccc gctacaccta ctggcagctg aaccagaacc tgctggagcg gctgtctcgg      1620
ctgggcatag acgctgaggg aaagctagag aaggagcccc atggcccgcg tgactttgtc      1680
aagatgttca aggacgtgga tgcggcggtg gacgccgaag tggtccagtt tatgaacagc      1740
atggccaaga acaacatcac ctacaaggac ctggtcaaga gctgctacca cgtgatgcag      1800
tactcgtgca accccttgc gcagcccgcc tgccccatct tcacccagct gtttttaccgc      1860 tcactgctga ccatcctgca ggacatctcc ctgcccatct gtatgtgcta tgagaatgac      1920
aaccccgggc ttggccagag cccccccagag tggctaaagg gtcactacca gacgctgtgc      1980
accaacttta ggagcctggc catcgacaag ggggtcctca cggccaagga ggccaaggta      2040
gtgcatgggg agcccacctg cgacctgcca gacctggacg cggccctgca gggccgggtg      2100
tacggccggc ggctgcctgt gcgcatgtcc aaggtgctga tgctgtgccc caggaacatc      2160
aagatcaaga acagggtggt cttcacgggg gagaatgccg ccctccagaa cagcttcatc      2220
aagtccacta ccaggaggga gaactacatc atcaacgggc cctacatgaa attcctcaac      2280
acctaccaca gaccctatt cccggacact aagctctcaa gcctgtacct gtggcacaac      2340 tttttccaggc ggcgctcggt ccctgtcccc agcggggcca gcgcggagga gtactctgac      2400
ctggccctct ttgtggacgg gggctcccgg gcccacgaag agagcaacgt catagatgtg      2460
gtgcctggca acctggtcac ttacgccaag cagaggctca acaacgccat cctgaaggcg      2520
tgcggccaga cccagttcta catcagcctg attcaggac tggtgccgag gacgcagtcg      2580
gtgcccgccc gtgactaccc ccacgtactg ggcacgcggg cggtggagtc ggcagcggcc      2640
tacgcggagg ccacctcctc ccttactgca accacggtgg tctgcgcggc cacagactgt      2700
cttagccagg tctgcaaggc acgtccggtt gtcacgctgc cagtgaccat caacaagtac      2760 acggggggtca acggcaacaa ccagatattc caggccggga acctgggata ctttatgggc      2820
cggggcgtgg acaggaacct gctgcaggcc cccgggggctg ggctgcgcaa gcaggccggg      2880
ggctcttcca tgcggaagaa gtttgtcttt gccacccccca ccatagggtt gaccgtgaag      2940
cgccggaccc aagccgcgac acatatgag attgagaaca tcagggctgg cctggaggcc      3000
attatatcac aaaaacagga ggaagactgt gtgtttgatg tggtgtgcaa ccttgtggat      3060
gccatgggcg aggcatgcgc ctcgctgact agggacgacg cggaatactt attgggccgc      3120
ttctccgtcc tggcggacag cgtcctagaa accctggcga ccattgcctc cagcgggata      3180
gagtggacgg cggggggccgc tcgggacttt ctggaggag tgtgggggtgg gcccgggggca      3240 gcccaggaca actttatcag cgtggccgag ccggtcggca ccgcgtcgca ggcctcggcc      3300
gggctgctgc tgggtggagg agggcagggc tccgggggca gacgcaagcg ccgtctggcc      3360
accgttctcc ccggactcga ggtctag                                         3387
```

<210> SEQ ID NO 31
<211> LENGTH: 1128
<212> TYPE: PRT
<213> ORGANISM: Artificial Sequence
<220> FEATURE:
<223> OTHER INFORMATION: Synthetic

<400> SEQUENCE: 31

```
Met Gln Gly Ala Gln Thr Ser Glu Asp Asn Leu Gly Ser Gln Ser Gln
1               5                   10                  15
```

```
Pro Gly Pro Cys Gly Tyr Ile Tyr Phe Tyr Pro Leu Ala Thr Tyr Pro
            20              25              30

Leu Arg Glu Val Ala Thr Leu Gly Thr Gly Tyr Ala Gly His Arg Cys
            35              40              45

Leu Thr Val Pro Leu Leu Cys Gly Ile Thr Val Glu Pro Gly Phe Ser
    50              55              60

Ile Asn Val Lys Ala Leu His Arg Arg Pro Asp Pro Asn Cys Gly Leu
65              70              75              80

Leu Arg Ala Thr Ser Tyr His Arg Asp Ile Tyr Val Phe His Asn Ala
                85              90              95

His Met Val Pro Pro Ile Phe Glu Gly Pro Gly Leu Glu Ala Leu Cys
            100             105             110

Gly Glu Thr Arg Glu Val Phe Gly Tyr Asp Ala Tyr Ser Ala Leu Pro
            115             120             125

Arg Glu Ser Ser Lys Pro Gly Asp Phe Phe Pro Glu Gly Leu Asp Pro
            130             135             140

Ser Ala Tyr Leu Gly Ala Val Ala Ile Thr Glu Ala Phe Lys Glu Arg
145             150             155             160

Leu Tyr Ser Gly Asn Leu Val Ala Ile Pro Ser Leu Lys Gln Glu Val
                165             170             175

Ala Val Gly Gln Ser Ala Ser Val Arg Val Pro Leu Tyr Asp Lys Glu
            180             185             190

Val Phe Pro Glu Gly Val Pro Gln Leu Arg Gln Phe Tyr Asn Ser Asp
            195             200             205

Leu Ser Arg Cys Met His Glu Ala Leu Tyr Thr Gly Leu Ala Gln Ala
    210             215             220

Leu Arg Val Arg Arg Val Gly Lys Leu Val Glu Leu Leu Glu Lys Gln
225             230             235             240

Ser Leu Gln Asp Gln Ala Lys Val Ala Lys Val Ala Pro Leu Lys Glu
            245             250             255

Phe Pro Ala Ser Thr Ile Ser His Pro Asp Ser Gly Ala Leu Met Ile
            260             265             270

Val Asp Ser Ala Ala Cys Glu Leu Ala Val Ser Tyr Ala Pro Ala Met
            275             280             285

Leu Glu Ala Ser His Glu Thr Pro Ala Ser Leu Asn Tyr Asp Ser Trp
    290             295             300

Pro Leu Phe Ala Asp Cys Glu Gly Pro Glu Ala Arg Val Ala Ala Leu
305             310             315             320

His Arg Tyr Asn Ala Ser Leu Ala Pro His Val Ser Thr Gln Ile Phe
            325             330             335

Ala Thr Asn Ser Val Leu Tyr Val Ser Gly Val Ser Lys Ser Thr Gly
            340             345             350

Gln Gly Lys Glu Ser Leu Phe Asn Ser Phe Tyr Met Thr His Gly Leu
            355             360             365

Gly Thr Leu Gln Glu Gly Thr Trp Asp Pro Cys Arg Arg Pro Cys Phe
    370             375             380

Ser Gly Trp Gly Gly Pro Asp Val Thr Gly Thr Asn Gly Pro Gly Asn
385             390             395             400

Tyr Ala Val Glu His Leu Val Tyr Ala Ala Ser Phe Ser Pro Asn Leu
            405             410             415

Leu Ala Arg Tyr Ala Tyr Tyr Leu Gln Phe Cys Gln Gly Gln Lys Ser
            420             425             430

Ser Leu Thr Pro Val Pro Glu Thr Gly Ser Tyr Val Ala Gly Ala Ala
```

-continued

```
                435                    440                    445

Ala Ser Pro Met Cys Ser Leu Cys Glu Gly Arg Ala Pro Ala Val Cys
        450                    455                    460

Leu Asn Thr Leu Phe Phe Arg Leu Arg Asp Arg Phe Pro Pro Val Met
465                    470                    475                    480

Ser Thr Gln Arg Arg Asp Pro Tyr Val Ile Ser Gly Ala Ser Gly Ser
                        485                    490                    495

Tyr Asn Glu Thr Asp Phe Leu Gly Asn Phe Leu Asn Phe Ile Asp Lys
                500                    505                    510

Glu Asp Asp Gly Gln Arg Pro Asp Asp Glu Pro Arg Tyr Thr Tyr Trp
                515                    520                    525

Gln Leu Asn Gln Asn Leu Leu Glu Arg Leu Ser Arg Leu Gly Ile Asp
        530                    535                    540

Ala Glu Gly Lys Leu Glu Lys Glu Pro His Gly Pro Arg Asp Phe Val
545                    550                    555                    560

Lys Met Phe Lys Asp Val Asp Ala Ala Val Asp Ala Glu Val Val Gln
                565                    570                    575

Phe Met Asn Ser Met Ala Lys Asn Asn Ile Thr Tyr Lys Asp Leu Val
                580                    585                    590

Lys Ser Cys Tyr His Val Met Gln Tyr Ser Cys Asn Pro Phe Ala Gln
        595                    600                    605

Pro Ala Cys Pro Ile Phe Thr Gln Leu Phe Tyr Arg Ser Leu Leu Thr
        610                    615                    620

Ile Leu Gln Asp Ile Ser Leu Pro Ile Cys Met Cys Tyr Glu Asn Asp
625                    630                    635                    640

Asn Pro Gly Leu Gly Gln Ser Pro Pro Glu Trp Leu Lys Gly His Tyr
                645                    650                    655

Gln Thr Leu Cys Thr Asn Phe Arg Ser Leu Ala Ile Asp Lys Gly Val
        660                    665                    670

Leu Thr Ala Lys Glu Ala Lys Val Val His Gly Glu Pro Thr Cys Asp
        675                    680                    685

Leu Pro Asp Leu Asp Ala Ala Leu Gln Gly Arg Val Tyr Gly Arg Arg
        690                    695                    700

Leu Pro Val Arg Met Ser Lys Val Leu Met Leu Cys Pro Arg Asn Ile
705                    710                    715                    720

Lys Ile Lys Asn Arg Val Val Phe Thr Gly Glu Asn Ala Ala Leu Gln
                725                    730                    735

Asn Ser Phe Ile Lys Ser Thr Thr Arg Arg Glu Asn Tyr Ile Ile Asn
                740                    745                    750

Gly Pro Tyr Met Lys Phe Leu Asn Thr Tyr His Lys Thr Leu Phe Pro
        755                    760                    765

Asp Thr Lys Leu Ser Ser Leu Tyr Leu Trp His Asn Phe Ser Arg Arg
        770                    775                    780

Arg Ser Val Pro Val Pro Ser Gly Ala Ser Ala Glu Glu Tyr Ser Asp
785                    790                    795                    800

Leu Ala Leu Phe Val Asp Gly Gly Ser Arg Ala His Glu Glu Ser Asn
                        805                    810                    815

Val Ile Asp Val Val Pro Gly Asn Leu Val Thr Tyr Ala Lys Gln Arg
                820                    825                    830

Leu Asn Asn Ala Ile Leu Lys Ala Cys Gly Gln Thr Gln Phe Tyr Ile
        835                    840                    845

Ser Leu Ile Gln Gly Leu Val Pro Arg Thr Gln Ser Val Pro Ala Arg
        850                    855                    860
```

-continued

```
Asp Tyr Pro His Val Leu Gly Thr Arg Ala Val Glu Ser Ala Ala Ala
865                 870                 875                 880

Tyr Ala Glu Ala Thr Ser Ser Leu Thr Ala Thr Thr Val Val Cys Ala
                885                 890                 895

Ala Thr Asp Cys Leu Ser Gln Val Cys Lys Ala Arg Pro Val Val Thr
                900                 905                 910

Leu Pro Val Thr Ile Asn Lys Tyr Thr Gly Val Asn Gly Asn Asn Gln
            915                 920                 925

Ile Phe Gln Ala Gly Asn Leu Gly Tyr Phe Met Gly Arg Gly Val Asp
        930                 935                 940

Arg Asn Leu Leu Gln Ala Pro Gly Ala Gly Leu Arg Lys Gln Ala Gly
945                 950                 955                 960

Gly Ser Ser Met Arg Lys Lys Phe Val Phe Ala Thr Pro Thr Ile Gly
                965                 970                 975

Leu Thr Val Lys Arg Arg Thr Gln Ala Ala Thr Thr Tyr Glu Ile Glu
            980                 985                 990

Asn Ile Arg Ala Gly Leu Glu Ala  Ile Ile Ser Gln Lys  Gln Glu Glu
            995                 1000                1005

Asp Cys  Val Phe Asp Val Val  Cys Asn Leu Val Asp  Ala Met Gly
    1010                1015                1020

Glu Ala  Cys Ala Ser Leu Thr  Arg Asp Asp Ala Glu  Tyr Leu Leu
    1025                1030                1035

Gly Arg  Phe Ser Val Leu Ala  Asp Ser Val Leu Glu  Thr Leu Ala
    1040                1045                1050

Thr Ile  Ala Ser Ser Gly Ile  Glu Trp Thr Ala Gly  Ala Ala Arg
    1055                1060                1065

Asp Phe  Leu Glu Gly Val Trp  Gly Gly Pro Gly Ala  Ala Gln Asp
    1070                1075                1080

Asn Phe  Ile Ser Val Ala Glu  Pro Val Gly Thr Ala  Ser Gln Ala
    1085                1090                1095

Ser Ala  Gly Leu Leu Leu Gly  Gly Gly Gly Gln Gly  Ser Gly Gly
    1100                1105                1110

Arg Arg  Lys Arg Arg Leu Ala  Thr Val Leu Pro Gly  Leu Glu Val
    1115                1120                1125
```

<210> SEQ ID NO 32
<211> LENGTH: 549
<212> TYPE: DNA
<213> ORGANISM: Artificial Sequence
<220> FEATURE:
<223> OTHER INFORMATION: Synthetic

<400> SEQUENCE: 32

```
atgaggccag ccaagtctac agattctgtg tttgtgagga ccccggtcga ggcgtgggtc      60
gcgccctcgc cgccggacga caaggtggct gagtccagct acctcatgtt cagggccatg     120
tacgcggtgt tcacccggga tgagaaagac ctgcctttgc cagccctggt cctctgccgg     180
ctcatcaagg cctccctgag gaaggatagg aagctgtacg cggagctggc ctgcaggaca     240
gccgacatcg ggggcaaaga cacgcacgta cggctcatca tcagcgtcct cgcgcgcagtg     300 tacaacgacc actacgacta ctggtcgcgg ctcagggtgg tgctgtgcta cacagtggtg     360
tttgcggtgc gaaactacct ggatgaccac aagagcgccg ccttcgtgct ggggggcaatc     420 gcccactacc tggccctcta tcgcagactc tggtttgcga ggctgggcgg catgccaaga     480
tcgctgagac gtcagttccc cgtgacgtgg gccctggcca gcctgactga cttcctgaaa     540
```

-continued tctttgtaa                                                                                  549

<210> SEQ ID NO 33
<211> LENGTH: 182
<212> TYPE: PRT
<213> ORGANISM: Artificial Sequence
<220> FEATURE:
<223> OTHER INFORMATION: Synthetic

<400> SEQUENCE: 33

Met Arg Pro Ala Lys Ser Thr Asp Ser Val Phe Val Arg Thr Pro Val
1               5                   10                  15

Glu Ala Trp Val Ala Pro Ser Pro Pro Asp Asp Lys Val Ala Glu Ser
            20                  25                  30

Ser Tyr Leu Met Phe Arg Ala Met Tyr Ala Val Phe Thr Arg Asp Glu
        35                  40                  45

Lys Asp Leu Pro Leu Pro Ala Leu Val Leu Cys Arg Leu Ile Lys Ala
    50                  55                  60

Ser Leu Arg Lys Asp Arg Lys Leu Tyr Ala Glu Leu Ala Cys Arg Thr
65                  70                  75                  80

Ala Asp Ile Gly Gly Lys Asp Thr His Val Arg Leu Ile Ile Ser Val
            85                  90                  95

Leu Arg Ala Val Tyr Asn Asp His Tyr Asp Tyr Trp Ser Arg Leu Arg
            100                 105                 110

Val Val Leu Cys Tyr Thr Val Val Phe Ala Val Arg Asn Tyr Leu Asp
        115                 120                 125

Asp His Lys Ser Ala Ala Phe Val Leu Gly Ala Ile Ala His Tyr Leu
        130                 135                 140

Ala Leu Tyr Arg Arg Leu Trp Phe Ala Arg Leu Gly Gly Met Pro Arg
145                 150                 155                 160

Ser Leu Arg Arg Gln Phe Pro Val Thr Trp Ala Leu Ala Ser Leu Thr
                165                 170                 175

Asp Phe Leu Lys Ser Leu
                180

<210> SEQ ID NO 34
<211> LENGTH: 666
<212> TYPE: DNA
<213> ORGANISM: Artificial Sequence
<220> FEATURE:
<223> OTHER INFORMATION: Synthetic

<400> SEQUENCE: 34
atggccaggt tcatcgctca gctcctcctg ttggcctcct gtgtggccgc cggccaggct     60
gtcaccgctt tcttgggtga gcgagccacc ctgacctcct actggaggag ggtgagcctc    120
ggtccagaga ttgaggtcag ctggtttaaa ctgggcccag agaggagca ggtacttatt     180 gggcgcatgc accacgatgt catctttata gagtggcctt caggggctt ctttgatatc      240 cacagaagtg ccaacacctt cttttagta gtcaccgctg ccaacatctc ccatgacggc     300
aactacctgt gccgcatgaa actgggcgag accgaggtca ccaagcagga acacctgagc    360
gtggtgaagc tctaacgct gtctgtccac tccgaaaggt ctcagttccc agacttctct     420
gtccttactg tgacatgcac tgtgaatgca tttccccatc cccacgtcca gtggctcatg     480
cccgagggcg tggagcccgc accaactgcg gcaaatggcg gtgttatgaa ggaaaaggat     540
gggagcctct ctgttgctgt tgacctgtca cttcccaagc cctggcacct gccagtgacc     600

-continued

```
tgcgttggga aaaatgacaa ggaggaagcc cacggggttt atgtttctgg atacttgtcg      660
caataa                                                                 666
```

<210> SEQ ID NO 35
<211> LENGTH: 221
<212> TYPE: PRT
<213> ORGANISM: Artificial Sequence
<220> FEATURE:
<223> OTHER INFORMATION: Synthetic

<400> SEQUENCE: 35

```
Met Ala Arg Phe Ile Ala Gln Leu Leu Leu Leu Ala Ser Cys Val Ala
1               5                   10                  15

Ala Gly Gln Ala Val Thr Ala Phe Leu Gly Glu Arg Ala Thr Leu Thr
            20                  25                  30

Ser Tyr Trp Arg Arg Val Ser Leu Gly Pro Glu Ile Glu Val Ser Trp
        35                  40                  45

Phe Lys Leu Gly Pro Gly Glu Glu Gln Val Leu Ile Gly Arg Met His
    50                  55                  60

His Asp Val Ile Phe Ile Glu Trp Pro Phe Arg Gly Phe Phe Asp Ile
65                  70                  75                  80

His Arg Ser Ala Asn Thr Phe Phe Leu Val Val Thr Ala Ala Asn Ile
                85                  90                  95

Ser His Asp Gly Asn Tyr Leu Cys Arg Met Lys Leu Gly Glu Thr Glu
            100                 105                 110

Val Thr Lys Gln Glu His Leu Ser Val Val Lys Pro Leu Thr Leu Ser
        115                 120                 125

Val His Ser Glu Arg Ser Gln Phe Pro Asp Phe Ser Val Leu Thr Val
    130                 135                 140

Thr Cys Thr Val Asn Ala Phe Pro His Pro His Val Gln Trp Leu Met
145                 150                 155                 160

Pro Glu Gly Val Glu Pro Ala Pro Thr Ala Ala Asn Gly Gly Val Met
                165                 170                 175

Lys Glu Lys Asp Gly Ser Leu Ser Val Ala Val Asp Leu Ser Leu Pro
            180                 185                 190

Lys Pro Trp His Leu Pro Val Thr Cys Val Gly Lys Asn Asp Lys Glu
        195                 200                 205

Glu Ala His Gly Val Tyr Val Ser Gly Tyr Leu Ser Gln
    210                 215                 220
```

<210> SEQ ID NO 36
<211> LENGTH: 1440
<212> TYPE: DNA
<213> ORGANISM: Artificial Sequence
<220> FEATURE:
<223> OTHER INFORMATION: Synthetic

<400> SEQUENCE: 36

```
atggttcctt ctcagagact ctcccgaact agcagcattt cctccaacga ggatcccgca      60
gagagccaca ttctggaact cgaagcggtc tcagacacca acacagactg cgatatggac     120
cccatggagg gcagcgaaga acactccaca gatggagaga tttcatcctc agaggaggag     180
gatgaagatc caactccggc ccacgccata cctgcacagc cctccagcgt ggtcataacc     240
cctacctcgg catcgtttgt gattcccaga aagaagtggg acctacagga caagacagtc     300
acattgcatc gctcacccct gtgcagggac gaggacgaga aggaggagac tggcaactcc     360
tcttacacca gaggccacaa aaggcgacgc ggagaggtcc atggctgcac cgatgaaagt     420
```

```
tatggcaagc gccgacacct gcccccggga gcaagaatgc ccagagcccc aagggccccc   480
aggatgccta gagcaccgag gtctccaaga gctccccgaa gcaacagagc aaccagaggt   540
ccccggtcag aatctagagg ggccggcagg agcacaagga agcaggcgag gcaagaacgc   600
agccagaggc ccctgcccaa caaaccgtgg tttgacatga gtctggttaa gcctgtctcc   660
aagattacat ttgtcacctt gcccagcccc ctggcctctc tgaccctaga gcccatccaa   720
gacccgttcc tacagtcgat gctggcggtg gccgcccatc cagagattgg agcctggcag   780
aaagtgcaac ccagacacga gctgcgcagg agctacaaga cgctacgtga gttttttcacc   840 aagtcaacca acaaggacac atggctggat gcacgcatgc aggcgatcca gaacgcgggg   900
ctctgcaccc tggtagccat gctagaagag accatctttt ggctccagga gatcacctac   960
cacggcgacc tgcccctagc tcccgcggaa gacatcctcc tggcctgcgc catgagtctc   1020
agcaaggtga tcctgaccaa gctcaaagag ctggcaccct gcttccttcc taacacgcga   1080
gactacaact ttgtgaagca actcttctac atcacctgtg ccacggcccg tcaaaacaag   1140
gtggtggaga ccctgagcag ctcatatgtg aagcagcccc tctgtctctt ggcagcatat   1200
gcggcagtag ccccagccta cattaacgcc cactgcagac ggagacacga tgaagttgaa   1260
ttcctgggcc actacatcaa gaattacaac cctggcacgc taagctccct tttgacagag   1320
gccgtggaga ctcacacacg tgactgccga agtgcatcct gcagccgact tgtcagggcc   1380
attctctccc cgggcactgg gtcactcgga ctgtttttg ttcctggatt aaatcaataa   1440
```

```
<210> SEQ ID NO 37
<211> LENGTH: 479
<212> TYPE: PRT
<213> ORGANISM: Artificial Sequence
<220> FEATURE:
<223> OTHER INFORMATION: Synthetic

<400> SEQUENCE: 37

Met Val Pro Ser Gln Arg Leu Ser Arg Thr Ser Ser Ile Ser Ser Asn
1               5                   10                  15

Glu Asp Pro Ala Glu Ser His Ile Leu Glu Leu Glu Ala Val Ser Asp
                20                  25                  30

Thr Asn Thr Asp Cys Asp Met Asp Pro Met Glu Gly Ser Glu Glu His
            35                  40                  45

Ser Thr Asp Gly Glu Ile Ser Ser Ser Glu Glu Glu Asp Glu Asp Pro
        50                  55                  60

Thr Pro Ala His Ala Ile Pro Ala Gln Pro Ser Ser Val Val Ile Thr
65                  70                  75                  80

Pro Thr Ser Ala Ser Phe Val Ile Pro Arg Lys Lys Trp Asp Leu Gln
                85                  90                  95

Asp Lys Thr Val Thr Leu His Arg Ser Pro Leu Cys Arg Asp Glu Asp
                100                 105                 110

Glu Lys Glu Glu Thr Gly Asn Ser Ser Tyr Thr Arg Gly His Lys Arg
            115                 120                 125

Arg Arg Gly Glu Val His Gly Cys Thr Asp Glu Ser Tyr Gly Lys Arg
        130                 135                 140

Arg His Leu Pro Pro Gly Ala Arg Met Pro Ala Pro Arg Ala Pro
145                 150                 155                 160

Arg Met Pro Arg Ala Pro Arg Ser Pro Arg Ala Pro Arg Ser Asn Arg
                165                 170                 175

Ala Thr Arg Gly Pro Arg Ser Glu Ser Arg Gly Ala Gly Arg Ser Thr
```

-continued

```
              180               185               190
Arg Lys Gln Ala Arg Gln Glu Arg Ser Gln Arg Pro Leu Pro Asn Lys
         195               200               205
Pro Trp Phe Asp Met Ser Leu Val Lys Pro Val Ser Lys Ile Thr Phe
    210               215               220
Val Thr Leu Pro Ser Pro Leu Ala Ser Leu Thr Leu Glu Pro Ile Gln
225               230               235               240
Asp Pro Phe Leu Gln Ser Met Leu Ala Val Ala Ala His Pro Glu Ile
             245               250               255
Gly Ala Trp Gln Lys Val Gln Pro Arg His Glu Leu Arg Arg Ser Tyr
         260               265               270
Lys Thr Leu Arg Glu Phe Phe Thr Lys Ser Thr Asn Lys Asp Thr Trp
         275               280               285
Leu Asp Ala Arg Met Gln Ala Ile Gln Asn Ala Gly Leu Cys Thr Leu
         290               295               300
Val Ala Met Leu Glu Glu Thr Ile Phe Trp Leu Gln Glu Ile Thr Tyr
305               310               315               320
His Gly Asp Leu Pro Leu Ala Pro Ala Glu Asp Ile Leu Leu Ala Cys
             325               330               335
Ala Met Ser Leu Ser Lys Val Ile Leu Thr Lys Leu Lys Glu Leu Ala
         340               345               350
Pro Cys Phe Leu Pro Asn Thr Arg Asp Tyr Asn Phe Val Lys Gln Leu
         355               360               365
Phe Tyr Ile Thr Cys Ala Thr Ala Arg Gln Asn Lys Val Val Glu Thr
    370               375               380
Leu Ser Ser Ser Tyr Val Lys Gln Pro Leu Cys Leu Leu Ala Ala Tyr
385               390               395               400
Ala Ala Val Ala Pro Ala Tyr Ile Asn Ala His Cys Arg Arg Arg His
             405               410               415
Asp Glu Val Glu Phe Leu Gly His Tyr Ile Lys Asn Tyr Asn Pro Gly
         420               425               430
Thr Leu Ser Ser Leu Leu Thr Glu Ala Val Glu Thr His Thr Arg Asp
         435               440               445
Cys Arg Ser Ala Ser Cys Ser Arg Leu Val Arg Ala Ile Leu Ser Pro
    450               455               460
Gly Thr Gly Ser Leu Gly Leu Phe Phe Val Pro Gly Leu Asn Gln
465               470               475
```

<210> SEQ ID NO 38
<211> LENGTH: 3048
<212> TYPE: DNA
<213> ORGANISM: Artificial Sequence
<220> FEATURE:
<223> OTHER INFORMATION: Synthetic

<400> SEQUENCE: 38

```
atgtctgggg gactcttcta taaccctttc ctaagaccta ataaaggcct tctgaaaaag      60
cctgacaagg agtacctgcg tctcattccc aagtgtttcc agacaccagg cgccgcaggg     120
gtggtggatg tgcgggggcc tcagcccccc ctgtgcttct accaagactc cctgacggtg     180
gtggggggtg acgaggatgg aaagggcatg tggtggcgcc agcgtgccca agagggcacg     240
gcaaggccgg aggcagacac ccacggaagc cctctggact tccatgtcta cgacatactc     300
gagacggtgt acacgcacga gaaatgcgcc gtcattccat cggataaaca ggggtatgtg     360
gtgccatgtg gcatcgtcat caagctactg ggccggcgca aggccgatgg ggccagcgtg     420
```

```
tgtgtgaacg tgtttgggca gcaggcctac ttctacgcca gcgcgcctca gggtctggac      480
gtggagtttg cagtcctcag cgccctcaag gccagcacct tcgaccgcag gaccccctgc      540
cgggtctcgg tggagaaggt cacgcgccgt tccattatgg gctacggcaa ccatgccggc      600
gactaccaca agataacccct ctcccatccc aacagtgtgt gtcacgtggc cacgtggctg     660
caagacaagc acgggtgtcg gatctttgag gccaacgtgg atgccacgcg ccgctttgtc      720
ctggacaatg actttgtcac ctttggctgg tacagctgcc gccgcgccat cccccgcctc      780
cagcaccggg actcgtacgc cgagctcgag tacgactgtg aggtgggcga cctctcggtc      840
cggcgtgaag acagctcctg gccctcctac caggccctgg ccttcgatat cgagtgtcta      900
ggggaggagg gcttccccac ggccaccaac gaggctgacc tgatcctgca gatatcctgc      960
gtcctctggt cgacaggtga ggaggccggg cgctataggc gcatcctgct gacgctgggc      1020
acctgcgaag acatagaggg ggttgaggtc tacgagttcc catcggagct ggacatgctc      1080
tacgccttct tccagctcat cagagacctc agcgtggaga ttgtgaccgg ctacaacgtg      1140
gccaactttg actggcccta cattctggac agagccaggc acatctacag catcaaccca      1200
gcctctctgg gcaaaattag ggctgggggc gtctgcgagg tcaggcgacc ccatgatgcg      1260
ggcaagggct tcttgcgggc caacaccaag gtccgcatca ccggcctcat ccccatagac      1320
atgtacgccg tgtgccggga caagctcagt ctctcagact acaagctgga cacagtagcc      1380
aggcacctac tgggggccaa gaaggaggat gtgcattaca aggagattcc tcgcctcttt      1440
gcagcgggcc ccgaggggcg caggcggctc ggcatgtact gcgtgcagga ctcggccctg      1500
gtcatggatc tgctaaacca tttcgtgatc cacgtggagg tggcagagat tgccaagatc      1560
gctcacatcc cctgcaggcg ggtgctggac gatgggcagc agatccgcgt gttctcctgc      1620
ctcctggcgg ccgcccaaaa ggaaaacttt atcctgccca tgccctcggc ctctgaccgg      1680
gacggctacc aggggggccac cgtcatccag ccccctgtccg gattctacaa ctccccggtt     1740
ctggtggtgg actttgccag cctctacccg agcatcattc aggctcataa tctctgttat      1800
tctaccatga taacgccggg agaagagcac aggctagccg gcctgcgccc gggagaagac      1860
tatgagtcct tcaggctcac ggggggcgtc taccactttg tgaagaagca cgtgcacgag      1920
tccttcttgg ctagtctgtt gacctcctgg ctggccaagc gcaaggccat caagaagctg      1980
ctggcggcct gcgaggatcc gcgccaaagg accatcctcg acaagcagca gctggccatc      2040
aagtgcacgt gcaacgccgt ctacggcttc accggggtgg ccaatggcct ctttccctgc      2100
ctctccatcg ccgagacggt gacgctgcag ggccgcacga tgttggagcg ggccaaggcc      2160
ttcgtggagg ccctgagccc cgccaacctg caggccctgg cccctcccc ggacgcctgg      2220 gcgcccctca accccgaggg ccagcttcga gtcatctacg gggacacaga ctcgctgttt      2280
atcgagtgcc gggggttttc agagagcgag accctgcgct ttgccgaggc cctggccgcc      2340
cacaccacca ggagcctgtt tgtggcccccc atctccctgg aggccgagaa gaccttctcc      2400
tgcctgatgc tgattacaaa gaagagatat gtggggggtgc tgacggacgg caagaccctg      2460
atgaaggggg tggagctcgt ccggaagacg gcctgcaagt ttgtgcagac acgctgccgg      2520
cgcgtgctcg acctggtgct ggcggatgcc cgggtaaagg aggcggccag cctcctctcc      2580
caccggccct tccaagagtc atttacacaa gggctacctg tgggcttttt gcccgtcatt      2640
gacatcctaa accaggccta cgcagacctc cgtgaaggca gggtccccat gggggagctc      2700
tgcttttcaa cggagctcag ccgcaagctc tcagcctaca agagcaccca gatgcctcac      2760
```

-continued

```
ctggctgtct accagaagtt cgtcgagcgc aacgaggaac tgccccagat ccacgaccgc    2820
atccagtacg tctttgtgga gcccaagggg ggagtgaagg gggcgagaaa gacggagatg    2880
gccgaggacc cggcctatgc cgagcggcac ggcgttcccg tggccgtgga tcattatttc    2940
gacaagctgc tccaaggagc ggccaacatc ctccagtgcc tctttgataa caactccggg    3000
gccgccctct ccgtcctcca gaattttaca gcccgcccac cattctaa                 3048
```

```
<210> SEQ ID NO 39
<211> LENGTH: 1015
<212> TYPE: PRT
<213> ORGANISM: Artificial Sequence
<220> FEATURE:
<223> OTHER INFORMATION: Synthetic

<400> SEQUENCE: 39

Met Ser Gly Gly Leu Phe Tyr Asn Pro Phe Leu Arg Pro Asn Lys Gly
1               5                   10                  15

Leu Leu Lys Lys Pro Asp Lys Glu Tyr Leu Arg Leu Ile Pro Lys Cys
                20                  25                  30

Phe Gln Thr Pro Gly Ala Ala Gly Val Val Asp Val Arg Gly Pro Gln
            35                  40                  45

Pro Pro Leu Cys Phe Tyr Gln Asp Ser Leu Thr Val Val Gly Gly Asp
        50                  55                  60

Glu Asp Gly Lys Gly Met Trp Trp Arg Gln Arg Ala Gln Glu Gly Thr
65                  70                  75                  80

Ala Arg Pro Glu Ala Asp Thr His Gly Ser Pro Leu Asp Phe His Val
                85                  90                  95

Tyr Asp Ile Leu Glu Thr Val Tyr Thr His Glu Lys Cys Ala Val Ile
            100                 105                 110

Pro Ser Asp Lys Gln Gly Tyr Val Val Pro Cys Gly Ile Val Ile Lys
        115                 120                 125

Leu Leu Gly Arg Arg Lys Ala Asp Gly Ala Ser Val Cys Val Asn Val
        130                 135                 140

Phe Gly Gln Gln Ala Tyr Phe Tyr Ala Ser Ala Pro Gln Gly Leu Asp
145                 150                 155                 160

Val Glu Phe Ala Val Leu Ser Ala Leu Lys Ala Ser Thr Phe Asp Arg
                165                 170                 175

Arg Thr Pro Cys Arg Val Ser Val Glu Lys Val Thr Arg Arg Ser Ile
            180                 185                 190

Met Gly Tyr Gly Asn His Ala Gly Asp Tyr His Lys Ile Thr Leu Ser
            195                 200                 205

His Pro Asn Ser Val Cys His Val Ala Thr Trp Leu Gln Asp Lys His
        210                 215                 220

Gly Cys Arg Ile Phe Glu Ala Asn Val Asp Ala Thr Arg Arg Phe Val
225                 230                 235                 240

Leu Asp Asn Asp Phe Val Thr Phe Gly Trp Tyr Ser Cys Arg Arg Ala
                245                 250                 255

Ile Pro Arg Leu Gln His Arg Asp Ser Tyr Ala Glu Leu Glu Tyr Asp
            260                 265                 270

Cys Glu Val Gly Asp Leu Ser Val Arg Arg Glu Asp Ser Ser Trp Pro
        275                 280                 285

Ser Tyr Gln Ala Leu Ala Phe Asp Ile Glu Cys Leu Gly Glu Glu Gly
        290                 295                 300

Phe Pro Thr Ala Thr Asn Glu Ala Asp Leu Ile Leu Gln Ile Ser Cys
305                 310                 315                 320
```

-continued

```
Val Leu Trp Ser Thr Gly Glu Glu Ala Gly Arg Tyr Arg Arg Ile Leu
            325             330             335

Leu Thr Leu Gly Thr Cys Glu Asp Ile Glu Gly Val Glu Val Tyr Glu
            340             345             350

Phe Pro Ser Glu Leu Asp Met Leu Tyr Ala Phe Phe Gln Leu Ile Arg
            355             360             365

Asp Leu Ser Val Glu Ile Val Thr Gly Tyr Asn Val Ala Asn Phe Asp
            370             375             380

Trp Pro Tyr Ile Leu Asp Arg Ala Arg His Ile Tyr Ser Ile Asn Pro
385             390             395             400

Ala Ser Leu Gly Lys Ile Arg Ala Gly Gly Val Cys Glu Val Arg Arg
            405             410             415

Pro His Asp Ala Gly Lys Gly Phe Leu Arg Ala Asn Thr Lys Val Arg
            420             425             430

Ile Thr Gly Leu Ile Pro Ile Asp Met Tyr Ala Val Cys Arg Asp Lys
            435             440             445

Leu Ser Leu Ser Asp Tyr Lys Leu Asp Thr Val Ala Arg His Leu Leu
            450             455             460

Gly Ala Lys Lys Glu Asp Val His Tyr Lys Glu Ile Pro Arg Leu Phe
465             470             475             480

Ala Ala Gly Pro Glu Gly Arg Arg Arg Leu Gly Met Tyr Cys Val Gln
            485             490             495

Asp Ser Ala Leu Val Met Asp Leu Leu Asn His Phe Val Ile His Val
            500             505             510

Glu Val Ala Glu Ile Ala Lys Ile Ala His Ile Pro Cys Arg Arg Val
            515             520             525

Leu Asp Asp Gly Gln Gln Ile Arg Val Phe Ser Cys Leu Leu Ala Ala
            530             535             540

Ala Gln Lys Glu Asn Phe Ile Leu Pro Met Pro Ser Ala Ser Asp Arg
545             550             555             560

Asp Gly Tyr Gln Gly Ala Thr Val Ile Gln Pro Leu Ser Gly Phe Tyr
            565             570             575

Asn Ser Pro Val Leu Val Val Asp Phe Ala Ser Leu Tyr Pro Ser Ile
            580             585             590

Ile Gln Ala His Asn Leu Cys Tyr Ser Thr Met Ile Thr Pro Gly Glu
            595             600             605

Glu His Arg Leu Ala Gly Leu Arg Pro Gly Glu Asp Tyr Glu Ser Phe
            610             615             620

Arg Leu Thr Gly Gly Val Tyr His Phe Val Lys Lys His Val His Glu
625             630             635             640

Ser Phe Leu Ala Ser Leu Leu Thr Ser Trp Leu Ala Lys Arg Lys Ala
            645             650             655

Ile Lys Lys Leu Leu Ala Ala Cys Glu Asp Pro Arg Gln Arg Thr Ile
            660             665             670

Leu Asp Lys Gln Gln Leu Ala Ile Lys Cys Thr Cys Asn Ala Val Tyr
            675             680             685

Gly Phe Thr Gly Val Ala Asn Gly Leu Phe Pro Cys Leu Ser Ile Ala
            690             695             700

Glu Thr Val Thr Leu Gln Gly Arg Thr Met Leu Glu Arg Ala Lys Ala
705             710             715             720

Phe Val Glu Ala Leu Ser Pro Ala Asn Leu Gln Ala Leu Ala Pro Ser
            725             730             735
```

-continued

```
Pro Asp Ala Trp Ala Pro Leu Asn Pro Glu Gly Gln Leu Arg Val Ile
            740                 745                 750

Tyr Gly Asp Thr Asp Ser Leu Phe Ile Glu Cys Arg Gly Phe Ser Glu
            755                 760                 765

Ser Glu Thr Leu Arg Phe Ala Glu Ala Leu Ala Ala His Thr Thr Arg
            770                 775                 780

Ser Leu Phe Val Ala Pro Ile Ser Leu Glu Ala Glu Lys Thr Phe Ser
785                 790                 795                 800

Cys Leu Met Leu Ile Thr Lys Lys Arg Tyr Val Gly Val Leu Thr Asp
                805                 810                 815

Gly Lys Thr Leu Met Lys Gly Val Glu Leu Val Arg Lys Thr Ala Cys
            820                 825                 830

Lys Phe Val Gln Thr Arg Cys Arg Arg Val Leu Asp Leu Val Leu Ala
            835                 840                 845

Asp Ala Arg Val Lys Glu Ala Ala Ser Leu Leu Ser His Arg Pro Phe
    850                 855                 860

Gln Glu Ser Phe Thr Gln Gly Leu Pro Val Gly Phe Leu Pro Val Ile
865                 870                 875                 880

Asp Ile Leu Asn Gln Ala Tyr Ala Asp Leu Arg Glu Gly Arg Val Pro
                885                 890                 895

Met Gly Glu Leu Cys Phe Ser Thr Glu Leu Ser Arg Lys Leu Ser Ala
            900                 905                 910

Tyr Lys Ser Thr Gln Met Pro His Leu Ala Val Tyr Gln Lys Phe Val
            915                 920                 925

Glu Arg Asn Glu Glu Leu Pro Gln Ile His Asp Arg Ile Gln Tyr Val
    930                 935                 940

Phe Val Glu Pro Lys Gly Gly Val Lys Gly Ala Arg Lys Thr Glu Met
945                 950                 955                 960

Ala Glu Asp Pro Ala Tyr Ala Glu Arg His Gly Val Pro Val Ala Val
                965                 970                 975

Asp His Tyr Phe Asp Lys Leu Leu Gln Gly Ala Ala Asn Ile Leu Gln
            980                 985                 990

Cys Leu Phe Asp Asn Asn Ser Gly  Ala Ala Leu Ser Val  Leu Gln Asn
            995                 1000                1005

Phe Thr  Ala Arg Pro Pro Phe
    1010                1015
```

<210> SEQ ID NO 40
<211> LENGTH: 1437
<212> TYPE: DNA
<213> ORGANISM: Artificial Sequence
<220> FEATURE:
<223> OTHER INFORMATION: Synthetic
<400> SEQUENCE: 40

```
atggttcctt ctcagagact ctcccgaact agcagcattt cctccaacga ggatcccgca      60
gagagccaca ttctggaact cgaagcggtc tcagacacca acacagactg cgatatggac     120
cccatggagg gcagcgaaga acactccaca gatggagaga tttcatcctc agaggaggag     180
gatgaagatc caactccggc ccacgccata cctgcacagc cctccagcgt ggtcataacc     240
cctacctcgg catcgtttgt gattcccaga aagaagtggg acctacagga caagacagtc     300
acattgcatc gctcacccct gtgcagggac gaggacgaga aggaggagac tggcaactcc     360
tcttacacca gaggccacaa aaggcgacgc ggagaggtcc atggctgcac cgatgaaagt     420
tatggcaagc gccgacacct gccccccggga gcaagaatgc ccagagcccc aagggcccccc    480
```

-continued

```
aggatgccta gagcaccgag gtctccaaga gctccccgaa gcaacagagc aaccagaggt      540
ccccggtcag aatctagagg ggccggcagg agcacaagga agcaggcgag gcaagaacgc      600
agccagaggc ccctgcccaa caaaccgtgg tttgacatga gtctggttaa gcctgtctcc      660
aagattacat ttgtcacctt gcccagcccc ctggcctctc tgaccctaga gcccatccaa      720
gacccgttcc tacagtcgat gctggcggtg gccgcccatc cagagattgg agcctggcag      780
aaagtgcaac ccagacacga gctgcgcagg agctacaaga cgctacgtga gttttttcacc     840 aagtcaacca acaaggacac atggctggat gcacgcatgc aggcgatcca gaacgcgggg      900
ctctgcaccc tggtagccat gctagaagag accatctttt ggctccagga gatcaccctac     960 cacggcgacc tgcccctagc tcccgcggaa gacatcctcc tggcctgcgc catgagtctc      1020
agcaaggtga tcctgaccaa gctcaaagag ctggcacccct gcttccttcc taacacgcga     1080
gactacaact ttgtgaagca actcttctac atcacctgtg ccacggcccg tcaaaacaag      1140
gtggtggaga ccctgagcag ctcatatgtg aagcagcccc tctgtctctt ggcagcatat      1200
gcggcagtag ccccagccta cattaacgcc cactgcagac ggagacacga tgaagttgaa      1260
ttcctgggcc actacatcaa gaattacaac cctggcacgc taagctccct tttgacagag      1320
gccgtggaga ctcacacacg tgactgccga agtgcatcct gcagccgact tgtcagggcc      1380
attctctccc cgggcactgg gtcactcgga ctgtttttg ttcctggatt aaatcaa         1437
```

<210> SEQ ID NO 41
<211> LENGTH: 479
<212> TYPE: PRT
<213> ORGANISM: Artificial Sequence
<220> FEATURE:
<223> OTHER INFORMATION: Synthetic

<400> SEQUENCE: 41

```
Met Val Pro Ser Gln Arg Leu Ser Arg Thr Ser Ser Ile Ser Ser Asn
1               5                   10                  15

Glu Asp Pro Ala Glu Ser His Ile Leu Glu Leu Glu Ala Val Ser Asp
            20                  25                  30

Thr Asn Thr Asp Cys Asp Met Asp Pro Met Glu Gly Ser Glu Glu His
        35                  40                  45

Ser Thr Asp Gly Glu Ile Ser Ser Ser Glu Glu Glu Asp Glu Asp Pro
    50                  55                  60

Thr Pro Ala His Ala Ile Pro Ala Gln Pro Ser Ser Val Val Ile Thr
65                  70                  75                  80

Pro Thr Ser Ala Ser Phe Val Ile Pro Arg Lys Lys Trp Asp Leu Gln
                85                  90                  95

Asp Lys Thr Val Thr Leu His Arg Ser Pro Leu Cys Arg Asp Glu Asp
            100                 105                 110

Glu Lys Glu Glu Thr Gly Asn Ser Ser Tyr Thr Arg Gly His Lys Arg
        115                 120                 125

Arg Arg Gly Glu Val His Gly Cys Thr Asp Glu Ser Tyr Gly Lys Arg
    130                 135                 140

Arg His Leu Pro Pro Gly Ala Arg Met Pro Arg Ala Pro Arg Ala Pro
145                 150                 155                 160

Arg Met Pro Arg Ala Pro Arg Ser Pro Arg Ala Pro Arg Ser Asn Arg
                165                 170                 175

Ala Thr Arg Gly Pro Arg Ser Glu Ser Arg Gly Ala Gly Arg Ser Thr
            180                 185                 190
```

```
Arg Lys Gln Ala Arg Gln Glu Arg Ser Gln Arg Pro Leu Pro Asn Lys
    195                 200                 205

Pro Trp Phe Asp Met Ser Leu Val Lys Pro Val Ser Lys Ile Thr Phe
    210                 215                 220

Val Thr Leu Pro Ser Pro Leu Ala Ser Leu Thr Leu Glu Pro Ile Gln
225                 230                 235                 240

Asp Pro Phe Leu Gln Ser Met Leu Ala Val Ala Ala His Pro Glu Ile
                245                 250                 255

Gly Ala Trp Gln Lys Val Gln Pro Arg His Glu Leu Arg Arg Ser Tyr
                260                 265                 270

Lys Thr Leu Arg Glu Phe Phe Thr Lys Ser Thr Asn Lys Asp Thr Trp
                275                 280                 285

Leu Asp Ala Arg Met Gln Ala Ile Gln Asn Ala Gly Leu Cys Thr Leu
    290                 295                 300

Val Ala Met Leu Glu Glu Thr Ile Phe Trp Leu Gln Glu Ile Thr Tyr
305                 310                 315                 320

His Gly Asp Leu Pro Leu Ala Pro Ala Glu Asp Ile Leu Leu Ala Cys
                325                 330                 335

Ala Met Ser Leu Ser Lys Val Ile Leu Thr Lys Leu Lys Glu Leu Ala
                340                 345                 350

Pro Cys Phe Leu Pro Asn Thr Arg Asp Tyr Asn Phe Val Lys Gln Leu
                355                 360                 365

Phe Tyr Ile Thr Cys Ala Thr Ala Arg Gln Asn Lys Val Val Glu Thr
    370                 375                 380

Leu Ser Ser Ser Tyr Val Lys Gln Pro Leu Cys Leu Leu Ala Ala Tyr
385                 390                 395                 400

Ala Ala Val Ala Pro Ala Tyr Ile Asn Ala His Cys Arg Arg Arg His
                405                 410                 415

Asp Glu Val Glu Phe Leu Gly His Tyr Ile Lys Asn Tyr Asn Pro Gly
                420                 425                 430

Thr Leu Ser Ser Leu Leu Thr Glu Ala Val Glu Thr His Thr Arg Asp
                435                 440                 445

Cys Arg Ser Ala Ser Cys Ser Arg Leu Val Arg Ala Ile Leu Ser Pro
    450                 455                 460

Gly Thr Gly Ser Leu Gly Leu Phe Phe Val Pro Gly Leu Asn Gln
465                 470                 475
```

```
<210> SEQ ID NO 42
<211> LENGTH: 2481
<212> TYPE: DNA
<213> ORGANISM: Artificial Sequence
<220> FEATURE:
<223> OTHER INFORMATION: Synthetic

<400> SEQUENCE: 42
atggcaacga ccagtcatgt cgagcatgag ctcctctcca aattgattga tgagttaaag      60
gtcaaggcca actcagaccc cgaggctgat gtcctggccg ggcgcctgct ccaccgcctt     120
aaggccgagt cagttacaca cacagtagcc gaatatctgg aggtcttctc tgacaaattc     180
tacgatgagg aattcttcca gatgcaccgg gatgagctgg agacccgagt ctctgctttc     240
gcgcagagcc cggcctacga gcgcatcgtc tccagcggct acctgtcggc cctgcgctac     300
tatgacacct atctgtatgt ggggcgcagc gggaagcagg agagtgtgca gcactttac     360 atgcggttag ccggcttctg tgcctcaacc acctgcctct acgcgggtct cagggcagcc     420
ctgcagcggg ccaggccgga gattgagagt gacatggagg tgtttgatta ctactttgag     480
```

```
cacctaacct cccagacggt gtgctgctcc acgccctta tgcgctttgc cggggtggaa      540
aactccactc tggccagctg catcctcacc accccgacc tcagctccga gtgggacgtg       600
acccaggccc tctataggca cctggggcgc tacctctttc agcgagccgg ggtgggtgta     660
ggggtgacgg gggctggcca ggatgggaaa cacatcagcc tcctgatgag gatgatcaac     720
agccacgtgg agtaccacaa ctatggctgc aagaggccgg tcagtgtggc ggcctacatg     780
gagccctggc acagccagat tttcaagttt ttggaaacga agctgccgga gaaccacgag     840
aggtgcccgg gcatctttac ggggctcttt gtccccgagc tcttcttcaa gctttttagg     900
gacacgccct ggtcggactg gtacctgttt gaccccaagg acgccgggga cctggagagg     960
ctctacgggg aggagtttga gcgcgagtac tatcggctgg tgacagcggg caagttttgt    1020
gggcgggtct ccatcaagtc cctgatgttc tctatcgtca actgcgccgt caaggccggc    1080
agccccttca tccttttgaa ggaggcctgc aacgcccact tttggcgcga cctgcagggc    1140
gaggccatga acgccgccaa cctgtgcgcc gaggtgctgc agccctcgag gaagtctgtg    1200
gccacctgca atctggccaa catctgcctc ccgcgctgcc tggtgaatgc gcctctggcg    1260
gtgcgggcac agcgggccga cacgcagggg gatgaactcc tgctggccct ccctcgactc    1320
tcagtcaccc tacctggaga gggggcagtc ggtgatggat tctcgctagc ccgcctcaga    1380
gatgccaccc agtgtgccac ctttgtggtg gcctgctcca ttcttcaggg atcccccact    1440
tatgattcca gggatatggc ctccatgggc ctcggggtgc agggcctggc cgatgtcttt    1500
gcggacctgg gctggcagta cactgaccct ccctctcgct cgttaaacaa ggaaatattc    1560
gaacatatgt actttacggc cctctgcacc agtagtctga ttggacttca caccaggaag    1620
atttttccgg gtttcaaaca gagcaagtat gccgggggt ggtttcactg gcacgattgg     1680
gcaggaacag acctttctat tcccagggaa atttggtctc gcctctctga acgcattgtg    1740
agggatgggc ttttcaattc acagtttatc gccctgatgc ccacctcagg ctgtgcccag    1800
gtgacgggct gttcggacgc cttctacccc ttctatgcca atgcgtccac caaggtcacc    1860
aacaaggagg aggcccttag gccaaaccgg tcttttttggc gtcatgtgcg tctggatgac    1920
agggaagctt tgaatcttgt cgggggccgt gtctcctgcc tcccggaggc tctgcggcag    1980
cgctacctgc gtttccaaac ggcctttgat tacaaccagg aggacctgat tcagatgtcc    2040
cgggacaggg cccccttgt ggaccagagc caatctcaca gcctgttttt gcgtgaggaa    2100
gatgccgcgc gggccagcac gctagccaac ctactggtgc gcagctacga gctgggcctg    2160
aagactatca tgtactattg tcgcattgag aaggccgccg atctggtggt gatggagtgt    2220
aaggccagcg cggctctgtc ggtgccgcgg gaggaacaga atgagcggag tcccgctgag    2280
cagatgccgc ctcgtcccat ggaaccggcg caggttgcgg ggccggttga catcatgagc    2340
aagggcccag gggagggacc aggtgggtgg tgtgtgcccg ggggattgga agtgtgctat    2400
aagtaccgtc agctcttctc agaggatgat ctgttggaga ctgacggttt tactgaacga    2460
gcctgtgaat cttgccaata a                                               2481
```

<210> SEQ ID NO 43
<211> LENGTH: 826
<212> TYPE: PRT
<213> ORGANISM: Artificial Sequence
<220> FEATURE:
<223> OTHER INFORMATION: Synthetic

<400> SEQUENCE: 43

-continued

```
Met Ala Thr Thr Ser His Val Glu His Glu Leu Leu Ser Lys Leu Ile
1               5                   10                  15

Asp Glu Leu Lys Val Lys Ala Asn Ser Asp Pro Glu Ala Asp Val Leu
            20                  25                  30

Ala Gly Arg Leu Leu His Arg Leu Lys Ala Glu Ser Val Thr His Thr
        35                  40                  45

Val Ala Glu Tyr Leu Glu Val Phe Ser Asp Lys Phe Tyr Asp Glu Glu
    50                  55                  60

Phe Phe Gln Met His Arg Asp Glu Leu Glu Thr Arg Val Ser Ala Phe
65                  70                  75                  80

Ala Gln Ser Pro Ala Tyr Glu Arg Ile Val Ser Ser Gly Tyr Leu Ser
                85                  90                  95

Ala Leu Arg Tyr Tyr Asp Thr Tyr Leu Tyr Val Gly Arg Ser Gly Lys
            100                 105                 110

Gln Glu Ser Val Gln His Phe Tyr Met Arg Leu Ala Gly Phe Cys Ala
        115                 120                 125

Ser Thr Thr Cys Leu Tyr Ala Gly Leu Arg Ala Ala Leu Gln Arg Ala
    130                 135                 140

Arg Pro Glu Ile Glu Ser Asp Met Glu Val Phe Asp Tyr Tyr Phe Glu
145                 150                 155                 160

His Leu Thr Ser Gln Thr Val Cys Cys Ser Thr Pro Phe Met Arg Phe
                165                 170                 175

Ala Gly Val Glu Asn Ser Thr Leu Ala Ser Cys Ile Leu Thr Thr Pro
            180                 185                 190

Asp Leu Ser Ser Glu Trp Asp Val Thr Gln Ala Leu Tyr Arg His Leu
        195                 200                 205

Gly Arg Tyr Leu Phe Gln Arg Ala Gly Val Gly Val Gly Val Thr Gly
    210                 215                 220

Ala Gly Gln Asp Gly Lys His Ile Ser Leu Leu Met Arg Met Ile Asn
225                 230                 235                 240

Ser His Val Glu Tyr His Asn Tyr Gly Cys Lys Arg Pro Val Ser Val
                245                 250                 255

Ala Ala Tyr Met Glu Pro Trp His Ser Gln Ile Phe Lys Phe Leu Glu
            260                 265                 270

Thr Lys Leu Pro Glu Asn His Glu Arg Cys Pro Gly Ile Phe Thr Gly
        275                 280                 285

Leu Phe Val Pro Glu Leu Phe Phe Lys Leu Phe Arg Asp Thr Pro Trp
    290                 295                 300

Ser Asp Trp Tyr Leu Phe Asp Pro Lys Asp Ala Gly Asp Leu Glu Arg
305                 310                 315                 320

Leu Tyr Gly Glu Glu Phe Glu Arg Glu Tyr Tyr Arg Leu Val Thr Ala
            325                 330                 335

Gly Lys Phe Cys Gly Arg Val Ser Ile Lys Ser Leu Met Phe Ser Ile
            340                 345                 350

Val Asn Cys Ala Val Lys Ala Gly Ser Pro Phe Ile Leu Leu Lys Glu
        355                 360                 365

Ala Cys Asn Ala His Phe Trp Arg Asp Leu Gln Gly Glu Ala Met Asn
    370                 375                 380

Ala Ala Asn Leu Cys Ala Glu Val Leu Gln Pro Ser Arg Lys Ser Val
385                 390                 395                 400

Ala Thr Cys Asn Leu Ala Asn Ile Cys Leu Pro Arg Cys Leu Val Asn
            405                 410                 415

Ala Pro Leu Ala Val Arg Ala Gln Arg Ala Asp Thr Gln Gly Asp Glu
```

```
                    420                425                430
Leu Leu Leu Ala Leu Pro Arg Leu Ser Val Thr Leu Pro Gly Glu Gly
            435                440                445

Ala Val Gly Asp Gly Phe Ser Leu Ala Arg Leu Arg Asp Ala Thr Gln
        450                455                460

Cys Ala Thr Phe Val Val Ala Cys Ser Ile Leu Gln Gly Ser Pro Thr
465                470                475                480

Tyr Asp Ser Arg Asp Met Ala Ser Met Gly Leu Gly Val Gln Gly Leu
            485                490                495

Ala Asp Val Phe Ala Asp Leu Gly Trp Gln Tyr Thr Asp Pro Pro Ser
        500                505                510

Arg Ser Leu Asn Lys Glu Ile Phe Glu His Met Tyr Phe Thr Ala Leu
        515                520                525

Cys Thr Ser Ser Leu Ile Gly Leu His Thr Arg Lys Ile Phe Pro Gly
        530                535                540

Phe Lys Gln Ser Lys Tyr Ala Gly Gly Trp Phe His Trp His Asp Trp
545                550                555                560

Ala Gly Thr Asp Leu Ser Ile Pro Arg Glu Ile Trp Ser Arg Leu Ser
            565                570                575

Glu Arg Ile Val Arg Asp Gly Leu Phe Asn Ser Gln Phe Ile Ala Leu
            580                585                590

Met Pro Thr Ser Gly Cys Ala Gln Val Thr Gly Cys Ser Asp Ala Phe
        595                600                605

Tyr Pro Phe Tyr Ala Asn Ala Ser Thr Lys Val Thr Asn Lys Glu Glu
        610                615                620

Ala Leu Arg Pro Asn Arg Ser Phe Trp Arg His Val Arg Leu Asp Asp
625                630                635                640

Arg Glu Ala Leu Asn Leu Val Gly Gly Arg Val Ser Cys Leu Pro Glu
            645                650                655

Ala Leu Arg Gln Arg Tyr Leu Arg Phe Gln Thr Ala Phe Asp Tyr Asn
            660                665                670

Gln Glu Asp Leu Ile Gln Met Ser Arg Asp Arg Ala Pro Phe Val Asp
            675                680                685

Gln Ser Gln Ser His Ser Leu Phe Leu Arg Glu Glu Asp Ala Ala Arg
        690                695                700

Ala Ser Thr Leu Ala Asn Leu Leu Val Arg Ser Tyr Glu Leu Gly Leu
705                710                715                720

Lys Thr Ile Met Tyr Tyr Cys Arg Ile Glu Lys Ala Ala Asp Leu Gly
            725                730                735

Val Met Glu Cys Lys Ala Ser Ala Ala Leu Ser Val Pro Arg Glu Glu
            740                745                750

Gln Asn Glu Arg Ser Pro Ala Glu Gln Met Pro Pro Arg Pro Met Glu
        755                760                765

Pro Ala Gln Val Ala Gly Pro Val Asp Ile Met Ser Lys Gly Pro Gly
        770                775                780

Glu Gly Pro Gly Gly Trp Cys Val Pro Gly Gly Leu Glu Val Cys Tyr
785                790                795                800

Lys Tyr Arg Gln Leu Phe Ser Glu Asp Asp Leu Leu Glu Thr Asp Gly
            805                810                815

Phe Thr Glu Arg Ala Cys Glu Ser Cys Gln
            820                825
```

<210> SEQ ID NO 44

-continued

<211> LENGTH: 1215
<212> TYPE: DNA
<213> ORGANISM: Artificial Sequence
<220> FEATURE:
<223> OTHER INFORMATION: Synthetic

<400> SEQUENCE: 44

```
atggaaacca ctcagactct ccgctttaag accaaggccc tagccgtcct gtccaagtgc      60
tatgaccatg cccagactca tctcaaggga ggagtgctgc aggtaaacct tctgtctgta     120
aactatggag ccccccggct ggccgccgtg gccaacgcag gcacggccgg gctaatcagc     180
ttcgaggtct cccctgacgc tgtggccgag tggcagaatc accagagccc agaggaggcc     240
ccggccgccg tgtcatttag aaaccttgcc tacgggcgca cctgtgtcct gggcaaggag     300
ctgtttggct cggctgtgga gcaggcttcc ctgcaatttt acaagcggcc acaagggggt     360
tcccggcctg aatttgttaa gctcactatg gaatatgatg ataaggtgtc caagagccac     420
cacacctgcg ccctgatgcc ctatatgccc ccggccagcg acaggctgag gaacgagcag     480
atgattgggc aggtgctgtt gatgcccaag acggcttcct cgttgcagaa gtgggcacgc     540
cagcaaggct caggcggcgt taaggtgaca ctcaatccgg atctctacgt caccacgtat     600
acttctgggg aggcctgcct caccctagac tacaagcctc tgagtgtggg gccatacgag     660
gccttcactg ccctgtggc caaggctcag gacgtggggg ccgttgaggc ccacgttgtc     720
tgctcggtag cagcggactc gctggcggcg gcgcttagcc tctgccgcat tccggccgtt     780
agcgtgccaa tcttgaggtt ttacaggtct ggcatcatag ctgtggtggc cggcctgctg     840
acgtcagcgg gggacctgcc gttggatctt agtgttattt tatttaacca cgcctccgaa     900
gaggcggccg ccagtacggc ctctgagcca gaagataaaa gtccccgggt gcaaccactg     960
ggcacaggac tccaacaacg ccccagacat acggtcagtc catctccttc acctccgcca    1020
cctcctagga cccctacttg ggagagtccg gcaaggccag agacaccctc gcctgccatt    1080
cccagccact ccagcaacac cgcactggag aggcctctgg ctgttcagct cgcgaggaaa    1140
aggacatcgt cggaggccag gcagaagcag aagcacccca agaaagtgaa gcaggccttt    1200
aaccccctca tttaa                                                     1215
```

<210> SEQ ID NO 45
<211> LENGTH: 404
<212> TYPE: PRT
<213> ORGANISM: Artificial Sequence
<220> FEATURE:
<223> OTHER INFORMATION: Synthetic

<400> SEQUENCE: 45

```
Met Glu Thr Thr Gln Thr Leu Arg Phe Lys Thr Lys Ala Leu Ala Val
1               5                   10                  15

Leu Ser Lys Cys Tyr Asp His Ala Gln Thr His Leu Lys Gly Gly Val
            20                  25                  30

Leu Gln Val Asn Leu Leu Ser Val Asn Tyr Gly Gly Pro Arg Leu Ala
        35                  40                  45

Ala Val Ala Asn Ala Gly Thr Ala Gly Leu Ile Ser Phe Glu Val Ser
    50                  55                  60

Pro Asp Ala Val Ala Glu Trp Gln Asn His Gln Ser Pro Glu Glu Ala
65                  70                  75                  80

Pro Ala Ala Val Ser Phe Arg Asn Leu Ala Tyr Gly Arg Thr Cys Val
                85                  90                  95

Leu Gly Lys Glu Leu Phe Gly Ser Ala Val Glu Gln Ala Ser Leu Gln
```

```
            100              105              110
Phe Tyr Lys Arg Pro Gln Gly Gly Ser Arg Pro Glu Phe Val Lys Leu
        115              120              125

Thr Met Glu Tyr Asp Asp Lys Val Ser Lys Ser His His Thr Cys Ala
    130              135              140

Leu Met Pro Tyr Met Pro Pro Ala Ser Asp Arg Leu Arg Asn Glu Gln
145              150              155              160

Met Ile Gly Gln Val Leu Leu Met Pro Lys Thr Ala Ser Ser Leu Gln
            165              170              175

Lys Trp Ala Arg Gln Gln Gly Ser Gly Gly Val Lys Val Thr Leu Asn
        180              185              190

Pro Asp Leu Tyr Val Thr Thr Tyr Thr Ser Gly Glu Ala Cys Leu Thr
        195              200              205

Leu Asp Tyr Lys Pro Leu Ser Val Gly Pro Tyr Glu Ala Phe Thr Gly
    210              215              220

Pro Val Ala Lys Ala Gln Asp Val Gly Ala Val Glu Ala His Val Val
225              230              235              240

Cys Ser Val Ala Ala Asp Ser Leu Ala Ala Ala Leu Ser Leu Cys Arg
            245              250              255

Ile Pro Ala Val Ser Val Pro Ile Leu Arg Phe Tyr Arg Ser Gly Ile
            260              265              270

Ile Ala Val Val Ala Gly Leu Leu Thr Ser Ala Gly Asp Leu Pro Leu
            275              280              285

Asp Leu Ser Val Ile Leu Phe Asn His Ala Ser Glu Glu Ala Ala Ala
    290              295              300

Ser Thr Ala Ser Glu Pro Glu Asp Lys Ser Pro Arg Val Gln Pro Leu
305              310              315              320

Gly Thr Gly Leu Gln Gln Arg Pro Arg His Thr Val Ser Pro Ser Pro
            325              330              335

Ser Pro Pro Pro Pro Pro Arg Thr Pro Thr Trp Glu Ser Pro Ala Arg
            340              345              350

Pro Glu Thr Pro Ser Pro Ala Ile Pro Ser His Ser Ser Asn Thr Ala
            355              360              365

Leu Glu Arg Pro Leu Ala Val Gln Leu Ala Arg Lys Arg Thr Ser Ser
    370              375              380

Glu Ala Arg Gln Lys Gln Lys His Pro Lys Lys Val Lys Gln Ala Phe
385              390              395              400

Asn Pro Leu Ile
```

<210> SEQ ID NO 46
<211> LENGTH: 957
<212> TYPE: DNA
<213> ORGANISM: Artificial Sequence
<220> FEATURE:
<223> OTHER INFORMATION: Synthetic

<400> SEQUENCE: 46

```
atggccccgg tcaccccaga tgccgtgaat gcacgccaac agcgaccggc agatcccgca      60
ttgcgccgcc taatgcatcc gcaccacaga aactacacgg cctcaaaggc ctcggcgcat     120
agcgtgaagt cggtgtccag gtgtggaaaa tctcgctcag agctgggaag aatggaaagg     180
gttggcagtg tggcccgatc aatatgttcc cggcacacca gacatggtgt agacagatcc     240
catttttcac tacgggactt cttcagggga atctctgcca actttgagct gggcaaagat     300
tttctgcgtg agatgaacac ccccatacat gtctcagagg ccgtgtttct cccactgtca     360
```

-continued

```
ctgtgcactc tctcccccgg gcgctgcctt cgcctgtctc ccttcggcca cagcctgact    420
ctggggtctc actgcgagat ctgcatcaat aggtcccagg ttcatgtgcc tcaggagttt    480
agctccaccc agctctcctt cttcaacaat gtccacaaga taatacccaa caagaccttc    540
tatgtgtctc tgctcagcag ctctcccagt gcagtaaagg ctggactttc ccaacccagc    600
cttctctacg cttacctggt caccggacac ttttgtggca ccatctgccc catcttcagc    660
acaaatggaa aagggcgcct aatcatgcat ctcctgctcc agggcacctc ccttcacatc    720
ccagagacct gcttgaaact gttatgtgaa aacataggcc ccacctacga gctggccgtg    780
gacctagtag gggacgcctt ctgtataaag gtcagcccca gagacacggt atatgagaag    840
gctgtcaatg tcgacgaaga tgccatctac gaggccatca aggacctgga atgtggggat    900
gagctgcgcc tacagatcat caactatacc cagctcattt tggaaaataa acagtag       957
```

```
<210> SEQ ID NO 47
<211> LENGTH: 318
<212> TYPE: PRT
<213> ORGANISM: Artificial Sequence
<220> FEATURE:
<223> OTHER INFORMATION: Synthetic

<400> SEQUENCE: 47

Met Ala Pro Val Thr Pro Asp Ala Val Asn Ala Arg Gln Gln Arg Pro
1               5                   10                  15

Ala Asp Pro Ala Leu Arg Arg Leu Met His Pro His His Arg Asn Tyr
                20                  25                  30

Thr Ala Ser Lys Ala Ser Ala His Ser Val Lys Ser Val Ser Arg Cys
            35                  40                  45

Gly Lys Ser Arg Ser Glu Leu Gly Arg Met Glu Arg Val Gly Ser Val
        50                  55                  60

Ala Arg Ser Ile Cys Ser Arg His Thr Arg His Gly Val Asp Arg Ser
65                  70                  75                  80

His Phe Ser Leu Arg Asp Phe Phe Arg Gly Ile Ser Ala Asn Phe Glu
                85                  90                  95

Leu Gly Lys Asp Phe Leu Arg Glu Met Asn Thr Pro Ile His Val Ser
            100                 105                 110

Glu Ala Val Phe Leu Pro Leu Ser Leu Cys Thr Leu Ser Pro Gly Arg
            115                 120                 125

Cys Leu Arg Leu Ser Pro Phe Gly His Ser Leu Thr Leu Gly Ser His
        130                 135                 140

Cys Glu Ile Cys Ile Asn Arg Ser Gln Val His Val Pro Gln Glu Phe
145                 150                 155                 160

Ser Ser Thr Gln Leu Ser Phe Phe Asn Asn Val His Lys Ile Ile Pro
                165                 170                 175

Asn Lys Thr Phe Tyr Val Ser Leu Leu Ser Ser Ser Pro Ser Ala Val
                180                 185                 190

Lys Ala Gly Leu Ser Gln Pro Ser Leu Leu Tyr Ala Tyr Leu Val Thr
            195                 200                 205

Gly His Phe Cys Gly Thr Ile Cys Pro Ile Phe Ser Thr Asn Gly Lys
        210                 215                 220

Gly Arg Leu Ile Met His Leu Leu Leu Gln Gly Thr Ser Leu His Ile
225                 230                 235                 240

Pro Glu Thr Cys Leu Lys Leu Leu Cys Glu Asn Ile Gly Pro Thr Tyr
                245                 250                 255
```

-continued

```
Glu Leu Ala Val Asp Leu Val Gly Asp Ala Phe Cys Ile Lys Val Ser
        260                 265                 270

Pro Arg Asp Thr Val Tyr Glu Lys Ala Val Asn Val Asp Glu Asp Ala
        275                 280                 285

Ile Tyr Glu Ala Ile Lys Asp Leu Glu Cys Gly Asp Glu Leu Arg Leu
        290                 295                 300

Gln Ile Ile Asn Tyr Thr Gln Leu Ile Leu Glu Asn Lys Gln
305                 310                 315
```

```
<210> SEQ ID NO 48
<211> LENGTH: 1011
<212> TYPE: DNA
<213> ORGANISM: Artificial Sequence
<220> FEATURE:
<223> OTHER INFORMATION: Synthetic

<400> SEQUENCE: 48
atggcgagcc cggaagagag gctcctagac gagctcaata acgtaattgt gtcatttctg      60
tgtgactctg ggtctctgga agtggagaga tgctccgggg cgcatgtgtt ctccaggggc     120
agctcccaac ccctctgcac cgtgaagctg cgccacggac agatttacca cctggagttt     180
gtctacaagt tcctggcctt taagctgaag aactgcaact accctcctc gcccgtgttt      240 gtgatatcca caacggcct ggccaccacc ctgaggtgct ttttgcacga gccgtcgggt      300
ctcagatcgg gccagagcgg cccttgcctg ggtctctcaa cggatgttga cctaccaaag     360
aactccatca ttatgctggg ccaggatgac ttcattaagt tcaaaagccc cctggtcttc     420
cctgctgagc ttgatctcct gaaatctatg gtggtctgcc gggcctacat cacggaacac     480
cggacgacga tgcagtttct ggtgtttcag gccgccaacg cccagaaggc ctcgcgggtc     540
atggatatga ttagtgatat gtctcagcaa ctgtctcggt ctggtcaagt cgaggatacg     600
ggcgccagag tcacaggtgg aggaggtccc aggcctggcg tcacgcactc ggggtgtctt     660
ggggactcac acgttagggg gcgcggtggt tgggacttgg ataactttc agaagctgag      720 accgaagacg aggcgagtta cgctccttgg agggacaaag actcgtggtc ggaatccgag     780
gcggcgccgt ggaagaagga actcgtgagg caccccatcc gcaggcaccg gacacgcgag     840
actcgccgta tgcgcgggag ccattcacgg gtggaacacg tgccccccga ccccgggag     900 acggtggtgg ggggagcatg gcgttattct tggcgcgcca cacttatct ggcacgggtg      960 ctggctgtca cggccgtggc cctgctcctg atgtttctga ggtggacctg a            1011
```

```
<210> SEQ ID NO 49
<211> LENGTH: 336
<212> TYPE: PRT
<213> ORGANISM: Artificial Sequence
<220> FEATURE:
<223> OTHER INFORMATION: Synthetic

<400> SEQUENCE: 49

Met Ala Ser Pro Glu Glu Arg Leu Leu Asp Glu Leu Asn Asn Val Ile
1               5                   10                  15

Val Ser Phe Leu Cys Asp Ser Gly Ser Leu Glu Val Glu Arg Cys Ser
            20                  25                  30

Gly Ala His Val Phe Ser Arg Gly Ser Ser Gln Pro Leu Cys Thr Val
        35                  40                  45

Lys Leu Arg His Gly Gln Ile Tyr His Leu Glu Phe Val Tyr Lys Phe
    50                  55                  60

Leu Ala Phe Lys Leu Lys Asn Cys Asn Tyr Pro Ser Ser Pro Val Phe
```

-continued

```
65                70                75                80

Val Ile Ser Asn Asn Gly Leu Ala Thr Thr Leu Arg Cys Phe Leu His
              85                90                95

Glu Pro Ser Gly Leu Arg Ser Gly Gln Ser Gly Pro Cys Leu Gly Leu
              100               105               110

Ser Thr Asp Val Asp Leu Pro Lys Asn Ser Ile Ile Met Leu Gly Gln
              115               120               125

Asp Asp Phe Ile Lys Phe Lys Ser Pro Leu Val Phe Pro Ala Glu Leu
        130               135               140

Asp Leu Leu Lys Ser Met Val Val Cys Arg Ala Tyr Ile Thr Glu His
145               150               155               160

Arg Thr Thr Met Gln Phe Leu Val Phe Gln Ala Ala Asn Ala Gln Lys
              165               170               175

Ala Ser Arg Val Met Asp Met Ile Ser Asp Met Ser Gln Gln Leu Ser
              180               185               190

Arg Ser Gly Gln Val Glu Asp Thr Gly Ala Arg Val Thr Gly Gly Gly
              195               200               205

Gly Pro Arg Pro Gly Val Thr His Ser Gly Cys Leu Gly Asp Ser His
        210               215               220

Val Arg Gly Arg Gly Gly Trp Asp Leu Asp Asn Phe Ser Glu Ala Glu
225               230               235               240

Thr Glu Asp Glu Ala Ser Tyr Ala Pro Trp Arg Asp Lys Asp Ser Trp
              245               250               255

Ser Glu Ser Glu Ala Ala Pro Trp Lys Lys Glu Leu Val Arg His Pro
              260               265               270

Ile Arg Arg His Arg Thr Arg Glu Thr Arg Arg Met Arg Gly Ser His
              275               280               285

Ser Arg Val Glu His Val Pro Pro Glu Thr Arg Glu Thr Val Val Gly
        290               295               300

Gly Ala Trp Arg Tyr Ser Trp Arg Ala Thr Pro Tyr Leu Ala Arg Val
305               310               315               320

Leu Ala Val Thr Ala Val Ala Leu Leu Leu Met Phe Leu Arg Trp Thr
              325               330               335
```

<210> SEQ ID NO 50
<211> LENGTH: 1776
<212> TYPE: DNA
<213> ORGANISM: Artificial Sequence
<220> FEATURE:
<223> OTHER INFORMATION: Synthetic

<400> SEQUENCE: 50

```
atggcgttat tcttggcgcg ccacacctta tctggcacgg gtgctggcgg tcacggccgt      60
ggccctgctc ctgatgtttc tgaggtggac ctgacgttgc cggcccttgg ggagcgggag     120
ttctccaggc tcctggatct ggggctggcc tgcctggatc tgagctatgt ggaaatgagg     180
gaatttgtgg tttggggcag gcccccagct tctgaggcgg ctgtggcctc tacgccaggc     240
tcgcttttcc gaagccactc gtccgcctac tggttgtcgg aggtggagag gcccgggggc     300
cttgtccgct gggccaggtc acagaccagc ccctcatccc tgaccctcgc gccccatctt     360
ggcccgtccc tcttgtccct tcagcgttc accggtggtg ggtgtggagc cgtggccttt     420
tgcaacgcct ttttcctagc ttattttttg gttgtgcggt ctgttttcc cgcgttttcc     480 gatagaaatag ctgcctggat ctgcgcccgg tcccctttct gcgaaaacac ccgggccgtg    540 gccagggggtt accgaggcct cgtgaagagg ttcttggcat tcgtgtttga gcgtagtagc    600
```

-continued

```
tatgaccccc ccttgttgag gcaaaactct aggcctgtgg agcgctgctt tgccatcaag      660
aattatgtcc cgggcctgga ctcacaaagc tgtgtgacgg tcccgagctt ctcccgctgg      720
gcccagtctc acgccagcga gctcgatccc cgggagattc gcgacagagt tacaccagcg      780
actgcacctt cgttcgtggc tgatcatgcc tcggctctat tggcctccct ccagaagaag      840
gcctccgaca cccccgtgg gaatcccatt cagtggatgt ggtaccgcct gttggtaaac      900
tcgtgcctga ggagtgccca ctgtcttctg cctatacctg ccgtctctga ggggggggaga     960 aagacgggcg ggggcgtagg ggaggagctc gtgggggccg gggggccctg cctgagccgg     1020
gatgttttcg tggcgatcgt aagccgcaat gttctctcgt gtctgctgaa cgtgcctgcc     1080
gcgggtcccc gggcctacaa gtgtttcaga tcccacgctt ccagaccggt gtctggcccg     1140
gattaccctc ccttggccgt gttttgcatg gactgcggtt actgcttgaa ctttggaaag     1200
cagacaggtg taggaggcag gctcaattcc tttagaccca ctctccagtt ttatccccgt     1260
gaccagaagg agaagcatgt gctgacctgc catgccagcg gccgtgtgta ctgctccaac     1320
tgcggctctg cggcggtggg ctgccagagg ctggctgagc caccgagcgc ccgctcgggc     1380
tggcggcccc gaatccgggc agtgctgccg cacaacgcgg cctacgagct cgaccgtggc     1440
tcccgcctct tggatgccat catcccctgc ttgggacccg accgcacttg catgcggccg     1500
gtggtcctgc gggggggtgac ggtcaggcag ctcctgtatt taactttgcg gacagaggcc     1560
agagccgttt gctccatctg tcagcaacgc caagctccag aggacgcccg cgacgagcct     1620
cacctgttct cctcctgttt agaggtagaa ttgccacctg gtgagcggtg tgcgggctgc     1680
cgtctctatc agacgcgtta tggcacgccg gctgcccaag cccaccctcc aggggaggct     1740
ggaggcggat tttccagaca gtcccctgct tcctaa                               1776
```

<210> SEQ ID NO 51
<211> LENGTH: 591
<212> TYPE: PRT
<213> ORGANISM: Artificial Sequence
<220> FEATURE:
<223> OTHER INFORMATION: Synthetic

<400> SEQUENCE: 51

```
Met Ala Leu Phe Leu Ala Arg His Thr Leu Ser Gly Thr Gly Ala Gly
1               5                   10                  15

Gly His Gly Arg Gly Pro Ala Pro Asp Val Ser Glu Val Asp Leu Thr
            20                  25                  30

Leu Pro Ala Leu Gly Glu Arg Glu Phe Ser Arg Leu Leu Asp Leu Gly
        35                  40                  45

Leu Ala Cys Leu Asp Leu Ser Tyr Val Glu Met Arg Glu Phe Val Val
    50                  55                  60

Trp Gly Arg Pro Pro Ala Ser Glu Ala Ala Val Ala Ser Thr Pro Gly
65                  70                  75                  80

Ser Leu Phe Arg Ser His Ser Ser Ala Tyr Trp Leu Ser Glu Val Glu
                85                  90                  95

Arg Pro Gly Gly Leu Val Arg Trp Ala Arg Ser Gln Thr Ser Pro Ser
            100                 105                 110

Ser Leu Thr Leu Ala Pro His Leu Gly Pro Ser Leu Leu Ser Leu Ser
            115                 120                 125

Ala Phe Thr Gly Gly Gly Cys Gly Ala Val Ala Phe Cys Asn Ala Phe
        130                 135                 140

Phe Leu Ala Tyr Phe Leu Val Val Arg Ser Val Phe Pro Ala Phe Ser
```

-continued

```
145                 150                 155                 160

Asp Arg Ile Ala Ala Trp Ile Cys Ala Arg Ser Pro Phe Cys Glu Asn
                165                 170                 175

Thr Arg Ala Val Ala Arg Gly Tyr Arg Gly Leu Val Lys Arg Phe Leu
                180                 185                 190

Ala Phe Val Phe Glu Arg Ser Ser Tyr Asp Pro Pro Leu Leu Arg Gln
                195                 200                 205

Asn Ser Arg Pro Val Glu Arg Cys Phe Ala Ile Lys Asn Tyr Val Pro
    210                 215                 220

Gly Leu Asp Ser Gln Ser Cys Val Thr Val Pro Ser Phe Ser Arg Trp
225                 230                 235                 240

Ala Gln Ser His Ala Ser Glu Leu Asp Pro Arg Glu Ile Arg Asp Arg
                245                 250                 255

Val Thr Pro Ala Thr Ala Pro Ser Phe Val Ala Asp His Ala Ser Ala
                260                 265                 270

Leu Leu Ala Ser Leu Gln Lys Lys Ala Ser Asp Thr Pro Cys Gly Asn
                275                 280                 285

Pro Ile Gln Trp Met Trp Tyr Arg Leu Leu Val Asn Ser Cys Leu Arg
    290                 295                 300

Ser Ala His Cys Leu Leu Pro Ile Pro Ala Val Ser Glu Gly Gly Arg
305                 310                 315                 320

Lys Thr Gly Gly Gly Val Gly Glu Glu Leu Val Gly Ala Gly Gly Pro
                325                 330                 335

Cys Leu Ser Arg Asp Val Phe Val Ala Ile Val Ser Arg Asn Val Leu
                340                 345                 350

Ser Cys Leu Leu Asn Val Pro Ala Ala Gly Pro Arg Ala Tyr Lys Cys
    355                 360                 365

Phe Arg Ser His Ala Ser Arg Pro Val Ser Gly Pro Asp Tyr Pro Pro
    370                 375                 380

Leu Ala Val Phe Cys Met Asp Cys Gly Tyr Cys Leu Asn Phe Gly Lys
385                 390                 395                 400

Gln Thr Gly Val Gly Gly Arg Leu Asn Ser Phe Arg Pro Thr Leu Gln
                405                 410                 415

Phe Tyr Pro Arg Asp Gln Lys Glu Lys His Val Leu Thr Cys His Ala
                420                 425                 430

Ser Gly Arg Val Tyr Cys Ser Asn Cys Gly Ser Ala Ala Val Gly Cys
                435                 440                 445

Gln Arg Leu Ala Glu Pro Pro Ser Ala Arg Ser Gly Trp Arg Pro Arg
    450                 455                 460

Ile Arg Ala Val Leu Pro His Asn Ala Ala Tyr Glu Leu Asp Arg Gly
465                 470                 475                 480

Ser Arg Leu Leu Asp Ala Ile Ile Pro Cys Leu Gly Pro Asp Arg Thr
                485                 490                 495

Cys Met Arg Pro Val Val Leu Arg Gly Val Thr Val Arg Gln Leu Leu
                500                 505                 510

Tyr Leu Thr Leu Arg Thr Glu Ala Arg Ala Val Cys Ser Ile Cys Gln
                515                 520                 525

Gln Arg Gln Ala Pro Glu Asp Ala Arg Asp Glu Pro His Leu Phe Ser
    530                 535                 540

Ser Cys Leu Glu Val Glu Leu Pro Pro Gly Glu Arg Cys Ala Gly Cys
545                 550                 555                 560

Arg Leu Tyr Gln Thr Arg Tyr Gly Thr Pro Ala Ala Gln Ala His Pro
                565                 570                 575
```

-continued

Pro Gly Glu Ala Gly Gly Gly Phe Ser Arg Gln Ser Pro Ala Ser
        580                         585                 590

<210> SEQ ID NO 52
<211> LENGTH: 1713
<212> TYPE: DNA
<213> ORGANISM: Artificial Sequence
<220> FEATURE:
<223> OTHER INFORMATION: Synthetic

<400> SEQUENCE: 52
atggcgctct ccgggcacgt cttgatagac cccgcccgac tgcccaggga cacaggcccc      60
gaactcatgt gggccccaag ccttcgcaac tcactgcgcg tgtcccccga agcgctcgag     120
ctggcagagc gggaggccga aagggccagg tcggagcggt gggacaggtg tgcccaggtg     180
ctcaaaaata ggctgctccg cgtggagctg gacggcatca tgcgtgacca cctggccagg     240
gcggaggaga tccgccagga cctggatgct gtagtggcct tctctgatgg cctggagagc     300
atgcaggtca ggtccccctc cacgggaggg cgctctgcgc cagccccgcc ctccccatcc     360
ccagcccagc cgttcactcg gctcaccggg aacgcccagt atgcagtctc aatctctccc     420 acggacccc ctctgatggt ggccggcagc ctggctcaaa cgctgcttgg taatctgtac     480
gggaacatca accagtgggt accgtccttc ggaccctggt acaggaccat gtcggctaat     540
gccatgcagc ggcgcgtgtt ccctaagcag ctgaggggca acctgaactt taccaactcc     600
gtctccctaa agctgatgac agaagtggtg gcggtgcttg agggcaccac ccaggacttt     660
ttctcagacg tcaggcacct gccagacctc caggctgccc tgatcctctc ggtggcctac     720
ctgctactcc aggggggctc ctcacaccag cagcgccccc tccctgcctc acgggaagag     780
ctgctggagc tgggcccgga gagcctagag aaaatcatcg ccgacctcaa ggccaagtca     840
cccggcggaa attttatgat tttaacaagc ggaaacaagg aagcgcgcca gtcaatagcc     900
cctctcaacc gacaggcggc atatccaccc ggcacattcg cggacaataa gatttacaac     960
ctgtttgtgg gagcgggact actgcccacg acggccgcgc tgaacgtgcc cggggcggcg    1020
ggtcgggacc gggacctggt gtaccggatc gccaaccaga tctttgggga ggatgtgccc    1080
cccttctcat ctcaccagtg gaacctgcgc gtaggtttag ccgcactcga ggccctgatg    1140
ctcgtctaca cgctctgcga gaccgccaac ctggccgagg cggccacccg cgcgtctacac   1200 ctatcgtccc tgctccccca ggcaatgcag cggcgcaagc ctgccatggc gtcagctggt    1260
atgccgggcg cctatccagt ccagacgctt ttccgccacg gggagctctt ccgcttcatc    1320
tgggcccact acgtgaggcc cacggtggcg gcagaccccc aggcctccat cagctctctt    1380
ttccccgggc tggttttgct ggccctggag ctgaagttga tggatgggca ggctccctcc    1440
cattatgcca taaacctgac cggacaaaag tttgacaccc tctttgagat tatcaaccag    1500
aagcttttat ttcacgaccc ggctgccatg ctggcggcgc gcacacagct gcgtctagcc    1560
ttcgaggacg gcgtcggtgt tgccctgggg cgccctcgc ccatgcttgc ggcgcgggag    1620
atcctggagc gtcagttctc agcctcggat gactacgacc ggctgtactt cctgacgctg    1680
ggctacctgg cctccccggt ggccccaagc tga                                 1713

<210> SEQ ID NO 53
<211> LENGTH: 570
<212> TYPE: PRT
<213> ORGANISM: Artificial Sequence
<220> FEATURE:
<223> OTHER INFORMATION: Synthetic -continued

```
<400> SEQUENCE: 53

Met Ala Leu Ser Gly His Val Leu Ile Asp Pro Ala Arg Leu Pro Arg
1               5                   10                  15

Asp Thr Gly Pro Glu Leu Met Trp Ala Pro Ser Leu Arg Asn Ser Leu
            20                  25                  30

Arg Val Ser Pro Glu Ala Leu Glu Leu Ala Glu Arg Glu Ala Glu Arg
        35                  40                  45

Ala Arg Ser Glu Arg Trp Asp Arg Cys Ala Gln Val Leu Lys Asn Arg
    50                  55                  60

Leu Leu Arg Val Glu Leu Asp Gly Ile Met Arg Asp His Leu Ala Arg
65                  70                  75                  80

Ala Glu Glu Ile Arg Gln Asp Leu Asp Ala Val Val Ala Phe Ser Asp
                85                  90                  95

Gly Leu Glu Ser Met Gln Val Arg Ser Pro Ser Thr Gly Gly Arg Ser
            100                 105                 110

Ala Pro Ala Pro Pro Ser Pro Ser Pro Ala Gln Pro Phe Thr Arg Leu
        115                 120                 125

Thr Gly Asn Ala Gln Tyr Ala Val Ser Ile Ser Pro Thr Asp Pro Pro
    130                 135                 140

Leu Met Val Ala Gly Ser Leu Ala Gln Thr Leu Leu Gly Asn Leu Tyr
145                 150                 155                 160

Gly Asn Ile Asn Gln Trp Val Pro Ser Phe Gly Pro Trp Tyr Arg Thr
                165                 170                 175

Met Ser Ala Asn Ala Met Gln Arg Arg Val Phe Pro Lys Gln Leu Arg
            180                 185                 190

Gly Asn Leu Asn Phe Thr Asn Ser Val Ser Leu Lys Leu Met Thr Glu
        195                 200                 205

Val Val Ala Val Leu Glu Gly Thr Thr Gln Asp Phe Phe Ser Asp Val
    210                 215                 220

Arg His Leu Pro Asp Leu Gln Ala Ala Leu Ile Leu Ser Val Ala Tyr
225                 230                 235                 240

Leu Leu Leu Gln Gly Gly Ser Ser His Gln Gln Arg Pro Leu Pro Ala
                245                 250                 255

Ser Arg Glu Glu Leu Leu Glu Leu Gly Pro Glu Ser Leu Glu Lys Ile
            260                 265                 270

Ile Ala Asp Leu Lys Ala Lys Ser Pro Gly Gly Asn Phe Met Ile Leu
        275                 280                 285

Thr Ser Gly Asn Lys Glu Ala Arg Gln Ser Ile Ala Pro Leu Asn Arg
    290                 295                 300

Gln Ala Ala Tyr Pro Pro Gly Thr Phe Ala Asp Asn Lys Ile Tyr Asn
305                 310                 315                 320

Leu Phe Val Gly Ala Gly Leu Leu Pro Thr Thr Ala Ala Leu Asn Val
                325                 330                 335

Pro Gly Ala Ala Gly Arg Asp Arg Asp Leu Val Tyr Arg Ile Ala Asn
            340                 345                 350

Gln Ile Phe Gly Glu Asp Val Pro Pro Phe Ser Ser His Gln Trp Asn
        355                 360                 365

Leu Arg Val Gly Leu Ala Ala Leu Glu Ala Leu Met Leu Val Tyr Thr
    370                 375                 380

Leu Cys Glu Thr Ala Asn Leu Ala Glu Ala Ala Thr Arg Arg Leu His
385                 390                 395                 400

Leu Ser Ser Leu Leu Pro Gln Ala Met Gln Arg Arg Lys Pro Ala Met
```

-continued

```
                    405                   410                   415

Ala Ser Ala Gly Met Pro Gly Ala Tyr Pro Val Gln Thr Leu Phe Arg
            420                   425                   430

His Gly Glu Leu Phe Arg Phe Ile Trp Ala His Tyr Val Arg Pro Thr
        435                   440                   445

Val Ala Ala Asp Pro Gln Ala Ser Ile Ser Ser Leu Phe Pro Gly Leu
    450                   455                   460

Val Leu Leu Ala Leu Glu Leu Lys Leu Met Asp Gly Gln Ala Pro Ser
465                   470                   475                   480

His Tyr Ala Ile Asn Leu Thr Gly Gln Lys Phe Asp Thr Leu Phe Glu
                485                   490                   495

Ile Ile Asn Gln Lys Leu Leu Phe His Asp Pro Ala Ala Met Leu Ala
            500                   505                   510

Ala Arg Thr Gln Leu Arg Leu Ala Phe Glu Asp Gly Val Gly Val Ala
            515                   520                   525

Leu Gly Arg Pro Ser Pro Met Leu Ala Ala Arg Glu Ile Leu Glu Arg
        530                   535                   540

Gln Phe Ser Ala Ser Asp Asp Tyr Asp Arg Leu Tyr Phe Leu Thr Leu
545                   550                   555                   560

Gly Tyr Leu Ala Ser Pro Val Ala Pro Ser
                565                   570
```

```
<210> SEQ ID NO 54
<211> LENGTH: 309
<212> TYPE: DNA
<213> ORGANISM: Artificial Sequence
<220> FEATURE:
<223> OTHER INFORMATION: Synthetic

<400> SEQUENCE: 54
atggaagcca ccatgcgacc gggtagacca ctggctggat tctacgctac tctccgccgt      60
tccttcagaa gaatgtccaa aaggtcaaag aacaaggcca agaaggagcg tgtcccagtg     120
gaggaccgcc caccgactcc gatgcccacc agccagcgac tgatccgcag aaacgcgttg     180
ggaggaggcg tccgccccga tgcggaggac tgcatcaaac gctgccaccc cctggagccc     240
gcgctggggg tgtcaacaaa gaactttgac ctgttgtccc tgagatgtga attgggatgg     300
tgtggataa                                                             309
```

```
<210> SEQ ID NO 55
<211> LENGTH: 102
<212> TYPE: PRT
<213> ORGANISM: Artificial Sequence
<220> FEATURE:
<223> OTHER INFORMATION: Synthetic

<400> SEQUENCE: 55

Met Glu Ala Thr Met Arg Pro Gly Arg Pro Leu Ala Gly Phe Tyr Ala
1               5                   10                  15

Thr Leu Arg Arg Ser Phe Arg Arg Met Ser Lys Arg Ser Lys Asn Lys
            20                  25                  30

Ala Lys Lys Glu Arg Val Pro Val Glu Asp Arg Pro Pro Thr Pro Met
        35                  40                  45

Pro Thr Ser Gln Arg Leu Ile Arg Arg Asn Ala Leu Gly Gly Gly Val
    50                  55                  60

Arg Pro Asp Ala Glu Asp Cys Ile Lys Arg Cys His Pro Leu Glu Pro
65                  70                  75                  80
```

Ala Leu Gly Val Ser Thr Lys Asn Phe Asp Leu Leu Ser Leu Arg Cys
                85                  90                  95

Glu Leu Gly Trp Cys Gly
            100

<210> SEQ ID NO 56
<211> LENGTH: 183
<212> TYPE: DNA
<213> ORGANISM: Artificial Sequence
<220> FEATURE:
<223> OTHER INFORMATION: Synthetic

<400> SEQUENCE: 56
atggtacacg tcctggagcg tactttgcta gagcagcagt cctctgcctg cggcctgccc      60
ggctcttcta cggagaccag gcctagccac ccctgccccg aggacccaga cgtcagcaaa     120
ctaagactac tcctggtggt actctgtgtc ctgtttggac ttttatgcct gctcctcatc     180
taa                                                                   183

<210> SEQ ID NO 57
<211> LENGTH: 60
<212> TYPE: PRT
<213> ORGANISM: Artificial Sequence
<220> FEATURE:
<223> OTHER INFORMATION: Synthetic

<400> SEQUENCE: 57

Met Val His Val Leu Glu Arg Thr Leu Leu Glu Gln Gln Ser Ser Ala
1               5                   10                  15

Cys Gly Leu Pro Gly Ser Ser Thr Glu Thr Arg Pro Ser His Pro Cys
            20                  25                  30

Pro Glu Asp Pro Asp Val Ser Lys Leu Arg Leu Leu Leu Val Val Leu
        35                  40                  45

Cys Val Leu Phe Gly Leu Leu Cys Leu Leu Leu Ile
    50                  55                  60

<210> SEQ ID NO 58
<211> LENGTH: 738
<212> TYPE: DNA
<213> ORGANISM: Artificial Sequence
<220> FEATURE:
<223> OTHER INFORMATION: Synthetic

<400> SEQUENCE: 58
atgatggacc caaactcgac ttctgaagat gtaaaattta cacctgaccc ataccaggtg      60
ccttttgtac aagcttttga ccaagctacc agagtctatc aggacctggg agggccatcg     120
caagctcctt tgccttgtgt gctgtggccg gtgctgccag agcctctgcc acaaggccag     180
ctaactgcct atcatgtttc aactgctccg actgggtcgt ggttttctgc ccctcagcct     240
gctcctgaga atgcttatca agcttatgca gcacctcagc tgttcccagt ctccgacata     300
acccagaatc aacagactaa ccaagccggg ggagaagcac ctcaacctgg agacaattct     360
actgttcaaa cagcagcagc agtggtgttt gcttgccccg gggctaacca aggacaacag     420
ctagcagaca ttggtgttcc acagcctgca ccagtggctg ccccggcacg acgcacacgg     480
aaaccacaac agccagaatc gctggaggaa tgcgattctg aactagaaat aaagcgatac     540
aagaatcggg tggcttccag aaaatgccgg gccaagttta gcaactgct gcagcactac     600 cgtgaggtgg ctgctgccaa tcatctgaa aatgacaggc tgcgcctcct gttgaagcag     660
atgtgcccaa gcctggatgt tgactccatt atccccggga caccagatgt tttacacgag     720

-continued gatctcttaa atttctaa                                                  738

<210> SEQ ID NO 59
<211> LENGTH: 245
<212> TYPE: PRT
<213> ORGANISM: Artificial Sequence
<220> FEATURE:
<223> OTHER INFORMATION: Synthetic

<400> SEQUENCE: 59

Met Met Asp Pro Asn Ser Thr Ser Glu Asp Val Lys Phe Thr Pro Asp
1               5                   10                  15

Pro Tyr Gln Val Pro Phe Val Gln Ala Phe Asp Gln Ala Thr Arg Val
            20                  25                  30

Tyr Gln Asp Leu Gly Gly Pro Ser Gln Ala Pro Leu Pro Cys Val Leu
        35                  40                  45

Trp Pro Val Leu Pro Glu Pro Leu Pro Gln Gly Gln Leu Thr Ala Tyr
    50                  55                  60

His Val Ser Thr Ala Pro Thr Gly Ser Trp Phe Ser Ala Pro Gln Pro
65                  70                  75                  80

Ala Pro Glu Asn Ala Tyr Gln Ala Tyr Ala Ala Pro Gln Leu Phe Pro
                85                  90                  95

Val Ser Asp Ile Thr Gln Asn Gln Gln Thr Asn Gln Ala Gly Gly Glu
            100                 105                 110

Ala Pro Gln Pro Gly Asp Asn Ser Thr Val Gln Thr Ala Ala Ala Val
        115                 120                 125

Val Phe Ala Cys Pro Gly Ala Asn Gln Gly Gln Gln Leu Ala Asp Ile
    130                 135                 140

Gly Val Pro Gln Pro Ala Pro Val Ala Ala Pro Ala Arg Arg Thr Arg
145                 150                 155                 160

Lys Pro Gln Gln Pro Glu Ser Leu Glu Glu Cys Asp Ser Glu Leu Glu
                165                 170                 175

Ile Lys Arg Tyr Lys Asn Arg Val Ala Ser Arg Lys Cys Arg Ala Lys
                180                 185                 190

Phe Lys Gln Leu Leu Gln His Tyr Arg Glu Val Ala Ala Ala Lys Ser
            195                 200                 205

Ser Glu Asn Asp Arg Leu Arg Leu Leu Leu Lys Gln Met Cys Pro Ser
    210                 215                 220

Leu Asp Val Asp Ser Ile Ile Pro Arg Thr Pro Asp Val Leu His Glu
225                 230                 235                 240

Asp Leu Leu Asn Phe
                245

<210> SEQ ID NO 60
<211> LENGTH: 1818
<212> TYPE: DNA
<213> ORGANISM: Artificial Sequence
<220> FEATURE:
<223> OTHER INFORMATION: Synthetic

<400> SEQUENCE: 60
atgaggccta aaaaggatgg cttggaagac tttctgaggc taactcctga aatcaaaaag       60
cagctgggct ctctggtctc tgactactgc aacgtcctca acaaggaatt tacagccggg      120
agtgtggaga ttactctgag atcctacaaa atatgcaagg catttataaa tgaggccaag      180
gcccacgggc gagaatgggg cgggctaatg gccacgctca acatctgcaa tttttgggcc      240

-continued

```
attctccgaa acaacagggt aagaagacgg gctgagaatg ccggcaacga cgcatgttcc      300
atcgcgtgcc ctatagtgat gcgctacgtg ttagaccacc tgatagtggt cactgacaga      360
ttcttcatcc aggcccccag caaccgggtg atgattcctg ccaccatagg caccgctatg      420
tacaagctcc taaaacacag tcgggtgcgg gcctacacct acagcaaggt gctgggcgtg      480
gaccgcgcgg ccatcatggc ctccggcaag caggtagtgg aacacctgaa caggatggag      540
aaggaaggcc tcctaagctc caagttcaag gccttttgca agtgggtgtt cacctatccc      600
gtcctcgagg agatgttcca gactatggtc tcgtccaaga caggccatct gacggacgat      660
gttaaggatg tcagggctct gattaagaca ctgccccggg cctcctactc cagccacgcc      720
ggacagagga gctacgtgag cggcgtgctt cccgcgtgcc tgctgtcaac caagtccaag      780
gcagtggaaa ctcctatcct cgtgtccgga gccgacagga tggacgagga gctcatgggg      840
aatgatgggg gtgcctctca caccgaggcc cgctactcgg agtccggaca gtttcatgct      900
tttacagatg aactcgaaag tctcccgagc ccgaccatgc ccctgaagcc cggtgcccaa      960
agcgccgact gcggtgacag cagttccagc agcagtgact cgggcaacag tgacaccgag     1020
cagagcgagc gggaagaggc cagggccgag gccccgcgcc tgcgggcccc aaagtcgcgc     1080
cggacatcca ggcccaaccg tggtcaaact ccatgtcctt ccaacgcggc ggaacctgaa     1140
cagccttgga tagcagcggt ccaccaagag agcgatgaga gacccatatt ccccccacccc     1200 tcaaagccca ccttttcttcc tcccgttaaa aggaagaagg gcctcaggga tagccgggaa     1260
ggtatgttcc tgccaaagcc ggaagcgggc agtgccatat ctgacgtgtt cgaggggcga     1320
gaggtgtgtc agccaaagag gatcaggccc ttccatccac ccggatcccc gtgggccaac     1380
cggcccctgc ctgcctcttt ggctcccacc cccacaggac ctgtccatga accggtcgga     1440
tccctaacgc cagccccggt gccccagcca cttgacccgg ccccccgcagt aacccccgag     1500 gcaagtcatc tgttggagga ccctgatgaa gaaaccagtc aggccgtgaa ggccctaagg     1560
gagatggctg acactgttat tccccagaag gaggaagcag ccatatgtgg acagatggac     1620
ctgagccacc cgcccccctcg tggccatttg gacgaactga ccacaacact agagtccatg     1680
acagaggatt tgaatctgga ctcccccctg accccgaac ttaatgaaat cttggataca     1740
tttctaaatg atgaatgtct gctgcatgcc atgcatattt caactgggct gtctattttt     1800
gacaccagct tattttag                                                  1818
```

<210> SEQ ID NO 61
<211> LENGTH: 605
<212> TYPE: PRT
<213> ORGANISM: Artificial Sequence
<220> FEATURE:
<223> OTHER INFORMATION: Synthetic

<400> SEQUENCE: 61

```
Met Arg Pro Lys Lys Asp Gly Leu Glu Asp Phe Leu Arg Leu Thr Pro
1               5                   10                  15

Glu Ile Lys Lys Gln Leu Gly Ser Leu Val Ser Asp Tyr Cys Asn Val
            20                  25                  30

Leu Asn Lys Glu Phe Thr Ala Gly Ser Val Glu Ile Thr Leu Arg Ser
        35                  40                  45

Tyr Lys Ile Cys Lys Ala Phe Ile Asn Glu Ala Lys Ala His Gly Arg
    50                  55                  60

Glu Trp Gly Gly Leu Met Ala Thr Leu Asn Ile Cys Asn Phe Trp Ala
65                  70                  75                  80
```

-continued

```
Ile Leu Arg Asn Asn Arg Val Arg Arg Arg Ala Glu Asn Ala Gly Asn
                85              90                  95

Asp Ala Cys Ser Ile Ala Cys Pro Ile Val Met Arg Tyr Val Leu Asp
            100             105             110

His Leu Ile Val Val Thr Asp Arg Phe Phe Ile Gln Ala Pro Ser Asn
        115             120             125

Arg Val Met Ile Pro Ala Thr Ile Gly Thr Ala Met Tyr Lys Leu Leu
    130             135             140

Lys His Ser Arg Val Arg Ala Tyr Thr Tyr Ser Lys Val Leu Gly Val
145             150             155             160

Asp Arg Ala Ala Ile Met Ala Ser Gly Lys Gln Val Val Glu His Leu
            165             170             175

Asn Arg Met Glu Lys Glu Gly Leu Leu Ser Ser Lys Phe Lys Ala Phe
        180             185             190

Cys Lys Trp Val Phe Thr Tyr Pro Val Leu Glu Glu Met Phe Gln Thr
        195             200             205

Met Val Ser Ser Lys Thr Gly His Leu Thr Asp Asp Val Lys Asp Val
    210             215             220

Arg Ala Leu Ile Lys Thr Leu Pro Arg Ala Ser Tyr Ser Ser His Ala
225             230             235             240

Gly Gln Arg Ser Tyr Val Ser Gly Val Leu Pro Ala Cys Leu Leu Ser
            245             250             255

Thr Lys Ser Lys Ala Val Glu Thr Pro Ile Leu Val Ser Gly Ala Asp
        260             265             270

Arg Met Asp Glu Glu Leu Met Gly Asn Asp Gly Gly Ala Ser His Thr
        275             280             285

Glu Ala Arg Tyr Ser Glu Ser Gly Gln Phe His Ala Phe Thr Asp Glu
    290             295             300

Leu Glu Ser Leu Pro Ser Pro Thr Met Pro Leu Lys Pro Gly Ala Gln
305             310             315             320

Ser Ala Asp Cys Gly Asp Ser Ser Ser Ser Ser Asp Ser Gly Asn
            325             330             335

Ser Asp Thr Glu Gln Ser Glu Arg Glu Glu Ala Arg Ala Glu Ala Pro
            340             345             350

Arg Leu Arg Ala Pro Lys Ser Arg Arg Thr Ser Arg Pro Asn Arg Gly
        355             360             365

Gln Thr Pro Cys Pro Ser Asn Ala Ala Glu Pro Glu Gln Pro Trp Ile
    370             375             380

Ala Ala Val His Gln Glu Ser Asp Glu Arg Pro Ile Phe Pro His Pro
385             390             395             400

Ser Lys Pro Thr Phe Leu Pro Pro Val Lys Arg Lys Lys Gly Leu Arg
            405             410             415

Asp Ser Arg Glu Gly Met Phe Leu Pro Lys Pro Glu Ala Gly Ser Ala
            420             425             430

Ile Ser Asp Val Phe Glu Gly Arg Glu Val Cys Gln Pro Lys Arg Ile
        435             440             445

Arg Pro Phe His Pro Pro Gly Ser Pro Trp Ala Asn Arg Pro Leu Pro
    450             455             460

Ala Ser Leu Ala Pro Thr Pro Thr Gly Pro Val His Glu Pro Val Gly
465             470             475             480

Ser Leu Thr Pro Ala Pro Val Pro Gln Pro Leu Asp Pro Ala Pro Ala
            485             490             495

Val Thr Pro Glu Ala Ser His Leu Leu Glu Asp Pro Asp Glu Glu Thr
```

-continued

```
                  500                 505                 510

Ser Gln Ala Val Lys Ala Leu Arg Glu Met Ala Asp Thr Val Ile Pro
        515                 520                 525

Gln Lys Glu Glu Ala Ala Ile Cys Gly Gln Met Asp Leu Ser His Pro
    530                 535                 540

Pro Pro Arg Gly His Leu Asp Glu Leu Thr Thr Thr Leu Glu Ser Met
545                 550                 555                 560

Thr Glu Asp Leu Asn Leu Asp Ser Pro Leu Thr Pro Glu Leu Asn Glu
                565                 570                 575

Ile Leu Asp Thr Phe Leu Asn Asp Glu Cys Leu Leu His Ala Met His
                580                 585                 590

Ile Ser Thr Gly Leu Ser Ile Phe Asp Thr Ser Leu Phe
                595                 600                 605

<210> SEQ ID NO 62
<211> LENGTH: 513
<212> TYPE: DNA
<213> ORGANISM: Artificial Sequence
<220> FEATURE:
<223> OTHER INFORMATION: Synthetic

<400> SEQUENCE: 62
atggagcgaa ggttagtggt cactctgcag tgcctggtgc tgctttacct ggcacctgag      60
tgtggaggta cagaccaatg tgacaatttt ccccaaatgt tgagggacct aagagatgcc     120
ttcagtcgtg ttaaaacctt tttccagaca aaggacgagg tagataacct tttgctcaag     180
gagtctctgc tagaggactt taagggctac cttggatgcc aggccctgtc agaaatgatc     240
caattctacc tggaggaagt catgccacag gctgaaaacc aggaccctga agccaaagac     300
catgtaaatt ctttgggtga aaatctaaag accctacggc tccgcctgcg caggtgccac     360
aggttcctgc cgtgtgagaa caagagtaaa gctgtggaac agataaaaaa tgcctttaac     420
aagctgcaag aaaaaggaat ttacaaagcc atgagtgaat ttgacatttt tattaactac     480
atagaagcat acatgacaat aaagccaggt gga                                  513

<210> SEQ ID NO 63
<211> LENGTH: 170
<212> TYPE: PRT
<213> ORGANISM: Artificial Sequence
<220> FEATURE:
<223> OTHER INFORMATION: Synthetic

<400> SEQUENCE: 63

Met Glu Arg Arg Leu Val Val Thr Leu Gln Cys Leu Val Leu Leu Tyr
1               5                   10                  15

Leu Ala Pro Glu Cys Gly Gly Thr Asp Gln Cys Asp Asn Phe Pro Gln
            20                  25                  30

Met Leu Arg Asp Leu Arg Asp Ala Phe Ser Arg Val Lys Thr Phe Phe
        35                  40                  45

Gln Thr Lys Asp Glu Val Asp Asn Leu Leu Leu Lys Glu Ser Leu Leu
    50                  55                  60

Glu Asp Phe Lys Gly Tyr Leu Gly Cys Gln Ala Leu Ser Glu Met Ile
65                  70                  75                  80

Gln Phe Tyr Leu Glu Glu Val Met Pro Gln Ala Glu Asn Gln Asp Pro
                85                  90                  95

Glu Ala Lys Asp His Val Asn Ser Leu Gly Glu Asn Leu Lys Thr Leu
            100                 105                 110
```

-continued

Arg Leu Arg Leu Arg Arg Cys His Arg Phe Leu Pro Cys Glu Asn Lys
            115                 120                 125

Ser Lys Ala Val Glu Gln Ile Lys Asn Ala Phe Asn Lys Leu Gln Glu
        130                 135                 140

Lys Gly Ile Tyr Lys Ala Met Ser Glu Phe Asp Ile Phe Ile Asn Tyr
145                 150                 155                 160

Ile Glu Ala Tyr Met Thr Ile Lys Ala Arg
                165                 170

<210> SEQ ID NO 64
<211> LENGTH: 309
<212> TYPE: DNA
<213> ORGANISM: Artificial Sequence
<220> FEATURE:
<223> OTHER INFORMATION: Synthetic

<400> SEQUENCE: 64 atgggggaagg tcctaagaaa gccgtttgca aaggctgtgc cactgctctt cctcgccgcc      60
acctggcttc tgaccggggt gctgccggcc ggcgcttcca gtcccacaaa cgcggcggcg      120
gcttccctga ctgaagccca ggaccagttc tactcctaca catgtaatgc ggacacattc      180
tcgccttctt tgaccagctt tgcctccatc tgggcacttc tgacgcttgt cttagtcatt      240
atagcctcag ccatctacct gatgtacgtc tgctttaaca gtttgtgaa cacgctgctg      300 acggattag                                                              309

<210> SEQ ID NO 65
<211> LENGTH: 102
<212> TYPE: PRT
<213> ORGANISM: Artificial Sequence
<220> FEATURE:
<223> OTHER INFORMATION: Synthetic

<400> SEQUENCE: 65

Met Gly Lys Val Leu Arg Lys Pro Phe Ala Lys Ala Val Pro Leu Leu
1                 5                 10                  15

Phe Leu Ala Ala Thr Trp Leu Leu Thr Gly Val Leu Pro Ala Gly Ala
            20                  25                  30

Ser Ser Pro Thr Asn Ala Ala Ala Ala Ser Leu Thr Glu Ala Gln Asp
        35                  40                  45

Gln Phe Tyr Ser Tyr Thr Cys Asn Ala Asp Thr Phe Ser Pro Ser Leu
    50                  55                  60

Thr Ser Phe Ala Ser Ile Trp Ala Leu Leu Thr Leu Val Leu Val Ile
65                  70                  75                  80

Ile Ala Ser Ala Ile Tyr Leu Met Tyr Val Cys Phe Asn Lys Phe Val
                85                  90                  95

Asn Thr Leu Leu Thr Asp
            100

<210> SEQ ID NO 66
<211> LENGTH: 489
<212> TYPE: DNA
<213> ORGANISM: Artificial Sequence
<220> FEATURE:
<223> OTHER INFORMATION: Synthetic

<400> SEQUENCE: 66
atgtcagctc cacgcaaagt cagattgcct tctgttaagg ctgttgacat gagcatggaa      60
gacatggccg cccgcctggc tcgcctggag tctgagaata aggctctgaa gcaacaggtc      120

-continued

```
ctcagagggg gtgcctgtgc ctcgtctacc tctgttcctt ctgctccagt gcctccgcct      180
gagccgctta cagctcgaca gcgagaggta atgattacgc aggccacggg ccgtttggcg      240
tctcaggcta tgaagaagat tgaagacaag gttcggaaat ctgttgacgg tgtaactacc      300
cgcaatgaaa tggaaaatat attgcaaaat ctgaccctcc gcattcaagt atctatgttg      360
ggtgcaaaag gccaacccag ccctggtgag ggaacacgac cacgagaatc aaacgacccc      420
aacgccaccc gacgtgcccg ctcccgctcc cggggacgtg aagcaaagaa agtgcaaatt      480
tctgattaa                                                              489
```

```
<210> SEQ ID NO 67
<211> LENGTH: 162
<212> TYPE: PRT
<213> ORGANISM: Artificial Sequence
<220> FEATURE:
<223> OTHER INFORMATION: Synthetic

<400> SEQUENCE: 67

Met Ser Ala Pro Arg Lys Val Arg Leu Pro Ser Val Lys Ala Val Asp
1               5                   10                  15

Met Ser Met Glu Asp Met Ala Ala Arg Leu Ala Arg Leu Glu Ser Glu
            20                  25                  30

Asn Lys Ala Leu Lys Gln Gln Val Leu Arg Gly Gly Ala Cys Ala Ser
        35                  40                  45

Ser Thr Ser Val Pro Ser Ala Pro Val Pro Pro Glu Pro Leu Thr
    50                  55                  60

Ala Arg Gln Arg Glu Val Met Ile Thr Gln Ala Thr Gly Arg Leu Ala
65                  70                  75                  80

Ser Gln Ala Met Lys Lys Ile Glu Asp Lys Val Arg Lys Ser Val Asp
                85                  90                  95

Gly Val Thr Thr Arg Asn Glu Met Glu Asn Ile Leu Gln Asn Leu Thr
            100                 105                 110

Leu Arg Ile Gln Val Ser Met Leu Gly Ala Lys Gly Gln Pro Ser Pro
        115                 120                 125

Gly Glu Gly Thr Arg Pro Arg Glu Ser Asn Asp Pro Asn Ala Thr Arg
    130                 135                 140

Arg Ala Arg Ser Arg Ser Arg Gly Arg Glu Ala Lys Lys Val Gln Ile
145                 150                 155                 160

Ser Asp
```

```
<210> SEQ ID NO 68
<211> LENGTH: 1218
<212> TYPE: DNA
<213> ORGANISM: Artificial Sequence
<220> FEATURE:
<223> OTHER INFORMATION: Synthetic

<400> SEQUENCE: 68
atgaagtcct ccaagaatga cacgttcgtc tatagaacgt gggtcaaaac gcttgttgtg       60
tactttgtga tgtttgtcat gtcggcggtg gtccccatca ccgccatgtt ccccaacctg      120
gggtacccct gctactttaa cgcactggtt gattacgggg cacttaacct gaccaattac      180
aacctggccc accacctgac ccccacgctc tatctggagc cgccggagat gtttgtctac      240
atcacactgg tctttatcgc ggactgcgtg gctttcatct actacgcctg cggcgaggtg      300
gcgctaatca aggcccgaaa aaaggtctcg ggtcttacag acctctcggc ctgggtctcg      360
gcagtgggct ccccaaccgt gctgtttttg gccatcctca gctctggtc catacaggtc      420
```

-continued

```
ttcatccagg tcctttccta caagcacgtc tttctctcgg cctttgtgta cttttttgcac        480 tttctggcct cagttctaca cgcctgcgca tgtgtgaccc gcttctcccc ggtctgggtg        540
gtcaaggccc aggacaactc tattccccag gacaccttct tgtggtgggt ggtcttctac        600
ctgaagcccg tagttacaaa cctgtacctg gggtgccttg ccctggagac gctggtcttc        660
tcgctcagcg tgttcctggc cctgggcaac agcttttact ttatggtggg ggacatggtg        720
ctgggagccg tgaacctctt cctcatcctg cccatcttct ggtacattct gacggaggtg        780
tggctggcct ccttcctgcg gcacaacttt ggcttctact gcggcatgtt catcgcctcc        840
atcatcctga tcctgccctt ggtcaggtac gaggccgtct ttgtctccgc caagctgcac        900
accactgtgg ccatcaatgt ggccatcata cctatcctgt gctcggtggc catgctcatc        960
aggatatgcc ggattttcaa aagcatgcgc cagggcactg actatgtccc tgtctcggag       1020
acggtggaac tggagctaga gtcagagccg aggcctaggc cctcgcgcac gccatcaccc       1080
gggcgcaacc gccgccgctc ttctacgtcc tcatcttcct ccaggtcaac caggagacag       1140
aggcccgtct ctacccaagc cctcgtctcc tccgttttac cgatgacgac ggacagcgag       1200
gaggagatct tcccctaa                                                      1218
```

```
<210> SEQ ID NO 69
<211> LENGTH: 405
<212> TYPE: PRT
<213> ORGANISM: Artificial Sequence
<220> FEATURE:
<223> OTHER INFORMATION: Synthetic

<400> SEQUENCE: 69

Met Lys Ser Ser Lys Asn Asp Thr Phe Val Tyr Arg Thr Trp Val Lys
1               5                   10                  15

Thr Leu Val Val Tyr Phe Val Met Phe Val Met Ser Ala Val Val Pro
            20                  25                  30

Ile Thr Ala Met Phe Pro Asn Leu Gly Tyr Pro Cys Tyr Phe Asn Ala
        35                  40                  45

Leu Val Asp Tyr Gly Ala Leu Asn Leu Thr Asn Tyr Asn Leu Ala His
    50                  55                  60

His Leu Thr Pro Thr Leu Tyr Leu Glu Pro Pro Glu Met Phe Val Tyr
65                  70                  75                  80

Ile Thr Leu Val Phe Ile Ala Asp Cys Val Ala Phe Ile Tyr Tyr Ala
                85                  90                  95

Cys Gly Glu Val Ala Leu Ile Lys Ala Arg Lys Lys Val Ser Gly Leu
            100                 105                 110

Thr Asp Leu Ser Ala Trp Val Ser Ala Val Gly Ser Pro Thr Val Leu
        115                 120                 125

Phe Leu Ala Ile Leu Lys Leu Trp Ser Ile Gln Val Phe Ile Gln Val
    130                 135                 140

Leu Ser Tyr Lys His Val Phe Leu Ser Ala Phe Val Tyr Phe Leu His
145                 150                 155                 160

Phe Leu Ala Ser Val Leu His Ala Cys Ala Cys Val Thr Arg Phe Ser
                165                 170                 175

Pro Val Trp Val Val Lys Ala Gln Asp Asn Ser Ile Pro Gln Asp Thr
            180                 185                 190

Phe Leu Trp Trp Val Val Phe Tyr Leu Lys Pro Val Val Thr Asn Leu
        195                 200                 205

Tyr Leu Gly Cys Leu Ala Leu Glu Thr Leu Val Phe Ser Leu Ser Val
```

```
        210              215              220
Phe Leu Ala Leu Gly Asn Ser Phe Tyr Phe Met Val Gly Asp Met Val
225              230              235              240

Leu Gly Ala Val Asn Leu Phe Leu Ile Leu Pro Ile Phe Trp Tyr Ile
                 245              250              255

Leu Thr Glu Val Trp Leu Ala Ser Phe Leu Arg His Asn Phe Gly Phe
                 260              265              270

Tyr Cys Gly Met Phe Ile Ala Ser Ile Ile Leu Ile Leu Pro Leu Val
                 275              280              285

Arg Tyr Glu Ala Val Phe Val Ser Ala Lys Leu His Thr Thr Val Ala
                 290              295              300

Ile Asn Val Ala Ile Ile Pro Ile Leu Cys Ser Val Ala Met Leu Ile
305              310              315              320

Arg Ile Cys Arg Ile Phe Lys Ser Met Arg Gln Gly Thr Asp Tyr Val
                 325              330              335

Pro Val Ser Glu Thr Val Glu Leu Glu Leu Glu Ser Glu Pro Arg Pro
                 340              345              350

Arg Pro Ser Arg Thr Pro Ser Pro Gly Arg Asn Arg Arg Arg Ser Ser
                 355              360              365

Thr Ser Ser Ser Ser Ser Arg Ser Thr Arg Arg Gln Arg Pro Val Ser
                 370              375              380

Thr Gln Ala Leu Val Ser Ser Val Leu Pro Met Thr Thr Asp Ser Glu
385              390              395              400

Glu Glu Ile Phe Pro
                405
```

```
<210> SEQ ID NO 70
<211> LENGTH: 1011
<212> TYPE: DNA
<213> ORGANISM: Artificial Sequence
<220> FEATURE:
<223> OTHER INFORMATION: Synthetic

<400> SEQUENCE: 70
atggcatccg ccgcgaacag tagccgggaa cagcttcgca agttcctcaa caaggagtgc      60
ctctgggtgc tgagcgatgc ctctacgccc cagatgaaag tctatacggc cacaaccgcc     120
gtgtcagctg tgtacgtgcc tcagatagcc ggacctccta aaacctacat gaatgttacc     180
ctcattgtgc tgaagcccaa gaagaagccc acctatgtga ccgtctacat caatggaacc     240
ctagccaccg tggccaggcc cgaggttctc ttcactaagg cagtccaggg gccacacagc     300
ctgactctca tgtactttgg ggtattctca gatgcagtgg gtgaggcggt gcctgtggag     360
attaggggta accctgtagt cacctgcaca gatctgacca cggcccacgt ctttaccacc     420
tcaaccgccg ttaaaacagt agaagaactg caagatatca caccctcgga gatcatccca     480
ctgggacggg gtggtgcctg gtatgcagaa ggggccctgt acatgttttt cgttaacatg     540
gacatgctga tgtgctgccc caatatgcca acctttccat cactgaccca ttttatcaac     600
ctgctaacca gatgtgataa cggggaatgt gtgacatgct atggtgccgg ggcccacgtg     660
aacatcctgc gtggctggac ggaggacgat agcccaggca catctggcac ctgtccttgt     720
ctgctgccat gcacggccct gaacaacgac tacgtaccca taactgggca tcgggctttg     780
ttgggtctga tgttcaaacc ggaggatgcc cactttgtgg tgggactgag atttaaccca     840
cccaaaatgc acccgacat gtcacgcgtc ctgcaggggg ttcttgctaa tgggaaagag     900
gtcccatgta cagcacaacc ttggaccctg ctgcgatttt ctgacctta cagccgggct     960
```

-continued atgctctaca attgccaagt actgaaacgt caggtcttac attcttattg a                1011

<210> SEQ ID NO 71
<211> LENGTH: 336
<212> TYPE: PRT
<213> ORGANISM: Artificial Sequence
<220> FEATURE:
<223> OTHER INFORMATION: Synthetic

<400> SEQUENCE: 71

Met Ala Ser Ala Ala Asn Ser Ser Arg Glu Gln Leu Arg Lys Phe Leu
1               5                   10                  15

Asn Lys Glu Cys Leu Trp Val Leu Ser Asp Ala Ser Thr Pro Gln Met
            20                  25                  30

Lys Val Tyr Thr Ala Thr Thr Ala Val Ser Ala Val Tyr Val Pro Gln
        35                  40                  45

Ile Ala Gly Pro Pro Lys Thr Tyr Met Asn Val Thr Leu Ile Val Leu
    50                  55                  60

Lys Pro Lys Lys Lys Pro Thr Tyr Val Thr Val Tyr Ile Asn Gly Thr
65                  70                  75                  80

Leu Ala Thr Val Ala Arg Pro Glu Val Leu Phe Thr Lys Ala Val Gln
                85                  90                  95

Gly Pro His Ser Leu Thr Leu Met Tyr Phe Gly Val Phe Ser Asp Ala
            100                 105                 110

Val Gly Glu Ala Val Pro Val Glu Ile Arg Gly Asn Pro Val Val Thr
        115                 120                 125

Cys Thr Asp Leu Thr Thr Ala His Val Phe Thr Thr Ser Thr Ala Val
    130                 135                 140

Lys Thr Val Glu Glu Leu Gln Asp Ile Thr Pro Ser Glu Ile Ile Pro
145                 150                 155                 160

Leu Gly Arg Gly Gly Ala Trp Tyr Ala Glu Gly Ala Leu Tyr Met Phe
                165                 170                 175

Phe Val Asn Met Asp Met Leu Met Cys Cys Pro Asn Met Pro Thr Phe
            180                 185                 190

Pro Ser Leu Thr His Phe Ile Asn Leu Leu Thr Arg Cys Asp Asn Gly
            195                 200                 205

Glu Cys Val Thr Cys Tyr Gly Ala Gly Ala His Val Asn Ile Leu Arg
    210                 215                 220

Gly Trp Thr Glu Asp Asp Ser Pro Gly Thr Ser Gly Thr Cys Pro Cys
225                 230                 235                 240

Leu Leu Pro Cys Thr Ala Leu Asn Asn Asp Tyr Val Pro Ile Thr Gly
            245                 250                 255

His Arg Ala Leu Leu Gly Leu Met Phe Lys Pro Glu Asp Ala His Phe
            260                 265                 270

Val Val Gly Leu Arg Phe Asn Pro Pro Lys Met His Pro Asp Met Ser
        275                 280                 285

Arg Val Leu Gln Gly Val Leu Ala Asn Gly Lys Glu Val Pro Cys Thr
    290                 295                 300

Ala Gln Pro Trp Thr Leu Leu Arg Phe Ser Asp Leu Tyr Ser Arg Ala
305                 310                 315                 320

Met Leu Tyr Asn Cys Gln Val Leu Lys Arg Gln Val Leu His Ser Tyr
                325                 330                 335

<210> SEQ ID NO 72
<211> LENGTH: 1521

<212> TYPE: DNA
<213> ORGANISM: Artificial Sequence
<220> FEATURE:
<223> OTHER INFORMATION: Synthetic

<400> SEQUENCE: 72

```
atggatgtcc acattgacaa ccaagtgctg agtggcctcg ggacccccct cctcgtgcac      60
ctatttgttc ccgacacggt tatggcagag ctttgcccca atcgcgtgcc aaactgcgag     120
ggagcctggt gccagactct cttcagtgac cggacgggtc tcacgagggt ctgccgcgtg     180
tttgctgctc ggggcatgct gcccggacgg cctagccatc ggggcacgtt taccagtgtg     240
ccagtgtact gcgaggaggg ccttccagag ctctacaacc ccttccacgt ggccgccctt     300
cgattttacg atgaaggagg gctggttggg gagctacaga tttattacct gtctctcttc     360
gagggggcca aaagggctct gacggacggg catctgatca gagaggcctc tggggtccag     420
gagtctgctg cggctatgca gcccatgcct atagatcctg gcccccctgg aggggcgggt     480
atagagcata tgccggtggc cgcggcccag gtcgagcacc ctaaaacgta tgacctcaag     540
caaattctat tggagataac gcaagaggag aatagagggg agcagaggtt gggccacgct     600
gggagtccgg ccctttgcct ggggctcaga cttaggccg gggccgagac caaggcggct     660
gctgagacct ctgtgcccaa gcaccaccca gccctcgaga accccagcaa catccggggt     720
agcgccggtg gggaaggcgg cggggccga gcagggactg cgcggcactgt ggggtcggg     780 tcggggcac cctcgagggt gcctgtttct ttctctaaga cccgtcgggc cattcgtgag     840
tccagggccc tggtcagggg aattgctcat attttagcc cccacgctct ctatgttgtc     900
acatatccag agctgagtgc ccaggcaga ctgcacagga tgacagctgt cacccatgcc     960
tccccagcaa cagatcttgc tgaggtttca attttgggag ctccagagag ggagtttcgc    1020
ttcctcattt cagtggccct cagaatttct gctagcttca gggaaaaact ggccacgcag    1080
gcctggacag cacaacaaga aatcccagtt gttattccca cctcctactc ccgtatctat    1140
aaaaattcag acctgatcag ggaagcgttc ttcactgtcc agacacgggt tagttgggaa    1200
agttgttggg tgaaagctat ctccaatgca ccaaagacgc cggatgcctg cctatggata    1260
gatagccacc cgctgtatga ggaaggggcc tcggcctggg gtaaggtgat cgactccagg    1320 cccccggtg ggctggttgg ggctgcttcc cagctagtag cccttggaac tgacgggcac    1380
tgcgtccacc tggccaccac atcggacggg caggcatttt tggtgctgcc tgggggcttt    1440
gttattaaag gccaattggc actcaccccc gaggagaggg gatatattct ggcacgtcat    1500
ggcatccgcc gcgaacagta g                                             1521
```

<210> SEQ ID NO 73
<211> LENGTH: 506
<212> TYPE: PRT
<213> ORGANISM: Artificial Sequence
<220> FEATURE:
<223> OTHER INFORMATION: Synthetic

<400> SEQUENCE: 73

```
Met Asp Val His Ile Asp Asn Gln Val Leu Ser Gly Leu Gly Thr Pro
1               5                   10                  15

Leu Leu Val His Leu Phe Val Pro Asp Thr Val Met Ala Glu Leu Cys
            20                  25                  30

Pro Asn Arg Val Pro Asn Cys Glu Gly Ala Trp Cys Gln Thr Leu Phe
        35                  40                  45

Ser Asp Arg Thr Gly Leu Thr Arg Val Cys Arg Val Phe Ala Ala Arg
```

-continued

```
                50                 55                 60

Gly Met Leu Pro Gly Arg Pro Ser His Arg Gly Thr Phe Thr Ser Val
65                  70                  75                  80

Pro Val Tyr Cys Glu Glu Gly Leu Pro Glu Leu Tyr Asn Pro Phe His
                85                  90                  95

Val Ala Ala Leu Arg Phe Tyr Asp Glu Gly Gly Leu Val Gly Glu Leu
                100                 105                 110

Gln Ile Tyr Tyr Leu Ser Leu Phe Glu Gly Ala Lys Arg Ala Leu Thr
                115                 120                 125

Asp Gly His Leu Ile Arg Glu Ala Ser Gly Val Gln Glu Ser Ala Ala
                130                 135                 140

Ala Met Gln Pro Met Pro Ile Asp Pro Gly Pro Pro Gly Gly Ala Gly
145                 150                 155                 160

Ile Glu His Met Pro Val Ala Ala Ala Gln Val Glu His Pro Lys Thr
                165                 170                 175

Tyr Asp Leu Lys Gln Ile Leu Leu Glu Ile Thr Gln Glu Glu Asn Arg
                180                 185                 190

Gly Glu Gln Arg Leu Gly His Ala Gly Ser Pro Ala Leu Cys Leu Gly
                195                 200                 205

Leu Arg Leu Arg Ala Gly Ala Glu Thr Lys Ala Ala Ala Glu Thr Ser
210                 215                 220

Val Pro Lys His His Pro Ala Leu Glu Asn Pro Ser Asn Ile Arg Gly
225                 230                 235                 240

Ser Ala Gly Gly Glu Gly Gly Gly Arg Ala Gly Thr Gly Gly Thr
                245                 250                 255

Val Gly Val Gly Ser Gly Ala Pro Ser Arg Val Pro Val Ser Phe Ser
                260                 265                 270

Lys Thr Arg Arg Ala Ile Arg Glu Ser Arg Ala Leu Val Arg Gly Ile
                275                 280                 285

Ala His Ile Phe Ser Pro His Ala Leu Tyr Val Val Thr Tyr Pro Glu
                290                 295                 300

Leu Ser Ala Gln Gly Arg Leu His Arg Met Thr Ala Val Thr His Ala
305                 310                 315                 320

Ser Pro Ala Thr Asp Leu Ala Glu Val Ser Ile Leu Gly Ala Pro Glu
                325                 330                 335

Arg Glu Phe Arg Phe Leu Ile Ser Val Ala Leu Arg Ile Ser Ala Ser
                340                 345                 350

Phe Arg Glu Lys Leu Ala Thr Gln Ala Trp Thr Ala Gln Gln Glu Ile
                355                 360                 365

Pro Val Val Ile Pro Thr Ser Tyr Ser Arg Ile Tyr Lys Asn Ser Asp
                370                 375                 380

Leu Ile Arg Glu Ala Phe Phe Thr Val Gln Thr Arg Val Ser Trp Glu
385                 390                 395                 400

Ser Cys Trp Val Lys Ala Ile Ser Asn Ala Pro Lys Thr Pro Asp Ala
                405                 410                 415

Cys Leu Trp Ile Asp Ser His Pro Leu Tyr Glu Glu Gly Ala Ser Ala
                420                 425                 430

Trp Gly Lys Val Ile Asp Ser Arg Pro Pro Gly Gly Leu Val Gly Ala
                435                 440                 445

Ala Ser Gln Leu Val Ala Leu Gly Thr Asp Gly His Cys Val His Leu
                450                 455                 460

Ala Thr Thr Ser Asp Gly Gln Ala Phe Leu Val Leu Pro Gly Gly Phe
465                 470                 475                 480
```

-continued

```
Val Ile Lys Gly Gln Leu Ala Leu Thr Pro Glu Glu Arg Gly Tyr Ile
                485                 490                 495

Leu Ala Arg His Gly Ile Arg Arg Glu Gln
            500                 505

<210> SEQ ID NO 74
<211> LENGTH: 705
<212> TYPE: DNA
<213> ORGANISM: Artificial Sequence
<220> FEATURE:
<223> OTHER INFORMATION: Synthetic

<400> SEQUENCE: 74
atggcacacg ccagagacaa ggcaggcgct gtcctggcca tgatactcat ctgtgagaca        60
agccttatct ggacatctag tggcagttcg acggcctcgg cggggaacgt gacaggcaca       120
acggctgtga ctacaccatc accgtcggca tcgggtccta gcacaaacca gtctacgacc       180
ttgaccacga ccagcgcccc tataaccaca actgctatcc tgagcaccaa cacaaccacg       240
gtgacatcca ctgggacaac tgtcacacca gtcccaacaa cttccaacgc atccaccatc       300
aatgtcacca ctaaggttac tgcacagaac atcactgcca ccgaggccgg aacaggaacc       360
tccacgggtg tgactagcaa tgtcaccacc aggtcctcca ccaccaccag tgctactacc       420
cgtattacca acgctaccac cttggccccc acgctgtcct ccaaagggac gtccaatgcc       480
acaaaaacaa ctgctgagct tcccaccgtt ccagatgaga ggcagccatc tttatcttac       540
ggtcttcctc tctggacact ggtgtttgtg gggctcactt ttctgatgct aattctgata       600
tttgcggctg ggctaatgat gtccgccaag aacaagcccc tggacgaagc cctgctcacg       660
aatgccgtca cgcgagaccc gtcgctttac aagggactgg tgtag                        705

<210> SEQ ID NO 75
<211> LENGTH: 234
<212> TYPE: PRT
<213> ORGANISM: Artificial Sequence
<220> FEATURE:
<223> OTHER INFORMATION: Synthetic

<400> SEQUENCE: 75

Met Ala His Ala Arg Asp Lys Ala Gly Ala Val Leu Ala Met Ile Leu
1               5                   10                  15

Ile Cys Glu Thr Ser Leu Ile Trp Thr Ser Ser Gly Ser Ser Thr Ala
                20                  25                  30

Ser Ala Gly Asn Val Thr Gly Thr Thr Ala Val Thr Thr Pro Ser Pro
            35                  40                  45

Ser Ala Ser Gly Pro Ser Thr Asn Gln Ser Thr Thr Leu Thr Thr Thr
        50                  55                  60

Ser Ala Pro Ile Thr Thr Thr Ala Ile Leu Ser Thr Asn Thr Thr Thr
65                  70                  75                  80

Val Thr Ser Thr Gly Thr Thr Val Thr Pro Val Pro Thr Thr Ser Asn
                85                  90                  95

Ala Ser Thr Ile Asn Val Thr Thr Lys Val Thr Ala Gln Asn Ile Thr
            100                 105                 110

Ala Thr Glu Ala Gly Thr Gly Thr Ser Thr Gly Val Thr Ser Asn Val
        115                 120                 125

Thr Thr Arg Ser Ser Thr Thr Thr Ser Ala Thr Thr Arg Ile Thr Asn
    130                 135                 140

Ala Thr Thr Leu Ala Pro Thr Leu Ser Ser Lys Gly Thr Ser Asn Ala
```

```
145                 150                 155                 160

Thr Lys Thr Thr Ala Glu Leu Pro Thr Val Pro Asp Glu Arg Gln Pro
            165                 170                 175

Ser Leu Ser Tyr Gly Leu Pro Leu Trp Thr Leu Val Phe Val Gly Leu
            180                 185                 190

Thr Phe Leu Met Leu Ile Leu Ile Phe Ala Ala Gly Leu Met Met Ser
            195                 200                 205

Ala Lys Asn Lys Pro Leu Asp Glu Ala Leu Leu Thr Asn Ala Val Thr
    210                 215                 220

Arg Asp Pro Ser Leu Tyr Lys Gly Leu Val
225                 230
```

<210> SEQ ID NO 76
<211> LENGTH: 1263
<212> TYPE: DNA
<213> ORGANISM: Artificial Sequence
<220> FEATURE:
<223> OTHER INFORMATION: Synthetic

<400> SEQUENCE: 76

```
atggtcgatg aacaagtggc ggtggaacac ggcaccgtca gccacacaat cagccgggag    60
gaagatggcg tggtccacga gcggcgtgtc ttggccagcg gggagagggt ggaagtcttt   120
tataaggctc cggccccacg acctcgggag ggacgggcct ctaccttcca cgacttcacc   180
gtcccggcgg ctgctgccgt cccagggccg gaacctgagc ctgagccaca cccacctatg   240
ccaatccatg ccaatggggg aggagagacc aagaccaata cccaggatca gaatcaaaat   300
cagaccaccc ggacccggac caatgccaaa gctgaagaac ggactgcgga gatggatgac   360
accatggcct cgtcaggagg gcagagaggg gcaccaattt ccgcggacct actctctctc   420
tcctcgttaa ctggtagaat ggcagccatg gcccccctcct ggatgaagag cgaggtatgc   480
ggtgagagaa tgagattcaa ggaagatgtc tatgatggag aggcagagac cctagctgag   540
cctccacgct gtttcatgct gagctttgtt ttcatctatt actgctgcta tttggcgttc   600
ctggccctac tcgcctttgg tttttaaccca ctcttttttgc ccagctttat gccggtgggg   660
gccaaggtgc ttcggggtaa ggggcgtgat tttggggtgc ccctgtctta tgggtgtccg   720
accaatccat tctgcaaggt ttacaccctt atcccggccg tggtcattaa caatgtgact   780
tattacccca acaacacgga cagccatggg ggtcatggtg atttgaggc ggctgccctt   840 catgtagctg cactttttga gtctgggtgc ccaaatctac aggctgtgac taataggaac   900
aggacattta acgtcaccag agccagtggc cgagttgaaa ggcgccttgt acaagatatg   960
cagagggtcc tggcgagtgc tgtggtggtg atgcatcatc actgccacta tgagacatat  1020
tatgtctttg atggggtggg ccccgagttt ggtaccattc ctacgccctg cttcaaggat  1080
gtgttggcct ttaggccgtc attggtgacc aactgcaccg cgccgttaaa gacatccgtc  1140
aagggtccta actggtcagg ggcagctgga ggcatgaaac ggaagcaatg tcgtgttgac  1200
cggctcacgg accgctcatt ccctgcatac ctcgaggagg tcatgtatgt gatggttcag  1260
tag                                                                1263
```

<210> SEQ ID NO 77
<211> LENGTH: 1263
<212> TYPE: PRT
<213> ORGANISM: Artificial Sequence
<220> FEATURE:
<223> OTHER INFORMATION: Synthetic -continued

```
<400> SEQUENCE: 77

Ala Thr Gly Gly Thr Cys Gly Ala Thr Gly Ala Ala Cys Ala Ala Gly
1               5                   10                  15

Thr Gly Gly Cys Gly Gly Thr Gly Gly Ala Ala Cys Ala Cys Gly Gly
                20                  25                  30

Cys Ala Cys Cys Gly Thr Cys Ala Gly Cys Cys Ala Cys Ala Cys Ala
        35                  40                  45

Ala Thr Cys Ala Gly Cys Cys Gly Gly Gly Ala Gly Gly Ala Ala Gly
    50                  55                  60

Ala Thr Gly Gly Cys Gly Thr Gly Gly Thr Cys Cys Ala Cys Gly Ala
65                  70                  75                  80

Gly Cys Gly Gly Cys Gly Thr Gly Thr Cys Thr Thr Gly Gly Cys Cys
                85                  90                  95

Ala Gly Cys Gly Gly Gly Gly Ala Gly Ala Gly Gly Thr Gly Gly
        100                 105                 110

Ala Ala Gly Thr Cys Thr Thr Thr Thr Ala Thr Ala Ala Gly Gly Cys
        115                 120                 125

Thr Cys Cys Gly Gly Cys Cys Cys Cys Ala Cys Gly Ala Cys Cys Thr
    130                 135                 140

Cys Gly Gly Gly Ala Gly Gly Gly Ala Cys Gly Gly Gly Cys Cys Thr
145                 150                 155                 160

Cys Thr Ala Cys Cys Thr Thr Cys Cys Ala Cys Gly Ala Cys Thr Thr
            165                 170                 175

Cys Ala Cys Cys Gly Thr Cys Cys Gly Gly Cys Gly Gly Cys Thr
            180                 185                 190

Gly Cys Thr Gly Cys Cys Gly Thr Cys Cys Cys Ala Gly Gly Gly Cys
        195                 200                 205

Cys Gly Gly Ala Ala Cys Cys Thr Gly Ala Gly Cys Cys Thr Gly Ala
    210                 215                 220

Gly Cys Cys Ala Cys Ala Cys Cys Cys Ala Cys Cys Thr Ala Thr Gly
225                 230                 235                 240

Cys Cys Ala Ala Thr Cys Cys Ala Thr Gly Cys Cys Ala Ala Thr Gly
            245                 250                 255

Gly Gly Gly Gly Ala Gly Gly Ala Gly Ala Gly Ala Cys Cys Ala Ala
        260                 265                 270

Gly Ala Cys Cys Ala Ala Thr Ala Cys Cys Ala Gly Gly Ala Thr
        275                 280                 285

Cys Ala Gly Ala Ala Thr Cys Ala Ala Ala Thr Cys Ala Gly Ala
    290                 295                 300

Cys Cys Ala Cys Cys Cys Gly Gly Ala Cys Cys Cys Gly Gly Ala Cys
305                 310                 315                 320

Cys Ala Ala Thr Gly Cys Cys Ala Ala Ala Gly Cys Thr Gly Ala Ala
        325                 330                 335

Gly Ala Ala Cys Gly Gly Ala Cys Thr Gly Cys Gly Gly Ala Gly Ala
        340                 345                 350

Thr Gly Gly Ala Thr Gly Ala Cys Ala Cys Cys Ala Thr Gly Gly Cys
        355                 360                 365

Cys Thr Cys Gly Thr Cys Ala Gly Gly Ala Gly Gly Gly Cys Ala Gly
    370                 375                 380

Ala Gly Ala Gly Gly Gly Gly Cys Ala Cys Cys Ala Ala Thr Thr Thr
385                 390                 395                 400

Cys Cys Gly Cys Gly Gly Ala Cys Cys Thr Ala Cys Thr Cys Thr Cys
            405                 410                 415
```

-continued

```
Thr Cys Thr Cys Thr Cys Cys Thr Cys Gly Thr Thr Ala Ala Cys Thr
        420                 425                 430

Gly Gly Thr Ala Gly Ala Ala Thr Gly Gly Cys Ala Gly Cys Cys Ala
        435                 440                 445

Thr Gly Gly Cys Cys Cys Cys Thr Cys Cys Thr Gly Gly Ala Thr
        450                 455                 460

Gly Ala Ala Gly Ala Gly Cys Gly Ala Gly Gly Thr Ala Thr Gly Cys
465                 470                 475                 480

Gly Gly Thr Gly Ala Gly Ala Gly Ala Ala Thr Gly Ala Gly Ala Thr
                485                 490                 495

Thr Cys Ala Ala Gly Gly Ala Ala Gly Ala Thr Gly Thr Cys Thr Ala
                500                 505                 510

Thr Gly Ala Thr Gly Gly Ala Gly Ala Gly Gly Cys Ala Gly Ala Gly
        515                 520                 525

Ala Cys Cys Cys Thr Ala Gly Cys Thr Gly Ala Gly Cys Cys Thr Cys
        530                 535                 540

Cys Ala Cys Gly Cys Thr Gly Thr Thr Thr Cys Ala Thr Gly Cys Thr
545                 550                 555                 560

Gly Ala Gly Cys Thr Thr Thr Gly Thr Thr Thr Thr Cys Ala Thr Cys
                565                 570                 575

Thr Ala Thr Thr Ala Cys Thr Gly Cys Thr Gly Cys Thr Ala Thr Thr
                580                 585                 590

Thr Gly Gly Cys Gly Thr Thr Cys Cys Thr Gly Gly Cys Cys Cys Thr
        595                 600                 605

Ala Cys Thr Cys Gly Cys Cys Thr Thr Thr Gly Gly Thr Thr Thr Thr
        610                 615                 620

Ala Ala Cys Cys Cys Ala Cys Thr Cys Thr Thr Thr Thr Gly Cys
625                 630                 635                 640

Cys Cys Ala Gly Cys Thr Thr Thr Ala Thr Gly Cys Cys Gly Gly Thr
                645                 650                 655

Gly Gly Gly Gly Gly Cys Cys Ala Ala Gly Gly Thr Gly Cys Thr Thr
                660                 665                 670

Cys Gly Gly Gly Gly Thr Ala Ala Gly Gly Gly Gly Cys Gly Thr Gly
        675                 680                 685

Ala Thr Thr Thr Thr Gly Gly Gly Gly Thr Gly Cys Cys Cys Cys Thr
        690                 695                 700

Gly Thr Cys Thr Thr Ala Thr Gly Gly Gly Thr Gly Thr Cys Cys Gly
705                 710                 715                 720

Ala Cys Cys Ala Ala Thr Cys Cys Ala Thr Thr Cys Thr Gly Cys Ala
                725                 730                 735

Ala Gly Gly Thr Thr Thr Ala Cys Ala Cys Cys Cys Thr Thr Ala Thr
        740                 745                 750

Cys Cys Cys Gly Gly Cys Cys Gly Thr Gly Gly Thr Cys Ala Thr Thr
        755                 760                 765

Ala Ala Cys Ala Ala Thr Gly Thr Gly Ala Cys Thr Thr Ala Thr Thr
        770                 775                 780

Ala Cys Cys Cys Ala Ala Cys Ala Ala Cys Ala Cys Gly Gly Ala
785                 790                 795                 800

Cys Ala Gly Cys Cys Ala Thr Gly Gly Gly Gly Thr Cys Ala Thr
                805                 810                 815

Gly Gly Thr Gly Gly Ala Thr Thr Thr Gly Ala Gly Gly Cys Gly Gly
        820                 825                 830
```

-continued

```
Cys Thr Gly Cys Cys Cys Thr Thr Cys Ala Thr Gly Thr Ala Gly Cys
        835                 840                 845

Thr Gly Cys Ala Cys Thr Thr Thr Thr Thr Gly Ala Gly Thr Cys Thr
    850                 855                 860

Gly Gly Gly Thr Gly Cys Cys Ala Ala Ala Thr Cys Thr Ala Cys
865                 870                 875                 880

Ala Gly Gly Cys Thr Gly Thr Gly Ala Cys Thr Ala Ala Thr Ala Gly
                885                 890                 895

Gly Ala Ala Cys Ala Gly Gly Ala Cys Ala Thr Thr Thr Ala Ala Cys
            900                 905                 910

Gly Thr Cys Ala Cys Cys Ala Gly Ala Gly Cys Cys Ala Gly Thr Gly
        915                 920                 925

Gly Cys Cys Gly Ala Gly Thr Thr Gly Ala Ala Ala Gly Gly Cys Gly
    930                 935                 940

Cys Cys Thr Thr Gly Thr Ala Cys Ala Ala Gly Ala Thr Ala Thr Gly
945                 950                 955                 960

Cys Ala Gly Ala Gly Gly Gly Thr Cys Cys Thr Gly Gly Cys Gly Ala
            965                 970                 975

Gly Thr Gly Cys Thr Gly Thr Gly Gly Thr Gly Gly Thr Gly Ala Thr
        980                 985                 990

Gly Cys Ala Thr Cys Ala Thr Cys  Ala Cys Thr Gly Cys  Cys Ala Cys
        995                 1000                1005

Thr Ala  Thr Gly Ala Gly Ala  Cys Ala Thr Ala Thr  Thr Ala Thr
    1010                1015                1020

Gly Thr  Cys Thr Thr Thr Gly  Ala Thr Gly Gly Gly  Gly Thr Gly
    1025                1030                1035

Gly Gly  Cys Cys Cys Cys Gly  Ala Gly Thr Thr Thr  Gly Gly Thr
    1040                1045                1050

Ala Cys  Cys Ala Thr Thr Cys  Cys Thr Ala Cys Gly  Cys Cys Cys
    1055                1060                1065

Thr Gly  Cys Thr Thr Cys Ala  Ala Gly Gly Ala Thr  Gly Thr Gly
    1070                1075                1080

Thr Thr  Gly Gly Cys Cys Thr  Thr Thr Ala Gly Gly  Cys Cys Gly
    1085                1090                1095

Thr Cys  Ala Thr Thr Gly Gly  Thr Gly Ala Cys Cys  Ala Ala Cys
    1100                1105                1110

Thr Gly  Cys Ala Cys Cys Gly  Cys Gly Cys Cys Gly  Thr Thr Ala
    1115                1120                1125

Ala Ala  Gly Ala Cys Ala Thr  Cys Cys Gly Thr Cys  Ala Ala Gly
    1130                1135                1140

Gly Gly  Thr Cys Cys Thr Ala  Ala Cys Thr Gly Gly  Thr Cys Ala
    1145                1150                1155

Gly Gly  Gly Gly Cys Ala Gly  Cys Thr Gly Gly Ala  Gly Gly Cys
    1160                1165                1170

Ala Thr  Gly Ala Ala Ala Cys  Gly Gly Ala Ala Gly  Cys Ala Ala
    1175                1180                1185

Thr Gly  Thr Cys Gly Thr Gly  Thr Thr Gly Ala Cys  Cys Gly Gly
    1190                1195                1200

Cys Thr  Cys Ala Cys Gly Gly  Ala Cys Cys Gly Cys  Thr Cys Ala
    1205                1210                1215

Thr Thr  Cys Cys Cys Thr Gly  Cys Ala Thr Ala Cys  Cys Thr Cys
    1220                1225                1230

Gly Ala  Gly Gly Ala Gly Gly  Thr Cys Ala Thr Gly  Thr Ala Thr
```

-continued

```
          1235              1240              1245

Gly Thr  Gly Ala Thr Gly Gly  Thr Thr Cys Ala Gly  Thr Ala Gly
    1250              1255              1260
```

<210> SEQ ID NO 78
<211> LENGTH: 1215
<212> TYPE: DNA
<213> ORGANISM: Artificial Sequence
<220> FEATURE:
<223> OTHER INFORMATION: Synthetic

<400> SEQUENCE: 78

```
atgctcaagt gtaagcagcc cggggcccgc ttcattcacg gggccgtgca cctgccatcg        60
ggacagattg tcttccacac catccacagc cccactcttg cctcggcgct gggactgcct       120
ggggaaaatg tacccatccc ggccctcttc cgtgcctcgg gcctcaacgt ccgtgagagc       180
ctacccatga ccaacatgag ggcaccgatc atctcgctgg ctcgcctcat cctggccccc       240
aacccctata tcctagaggg acagctgacg gtgggcatga cacaggacaa cggcattccc       300
gtgctttttg ccaggcctgt cattgaggta aaaagcgggc ctgagtccaa cattaaagcc       360
tcctcgcaac ttatgatagc agaagactcc tgcctgaatc agatcgcccc cttttccgca       420
tcagagcacc ccgccttctc catggttgag tccgtaaaac gagtccgggt cgatgaggga       480
gcaaacaccc ggcgcaccat ccgggatatt ctggagatcc ccgtgactgt gctctcatcc       540
ctgcaactgt ctcccaccaa gtccatcctg aaaaaggcac cggagccccc acctccggag       600
ccccaagcca ccttcgatgc caccccctat gcccgcatct tttacgacat cgggcgacag       660
gtgcccaagc tgggcaatgc ccccgccgcg caggtcagca acgtgctcat cgccaaccgc       720
tcccacaact ctctaaggct ggtgcccaat ccggacttgc tgcctctcca gcatttgtac       780
ctcaagcacg tagtgctaaa gagtctgaat ctggagaata tagtgcagga ctttgaggcc       840
atcttcacct ccccgtctga taccatcagt gaggctgaaa ccaaggcctt tgagaagctg       900
gtggagcaag ccaaaaacac cgtagagaac atagtctttt gcctcaacag catctgttcc       960
acctctacac tcccagatgt cgtccccgat gtcaataacc caaacattag cctggctcta      1020
gagaagtatt ttctcatgtt ccctccctca ggcaccatta tgagaaatgt cagattcgcc      1080 accccccatcg tccggctctt gtgccaaggg gctgagcttg gcaccatggc acagtttcta      1140
ggaaagtaca tcaaggtcaa gaaggaaact ggaatgtaca cactggtcaa gctttattac      1200
ctgctgcgca ttcca                                                       1215
```

<210> SEQ ID NO 79
<211> LENGTH: 405
<212> TYPE: PRT
<213> ORGANISM: Artificial Sequence
<220> FEATURE:
<223> OTHER INFORMATION: Synthetic

<400> SEQUENCE: 79

```
Met Leu Lys Cys Lys Gln Pro Gly Ala Arg Phe Ile His Gly Ala Val
1               5                   10                  15

His Leu Pro Ser Gly Gln Ile Val Phe His Thr Ile His Ser Pro Thr
            20                  25                  30

Leu Ala Ser Ala Leu Gly Leu Pro Gly Glu Asn Val Pro Ile Pro Ala
        35                  40                  45

Leu Phe Arg Ala Ser Gly Leu Asn Val Arg Glu Ser Leu Pro Met Thr
    50                  55                  60
```

```
Asn Met Arg Ala Pro Ile Ile Ser Leu Ala Arg Leu Ile Leu Ala Pro
65              70                  75                  80

Asn Pro Tyr Ile Leu Glu Gly Gln Leu Thr Val Gly Met Thr Gln Asp
                85                  90                  95

Asn Gly Ile Pro Val Leu Phe Ala Arg Pro Val Ile Glu Val Lys Ser
            100                 105                 110

Gly Pro Glu Ser Asn Ile Lys Ala Ser Ser Gln Leu Met Ile Ala Glu
        115                 120                 125

Asp Ser Cys Leu Asn Gln Ile Ala Pro Phe Ser Ala Ser Glu His Pro
    130                 135                 140

Ala Phe Ser Met Val Glu Ser Val Lys Arg Val Arg Val Asp Glu Gly
145                 150                 155                 160

Ala Asn Thr Arg Arg Thr Ile Arg Asp Ile Leu Glu Ile Pro Val Thr
                165                 170                 175

Val Leu Ser Ser Leu Gln Leu Ser Pro Thr Lys Ser Ile Leu Lys Lys
            180                 185                 190

Ala Pro Glu Pro Pro Pro Glu Pro Gln Ala Thr Phe Asp Ala Thr
        195                 200                 205

Pro Tyr Ala Arg Ile Phe Tyr Asp Ile Gly Arg Gln Val Pro Lys Leu
    210                 215                 220

Gly Asn Ala Pro Ala Ala Gln Val Ser Asn Val Leu Ile Ala Asn Arg
225                 230                 235                 240

Ser His Asn Ser Leu Arg Leu Val Pro Asn Pro Asp Leu Leu Pro Leu
                245                 250                 255

Gln His Leu Tyr Leu Lys His Val Val Leu Lys Ser Leu Asn Leu Glu
            260                 265                 270

Asn Ile Val Gln Asp Phe Glu Ala Ile Phe Thr Ser Pro Ser Asp Thr
        275                 280                 285

Ile Ser Glu Ala Glu Thr Lys Ala Phe Glu Lys Leu Val Glu Gln Ala
    290                 295                 300

Lys Asn Thr Val Glu Asn Ile Val Phe Cys Leu Asn Ser Ile Cys Ser
305                 310                 315                 320

Thr Ser Thr Leu Pro Asp Val Val Pro Asp Val Asn Asn Pro Asn Ile
                325                 330                 335

Ser Leu Ala Leu Glu Lys Tyr Phe Leu Met Phe Pro Pro Ser Gly Thr
            340                 345                 350

Ile Met Arg Asn Val Arg Phe Ala Thr Pro Ile Val Arg Leu Leu Cys
        355                 360                 365

Gln Gly Ala Glu Leu Gly Thr Met Ala Gln Phe Leu Gly Lys Tyr Ile
    370                 375                 380

Lys Val Lys Lys Glu Thr Gly Met Tyr Thr Leu Val Lys Leu Tyr Tyr
385                 390                 395                 400

Leu Leu Arg Ile Pro
                405
```

```
<210> SEQ ID NO 80
<211> LENGTH: 1983
<212> TYPE: DNA
<213> ORGANISM: Artificial Sequence
<220> FEATURE:
<223> OTHER INFORMATION: Synthetic

<400> SEQUENCE: 80
agcctcagcg aggttaagct gcacctggac atagaggggc atgcttcgca ttacaccatc        60
ccatggaccg aactgatggc aaaggtccca ggccttagcc cagaggcgct gtggagagag       120
```

```
gcaaatgtca ccgaagattt ggcgtctatg cttaaccgct acaagttaat ttacaagacg      180
tctggtaccc ttggtattgc gctggccgag cctgtcgata tccctgctgt ctctgaagga      240
tccatgcaag tggatgcatc taaggtccat cccggagtca ttagcggcct gaattcccct      300
gcctgcatgc ttagtgcccc ccttgagaag cagctcttct actatattgg caccatgctg      360
cccaacacgc ggccacacag ctatgtcttt tatcagctgc gctgtcactt gtcttatgtg      420
gccctgtcca tcaacgggga caagtttcag tacacggggg ccatgacttc taaatttctg      480
atgggcacct acaagcgagt gaccgagaag ggagatgagc atgtgttgag cctggtcttt      540
ggcaagacga aggacctgcc ggatctgagg gggcctttta gttacccatc cttaaccagt      600
gcccaaagcg gggactattc cctggtgatt gttacaacct ttgtgcatta tgccaacttt      660
cacaactact ttgtacccaa cctgaaggat atgtttttccc gagccgtcac catgacagcc      720
gccagctacg ctcgctacgt tctccagaaa ctggtcctgc tggagatgaa gggaggctgc      780
cgggagccgg aactggacac ggaaacgctg actaccatgt ttgaggtttc tgtggccttc      840
tttaaggtgg gtcatgctgt gggtgagact ggcaatggct gcgtggacct ccgctggttg      900
gccaagagct ctctttgagct gactgtcctg aaagacatca tcggcatatg ttatggggcc      960
actgtcaagg gcatgcaatc ctacgggctg gagcgcttgg ccgccatgct gatggccacg     1020
gtcaagatgg aggagctggg tcacctgact actgagaaac aggagtacgc gctgaggtta     1080
gccaccgtcg gctaccccaa ggccggggtt tacagtggcc tcattggagg cgccacatct     1140
gtgcttctct cggcctacaa ccgccacccc cttttccagc ccctgcatac cgtgatgaga     1200
gagaccctgt ttatcggcag ccacgtggtg ctacgcgagt tgcggctgaa cgtgactacc     1260
cagggcccca accttgccct ataccaactg ctgtccaccg ccctgtgctc ggccctagag     1320
attggggagg ttttgcgggg gctagccctg gggacagaga gcgggctctt ctcaccgtgc     1380
tacctcagcc tacgatttga cctcacacga gacaagctgc tgagcatggc cccccaggag     1440
gcaacgctgg accaggcggc cgtttcaaat gctgtggatg ggtttcttgg gcggctctct     1500
ttggagcgag aagacaggga tgcgtggcat ctccccgcct acaaatgcgt ggacaggctc     1560
gacaaagttc tgatgattat cccgctcatc aatgtgacat tcataatctc tagtgaccgt     1620
gaggtccgag gctcggcgct atacgaggcc agcaccacct atctcagcag ctctctcttt     1680
ctctcccccg ttataatgaa taaatgttcg cagggtgctg tggctgggga gccccgccag     1740
attccaaaga tccagaattt taccaggacg cagaaatcct gcattttttg tggctttgcc     1800
ctgctcagtt atgatgaaaa ggaaggcctg gaaactacaa cctacatcac ctcccaggaa     1860
gtccaaaact ccatcttgag ctccaactac tttgattttg acaacctcca cgttcactat     1920
ctgctgctga ccaccaacgg gactgtcatg gaaattgcgg gcctgtatga agaaagagca     1980
cac                                                                   1983
```

<210> SEQ ID NO 81
<211> LENGTH: 661
<212> TYPE: PRT
<213> ORGANISM: Artificial Sequence
<220> FEATURE:
<223> OTHER INFORMATION: Synthetic

<400> SEQUENCE: 81

```
Ser Leu Ser Glu Val Lys Leu His Leu Asp Ile Glu Gly His Ala Ser
1               5                   10                  15

His Tyr Thr Ile Pro Trp Thr Glu Leu Met Ala Lys Val Pro Gly Leu
```

-continued

```
                20               25               30
Ser Pro Glu Ala Leu Trp Arg Glu Ala Asn Val Thr Glu Asp Leu Ala
            35               40               45

Ser Met Leu Asn Arg Tyr Lys Leu Ile Tyr Lys Thr Ser Gly Thr Leu
        50               55               60

Gly Ile Ala Leu Ala Glu Pro Val Asp Ile Pro Ala Val Ser Glu Gly
65               70               75               80

Ser Met Gln Val Asp Ala Ser Lys Val His Pro Gly Val Ile Ser Gly
                85               90               95

Leu Asn Ser Pro Ala Cys Met Leu Ser Ala Pro Leu Glu Lys Gln Leu
            100              105              110

Phe Tyr Tyr Ile Gly Thr Met Leu Pro Asn Thr Arg Pro His Ser Tyr
        115              120              125

Val Phe Tyr Gln Leu Arg Cys His Leu Ser Tyr Val Ala Leu Ser Ile
        130              135              140

Asn Gly Asp Lys Phe Gln Tyr Thr Gly Ala Met Thr Ser Lys Phe Leu
145              150              155              160

Met Gly Thr Tyr Lys Arg Val Thr Glu Lys Gly Asp Glu His Val Leu
                165              170              175

Ser Leu Val Phe Gly Lys Thr Lys Asp Leu Pro Asp Leu Arg Gly Pro
            180              185              190

Phe Ser Tyr Pro Ser Leu Thr Ser Ala Gln Ser Gly Asp Tyr Ser Leu
        195              200              205

Val Ile Val Thr Thr Phe Val His Tyr Ala Asn Phe His Asn Tyr Phe
        210              215              220

Val Pro Asn Leu Lys Asp Met Phe Ser Arg Ala Val Thr Met Thr Ala
225              230              235              240

Ala Ser Tyr Ala Arg Tyr Val Leu Gln Lys Leu Val Leu Leu Glu Met
            245              250              255

Lys Gly Gly Cys Arg Glu Pro Glu Leu Asp Thr Glu Thr Leu Thr Thr
            260              265              270

Met Phe Glu Val Ser Val Ala Phe Phe Lys Val Gly His Ala Val Gly
        275              280              285

Glu Thr Gly Asn Gly Cys Val Asp Leu Arg Trp Leu Ala Lys Ser Phe
    290              295              300

Phe Glu Leu Thr Val Leu Lys Asp Ile Ile Gly Ile Cys Tyr Gly Ala
305              310              315              320

Thr Val Lys Gly Met Gln Ser Tyr Gly Leu Glu Arg Leu Ala Ala Met
            325              330              335

Leu Met Ala Thr Val Lys Met Glu Glu Leu Gly His Leu Thr Thr Glu
            340              345              350

Lys Gln Glu Tyr Ala Leu Arg Leu Ala Thr Val Gly Tyr Pro Lys Ala
            355              360              365

Gly Val Tyr Ser Gly Leu Ile Gly Gly Ala Thr Ser Val Leu Leu Ser
        370              375              380

Ala Tyr Asn Arg His Pro Leu Phe Gln Pro Leu His Thr Val Met Arg
385              390              395              400

Glu Thr Leu Phe Ile Gly Ser His Val Val Leu Arg Glu Leu Arg Leu
            405              410              415

Asn Val Thr Thr Gln Gly Pro Asn Leu Ala Leu Tyr Gln Leu Leu Ser
            420              425              430

Thr Ala Leu Cys Ser Ala Leu Glu Ile Gly Glu Val Leu Arg Gly Leu
        435              440              445
```

-continued

```
Ala Leu Gly Thr Glu Ser Gly Leu Phe Ser Pro Cys Tyr Leu Ser Leu
    450             455                 460

Arg Phe Asp Leu Thr Arg Asp Lys Leu Leu Ser Met Ala Pro Gln Glu
465             470                 475                 480

Ala Thr Leu Asp Gln Ala Ala Val Ser Asn Ala Val Asp Gly Phe Leu
            485                 490                 495

Gly Arg Leu Ser Leu Glu Arg Glu Asp Arg Asp Ala Trp His Leu Pro
            500                 505                 510

Ala Tyr Lys Cys Val Asp Arg Leu Asp Lys Val Leu Met Ile Ile Pro
            515                 520                 525

Leu Ile Asn Val Thr Phe Ile Ile Ser Ser Asp Arg Glu Val Arg Gly
            530                 535                 540

Ser Ala Leu Tyr Glu Ala Ser Thr Thr Tyr Leu Ser Ser Ser Leu Phe
545             550                 555                 560

Leu Ser Pro Val Ile Met Asn Lys Cys Ser Gln Gly Ala Val Ala Gly
            565                 570                 575

Glu Pro Arg Gln Ile Pro Lys Ile Gln Asn Phe Thr Arg Thr Gln Lys
            580                 585                 590

Ser Cys Ile Phe Cys Gly Phe Ala Leu Leu Ser Tyr Asp Glu Lys Glu
            595                 600                 605

Gly Leu Glu Thr Thr Thr Tyr Ile Thr Ser Gln Glu Val Gln Asn Ser
    610                 615                 620

Ile Leu Ser Ser Asn Tyr Phe Asp Phe Asp Asn Leu His Val His Tyr
625                 630                 635                 640

Leu Leu Leu Thr Thr Asn Gly Thr Val Met Glu Ile Ala Gly Leu Tyr
            645                 650                 655

Glu Glu Arg Ala His
            660
```

```
<210> SEQ ID NO 82
<211> LENGTH: 2196
<212> TYPE: DNA
<213> ORGANISM: Artificial Sequence
<220> FEATURE:
<223> OTHER INFORMATION: Synthetic

<400> SEQUENCE: 82
atgactcggc gtagggtgct aagcgtggtc gtgctgctag ccgccctggc gtgccgtctc      60
ggtgcgcaga ccccagagca gcccgcaccc cccgccacca cggtgcagcc taccgccacg     120
cgtcagcaaa ccagctttcc tttccgagtc tgcgagctct ccagccacgg cgacctgttc     180
cgcttctcct cggacatcca gtgtccctcg tttggcacgc gggagaatca cacggagggc     240
ctgttgatgg tgtttaaaga caacattatt ccctactcgt ttaaggtccg ctcctacacc     300
aagatagtga ccaacattct catctacaat ggctggtacg cggactccgt gaccaaccgg     360
cacgaggaga agttctccgt tgacagctac gaaactgacc agatggatac catctaccag     420
tgctacaacg cggtcaagat gacaaaagat gggctgacgc gcgtgtatgt agaccgcgac     480
ggagttaaca tcaccgtcaa cctaaagccc accggggggcc tggccaacgg ggtgcgccgc     540
tacgccagcc agacggagct ctatgacgcc cccgggtggt tgatatggac ttacagaaca     600
agaactaccg tcaactgcct gataactgac atgatggcca gtccaacag ccccttcgac     660 ttctttgtga ccaccaccgg gcagactgtg gaaatgtccc ctttctatga cgggaaaaat     720
aaggaaacct ccatgagcg ggcagactcc ttccacgtga gaactaacta caagatagtg     780
```

-continued

```
gactacgaca accgagggac gaacccgcaa ggcgaacgcc gagccttcct ggacaagggc      840
acttacacgc tatcttggaa gctcgagaac aggacagcct actgcccgct tcaacactgg      900
caaacctttg actcgaccat cgccacagaa acagggaagt caatacattt tgtgactgac      960
gagggcacct ctagcttcgt gaccaacaca accgtgggca tagagctccc ggacgccttc     1020
aagtgcatcg aagagcaggt gaacaagacc atgcatgaga agtacgaggc cgtccaggat     1080
cgttacacga agggccagga agccattaca tattttataa cgagcggagg attgttatta     1140
gcttggctac ctctgacccc gcgctcgttg gccaccgtca agaacctgac ggagcttacc     1200
actccgactt cctcaccccc cagcagtcca tcgcccccag ccccatccgc ggcccgcggg     1260
agcacccccg ccgccgttct gaggcgtcgg aggcgggatg cggggaacgc caccacaccg     1320
gtgcccccca cggcccccgg gaagtccctg ggcaccctca acaatcccgc caccgtccag     1380
atccaatttg cctacgactc cctgcgccgc cagatcaacc gcatgctggg agaccttgcg     1440
cgggcctggt gcctggagca gaagaggcag aacatggtgc tgagagaact aaccaagatt     1500
aatccaacca ccgtcatgtc cagcatctac ggtaaggcgg tggcggccaa gcgcctgggg     1560
gatgtcatct cagtctccca gtgcgtgccc gttaaccagg ccaccgtcac cctgcgcaag     1620
agcatgaggg tccctggctc cgagaccatg tgctactcgc gccccctggt gtccttcagc     1680
tttatcaacg acaccaagac ctacgaggga cagctgggca ccgacaacga gatcttcctc     1740
acaaaaaaga tgacggaggt gtgccaggcg accagccagt actacttcca gtccggcaac     1800
gagatccacg tctacaacga ctaccaccac tttaaaacca tcgagctgga cggcattgcc     1860
accctgcaga ccttcatctc actaaacacc tccctcatcg agaacattga ctttgcctcc     1920
ctggagctgt actcacggga cgaacagcgt gcctccaacg tctttgacct ggagggcatc     1980
ttccgggagt acaacttcca ggcgcaaaac atcgccggcc tgcggaagga tttggacaat     2040
gcagtgtcaa acggaagaaa tcaattcgtg gacggcctgg gggaacttat ggacagtctg     2100
ggtagcgtgg gtcagtccat caccaaccta gtcagcacgg tggggggttt gtttagcagc     2160
ctggtctctg gtttcatctc cttcttcaaa aacccc                              2196
```

```
<210> SEQ ID NO 83
<211> LENGTH: 732
<212> TYPE: PRT
<213> ORGANISM: Artificial Sequence
<220> FEATURE:
<223> OTHER INFORMATION: Synthetic

<400> SEQUENCE: 83

Met Thr Arg Arg Arg Val Leu Ser Val Val Val Leu Leu Ala Ala Leu
1               5                   10                  15

Ala Cys Arg Leu Gly Ala Gln Thr Pro Glu Gln Pro Ala Pro Pro Ala
            20                  25                  30

Thr Thr Val Gln Pro Thr Ala Thr Arg Gln Gln Thr Ser Phe Pro Phe
        35                  40                  45

Arg Val Cys Glu Leu Ser Ser His Gly Asp Leu Phe Arg Phe Ser Ser
    50                  55                  60

Asp Ile Gln Cys Pro Ser Phe Gly Thr Arg Glu Asn His Thr Glu Gly
65                  70                  75                  80

Leu Leu Met Val Phe Lys Asp Asn Ile Ile Pro Tyr Ser Phe Lys Val
                85                  90                  95

Arg Ser Tyr Thr Lys Ile Val Thr Asn Ile Leu Ile Tyr Asn Gly Trp
            100                 105                 110
```

-continued

```
Tyr Ala Asp Ser Val Thr Asn Arg His Glu Glu Lys Phe Ser Val Asp
        115                 120                 125

Ser Tyr Glu Thr Asp Gln Met Asp Thr Ile Tyr Gln Cys Tyr Asn Ala
        130                 135                 140

Val Lys Met Thr Lys Asp Gly Leu Thr Arg Val Tyr Val Asp Arg Asp
145                 150                 155                 160

Gly Val Asn Ile Thr Val Asn Leu Lys Pro Thr Gly Gly Leu Ala Asn
                165                 170                 175

Gly Val Arg Arg Tyr Ala Ser Gln Thr Glu Leu Tyr Asp Ala Pro Gly
                180                 185                 190

Trp Leu Ile Trp Thr Tyr Arg Thr Arg Thr Thr Val Asn Cys Leu Ile
                195                 200                 205

Thr Asp Met Met Ala Lys Ser Asn Ser Pro Phe Asp Phe Phe Val Thr
        210                 215                 220

Thr Thr Gly Gln Thr Val Glu Met Ser Pro Phe Tyr Asp Gly Lys Asn
225                 230                 235                 240

Lys Glu Thr Phe His Glu Arg Ala Asp Ser Phe His Val Arg Thr Asn
                245                 250                 255

Tyr Lys Ile Val Asp Tyr Asp Asn Arg Gly Thr Asn Pro Gln Gly Glu
                260                 265                 270

Arg Arg Ala Phe Leu Asp Lys Gly Thr Tyr Thr Leu Ser Trp Lys Leu
        275                 280                 285

Glu Asn Arg Thr Ala Tyr Cys Pro Leu Gln His Trp Gln Thr Phe Asp
        290                 295                 300

Ser Thr Ile Ala Thr Glu Thr Gly Lys Ser Ile His Phe Val Thr Asp
305                 310                 315                 320

Glu Gly Thr Ser Ser Phe Val Thr Asn Thr Thr Val Gly Ile Glu Leu
                325                 330                 335

Pro Asp Ala Phe Lys Cys Ile Glu Glu Gln Val Asn Lys Thr Met His
                340                 345                 350

Glu Lys Tyr Glu Ala Val Gln Asp Arg Tyr Thr Lys Gly Gln Glu Ala
        355                 360                 365

Ile Thr Tyr Phe Ile Thr Ser Gly Gly Leu Leu Leu Ala Trp Leu Pro
        370                 375                 380

Leu Thr Pro Arg Ser Leu Ala Thr Val Lys Asn Leu Thr Glu Leu Thr
385                 390                 395                 400

Thr Pro Thr Ser Ser Pro Pro Ser Ser Pro Ser Pro Ala Pro Ser
                405                 410                 415

Ala Ala Arg Gly Ser Thr Pro Ala Ala Val Leu Arg Arg Arg Arg
                420                 425                 430

Asp Ala Gly Asn Ala Thr Thr Pro Val Pro Thr Ala Pro Gly Lys
        435                 440                 445

Ser Leu Gly Thr Leu Asn Asn Pro Ala Thr Val Gln Ile Gln Phe Ala
        450                 455                 460

Tyr Asp Ser Leu Arg Arg Gln Ile Asn Arg Met Leu Gly Asp Leu Ala
465                 470                 475                 480

Arg Ala Trp Cys Leu Glu Gln Lys Arg Gln Asn Met Val Leu Arg Glu
                485                 490                 495

Leu Thr Lys Ile Asn Pro Thr Thr Val Met Ser Ser Ile Tyr Gly Lys
                500                 505                 510

Ala Val Ala Ala Lys Arg Leu Gly Asp Val Ile Ser Val Ser Gln Cys
        515                 520                 525

Val Pro Val Asn Gln Ala Thr Val Thr Leu Arg Lys Ser Met Arg Val
```

-continued

```
        530               535                540

Pro Gly Ser Glu Thr Met Cys Tyr Ser Arg Pro Leu Val Ser Phe Ser
545               550                555                560

Phe Ile Asn Asp Thr Lys Thr Tyr Glu Gly Gln Leu Gly Thr Asp Asn
                565                570                575

Glu Ile Phe Leu Thr Lys Lys Met Thr Glu Val Cys Gln Ala Thr Ser
            580                585                590

Gln Tyr Tyr Phe Gln Ser Gly Asn Glu Ile His Val Tyr Asn Asp Tyr
            595                600                605

His His Phe Lys Thr Ile Glu Leu Asp Gly Ile Ala Thr Leu Gln Thr
    610                615                620

Phe Ile Ser Leu Asn Thr Ser Leu Ile Glu Asn Ile Asp Phe Ala Ser
625               630                635                640

Leu Glu Leu Tyr Ser Arg Asp Glu Gln Arg Ala Ser Asn Val Phe Asp
                645                650                655

Leu Glu Gly Ile Phe Arg Glu Tyr Asn Phe Gln Ala Gln Asn Ile Ala
            660                665                670

Gly Leu Arg Lys Asp Leu Asp Asn Ala Val Ser Asn Gly Arg Asn Gln
            675                680                685

Phe Val Asp Gly Leu Gly Glu Leu Met Asp Ser Leu Gly Ser Val Gly
    690                695                700

Gln Ser Ile Thr Asn Leu Val Ser Thr Val Gly Gly Leu Phe Ser Ser
705               710                715                720

Leu Val Ser Gly Phe Ile Ser Phe Phe Lys Asn Pro
                725                730
```

```
<210> SEQ ID NO 84
<211> LENGTH: 414
<212> TYPE: DNA
<213> ORGANISM: Artificial Sequence
<220> FEATURE:
<223> OTHER INFORMATION: Synthetic

<400> SEQUENCE: 84
atgcgtgctg ttggtgtatt tctggccatc tgtcttgtca ccattttcgt cctcccaaca      60
tggggcaatt gggcataccc atgttgtcac gtcactcagc tccgcgctca acaccttctc     120
gcgttggaaa acattagcga catttacctg gtgagcaatc agacatgcga cggctttagc     180
ctggcctcct taaattcacc taagaatggg agcaaccagc tggtcatcag ccgctgcgca     240
aacggactca acgtggtctc cttctttatc tccatcctga gcgaagcag ctccgccctc      300 acgggccatc tccgtgagtt gttaaccacc ctggagactc tttacggttc attctcagtg     360
gaagacctgt ttggtgccaa cttaaacaga tacgcatggc atcgcggggg ctag           414
```

```
<210> SEQ ID NO 85
<211> LENGTH: 137
<212> TYPE: PRT
<213> ORGANISM: Artificial Sequence
<220> FEATURE:
<223> OTHER INFORMATION: Synthetic

<400> SEQUENCE: 85

Met Arg Ala Val Gly Val Phe Leu Ala Ile Cys Leu Val Thr Ile Phe
1               5                10                15

Val Leu Pro Thr Trp Gly Asn Trp Ala Tyr Pro Cys Cys His Val Thr
            20                25                30

Gln Leu Arg Ala Gln His Leu Leu Ala Leu Glu Asn Ile Ser Asp Ile
```

-continued

```
                35                   40                   45
Tyr Leu Val Ser Asn Gln Thr Cys Asp Gly Phe Ser Leu Ala Ser Leu
    50                   55                   60
Asn Ser Pro Lys Asn Gly Ser Asn Gln Leu Val Ile Ser Arg Cys Ala
65                   70                   75                   80
Asn Gly Leu Asn Val Val Ser Phe Phe Ile Ser Ile Leu Lys Arg Ser
                85                   90                   95
Ser Ser Ala Leu Thr Gly His Leu Arg Glu Leu Leu Thr Thr Leu Glu
            100                  105                  110
Thr Leu Tyr Gly Ser Phe Ser Val Glu Asp Leu Phe Gly Ala Asn Leu
        115                  120                  125
Asn Arg Tyr Ala Trp His Arg Gly Gly
    130                  135

<210> SEQ ID NO 86
<211> LENGTH: 2121
<212> TYPE: DNA
<213> ORGANISM: Artificial Sequence
<220> FEATURE:
<223> OTHER INFORMATION: Synthetic

<400> SEQUENCE: 86
atgcagttgc tctgtgtttt ttgcctggtg ttgctatggg aggtgggggc tgccagcctc      60
agcgaggtta agctgcacct ggacatagag gggcatgctt cgcattacac catcccatgg     120
accgaactga tggcaaaggt cccaggcctt agcccagagg cgctgtggag agaggcaaat     180
gtcaccgaag atttggcgtc tatgcttaac cgctacaagt taatttacaa gacgtctggt     240
acccttggta ttgcgctggc cgagcctgtc gatatccctg ctgtctctga aggatccatg     300
caagtggatc catctaaggt ccatcccgga gtcattagcg gcctgaattc ccctgcctgc     360
atgcttagtg ccccccttga gaagcagctc ttctactata ttggcaccat gctgcccaac     420
acgcggccac acagctatgt cttttatcag ctgcgctgtc acttgtctta tgtgccctg     480 tccatcaacg gggacaagtt tcagtacacg ggggccatga cttctaaatt tctgatgggc     540
acctacaagc gagtgaccga aagggagat gagcatgtgt tgagcctggt ctttggcaag     600
acgaaggacc tgccggatct gagggggcct tttagttacc catccttaac cagtgcccaa     660 agcgggact attccctggt gattgttaca acctttgtgc attatgccaa ctttcacaac     720
tactttgtac ccaacctgaa ggatatgttt tcccgagccg tcaccatgac agccgccagc     780
tacgctcgct acgttctcca gaaactggtc ctgctggaga tgaagggagg ctgccgggag     840
ccggaactgg acacggaaac gctgactacc atgtttgagg tttctgtggc cttctttaag     900
gtgggtcatg ctgtgggtga gactggcaat ggctgcgtgg acctccgctg gttggccaag     960
agcttctttg agctgactgt cctgaaagac atcatcggca tatgttatgg ggccactgtc    1020
aagggcatgc aatcctacgg gctggagcgc ttggccgcca tgctgatggc cacggtcaag    1080
atggaggagc tgggtcacct gactactgag aaacaggagt acgcgctgag gttagccacc    1140
gtcggctacc ccaaggccgg ggtttacagt ggcctcattg gaggcgccac atctgtgctt    1200
ctctcggcct acaaccgcca cccccttttc cagcccctgc ataccgtgat gagagagacc    1260
ctgtttatcg gcagccacgt ggtgctacgc gagttgcggc tgaacgtgac tacccagggg    1320
cccaaccttg ccctatacca actgctgtcc accgccctgt gctcggccct agagattggg    1380
gaggttttgc gggggctagc cctggggaca gagagcgggc tcttctcacc gtgctacctc    1440
agcctacgat ttgacctcac acgagacaag ctgctgagca tggcccccca ggaggcaacg    1500
```

-continued

```
ctggaccagg cggccgtttc aaatgctgtg gatgggtttc ttgggcggct ctctttggag      1560
cgagaagaca gggatgcgtg gcatctcccc gcctacaaat gcgtggacag gctcgacaaa      1620
gttctgatga ttatcccgct catcaatgtg acattcataa tctctagtga ccgtgaggtc      1680
cgaggctcgg cgctatacga ggccagcacc acctatctca gcagctctct ctttctctcc      1740
cccgttataa tgaataaatg ttcgcagggt gctgtggctg gggagccccg ccagattcca      1800
aagatccaga attttaccag gacgcagaaa tcctgcattt tttgtggctt tgccctgctc      1860
agttatgatg aaaaggaagg cctggaaact acaacctaca tcacctccca ggaagtccaa      1920
aactccatct tgagctccaa ctactttgat tttgacaacc tccacgttca ctatctgctg      1980
ctgaccacca acgggactgt catggaaatt gcgggcctgt atgaagaaag agcacacgtt      2040
gttttggcaa taatcctgta ctttattgct tttgctctgg gtatctttct ggttcacaag      2100
attgttatgt ttttccttta g                                                2121
```

```
<210> SEQ ID NO 87
<211> LENGTH: 706
<212> TYPE: PRT
<213> ORGANISM: Artificial Sequence
<220> FEATURE:
<223> OTHER INFORMATION: Synthetic

<400> SEQUENCE: 87

Met Gln Leu Leu Cys Val Phe Cys Leu Val Leu Leu Trp Glu Val Gly
1               5                   10                  15

Ala Ala Ser Leu Ser Glu Val Lys Leu His Leu Asp Ile Glu Gly His
            20                  25                  30

Ala Ser His Tyr Thr Ile Pro Trp Thr Glu Leu Met Ala Lys Val Pro
        35                  40                  45

Gly Leu Ser Pro Glu Ala Leu Trp Arg Glu Ala Asn Val Thr Glu Asp
    50                  55                  60

Leu Ala Ser Met Leu Asn Arg Tyr Lys Leu Ile Tyr Lys Thr Ser Gly
65                  70                  75                  80

Thr Leu Gly Ile Ala Leu Ala Glu Pro Val Asp Ile Pro Ala Val Ser
                85                  90                  95

Glu Gly Ser Met Gln Val Asp Ala Ser Lys Val His Pro Gly Val Ile
            100                 105                 110

Ser Gly Leu Asn Ser Pro Ala Cys Met Leu Ser Ala Pro Leu Glu Lys
        115                 120                 125

Gln Leu Phe Tyr Tyr Ile Gly Thr Met Leu Pro Asn Thr Arg Pro His
    130                 135                 140

Ser Tyr Val Phe Tyr Gln Leu Arg Cys His Leu Ser Tyr Val Ala Leu
145                 150                 155                 160

Ser Ile Asn Gly Asp Lys Phe Gln Tyr Thr Gly Ala Met Thr Ser Lys
                165                 170                 175

Phe Leu Met Gly Thr Tyr Lys Arg Val Thr Glu Lys Gly Asp Glu His
            180                 185                 190

Val Leu Ser Leu Val Phe Gly Lys Thr Lys Asp Leu Pro Asp Leu Arg
        195                 200                 205

Gly Pro Phe Ser Tyr Pro Ser Leu Thr Ser Ala Gln Ser Gly Asp Tyr
    210                 215                 220

Ser Leu Val Ile Val Thr Thr Phe Val His Tyr Ala Asn Phe His Asn
225                 230                 235                 240

Tyr Phe Val Pro Asn Leu Lys Asp Met Phe Ser Arg Ala Val Thr Met
```

-continued

```
                    245                 250                 255

Thr Ala Ala Ser Tyr Ala Arg Tyr Val Leu Gln Lys Leu Val Leu Leu
                260                 265                 270

Glu Met Lys Gly Gly Cys Arg Glu Pro Glu Leu Asp Thr Glu Thr Leu
                275                 280                 285

Thr Thr Met Phe Glu Val Ser Val Ala Phe Phe Lys Val Gly His Ala
        290                 295                 300

Val Gly Glu Thr Gly Asn Gly Cys Val Asp Leu Arg Trp Leu Ala Lys
305                 310                 315                 320

Ser Phe Phe Glu Leu Thr Val Leu Lys Asp Ile Ile Gly Ile Cys Tyr
                325                 330                 335

Gly Ala Thr Val Lys Gly Met Gln Ser Tyr Gly Leu Glu Arg Leu Ala
                340                 345                 350

Ala Met Leu Met Ala Thr Val Lys Met Glu Glu Leu Gly His Leu Thr
                355                 360                 365

Thr Glu Lys Gln Glu Tyr Ala Leu Arg Leu Ala Thr Val Gly Tyr Pro
        370                 375                 380

Lys Ala Gly Val Tyr Ser Gly Leu Ile Gly Gly Ala Thr Ser Val Leu
385                 390                 395                 400

Leu Ser Ala Tyr Asn Arg His Pro Leu Phe Gln Pro Leu His Thr Val
                405                 410                 415

Met Arg Glu Thr Leu Phe Ile Gly Ser His Val Val Leu Arg Glu Leu
                420                 425                 430

Arg Leu Asn Val Thr Thr Gln Gly Pro Asn Leu Ala Leu Tyr Gln Leu
                435                 440                 445

Leu Ser Thr Ala Leu Cys Ser Ala Leu Glu Ile Gly Glu Val Leu Arg
        450                 455                 460

Gly Leu Ala Leu Gly Thr Glu Ser Gly Leu Phe Ser Pro Cys Tyr Leu
465                 470                 475                 480

Ser Leu Arg Phe Asp Leu Thr Arg Asp Lys Leu Leu Ser Met Ala Pro
                485                 490                 495

Gln Glu Ala Thr Leu Asp Gln Ala Ala Val Ser Asn Ala Val Asp Gly
                500                 505                 510

Phe Leu Gly Arg Leu Ser Leu Glu Arg Glu Asp Arg Asp Ala Trp His
                515                 520                 525

Leu Pro Ala Tyr Lys Cys Val Asp Arg Leu Asp Lys Val Leu Met Ile
        530                 535                 540

Ile Pro Leu Ile Asn Val Thr Phe Ile Ile Ser Ser Asp Arg Glu Val
545                 550                 555                 560

Arg Gly Ser Ala Leu Tyr Glu Ala Ser Thr Thr Tyr Leu Ser Ser Ser
                565                 570                 575

Leu Phe Leu Ser Pro Val Ile Met Asn Lys Cys Ser Gln Gly Ala Val
                580                 585                 590

Ala Gly Glu Pro Arg Gln Ile Pro Lys Ile Gln Asn Phe Thr Arg Thr
                595                 600                 605

Gln Lys Ser Cys Ile Phe Cys Gly Phe Ala Leu Leu Ser Tyr Asp Glu
        610                 615                 620

Lys Glu Gly Leu Glu Thr Thr Thr Tyr Ile Thr Ser Gln Glu Val Gln
625                 630                 635                 640

Asn Ser Ile Leu Ser Ser Asn Tyr Phe Asp Phe Asp Asn Leu His Val
                645                 650                 655

His Tyr Leu Leu Leu Thr Thr Asn Gly Thr Val Met Glu Ile Ala Gly
                660                 665                 670
```

-continued

```
Leu Tyr Glu Glu Arg Ala His Val Val Leu Ala Ile Ile Leu Tyr Phe
        675                 680                 685

Ile Ala Phe Ala Leu Gly Ile Phe Leu Val His Lys Ile Val Met Phe
    690                 695                 700

Phe Leu
705
```

```
<210> SEQ ID NO 88
<211> LENGTH: 747
<212> TYPE: DNA
<213> ORGANISM: Artificial Sequence
<220> FEATURE:
<223> OTHER INFORMATION: Synthetic

<400> SEQUENCE: 88
atgactcatt tagtgcttct attgtgctgc tgtgtggggt ctgtttgtgc attttttctca      60 gatctggtta aatttgaaaa tgtcaccgcc catgcaggtg ctagagtgaa tctcacctgc     120
agcgttccta gcaatgagtc ggtctctcgg atcgagttgg gccggggata cactcccggg     180
gatggacaac tgcccttggc cgtagctact tccaacaacg gaactcatat aactaacggg     240
ggttacaatt atagccttac cctagaatgg gtaaatgact ccaacacctc cgtctctctg     300
ataatcccca atgtgaccct tgcgcatgca ggttactaca cgtgcaatgt gacactgaga     360
aattgcagtg tggcctccgg ggtccactgc aattactctg caggggaaga agacgaccaa     420
taccatgcca accggaccct cactcagcgt atgcatctta ctgttatccc agccactacc     480
atagccccca ccacattagt ctcccacacc acaagcacca gtcacaggcc ccataggcgg     540
cctgtttcta aacgtcccac gcataagcca gtgaccctgg gccctttttcc aatcgatccc     600 tggcgcccta agaccacctg ggtgcactgg gccctgctcc taatcacttg tgctgtggtg     660
gctccggtgc tcctcatcat tatcatctcc tgtctggggt ggctggcggg ctgggggagg     720
cggcgcaagg gctggatacc cctgtga                                         747
```

```
<210> SEQ ID NO 89
<211> LENGTH: 248
<212> TYPE: PRT
<213> ORGANISM: Artificial Sequence
<220> FEATURE:
<223> OTHER INFORMATION: Synthetic

<400> SEQUENCE: 89

Met Thr His Leu Val Leu Leu Leu Cys Cys Cys Val Gly Ser Val Cys
1               5                   10                  15

Ala Phe Phe Ser Asp Leu Val Lys Phe Glu Asn Val Thr Ala His Ala
            20                  25                  30

Gly Ala Arg Val Asn Leu Thr Cys Ser Val Pro Ser Asn Glu Ser Val
        35                  40                  45

Ser Arg Ile Glu Leu Gly Arg Gly Tyr Thr Pro Gly Asp Gly Gln Leu
    50                  55                  60

Pro Leu Ala Val Ala Thr Ser Asn Asn Gly Thr His Ile Thr Asn Gly
65                  70                  75                  80

Gly Tyr Asn Tyr Ser Leu Thr Leu Glu Trp Val Asn Asp Ser Asn Thr
                85                  90                  95

Ser Val Ser Leu Ile Ile Pro Asn Val Thr Leu Ala His Ala Gly Tyr
            100                 105                 110

Tyr Thr Cys Asn Val Thr Leu Arg Asn Cys Ser Val Ala Ser Gly Val
        115                 120                 125
```

-continued

---

His Cys Asn Tyr Ser Ala Gly Glu Glu Asp Asp Gln Tyr His Ala Asn
    130                 135                 140

Arg Thr Leu Thr Gln Arg Met His Leu Thr Val Ile Pro Ala Thr Thr
145                 150                 155                 160

Ile Ala Pro Thr Thr Leu Val Ser His Thr Thr Ser Thr Ser His Arg
                165                 170                 175

Pro His Arg Arg Pro Val Ser Lys Arg Pro Thr His Lys Pro Val Thr
                180                 185                 190

Leu Gly Pro Phe Pro Ile Asp Pro Trp Arg Pro Lys Thr Thr Trp Val
                195                 200                 205

His Trp Ala Leu Leu Leu Ile Thr Cys Ala Val Val Ala Pro Val Leu
    210                 215                 220

Leu Ile Ile Ile Ile Ser Cys Leu Gly Trp Leu Ala Gly Trp Gly Arg
225                 230                 235                 240

Arg Arg Lys Gly Trp Ile Pro Leu
                245

<210> SEQ ID NO 90
<211> LENGTH: 531
<212> TYPE: DNA
<213> ORGANISM: Artificial Sequence
<220> FEATURE:
<223> OTHER INFORMATION: Synthetic

<400> SEQUENCE: 90
atggcacgcc ggctgcccaa gcccaccctc caggggaggc tggaggcgga ttttccagac      60
agtcccctgc ttcctaaatt tcaagagctg aaccagaata atctccccaa tgatgttttt     120
cgggaggctc aaaggagtta cctggtattt ctgacgtccc agttctgcta cgaagagtac     180
gtgcagagga cttttggggt gcctcggcgc caacgcgcca tagacaagag gcagagagcc     240
agtgtggctg gggctggtgc tcatgcacac cttggcgggt catccgccac ccccgtccag     300
caggctcagg ccgccgcatc cgctgggact ggggccttgg catcatcagc gccgtccacg     360
gccgtagccc agtccgcgac cccctctgtt tcttcatcta ttagcagcct ccgggccgcg     420
acttcggggg cgactgccgc cgcctctgcc gccgcagccg tcgataccgg gtcaggtggc     480
gggggacaac cccaagacac cgccccgcgc ggggcacgta agaaacagta g             531

<210> SEQ ID NO 91
<211> LENGTH: 176
<212> TYPE: PRT
<213> ORGANISM: Artificial Sequence
<220> FEATURE:
<223> OTHER INFORMATION: Synthetic

<400> SEQUENCE: 91

Met Ala Arg Arg Leu Pro Lys Pro Thr Leu Gln Gly Arg Leu Glu Ala
1               5                   10                  15

Asp Phe Pro Asp Ser Pro Leu Leu Pro Lys Phe Gln Glu Leu Asn Gln
                20                  25                  30

Asn Asn Leu Pro Asn Asp Val Phe Arg Glu Ala Gln Arg Ser Tyr Leu
        35                  40                  45

Val Phe Leu Thr Ser Gln Phe Cys Tyr Glu Glu Tyr Val Gln Arg Thr
    50                  55                  60

Phe Gly Val Pro Arg Arg Gln Arg Ala Ile Asp Lys Arg Gln Arg Ala
65                  70                  75                  80

Ser Val Ala Gly Ala Gly Ala His Ala His Leu Gly Gly Ser Ser Ala

```
                   85                    90                    95

Thr Pro Val Gln Gln Ala Gln Ala Ala Ala Ser Ala Gly Thr Gly Ala
                  100                   105                   110

Leu Ala Ser Ser Ala Pro Ser Thr Ala Val Ala Gln Ser Ala Thr Pro
         115                   120                   125

Ser Val Ser Ser Ser Ile Ser Ser Leu Arg Ala Ala Thr Ser Gly Ala
    130                   135                   140

Thr Ala Ala Ala Ser Ala Ala Ala Ala Val Asp Thr Gly Ser Gly Gly
145                   150                   155                   160

Gly Gly Gln Pro Gln Asp Thr Ala Pro Arg Gly Ala Arg Lys Lys Gln
              165                   170                   175

<210> SEQ ID NO 92
<211> LENGTH: 3000
<212> TYPE: DNA
<213> ORGANISM: Artificial Sequence
<220> FEATURE:
<223> OTHER INFORMATION: Synthetic

<400> SEQUENCE: 92
cgggcacaat ttctggcggc ggcagggccg gcgaaatacg ccggcaccct ctggctggaa      60
acagagtctc cctgcgaccc ccttaacccg gcctacgtct ccgcagacac ccaggagccg     120
ctcaactaca tccccgtcta ccacaacttt ctggaatatg tcatgcccac cgtgctggag     180
aacccagagg ccttttccct gaccccagcc ggacgccccc aagctattgg tcccccgcag     240
gatgaccaag agaggaggag aagaaccctg gccagtgtag cttccgcccg cctcagcgcc     300
gccgccgccg actcctactg ggacacctgg cccgacgtgg agtccaacgc cggggagctg     360
cttcgggaat acgtctctgc gcccaaagcc ctgatggaag acctggcaga caaccccatt     420
gtggccatga cactttttagc gcacgccagt ctcatcgcct ctaggaatca ccccccttat     480
ccagccccgg ccacagaccg ggaagttatt ctattggaac aacgggagat gatggcgctg     540
ctggtcggca cacatccggc ctacgctgcc gccttcctgg gcgcccccatc gttctacgca     600 ggactcggcc tggtctcggc tctagcgaga gatgggggtt tgggagacct cctgtcggac     660
tcggtcctca cctacaggct ggtcaggagt ccagcctccg ggagggggggg catgccctca     720 accacccgcg gcagcaacga cggggaagac gcgcgccgcc tcacccgcca ccgcatcgcc     780
ggtccaccca ccggcttcat cttcttccag gacgcctggg aggagatgga tacccgagcc     840
gccctctggc cgcaccccga gttcttgggc ctggtccaca accaaagtac ggcccgcgcc     900
cgagcctgca tgctgctcct cgcacgccgg tgcttcgccc ccgaggccct tcagcagctc     960
tggcactcat tgcgcccgct ggagggcccg gtcgcatttc aggactacct gcgcgacttt    1020
gtgaagcagg cctatacacg cggagaagag ctccccaggg cggagggact cgaggtcccc    1080
cgcgaaaccc cgtcttccta cggcaccgtt accggccggg ccctgagaaa tcttatgcct    1140
tatggcactc ccattaccgg tcctaagagg ggctccggtg acaccatccc cgtctccgtt    1200
tttgaggcgg ccgtggcggc ggccttcctc ggtcggcccc taactctctt tgtctcctct    1260
caatatctgt ttaacctgaa gaccctggga caggtcaggg tcgttgctcc cctcctctac    1320
tgcgacgggc actctgagcc cttccggtcc ctggtggaga ccatctcgct gaattttctg    1380
caggacctgg acggctactc cgagtctttc gagccagaga tgtccatctt gcacgccag     1440 gccgtgtggc tacgcgagct tctcaccgag gccaggggccg ccaaacctaa ggaggccagg    1500 cccccccaccg tggccatcct ggccaacaga aaaaacatca tctggaagtg tttcacctat    1560
```

```
cggcacaatc tgccggacgt gcagttctac tttaacgcgg ccggggcctc acgatggccg    1620
accgatgtac tcaacccctc cttctacgag cacgaagatc ctccactgcc ggttggatac    1680
cagcttcccc cgaatccacg caacgtccag gagctgttct ccggtttccc cccaagggtg    1740
gggcacggac tggtcagcgg ggacgggttt cagtcagcag ataacacccc ggcctcctcc    1800
gaccggctcc agcagttggg aggaggggag acggaccagg gggaaaaggg gagcactact    1860
gctgaatctg aggcctctgg ccctcccagc ccacagagcc ccctcttaga gaaggtggcc    1920
cctggcaggc ccagggactg gctgtctcct acctcctccc cccgggacgt gacagttacc    1980
ccggattggg ccgcccccat cactctccca ggccccgat tgatggcaag ccctatttc     2040 ggggccgaaa cgagggcttc cgagagccca gaccggtctc cgggaagctc cccaaggcca    2100
tggcccaaag attccctgga gctccttccc caaccagcac cacaacagcc cccctcaagt    2160
ccctgggctt ctgaacaagg gcccatcgtc tacacattgt ctccacactc tacaccatcg    2220
actgcctcgg ggtcacagaa gaaacatacc atccagattc cagggttggt gccttcacag    2280
aagcccagtt atccaccctc agcccctac aagcccggcc agtcgacggg aggcatagct    2340
cccacaccat cagcggcatc tttaacgact tttgggctcc agccccagga cacacaagcc    2400
tcctctcagg acccaccta tggccattct atcatgcaac gggagaagaa acagcagggg    2460
ggccgggaag aagccgcgga gattcggccc tccgccaccc gcctccccac ggccgtcggg    2520
ctgcgacccc gtgcgcccgt ggtggccgcc ggcgcagcag cctccgctac tccagcgttc    2580
gacccgggag aagcgccgtc cggctttccc atccccagg cacccgccct ggggtccggc    2640
ttggccgccc cggcgcacac cccagttggt gcattggcac cgcgcccca aaaaacgcaa    2700 gcacaaaggc cccaagatgc agctgccctg cccaccccca caattaaagc ggtgggtgcc    2760
aggcccgtgc caaaggccac gggggcgctg gcggccggcg cccgtcctcg ggggcagccc    2820
accgcggccc cgccgtcggc tgcatctccg ccgcgcgtgt ctctccctgt caggagcaga    2880
cagcaacaat cccccgcaat cccattgccc ccaatgcatt ccggctcgga gcctggcgcg    2940
cggcccgagg tgcgcctatc ccagtaccgg catgcgggtc cccaaacata caccgtgcga    3000
```

```
<210> SEQ ID NO 93
<211> LENGTH: 1000
<212> TYPE: PRT
<213> ORGANISM: Artificial Sequence
<220> FEATURE:
<223> OTHER INFORMATION: Synthetic

<400> SEQUENCE: 93

Arg Ala Gln Phe Leu Ala Ala Ala Gly Pro Ala Lys Tyr Ala Gly Thr
1               5                   10                  15

Leu Trp Leu Glu Thr Glu Ser Pro Cys Asp Pro Leu Asn Pro Ala Tyr
            20                  25                  30

Val Ser Ala Asp Thr Gln Glu Pro Leu Asn Tyr Ile Pro Val Tyr His
        35                  40                  45

Asn Phe Leu Glu Tyr Val Met Pro Thr Val Leu Glu Asn Pro Glu Ala
        50                  55                  60

Phe Ser Leu Thr Pro Ala Gly Arg Pro Gln Ala Ile Gly Pro Gln
65                  70                  75                  80

Asp Asp Gln Glu Arg Arg Arg Arg Thr Leu Ala Ser Val Ala Ser Ala
                85                  90                  95

Arg Leu Ser Ala Ala Ala Ala Asp Ser Tyr Trp Asp Thr Trp Pro Asp
            100                 105                 110
```

-continued

```
Val Glu Ser Asn Ala Gly Glu Leu Leu Arg Glu Tyr Val Ser Ala Pro
        115                 120                 125

Lys Ala Leu Met Glu Asp Leu Ala Asp Asn Pro Ile Val Ala Met Thr
        130                 135                 140

Leu Leu Ala His Ala Ser Leu Ile Ala Ser Arg Asn His Pro Pro Tyr
145                 150                 155                 160

Pro Ala Pro Ala Thr Asp Arg Glu Val Ile Leu Leu Glu Gln Arg Glu
                165                 170                 175

Met Met Ala Leu Leu Val Gly Thr His Pro Ala Tyr Ala Ala Ala Phe
                180                 185                 190

Leu Gly Ala Pro Ser Phe Tyr Ala Gly Leu Gly Leu Val Ser Ala Leu
                195                 200                 205

Ala Arg Asp Gly Gly Leu Gly Asp Leu Leu Ser Asp Ser Val Leu Thr
        210                 215                 220

Tyr Arg Leu Val Arg Ser Pro Ala Ser Gly Arg Gly Gly Met Pro Ser
225                 230                 235                 240

Thr Thr Arg Gly Ser Asn Asp Gly Glu Asp Ala Arg Arg Leu Thr Arg
                245                 250                 255

His Arg Ile Ala Gly Pro Pro Thr Gly Phe Ile Phe Phe Gln Asp Ala
                260                 265                 270

Trp Glu Glu Met Asp Thr Arg Ala Ala Leu Trp Pro His Pro Glu Phe
        275                 280                 285

Leu Gly Leu Val His Asn Gln Ser Thr Ala Arg Ala Arg Ala Cys Met
        290                 295                 300

Leu Leu Leu Ala Arg Arg Cys Phe Ala Pro Glu Ala Leu Gln Gln Leu
305                 310                 315                 320

Trp His Ser Leu Arg Pro Leu Glu Gly Pro Val Ala Phe Gln Asp Tyr
                325                 330                 335

Leu Arg Asp Phe Val Lys Gln Ala Tyr Thr Arg Gly Glu Glu Leu Pro
                340                 345                 350

Arg Ala Glu Gly Leu Glu Val Pro Arg Glu Thr Pro Ser Ser Tyr Gly
        355                 360                 365

Thr Val Thr Gly Arg Ala Leu Arg Asn Leu Met Pro Tyr Gly Thr Pro
        370                 375                 380

Ile Thr Gly Pro Lys Arg Gly Ser Gly Asp Thr Ile Pro Val Ser Val
385                 390                 395                 400

Phe Glu Ala Ala Val Ala Ala Ala Phe Leu Gly Arg Pro Leu Thr Leu
                405                 410                 415

Phe Val Ser Ser Gln Tyr Leu Phe Asn Leu Lys Thr Leu Gly Gln Val
                420                 425                 430

Arg Val Val Ala Pro Leu Leu Tyr Cys Asp Gly His Ser Glu Pro Phe
        435                 440                 445

Arg Ser Leu Val Glu Thr Ile Ser Leu Asn Phe Leu Gln Asp Leu Asp
        450                 455                 460

Gly Tyr Ser Glu Ser Phe Glu Pro Glu Met Ser Ile Phe Ala Arg Gln
465                 470                 475                 480

Ala Val Trp Leu Arg Glu Leu Leu Thr Glu Ala Arg Ala Ala Lys Pro
                485                 490                 495

Lys Glu Ala Arg Pro Pro Thr Val Ala Ile Leu Ala Asn Arg Lys Asn
                500                 505                 510

Ile Ile Trp Lys Cys Phe Thr Tyr Arg His Asn Leu Pro Asp Val Gln
        515                 520                 525

Phe Tyr Phe Asn Ala Ala Gly Ala Ser Arg Trp Pro Thr Asp Val Leu
```

```
                 530                 535                 540

Asn Pro Ser Phe Tyr Glu His Glu Asp Pro Pro Leu Pro Val Gly Tyr
545                 550                 555                 560

Gln Leu Pro Pro Asn Pro Arg Asn Val Gln Glu Leu Phe Ser Gly Phe
                565                 570                 575

Pro Pro Arg Val Gly His Gly Leu Val Ser Gly Asp Gly Phe Gln Ser
                580                 585                 590

Ala Asp Asn Thr Pro Ala Ser Ser Asp Arg Leu Gln Gln Leu Gly Gly
                595                 600                 605

Gly Glu Thr Asp Gln Gly Glu Lys Gly Ser Thr Thr Ala Glu Ser Glu
                610                 615                 620

Ala Ser Gly Pro Pro Ser Pro Gln Ser Pro Leu Leu Glu Lys Val Ala
625                 630                 635                 640

Pro Gly Arg Pro Arg Asp Trp Leu Ser Pro Thr Ser Ser Pro Arg Asp
                645                 650                 655

Val Thr Val Thr Pro Gly Leu Ala Ala Pro Ile Thr Leu Pro Gly Pro
                660                 665                 670

Arg Leu Met Ala Arg Pro Tyr Phe Gly Ala Glu Thr Arg Ala Ser Glu
                675                 680                 685

Ser Pro Asp Arg Ser Pro Gly Ser Ser Pro Arg Pro Trp Pro Lys Asp
                690                 695                 700

Ser Leu Glu Leu Leu Pro Gln Pro Ala Pro Gln Gln Pro Pro Ser Ser
705                 710                 715                 720

Pro Trp Ala Ser Glu Gln Gly Pro Ile Val Tyr Thr Leu Ser Pro His
                725                 730                 735

Ser Thr Pro Ser Thr Ala Ser Gly Ser Gln Lys Lys His Thr Ile Gln
                740                 745                 750

Ile Pro Gly Leu Val Pro Ser Gln Lys Pro Ser Tyr Pro Pro Ser Ala
                755                 760                 765

Pro Tyr Lys Pro Gly Gln Ser Thr Gly Gly Ile Ala Pro Thr Pro Ser
                770                 775                 780

Ala Ala Ser Leu Thr Thr Phe Gly Leu Gln Pro Gln Asp Thr Gln Ala
785                 790                 795                 800

Ser Ser Gln Asp Pro Pro Tyr Gly His Ser Ile Met Gln Arg Glu Lys
                805                 810                 815

Lys Gln Gln Gly Gly Arg Glu Glu Ala Ala Glu Ile Arg Pro Ser Ala
                820                 825                 830

Thr Arg Leu Pro Thr Ala Val Gly Leu Arg Pro Arg Ala Pro Val Val
                835                 840                 845

Ala Ala Gly Ala Ala Ala Ser Ala Thr Pro Ala Phe Asp Pro Gly Glu
850                 855                 860

Ala Pro Ser Gly Phe Pro Ile Pro Gln Ala Pro Ala Leu Gly Ser Gly
865                 870                 875                 880

Leu Ala Ala Pro Ala His Thr Pro Val Gly Ala Leu Ala Pro Arg Pro
                885                 890                 895

Gln Lys Thr Gln Ala Gln Arg Pro Gln Asp Ala Ala Ala Leu Pro Thr
                900                 905                 910

Pro Thr Ile Lys Ala Val Gly Ala Arg Pro Val Pro Lys Ala Thr Gly
                915                 920                 925

Ala Leu Ala Ala Gly Ala Arg Pro Arg Gly Gln Pro Thr Ala Ala Pro
                930                 935                 940

Pro Ser Ala Ala Ser Pro Pro Arg Val Ser Leu Pro Val Arg Ser Arg
945                 950                 955                 960
```

```
Gln Gln Gln Ser Pro Ala Ile Pro Leu Pro Pro Met His Ser Gly Ser
            965             970             975

Glu Pro Gly Ala Arg Pro Glu Val Arg Leu Ser Gln Tyr Arg His Ala
        980             985             990

Gly Pro Gln Thr Tyr Thr Val Arg
        995             1000

<210> SEQ ID NO 94
<211> LENGTH: 1614
<212> TYPE: DNA
<213> ORGANISM: Artificial Sequence
<220> FEATURE:
<223> OTHER INFORMATION: Synthetic

<400> SEQUENCE: 94
atgagtgggc agcagagagg ctcggttatt ttggttcctg aacatctggc tggggcatta       60
actaagctta tgagcgattt tatcacagga caagatgtca ctctttctgg aggaaatatt      120
gcagtcaaaa ttcgcgatgc tataaaccag accccgggg gtggtgatgt agctatactt      180
tcttccctgt ttgctttatg gaatgccctc ccaacatctg gtagacaatc ctccagggac      240
gatttaatcc cagccgccgt gcaggcctta accacggccc acaacttatg tctgggtgtt      300
attccaggtg agacctcaca caaggacaca cccgagtcat tgctccgggc tatcgtgacg      360
ggtctccaaa aattgtgggt ggattcgtgc ggatgtccag agtgcctaca atgtcttaag      420
ggattgaagg caattaagcc cggcctttat gaaatcccta ggataatacc acacactaag      480
cagtgtagtc ctgtcaatct cctgaacatg ttggtccaca agcttgtggc tttacgtggt      540
catgtgcagc ttgcatacga cgcccgtgtc ctgacgcctg actttcacga aatccctgac      600
ctcgatgact ccgatgctgt tttcgcacgc accttattgg cagccttatt tcacctcaat      660 atgttctta ttctcaaaga ttacataaca caagactcca tgagcttgaa gcaggccctc      720
agtggtcatt ggatgtctgc cacgggcaac ccctgcctg cagcaccgga aaccctgcga      780
gactacttgg aagctttccg aaattcggat aatcacttt atctcccgac gacagggcct      840
ttaaacacct tccaatttcc cgaagagctt ctggggcgcg ttgttgttat tgattcctct      900
ttgtgtgccg ccagtcacgt tcaggacgtt atcacccatg gtgttggggc gggtgttcct      960
cgtcctcggt tttcggccct gcctccggcc ccatcccgcg agccccagca gacatgctct     1020
cagttaacga gcagagggaa tgaaagctca cggcgaaact tgggccagcc cgggggggacc     1080 tcccctgctg ttccccagt ttgccccatc gtttccctga cggcctcagg gccaagcaa     1140 aaccgcgggg gcatgggatc cttgcactta gccaagcctg aggaaacctc ccccgccgtc     1200
tccccagtat gccccatcgc ttccccagcg gcctccaggt ccaagcagca ctgcggggtc     1260
actggatcct cacaggccgc acccagcttt tcttccgttg ccccagtagc atctctgtct     1320
ggtgaccttg aagaggaaga ggaggggtcc cgagaatccc catccctacc gtccagcaaa     1380 aaggggacg aggaatttga ggcctggctt gaggctcagg acgcaaatct tgaggatgtt     1440
cagcgggagt tttccgggct gcgagtaatt ggtgatgagg acgaggatgg ttcggaggat     1500
ggggaatttt cagacctgga tctgtctgac agcgaccatg aagggga tga gggtgggggg     1560 gctgttggag ggggcaggag tctgcactcc ctgtattcac tgagcgtcgt ctaa     1614

<210> SEQ ID NO 95
<211> LENGTH: 537
<212> TYPE: PRT
<213> ORGANISM: Artificial Sequence
```

-continued

<220> FEATURE:
<223> OTHER INFORMATION: Synthetic

<400> SEQUENCE: 95

Met Ser Gly Gln Gln Arg Gly Ser Val Ile Leu Val Pro Glu His Leu
1               5                   10                  15

Ala Gly Ala Leu Thr Lys Leu Met Ser Asp Phe Ile Thr Gly Gln Asp
            20                  25                  30

Val Thr Leu Ser Gly Gly Asn Ile Ala Val Lys Ile Arg Asp Ala Ile
        35                  40                  45

Asn Gln Thr Pro Gly Gly Gly Asp Val Ala Ile Leu Ser Ser Leu Phe
    50                  55                  60

Ala Leu Trp Asn Ala Leu Pro Thr Ser Gly Arg Gln Ser Ser Arg Asp
65                  70                  75                  80

Asp Leu Ile Pro Ala Ala Val Gln Ala Leu Thr Thr Ala His Asn Leu
            85                  90                  95

Cys Leu Gly Val Ile Pro Gly Glu Thr Ser His Lys Asp Thr Pro Glu
            100                 105                 110

Ser Leu Leu Arg Ala Ile Val Thr Gly Leu Gln Lys Leu Trp Val Asp
        115                 120                 125

Ser Cys Gly Cys Pro Glu Cys Leu Gln Cys Leu Lys Gly Leu Lys Ala
        130                 135                 140

Ile Lys Pro Gly Leu Tyr Glu Ile Pro Arg Ile Ile Pro His Thr Lys
145                 150                 155                 160

Gln Cys Ser Pro Val Asn Leu Leu Asn Met Leu Val His Lys Leu Val
            165                 170                 175

Ala Leu Arg Gly His Val Gln Leu Ala Tyr Asp Ala Arg Val Leu Thr
            180                 185                 190

Pro Asp Phe His Glu Ile Pro Asp Leu Asp Asp Ser Asp Ala Val Phe
            195                 200                 205

Ala Arg Thr Leu Leu Ala Ala Leu Phe His Leu Asn Met Phe Phe Ile
            210                 215                 220

Leu Lys Asp Tyr Ile Thr Gln Asp Ser Met Ser Leu Lys Gln Ala Leu
225                 230                 235                 240

Ser Gly His Trp Met Ser Ala Thr Gly Asn Pro Leu Pro Ala Ala Pro
            245                 250                 255

Glu Thr Leu Arg Asp Tyr Leu Glu Ala Phe Arg Asn Ser Asp Asn His
            260                 265                 270

Phe Tyr Leu Pro Thr Thr Gly Pro Leu Asn Thr Phe Gln Phe Pro Glu
            275                 280                 285

Glu Leu Leu Gly Arg Val Val Val Ile Asp Ser Ser Leu Cys Ala Ala
    290                 295                 300

Ser His Val Gln Asp Val Ile Thr His Gly Val Gly Ala Gly Val Pro
305                 310                 315                 320

Arg Pro Arg Phe Ser Ala Leu Pro Pro Ala Pro Ser Arg Glu Pro Gln
            325                 330                 335

Gln Thr Cys Ser Gln Leu Thr Ser Arg Gly Asn Glu Ser Ser Arg Arg
            340                 345                 350

Asn Leu Gly Gln Pro Gly Gly Thr Ser Pro Ala Val Pro Pro Val Cys
        355                 360                 365

Pro Ile Val Ser Leu Thr Ala Ser Gly Ala Lys Gln Asn Arg Gly Gly
    370                 375                 380

Met Gly Ser Leu His Leu Ala Lys Pro Glu Glu Thr Ser Pro Ala Val
385                 390                 395                 400

-continued

```
Ser Pro Val Cys Pro Ile Ala Ser Pro Ala Ala Ser Arg Ser Lys Gln
            405                 410                 415

His Cys Gly Val Thr Gly Ser Ser Gln Ala Ala Pro Ser Phe Ser Ser
            420                 425                 430

Val Ala Pro Val Ala Ser Leu Ser Gly Asp Leu Glu Glu Glu Glu Glu
            435                 440                 445

Gly Ser Arg Glu Ser Pro Ser Leu Pro Ser Ser Lys Lys Gly Asp Glu
        450                 455                 460

Glu Phe Glu Ala Trp Leu Glu Ala Gln Asp Ala Asn Leu Glu Asp Val
465                 470                 475                 480

Gln Arg Glu Phe Ser Gly Leu Arg Val Ile Gly Asp Glu Asp Glu Asp
                485                 490                 495

Gly Ser Glu Asp Gly Glu Phe Ser Asp Leu Asp Leu Ser Asp Ser Asp
            500                 505                 510

His Glu Gly Asp Glu Gly Gly Gly Ala Val Gly Gly Gly Arg Ser Leu
            515                 520                 525

His Ser Leu Tyr Ser Leu Ser Val Val
        530                 535

<210> SEQ ID NO 96
<211> LENGTH: 654
<212> TYPE: DNA
<213> ORGANISM: Artificial Sequence
<220> FEATURE:
<223> OTHER INFORMATION: Synthetic

<400> SEQUENCE: 96
atggccatgt ttctgaagtc gcgtggggtc cggtcttgca gggaccggcg cctcttgtcg       60
gacgaggagg aagagacttc acagagcagc agctacactc tggggtctca ggcctcccag      120
tctatccagg aggaggacgt gagtgacact gatgagtctg actactcaga tgaagacgag      180
gagattgatt tggaggaaga gtaccccagt gacgaagacc catctgaggg cagtgatagc      240 gaccctcgt ggcatccttc agattcagac gagtctgact acagcgagag cgacgaggat       300
gaagcaaccc ccggctctca ggcctcacga tcttcaagag tctcgccatc tacccaacag      360
tcttcaggtc tgacacccac gccttcgttc tcccgaccac gcacccgggc acctccgagg      420
ccgccggctc ccgcgccggt caggggacgg gcctcagcac ctcccaggcc accagcccca      480
gttcagcaat ccaccaaaga caagggtccc catagaccta cgcgacctgt acttagaggc      540
ccagctccac gccgcccccc tccaccttca agtcccaata catacaataa acacatgatg      600
gaaaccaccc cccccattaa gggcaataac aactacaatt ggccatggct gtaa            654

<210> SEQ ID NO 97
<211> LENGTH: 217
<212> TYPE: PRT
<213> ORGANISM: Artificial Sequence
<220> FEATURE:
<223> OTHER INFORMATION: Synthetic

<400> SEQUENCE: 97

Met Ala Met Phe Leu Lys Ser Arg Gly Val Arg Ser Cys Arg Asp Arg
1               5                   10                  15

Arg Leu Leu Ser Asp Glu Glu Glu Glu Thr Ser Gln Ser Ser Ser Tyr
                20                  25                  30

Thr Leu Gly Ser Gln Ala Ser Gln Ser Ile Gln Glu Glu Asp Val Ser
            35                  40                  45
```

-continued

```
Asp Thr Asp Glu Ser Asp Tyr Ser Asp Glu Asp Glu Glu Ile Asp Leu
    50                  55                  60

Glu Glu Glu Tyr Pro Ser Asp Glu Asp Pro Ser Glu Gly Ser Asp Ser
65                  70                  75                  80

Asp Pro Ser Trp His Pro Ser Asp Ser Asp Glu Ser Asp Tyr Ser Glu
                85                  90                  95

Ser Asp Glu Asp Glu Ala Thr Pro Gly Ser Gln Ala Ser Arg Ser Ser
            100                 105                 110

Arg Val Ser Pro Ser Thr Gln Gln Ser Ser Gly Leu Thr Pro Thr Pro
        115                 120                 125

Ser Phe Ser Arg Pro Arg Thr Arg Ala Pro Pro Arg Pro Pro Ala Pro
    130                 135                 140

Ala Pro Val Arg Gly Arg Ala Ser Ala Pro Pro Arg Pro Pro Ala Pro
145                 150                 155                 160

Val Gln Gln Ser Thr Lys Asp Lys Gly Pro His Arg Pro Thr Arg Pro
                165                 170                 175

Val Leu Arg Gly Pro Ala Pro Arg Arg Pro Pro Pro Ser Ser Pro
            180                 185                 190

Asn Thr Tyr Asn Lys His Met Met Glu Thr Thr Pro Pro Ile Lys Gly
            195                 200                 205

Asn Asn Asn Tyr Asn Trp Pro Trp Leu
    210                 215
```

<210> SEQ ID NO 98
<211> LENGTH: 1842
<212> TYPE: DNA
<213> ORGANISM: Artificial Sequence
<220> FEATURE:
<223> OTHER INFORMATION: Synthetic

<400> SEQUENCE: 98

```
atgttcaaca tgaacgtgga cgagagcgcc tctggcgccc tcggctcctc ggccattcct      60
gttcacccca cgccggcctc ggtccgactt tttgagatcc tgcagggaaa gtacgcctac     120
gtccagggac agaccatcta cgccaacctc cgcaaccccg agtcttctc gaggcaggtg      180 tttacccatt tgtttaaacg agccatctct cattgcacgt acgatgacgt gctacatgac     240
tggaacaagt tcgaggcctg catccagaag cgatggccga gcgatgactc gtgtgcgagc     300
cggtttcgtg agtccacctt cgagtcgtgg tccacgacca tgaagctgac cgtgcgtgac     360
ctgctgacca ccaacatcta ccgagtgcta cacagccgct ccgtgctctc ctatgagcgt     420
tatgtggact ggatctgcgc caccggcatg gtgcccgccg ttaagaagcc cataacccaa     480
gagctccact ccaagataaa gagcctgagg acaggtgcg tctgtcggga attggggcac      540
gagaggacca tcaggagtat cgggacggaa ttatatgagg caacgaagga aataatagag     600
tcgctcaact ccacgttcat cccccagttt acggaggtga ccatcgagta ccttccgagg     660
agcgacgagt atgtggccta ctactgtggc cgccgcatca ggctgcatgt gctcttcccc     720
ccggccatct ttgccggaac ggtgaccttc gacagcccgg tgcagcgcct ctaccagaac     780
attttcatgt gctaccgcac gctggagcat gccaagatct gccagctcct gaacacggcc     840
cctctcaagg ccatcgtggg ccacgggggg cgagacatgt acaaggacat cctgccccat     900
ctggagcaga actcacagcg caaggacccc aagaaggagc tgctgaacct gctggtcaag     960
ctctcggaga acaagaccat cagcgggggtc acggacgtgg tggaggagtt cataacggat    1020
gcctccaaca acctggtgga ccgcaaccgt ctatttggcc agcccgggga gacagctgca    1080
```

```
cagggcctaa agaaaaaggt ctccaacacg gtggtcaagt gtctgactga tcagataaac    1140
gagcaatttg accagattaa tggcctagag aaggagaggg agctctatct aaagaagatc    1200
cgctccatgg agtctcagct gcaggcctcc ctgggtcccg gcggcaacaa cccagcggcg    1260
tcagcccccg ccgcagttgc ggcagaagcc gcgtctgtag atatactgac gggcagcacc    1320
gcctccgcaa tcgaaaagct gttcaactcc ccgtccgcca gcctgggtgc cagggtgtct    1380
ggtcacaatg aaagcatcct aaacagtttc gtttctcaat acatccccccc ttcgcgggaa   1440 atgactaagg atctgactga actttgggaa agcgagctgt ttaacacctt caagttaaca    1500
cccgtggttg ataatcaggg gcagcgtctc tacgtcagat actcgtcaga cacgatctct    1560
atattattgg gcccccttcac ctatctggtg gcagagcttt caccggtgga actcgtgaca    1620
gatgtctacg ccaccctagg catcgtggag atcatcgacg agctctaccg gagcagtcgc    1680
ctggccatct acatcgagga cctcggtcga aaatactgcc ccgcgagcgc gaccggggga    1740
gatcatggca tccggcaagc accatcagcc cggggggaca cggagcctga ccatgcaaaa    1800
agtaagcctg cgcgtgaccc cccgcctggt gctggaagtt aa                       1842
```

<210> SEQ ID NO 99
<211> LENGTH: 613
<212> TYPE: PRT
<213> ORGANISM: Artificial Sequence
<220> FEATURE:
<223> OTHER INFORMATION: Synthetic

<400> SEQUENCE: 99

```
Met Phe Asn Met Asn Val Asp Glu Ser Ala Ser Gly Ala Leu Gly Ser
1               5                   10                  15

Ser Ala Ile Pro Val His Pro Thr Pro Ala Ser Val Arg Leu Phe Glu
            20                  25                  30

Ile Leu Gln Gly Lys Tyr Ala Tyr Val Gln Gly Gln Thr Ile Tyr Ala
        35                  40                  45

Asn Leu Arg Asn Pro Gly Val Phe Ser Arg Gln Val Phe Thr His Leu
    50                  55                  60

Phe Lys Arg Ala Ile Ser His Cys Thr Tyr Asp Asp Val Leu His Asp
65                  70                  75                  80

Trp Asn Lys Phe Glu Ala Cys Ile Gln Lys Arg Trp Pro Ser Asp Asp
                85                  90                  95

Ser Cys Ala Ser Arg Phe Arg Glu Ser Thr Phe Glu Ser Trp Ser Thr
            100                 105                 110

Thr Met Lys Leu Thr Val Arg Asp Leu Leu Thr Thr Asn Ile Tyr Arg
        115                 120                 125

Val Leu His Ser Arg Ser Val Leu Ser Tyr Glu Arg Tyr Val Asp Trp
    130                 135                 140

Ile Cys Ala Thr Gly Met Val Pro Ala Val Lys Lys Pro Ile Thr Gln
145                 150                 155                 160

Glu Leu His Ser Lys Ile Lys Ser Leu Arg Asp Arg Cys Val Cys Arg
                165                 170                 175

Glu Leu Gly His Glu Arg Thr Ile Arg Ser Ile Gly Thr Glu Leu Tyr
            180                 185                 190

Glu Ala Thr Lys Glu Ile Ile Glu Ser Leu Asn Ser Thr Phe Ile Pro
        195                 200                 205

Gln Phe Thr Glu Val Thr Ile Glu Tyr Leu Pro Arg Ser Asp Glu Tyr
    210                 215                 220

Val Ala Tyr Tyr Cys Gly Arg Arg Ile Arg Leu His Val Leu Phe Pro
```

```
225             230             235             240

Pro Ala Ile Phe Ala Gly Thr Val Thr Phe Asp Ser Pro Val Gln Arg
                245             250             255

Leu Tyr Gln Asn Ile Phe Met Cys Tyr Arg Thr Leu Glu His Ala Lys
            260             265             270

Ile Cys Gln Leu Leu Asn Thr Ala Pro Leu Lys Ala Ile Val Gly His
            275             280             285

Gly Gly Arg Asp Met Tyr Lys Asp Ile Leu Ala His Leu Glu Gln Asn
    290             295             300

Ser Gln Arg Lys Asp Pro Lys Lys Glu Leu Leu Asn Leu Leu Val Lys
305             310             315             320

Leu Ser Glu Asn Lys Thr Ile Ser Gly Val Thr Asp Val Val Glu Glu
            325             330             335

Phe Ile Thr Asp Ala Ser Asn Asn Leu Val Asp Arg Asn Arg Leu Phe
            340             345             350

Gly Gln Pro Gly Glu Thr Ala Ala Gln Gly Leu Lys Lys Lys Val Ser
            355             360             365

Asn Thr Val Val Lys Cys Leu Thr Asp Gln Ile Asn Glu Gln Phe Asp
    370             375             380

Gln Ile Asn Gly Leu Glu Lys Glu Arg Glu Leu Tyr Leu Lys Lys Ile
385             390             395             400

Arg Ser Met Glu Ser Gln Leu Gln Ala Ser Leu Gly Pro Gly Gly Asn
            405             410             415

Asn Pro Ala Ala Ser Ala Pro Ala Ala Val Ala Ala Glu Ala Ala Ser
            420             425             430

Val Asp Ile Leu Thr Gly Ser Thr Ala Ser Ala Ile Glu Lys Leu Phe
            435             440             445

Asn Ser Pro Ser Ala Ser Leu Gly Ala Arg Val Ser Gly His Asn Glu
    450             455             460

Ser Ile Leu Asn Ser Phe Val Ser Gln Tyr Ile Pro Pro Ser Arg Glu
465             470             475             480

Met Thr Lys Asp Leu Thr Glu Leu Trp Glu Ser Glu Leu Phe Asn Thr
            485             490             495

Phe Lys Leu Thr Pro Val Val Asp Asn Gln Gly Gln Arg Leu Tyr Val
            500             505             510

Arg Tyr Ser Ser Asp Thr Ile Ser Ile Leu Leu Gly Pro Phe Thr Tyr
            515             520             525

Leu Val Ala Glu Leu Ser Pro Val Glu Leu Val Thr Asp Val Tyr Ala
    530             535             540

Thr Leu Gly Ile Val Glu Ile Ile Asp Glu Leu Tyr Arg Ser Ser Arg
545             550             555             560

Leu Ala Ile Tyr Ile Glu Asp Leu Gly Arg Lys Tyr Cys Pro Ala Ser
            565             570             575

Ala Thr Gly Gly Asp His Gly Ile Arg Gln Ala Pro Ser Ala Arg Gly
            580             585             590

Asp Thr Glu Pro Asp His Ala Lys Ser Lys Pro Ala Arg Asp Pro Pro
            595             600             605

Pro Gly Ala Gly Ser
    610
```

<210> SEQ ID NO 100
<211> LENGTH: 837
<212> TYPE: DNA
<213> ORGANISM: Artificial Sequence
<220> FEATURE:
<223> OTHER INFORMATION: Synthetic

<400> SEQUENCE: 100

```
atggcatccg gcaagcacca tcagcccggg gggacgcgga gcctgaccat gcaaaaagta      60
agcctgcgcg tgaccccccg cctggtgctg gaagttaacc gccataacgc catctgcgtg     120
gccaccaacg tccctgagtt ctacaatgcc aggggggacc ttaacatccg agacctccgg     180
gcccacgtca aggcccggat gatctcgtcc cagttttgcg gctacgtcct cgtgagtctg     240
ctggactccg aggaccaggt cgaccacctc aacatattcc cccacgtgtt ctccgagagg     300
atgatcctgt acaaacccaa caatgtgaac cttatggaga tgtgcgccct gctctcgatg     360
attgagaatg ccaagagccc ctccataggc ctctgccggg aggtgctggg tcgcctgacc     420
ctcttgcact ccaagtgcaa caatctggac tctctgtttc tgtacaacgg ggccaggacg     480
ctgctgtcca ccctggtcaa gtaccacgac ctggaggagg gggctgccac ccccgggccg     540
tggaatgagg gctgagtct ctttaagctg cacaaggagc tgaagcgcgc cccatccgaa     600
gcccgggacc tcatgcagag cctctttctg acctcgggga agatggggtg cctggccagg     660
tcacccaagg attactgcgc ggatctaaac aaggaggaag atgccaactc gggcttcaca     720
tttaacctgt tttatcaaga ttctttattg accaagcatt tccagtgcca gaccgtcctc     780
cagaccttga gacgcaagtg cctcgggagt gacacggtct caaaaataat tccctag       837
```

<210> SEQ ID NO 101
<211> LENGTH: 278
<212> TYPE: PRT
<213> ORGANISM: Artificial Sequence
<220> FEATURE:
<223> OTHER INFORMATION: Synthetic

<400> SEQUENCE: 101

```
Met Ala Ser Gly Lys His His Gln Pro Gly Gly Thr Arg Ser Leu Thr
1               5                   10                  15

Met Gln Lys Val Ser Leu Arg Val Thr Pro Arg Leu Val Leu Glu Val
            20                  25                  30

Asn Arg His Asn Ala Ile Cys Val Ala Thr Asn Val Pro Glu Phe Tyr
        35                  40                  45

Asn Ala Arg Gly Asp Leu Asn Ile Arg Asp Leu Arg Ala His Val Lys
    50                  55                  60

Ala Arg Met Ile Ser Ser Gln Phe Cys Gly Tyr Val Leu Val Ser Leu
65                  70                  75                  80

Leu Asp Ser Glu Asp Gln Val Asp His Leu Asn Ile Phe Pro His Val
                85                  90                  95

Phe Ser Glu Arg Met Ile Leu Tyr Lys Pro Asn Asn Val Asn Leu Met
            100                 105                 110

Glu Met Cys Ala Leu Leu Ser Met Ile Glu Asn Ala Lys Ser Pro Ser
        115                 120                 125

Ile Gly Leu Cys Arg Glu Val Leu Gly Arg Leu Thr Leu Leu His Ser
    130                 135                 140

Lys Cys Asn Asn Leu Asp Ser Leu Phe Leu Tyr Asn Gly Ala Arg Thr
145                 150                 155                 160

Leu Leu Ser Thr Leu Val Lys Tyr His Asp Leu Glu Glu Gly Ala Ala
                165                 170                 175

Thr Pro Gly Pro Trp Asn Glu Gly Leu Ser Leu Phe Lys Leu His Lys
            180                 185                 190
```

Glu Leu Lys Arg Ala Pro Ser Glu Ala Arg Asp Leu Met Gln Ser Leu
        195                 200                 205

Phe Leu Thr Ser Gly Lys Met Gly Cys Leu Ala Arg Ser Pro Lys Asp
        210                 215                 220

Tyr Cys Ala Asp Leu Asn Lys Glu Glu Asp Ala Asn Ser Gly Phe Thr
225                 230                 235                 240

Phe Asn Leu Phe Tyr Gln Asp Ser Leu Leu Thr Lys His Phe Gln Cys
                245                 250                 255

Gln Thr Val Leu Gln Thr Leu Arg Arg Lys Cys Leu Gly Ser Asp Thr
        260                 265                 270

Val Ser Lys Ile Ile Pro
        275

<210> SEQ ID NO 102
<211> LENGTH: 906
<212> TYPE: DNA
<213> ORGANISM: Artificial Sequence
<220> FEATURE:
<223> OTHER INFORMATION: Synthetic

<400> SEQUENCE: 102
atggatttga aagtggtagt gtctctctcc tctcgtctgt ataccgatga gattgccaag        60
atgcaacaga ggattggctg catcttaccc ctggcttcca ctcacgggac gcagaatgtg       120
cagggattgg gcttgggtca ggtgtactct ctagagacgg tcccggacta cgtgtccatg       180
tacaactacc tgtctgattg caccctggcc gtgctggatg aggttagcgt ggacagtttg       240
atactcacca agattgttcc aggtcagacc tacgccatta agaacaagta ccagcccttt       300
ttccagtggc atgggaccgg gagcctcagt gttatgcccc cggtatttgg acgagagcat       360
gccaccgtga agttagagtc caatgatgtg gacattgttt ccccatggt gctgcctacg       420 cccatagcag aggaggtgct gcagaagatt ctcctgttta cgtgtactc ccgggttgtc       480 atgcaggctc ccgggaacgc agacatgctc gatgtacaca tgcatcttgg ctctgtttca       540
tacctggggc accactacga gttggccctc ccggaggtgc cagggccct tggcttggcc       600 ctgctggaca tctgagtct ctacttttgc atcatggtga ccctgctgcc cagggccagt       660
atgcgcctgg tccgaggcct tatccggcat gagcatcacg acctcttgaa tctcttccag       720
gaaatggtgc cggatgagat agcccggata gacctggatg acctgtcagt ggcggatgat       780
ttatcacgca tgcgtgtgat gatgacctac ctacagtctt tggcatcact atttaatttg       840
gggcctcgct tggccacagc ggcatactct caagagaccc tgacggccac ttgctggtta       900
agataa                                                                   906

<210> SEQ ID NO 103
<211> LENGTH: 301
<212> TYPE: PRT
<213> ORGANISM: Artificial Sequence
<220> FEATURE:
<223> OTHER INFORMATION: Synthetic

<400> SEQUENCE: 103

Met Asp Leu Lys Val Val Val Ser Leu Ser Ser Arg Leu Tyr Thr Asp
1               5                   10                  15

Glu Ile Ala Lys Met Gln Gln Arg Ile Gly Cys Ile Leu Pro Leu Ala
            20                  25                  30

Ser Thr His Gly Thr Gln Asn Val Gln Gly Leu Gly Leu Gly Gln Val
        35                  40                  45

-continued

```
Tyr Ser Leu Glu Thr Val Pro Asp Tyr Val Ser Met Tyr Asn Tyr Leu
    50                  55                  60

Ser Asp Cys Thr Leu Ala Val Leu Asp Glu Val Ser Val Asp Ser Leu
65                  70                  75                  80

Ile Leu Thr Lys Ile Val Pro Gly Gln Thr Tyr Ala Ile Lys Asn Lys
                85                  90                  95

Tyr Gln Pro Phe Phe Gln Trp His Gly Thr Gly Ser Leu Ser Val Met
            100                 105                 110

Pro Pro Val Phe Gly Arg Glu His Ala Thr Val Lys Leu Glu Ser Asn
            115                 120                 125

Asp Val Asp Ile Val Phe Pro Met Val Leu Pro Thr Pro Ile Ala Glu
        130                 135                 140

Glu Val Leu Gln Lys Ile Leu Leu Phe Asn Val Tyr Ser Arg Val Val
145                 150                 155                 160

Met Gln Ala Pro Gly Asn Ala Asp Met Leu Asp Val His Met His Leu
                165                 170                 175

Gly Ser Val Ser Tyr Leu Gly His His Tyr Glu Leu Ala Leu Pro Glu
            180                 185                 190

Val Pro Gly Pro Leu Gly Leu Ala Leu Leu Asp Asn Leu Ser Leu Tyr
            195                 200                 205

Phe Cys Ile Met Val Thr Leu Leu Pro Arg Ala Ser Met Arg Leu Val
    210                 215                 220

Arg Gly Leu Ile Arg His Glu His His Asp Leu Leu Asn Leu Phe Gln
225                 230                 235                 240

Glu Met Val Pro Asp Glu Ile Ala Arg Ile Asp Leu Asp Asp Leu Ser
                245                 250                 255

Val Ala Asp Asp Leu Ser Arg Met Arg Val Met Met Thr Tyr Leu Gln
            260                 265                 270

Ser Leu Ala Ser Leu Phe Asn Leu Gly Pro Arg Leu Ala Thr Ala Ala
        275                 280                 285

Tyr Ser Gln Glu Thr Leu Thr Ala Thr Cys Trp Leu Arg
    290                 295                 300
```

```
<210> SEQ ID NO 104
<211> LENGTH: 4146
<212> TYPE: DNA
<213> ORGANISM: Artificial Sequence
<220> FEATURE:
<223> OTHER INFORMATION: Synthetic

<400> SEQUENCE: 104
atggcctcaa atgagggtgt ggaaaacaga cccttccct atctgacggt ggatgccgac      60
ctgctctcga acctgcggca gtcagcggct gagggggttgt ttcatagctt tgacctgctg     120
gtgggcaagg atgccagaga ggcgggcatc aagtttgagg tgctactcgg ggtctacacg     180
aacgccatcc aatatgttcg cttcctggag acggcactgg ccgtgtcctg tgtgaacacg     240
gaattcaaag acctgagtcg tatgacggat ggcaagattc aatttcgaat ctccgtcccc     300
accattgctc acgggacgg aaggagaccc agcaagcagc ggacattcat tgtggtcaaa     360
aattgccaca acaccacat tagtacgaaa atggaactgt ccatgctgga tctggagatc     420
ctgcatagta tccccgagac cccggtcgag tacgcagagt acgtgggggc tgtcaagacc     480
gtggcctcgg ccctacagtt tggggtcgat gccctggaga ggggcctcat taacaccgtc     540
ctgagtgtga agcttcgcca tgcccctccc atgtttatcc tgcagaccct ggcggatccc     600
accttcactg agaggggggtt ctccaagact gtcaagtctg acctcattgc catgttcaag     660
```

```
aggcatctgc tggagcactc cttcttcctg gaccgggccg agaacatggg ctccgggttt     720
tctcagtacg tgcgaagccg tctctctgag atggtagcgg ccgtgtccgg ggagagcgtg     780
ctcaaggggg tcagtaccta cacgaccgcc aaggggggag agccagtggg gggggtgttt     840
attgtcaccg acaacgttct gcgccagctc ttgaccttcc tgggtgagga ggccgacaac     900
cagattatgg ggccctcgag ctatgcttct tttgtggtac gggggggagaa cctggtcact    960 gccgtgagct acgggcgcgt gatgcgtacg tttgagcatt tcatggctag gatcgtggac    1020
tcaccggaaa aagccggaag caccaagtct gacctgccgg ctgtggccgc aggggtcgag    1080
gatcagcccc gggtgccgat ctcagccgcc gtcatcaagc tgggcaacca cgcggtggcc    1140
gtggaaagcc tgcaaaagat gtacaatgac actcagtccc cataccccct caacagaaga    1200
atgcagtaca gctactattt cccagtgggc ctgtttatgc ccaatcccaa gtacacgacc    1260
tccgccgcca tcaaaatgct ggacaacccc acacagcagc taccggtgga ggcatggatc    1320
gtaaacaaga ataaccttct cctcgcgttt aacctacaga atgctctcaa ggttctctgt    1380
cacccccgac tccacacacc cgcccatacc ctaaacagcc tcaacgcggc cccggccccg    1440
cgagacaggc gcgagaccta ctccctgcaa cacaggaggc ccaatcacat gaatgtgctt    1500
gttattgtgg acgagttcta tgataacaag tatgcagccc ccgtgacaga tatagctctc    1560
aagtgcgggc tgcccaccga agacttcctc cacccgtcca attatgacct gctgcggctg    1620
gagctgcacc cccttatga tatttacatt ggcagggatg ccggggagag ggccaggcac    1680
agggctgtgc accggctaat ggtgggtaac ctgccgactc ccctggcccc agctgcattc    1740
caagaggccc gggggcagca gtttgagacc gccacatctc tggcccacgt ggtggatcag    1800
gccgttattg agactgtgca ggatactgcc tatgacactg cctatccagc cttcttctac    1860
gtagtcgagg ctatgatcca cgggtttgag aaaagtttg tcatgaacgt gcctttggtg     1920
tccctgtgca tcaacaccta ctgggaacgg tcagggaggc ttgcctttgt gaacagcttt    1980
tccatgatca agttcatctg ccgccacctg ggaaataacg ccatctccaa ggaggcctat    2040
tccatgtata gaaaaatcta tgggaactt atagccctag agcaggccct gatgcgcctg    2100
gccgggtcag atgttgtggg ggatgagagc gtgggtcagt atgtctgcgc tctcctggac    2160
cctaacctgc tcccccggt ggcctacaca gacattttca cccatcttct caccgttagt    2220
gaccgggccc cccagattat tatcggaaat gaggtttacg ctgacaccct ggccgcgccc    2280
cagtttattg agagggttgg aaacatggat gagatggctg cccaatttgt ggccttgtac    2340
ggctaccggg ttaacggaga ccacgaccac gatttccgtc tgcacctagg cccttatgta    2400
gatgaggggc atgcggatgt gctggaaaag atcttttact acgttttcct cccaacctgc    2460
accaatgccc acatgtgcgg cctcgggtg gactttcagc acgtggccca gaccctggcc    2520
tacaacgggc cagccttcag ccaccatttt accagggacg aggacatcct cgacaatttg    2580
gagaatggga cgctcaggga tctgctggag atctccgacc tccgcccac cgtgggcatg    2640 atcagggacc tcagcgcctc attcatgacc tgccccactt tcacccgtgc cgtgcgtgtg    2700
tcggtggaca atgacgttac gcagcagctg gccccgaatc ccgccgacaa gcggacagag    2760
cagactgttt tggtgaacgg gctggtggcc tttgccttct ccgagaggac ccgggccgtc    2820
acccagtgtc tctttcacgc cattcctttc catatgtttt acggggaccc gcgagtggct    2880
gccaccatgc accaggatgt tgccacctttt gttatgcgca atcctcagca gcgggccgtg    2940
gaagccttca accggccaga gcagctcttt gcagagtacc gggagtggca ccgctcgccc    3000
```

-continued

```
atgggcaaat acgcggccga atgtcttcct tccctcgttt caatcagtgg aatgaccgcc    3060
atgcacatca agatgtcccc catggcctat attgcccagg ccaagctcaa gatccaccca    3120
ggggtggcca tgaccgtggt caggaccgat gagatcctct ctgaaaacat attgtttagc    3180
tccagggcct caacatccat gttcattggg accccaaatg ttagccgccg ggaggccagg    3240
gtggacgcgg taacctttga ggtgcatcac gagatggcct ccatcgacac cgggcttagt    3300
tatagctcga ccatgactcc ggccagggtg gcggccatca ctactgacat gggtatccac    3360
acccaagact tctttagcgt ctttccggcc gaggcctttg gcaaccagca agtcaatgac    3420
tacatcaagg ccaaggtggg cgctcagcgc aatgggacgc tgcttcggga ccccaggaca    3480
tacctggcag gtatgactaa tgttaatgga gctccaggac tctgccacgg ccagcaggcc    3540
acctgtgaga ttatcgtaac accggtcacg gcagacgtgg cttattttca aaagtccaac    3600
tctccaaggg gacgggccgc ctgtgtggtc tcctgtgaaa actacaatca ggaggttgcc    3660
gaggggctca tctatgacca ttctcgcccg gatgccgcct atgaataccg gagcactgtg    3720
aatccctggg catctcagct gggttctctg ggtgacatca tgtacaactc ctcctatcgc    3780
cagacggccg tcccgggcct ctacagcccc tgccgggcat tttttcaacaa ggaggagctt    3840 ctgcgcaaca cagggggact ctacaacatg gtcaacgagt acagccagcg acttggaggg    3900 caccccagcca ccagcaacac agaggtgcag tttgtagtga ttgctggcac tgacgtgttt    3960
ctggagcagc cctgcagctt tctgcaggag gcattccccg cactctcagc ctcctcccgg    4020
gcactcatcg atgagtttat gtctgtcaaa cagacccacg cccccatcca ttacggacac    4080
tatataattg aagaggtggc gccggtacga agaatattaa agtttggaaa taaggtggtt    4140
ttttga    4146
```

<210> SEQ ID NO 105
<211> LENGTH: 1381
<212> TYPE: PRT
<213> ORGANISM: Artificial Sequence
<220> FEATURE:
<223> OTHER INFORMATION: Synthetic

<400> SEQUENCE: 105

```
Met Ala Ser Asn Glu Gly Val Glu Asn Arg Pro Phe Pro Tyr Leu Thr
1               5                   10                  15

Val Asp Ala Asp Leu Leu Ser Asn Leu Arg Gln Ser Ala Ala Glu Gly
            20                  25                  30

Leu Phe His Ser Phe Asp Leu Leu Val Gly Lys Asp Ala Arg Glu Ala
        35                  40                  45

Gly Ile Lys Phe Glu Val Leu Leu Gly Val Tyr Thr Asn Ala Ile Gln
    50                  55                  60

Tyr Val Arg Phe Leu Glu Thr Ala Leu Ala Val Ser Cys Val Asn Thr
65                  70                  75                  80

Glu Phe Lys Asp Leu Ser Arg Met Thr Asp Gly Lys Ile Gln Phe Arg
                85                  90                  95

Ile Ser Val Pro Thr Ile Ala His Gly Asp Gly Arg Arg Pro Ser Lys
            100                 105                 110

Gln Arg Thr Phe Ile Val Val Lys Asn Cys His Lys His His Ile Ser
        115                 120                 125

Thr Glu Met Glu Leu Ser Met Leu Asp Leu Glu Ile Leu His Ser Ile
    130                 135                 140

Pro Glu Thr Pro Val Glu Tyr Ala Glu Tyr Val Gly Ala Val Lys Thr
145                 150                 155                 160
```

-continued

```
Val Ala Ser Ala Leu Gln Phe Gly Val Asp Ala Leu Glu Arg Gly Leu
            165                 170                 175

Ile Asn Thr Val Leu Ser Val Lys Leu Arg His Ala Pro Pro Met Phe
            180                 185                 190

Ile Leu Gln Thr Leu Ala Asp Pro Thr Phe Thr Glu Arg Gly Phe Ser
            195                 200                 205

Lys Thr Val Lys Ser Asp Leu Ile Ala Met Phe Lys Arg His Leu Leu
        210                 215                 220

Glu His Ser Phe Phe Leu Asp Arg Ala Glu Asn Met Gly Ser Gly Phe
    225                 230                 235                 240

Ser Gln Tyr Val Arg Ser Arg Leu Ser Glu Met Val Ala Ala Val Ser
            245                 250                 255

Gly Glu Ser Val Leu Lys Gly Val Ser Thr Tyr Thr Thr Ala Lys Gly
            260                 265                 270

Gly Glu Pro Val Gly Gly Val Phe Ile Val Thr Asp Asn Val Leu Arg
            275                 280                 285

Gln Leu Leu Thr Phe Leu Gly Glu Glu Ala Asp Asn Gln Ile Met Gly
        290                 295                 300

Pro Ser Ser Tyr Ala Ser Phe Val Val Arg Gly Glu Asn Leu Val Thr
    305                 310                 315                 320

Ala Val Ser Tyr Gly Arg Val Met Arg Thr Phe Glu His Phe Met Ala
            325                 330                 335

Arg Ile Val Asp Ser Pro Glu Lys Ala Gly Ser Thr Lys Ser Asp Leu
            340                 345                 350

Pro Ala Val Ala Ala Gly Val Glu Asp Gln Pro Arg Val Pro Ile Ser
            355                 360                 365

Ala Ala Val Ile Lys Leu Gly Asn His Ala Val Ala Val Glu Ser Leu
        370                 375                 380

Gln Lys Met Tyr Asn Asp Thr Gln Ser Pro Tyr Pro Leu Asn Arg Arg
    385                 390                 395                 400

Met Gln Tyr Ser Tyr Tyr Phe Pro Val Gly Leu Phe Met Pro Asn Pro
            405                 410                 415

Lys Tyr Thr Thr Ser Ala Ala Ile Lys Met Leu Asp Asn Pro Thr Gln
            420                 425                 430

Gln Leu Pro Val Glu Ala Trp Ile Val Asn Lys Asn Asn Leu Leu Leu
            435                 440                 445

Ala Phe Asn Leu Gln Asn Ala Leu Lys Val Leu Cys His Pro Arg Leu
        450                 455                 460

His Thr Pro Ala His Thr Leu Asn Ser Leu Asn Ala Ala Pro Ala Pro
    465                 470                 475                 480

Arg Asp Arg Arg Glu Thr Tyr Ser Leu Gln His Arg Arg Pro Asn His
            485                 490                 495

Met Asn Val Leu Val Ile Val Asp Glu Phe Tyr Asp Asn Lys Tyr Ala
            500                 505                 510

Ala Pro Val Thr Asp Ile Ala Leu Lys Cys Gly Leu Pro Thr Glu Asp
            515                 520                 525

Phe Leu His Pro Ser Asn Tyr Asp Leu Leu Arg Leu Glu Leu His Pro
        530                 535                 540

Leu Tyr Asp Ile Tyr Ile Gly Arg Asp Ala Gly Glu Arg Ala Arg His
    545                 550                 555                 560

Arg Ala Val His Arg Leu Met Val Gly Asn Leu Pro Thr Pro Leu Ala
            565                 570                 575
```

```
Pro Ala Ala Phe Gln Glu Ala Arg Gly Gln Gln Phe Glu Thr Ala Thr
        580             585             590

Ser Leu Ala His Val Val Asp Gln Ala Val Ile Glu Thr Val Gln Asp
        595             600             605

Thr Ala Tyr Asp Thr Ala Tyr Pro Ala Phe Phe Tyr Val Val Glu Ala
        610             615             620

Met Ile His Gly Phe Glu Glu Lys Phe Val Met Asn Val Pro Leu Val
625             630             635             640

Ser Leu Cys Ile Asn Thr Tyr Trp Glu Arg Ser Gly Arg Leu Ala Phe
        645             650             655

Val Asn Ser Phe Ser Met Ile Lys Phe Ile Cys Arg His Leu Gly Asn
        660             665             670

Asn Ala Ile Ser Lys Glu Ala Tyr Ser Met Tyr Arg Lys Ile Tyr Gly
        675             680             685

Glu Leu Ile Ala Leu Glu Gln Ala Leu Met Arg Leu Ala Gly Ser Asp
        690             695             700

Val Val Gly Asp Glu Ser Val Gly Gln Tyr Val Cys Ala Leu Leu Asp
705             710             715             720

Pro Asn Leu Leu Pro Pro Val Ala Tyr Thr Asp Ile Phe Thr His Leu
        725             730             735

Leu Thr Val Ser Asp Arg Ala Pro Gln Ile Ile Ile Gly Asn Glu Val
        740             745             750

Tyr Ala Asp Thr Leu Ala Ala Pro Gln Phe Ile Glu Arg Val Gly Asn
        755             760             765

Met Asp Glu Met Ala Ala Gln Phe Val Ala Leu Tyr Gly Tyr Arg Val
        770             775             780

Asn Gly Asp His Asp His Asp Phe Arg Leu His Leu Gly Pro Tyr Val
785             790             795             800

Asp Glu Gly His Ala Asp Val Leu Glu Lys Ile Phe Tyr Tyr Val Phe
        805             810             815

Leu Pro Thr Cys Thr Asn Ala His Met Cys Gly Leu Gly Val Asp Phe
        820             825             830

Gln His Val Ala Gln Thr Leu Ala Tyr Asn Gly Pro Ala Phe Ser His
        835             840             845

His Phe Thr Arg Asp Glu Asp Ile Leu Asp Asn Leu Glu Asn Gly Thr
        850             855             860

Leu Arg Asp Leu Leu Glu Ile Ser Asp Leu Arg Pro Thr Val Gly Met
865             870             875             880

Ile Arg Asp Leu Ser Ala Ser Phe Met Thr Cys Pro Thr Phe Thr Arg
        885             890             895

Ala Val Arg Val Ser Val Asp Asn Asp Val Thr Gln Gln Leu Ala Pro
        900             905             910

Asn Pro Ala Asp Lys Arg Thr Glu Gln Thr Val Leu Val Asn Gly Leu
        915             920             925

Val Ala Phe Ala Phe Ser Glu Arg Thr Arg Ala Val Thr Gln Cys Leu
        930             935             940

Phe His Ala Ile Pro Phe His Met Phe Tyr Gly Asp Pro Arg Val Ala
945             950             955             960

Ala Thr Met His Gln Asp Val Ala Thr Phe Val Met Arg Asn Pro Gln
        965             970             975

Gln Arg Ala Val Glu Ala Phe Asn Arg Pro Glu Gln Leu Phe Ala Glu
        980             985             990

Tyr Arg Glu Trp His Arg Ser Pro  Met Gly Lys Tyr Ala  Ala Glu Cys
```

-continued

```
            995                 1000                1005

Leu Pro  Ser Leu Val Ser Ile  Ser Gly Met Thr Ala  Met His Ile
    1010                1015                1020

Lys Met  Ser Pro Met Ala Tyr  Ile Ala Gln Ala Lys  Leu Lys Ile
    1025                1030                1035

His Pro  Gly Val Ala Met Thr  Val Val Arg Thr Asp  Glu Ile Leu
    1040                1045                1050

Ser Glu  Asn Ile Leu Phe Ser  Ser Arg Ala Ser Thr  Ser Met Phe
    1055                1060                1065

Ile Gly  Thr Pro Asn Val Ser  Arg Arg Glu Ala Arg  Val Asp Ala
    1070                1075                1080

Val Thr  Phe Glu Val His His  Glu Met Ala Ser Ile  Asp Thr Gly
    1085                1090                1095

Leu Ser  Tyr Ser Ser Thr Met  Thr Pro Ala Arg Val  Ala Ala Ile
    1100                1105                1110

Thr Thr  Asp Met Gly Ile His  Thr Gln Asp Phe Phe  Ser Val Phe
    1115                1120                1125

Pro Ala  Glu Ala Phe Gly Asn  Gln Gln Val Asn Asp  Tyr Ile Lys
    1130                1135                1140

Ala Lys  Val Gly Ala Gln Arg  Asn Gly Thr Leu Leu  Arg Asp Pro
    1145                1150                1155

Arg Thr  Tyr Leu Ala Gly Met  Thr Asn Val Asn Gly  Ala Pro Gly
    1160                1165                1170

Leu Cys  His Gly Gln Gln Ala  Thr Cys Glu Ile Ile  Val Thr Pro
    1175                1180                1185

Val Thr  Ala Asp Val Ala Tyr  Phe Gln Lys Ser Asn  Ser Pro Arg
    1190                1195                1200

Gly Arg  Ala Ala Cys Val Val  Ser Cys Glu Asn Tyr  Asn Gln Glu
    1205                1210                1215

Val Ala  Glu Gly Leu Ile Tyr  Asp His Ser Arg Pro  Asp Ala Ala
    1220                1225                1230

Tyr Glu  Tyr Arg Ser Thr Val  Asn Pro Trp Ala Ser  Gln Leu Gly
    1235                1240                1245

Ser Leu  Gly Asp Ile Met Tyr  Asn Ser Ser Tyr Arg  Gln Thr Ala
    1250                1255                1260

Val Pro  Gly Leu Tyr Ser Pro  Cys Arg Ala Phe Phe  Asn Lys Glu
    1265                1270                1275

Glu Leu  Leu Arg Asn Asn Arg  Gly Leu Tyr Asn Met  Val Asn Glu
    1280                1285                1290

Tyr Ser  Gln Arg Leu Gly Gly  His Pro Ala Thr Ser  Asn Thr Glu
    1295                1300                1305

Val Gln  Phe Val Val Ile Ala  Gly Thr Asp Val Phe  Leu Glu Gln
    1310                1315                1320

Pro Cys  Ser Phe Leu Gln Glu  Ala Phe Pro Ala Leu  Ser Ala Ser
    1325                1330                1335

Ser Arg  Ala Leu Ile Asp Glu  Phe Met Ser Val Lys  Gln Thr His
    1340                1345                1350

Ala Pro  Ile His Tyr Gly His  Tyr Ile Ile Glu Glu  Val Ala Pro
    1355                1360                1365

Val Arg  Arg Ile Leu Lys Phe  Gly Asn Lys Val Val  Phe
    1370                1375                1380
```

<210> SEQ ID NO 106

-continued

<211> LENGTH: 1818
<212> TYPE: DNA
<213> ORGANISM: Artificial Sequence
<220> FEATURE:
<223> OTHER INFORMATION: Synthetic

<400> SEQUENCE: 106
atggtgcagg caccgtctgt atacgtctgc ggcttcgtgg agcgcccgga cgccccaccc        60
aaggacgcct gccttcacct ggatcccctc accgtcaaga gccagctccc tctgaagaag       120
cccttgccac tcacggtgga acacctgccg gatgctccgg tcggctcagt ctttggcctt       180
taccagagcc gagcgggtct ctttagcgca gcctcgatta cctctgggga cttcctgtcc       240
ctgctggact caatttacca cgattgcgat attgcacaga gtcagcgcct gcccctccct       300
cgagaaccca aggtggaggc tctgcacgcc tggctcccct cactgtcact ggcctccctc       360
cacccagaca taccccaaac caccgcagat ggaggcaagc tgtccttctt tgaccacgtg       420
tctatctgtg ccctgggtcg tcggcgcggc accacggcag tctacggtac agaccttgcg       480
tgggtcctga agcactttag tgacctggaa ccgtctatcg ccgcccagat tgagaatgac       540
gccaatgccg caaagcgtga atccggatgc ccggaagacc accctctgcc cctcacgaag       600
ctcatagcta aggcaatcga tgctggattt ctgagaaacc gcgtggagac tctgaggcag       660
gacaggggtg tggccaatat cccagccgag tcgtatttaa aggccagcga cgccccggac       720
ctacaaaagc cggacaaggc acttcagagc ccaccaccgg cctccacaga cccagccacc       780
atgctatcag gtaacgcagg agaaggagca acagcctgcg gaggttcggc cgccgcgggc       840
caggacctca tcagcgtccc ccgcaacacc tttatgacac tgcttcagac caacctggac       900
aacaaaccgc cgaggcagac cccgctaccc tacgcggccc cgctgccccc cttttcccac       960
caggcaatag ccaccgcgcc ttcctacggt cctggggccg gagcggtcgc cccggccggc      1020
ggctacttta cctccccagg aggttactac gccgggcccg cgggcgggga cccgggtgcc      1080
ttcttggcga tggacgctca cacctaccac ccccacccac acccccctcc ggcctacttt      1140
ggcttgccgg gcctctttgg cccccctcca cccgtgcctc cttactacgg atcccacttg      1200
cgggcagact acgtccccgc tccctcgcga tccaacaagc ggaaaagaga ccccgaggag      1260
gatgaagaag gcggggggct attcccgggg gaggacgcca ccctctaccg caaggacata      1320
gcgggcctct ccaagagtgt gaatgagtta cagcacacgc tacaggccct gcgccgggag      1380
acgctgtcct acggccacac cggagtcgga tactgccccc agcagggccc ctgctacacc      1440
cactcggggc cttacggatt tcagcctcat caaaagctacg aagtgcccag atacgtccct      1500
catccgcccc caccaccaac ttctcaccag gcagctcagg cgcagcctcc accccccgggc      1560 acacaggccc ccgaagccca ctgtgtggcc gagtccacga tccctgaggc gggagcagcc      1620
gggaactctg accccgggga ggacaccaac cctcagcagc ccaccaccga gggccaccac      1680
cgcggaaaga aactggtgca ggcctctgcg tccggagtgg ctcagtctaa ggagcccacc      1740
acccccaagg ccaagtctgt gtcagcccac ctcaagtcca tcttttgcga ggaattgctg      1800
aataaacgcg tggcttga                                                   1818

<210> SEQ ID NO 107
<211> LENGTH: 605
<212> TYPE: PRT
<213> ORGANISM: Artificial Sequence
<220> FEATURE:
<223> OTHER INFORMATION: Synthetic

<400> SEQUENCE: 107

-continued

```
Met Val Gln Ala Pro Ser Val Tyr Val Cys Gly Phe Val Glu Arg Pro
1               5                   10                  15

Asp Ala Pro Pro Lys Asp Ala Cys Leu His Leu Asp Pro Leu Thr Val
            20                  25                  30

Lys Ser Gln Leu Pro Leu Lys Lys Pro Leu Pro Leu Thr Val Glu His
        35                  40                  45

Leu Pro Asp Ala Pro Val Gly Ser Val Phe Gly Leu Tyr Gln Ser Arg
    50                  55                  60

Ala Gly Leu Phe Ser Ala Ala Ser Ile Thr Ser Gly Asp Phe Leu Ser
65                  70                  75                  80

Leu Leu Asp Ser Ile Tyr His Asp Cys Asp Ile Ala Gln Ser Gln Arg
                85                  90                  95

Leu Pro Leu Pro Arg Glu Pro Lys Val Glu Ala Leu His Ala Trp Leu
            100                 105                 110

Pro Ser Leu Ser Leu Ala Ser Leu His Pro Asp Ile Pro Gln Thr Thr
        115                 120                 125

Ala Asp Gly Gly Lys Leu Ser Phe Phe Asp His Val Ser Ile Cys Ala
    130                 135                 140

Leu Gly Arg Arg Arg Gly Thr Thr Ala Val Tyr Gly Thr Asp Leu Ala
145                 150                 155                 160

Trp Val Leu Lys His Phe Ser Asp Leu Glu Pro Ser Ile Ala Ala Gln
            165                 170                 175

Ile Glu Asn Asp Ala Asn Ala Ala Lys Arg Glu Ser Gly Cys Pro Glu
            180                 185                 190

Asp His Pro Leu Pro Leu Thr Lys Leu Ile Ala Lys Ala Ile Asp Ala
        195                 200                 205

Gly Phe Leu Arg Asn Arg Val Glu Thr Leu Arg Gln Asp Arg Gly Val
    210                 215                 220

Ala Asn Ile Pro Ala Glu Ser Tyr Leu Lys Ala Ser Asp Ala Pro Asp
225                 230                 235                 240

Leu Gln Lys Pro Asp Lys Ala Leu Gln Ser Pro Pro Ala Ser Thr
            245                 250                 255

Asp Pro Ala Thr Met Leu Ser Gly Asn Ala Gly Glu Gly Ala Thr Ala
        260                 265                 270

Cys Gly Gly Ser Ala Ala Ala Gly Gln Asp Leu Ile Ser Val Pro Arg
        275                 280                 285

Asn Thr Phe Met Thr Leu Leu Gln Thr Asn Leu Asp Asn Lys Pro Pro
    290                 295                 300

Arg Gln Thr Pro Leu Pro Tyr Ala Ala Pro Leu Pro Pro Phe Ser His
305                 310                 315                 320

Gln Ala Ile Ala Thr Ala Pro Ser Tyr Gly Pro Gly Ala Gly Ala Val
            325                 330                 335

Ala Pro Ala Gly Gly Tyr Phe Thr Ser Pro Gly Gly Tyr Tyr Ala Gly
            340                 345                 350

Pro Ala Gly Gly Asp Pro Gly Ala Phe Leu Ala Met Asp Ala His Thr
        355                 360                 365

Tyr His Pro His Pro His Pro Pro Ala Tyr Phe Gly Leu Pro Gly
    370                 375                 380

Leu Phe Gly Pro Pro Pro Pro Val Pro Pro Tyr Tyr Gly Ser His Leu
385                 390                 395                 400

Arg Ala Asp Tyr Val Pro Ala Pro Ser Arg Ser Asn Lys Arg Lys Arg
            405                 410                 415
```

Asp Pro Glu Glu Asp Glu Glu Gly Gly Gly Leu Phe Pro Gly Glu Asp
            420                     425                 430

Ala Thr Leu Tyr Arg Lys Asp Ile Ala Gly Leu Ser Lys Ser Val Asn
            435                 440                 445

Glu Leu Gln His Thr Leu Gln Ala Leu Arg Arg Glu Thr Leu Ser Tyr
            450                 455                 460

Gly His Thr Gly Val Gly Tyr Cys Pro Gln Gln Gly Pro Cys Tyr Thr
465                 470                 475                 480

His Ser Gly Pro Tyr Gly Phe Gln Pro His Gln Ser Tyr Glu Val Pro
                    485                 490                 495

Arg Tyr Val Pro His Pro Pro Pro Pro Thr Ser His Gln Ala Ala
                500                 505                 510

Gln Ala Gln Pro Pro Pro Pro Gly Thr Gln Ala Pro Glu Ala His Cys
            515                 520                 525

Val Ala Glu Ser Thr Ile Pro Glu Ala Gly Ala Ala Gly Asn Ser Gly
            530                 535                 540

Pro Arg Glu Asp Thr Asn Pro Gln Gln Pro Thr Thr Glu Gly His His
545                 550                 555                 560

Arg Gly Lys Lys Leu Val Gln Ala Ser Ala Ser Gly Val Ala Gln Ser
                565                 570                 575

Lys Glu Pro Thr Thr Pro Lys Ala Lys Ser Val Ser Ala His Leu Lys
                580                 585                 590

Ser Ile Phe Cys Glu Glu Leu Leu Asn Lys Arg Val Ala
                595                 600                 605

<210> SEQ ID NO 108
<211> LENGTH: 1038
<212> TYPE: DNA
<213> ORGANISM: Artificial Sequence
<220> FEATURE:
<223> OTHER INFORMATION: Synthetic

<400> SEQUENCE: 108
atgctatcag gtaacgcagg agaaggagca acagcctgcg gaggttcggc cgccgcgggc        60
caggacctca tcagcgtccc ccgcaacacc tttatgacac tgcttcagac caacctggac       120
aacaaaccgc cgaggcagac cccgctaccc tacgcggccc cgctgccccc cttttcccac       180
caggcaatag ccaccgcgcc ttcctacggt cctggggccg gagcggtcgc cccggccggc       240
ggctacttta cctccccagg aggttactac gccgggcccg cgggcgggga cccgggtgcc       300
ttcttggcga tggacgctca cacctaccac ccccacccac accccctcc ggcctacttt        360 ggcttgccgg gcctctttgg ccccccctcca cccgtgcctc cttactacgg atcccacttg      420
cgggcagact acgtccccgc tccctcgcga tccaacaagc ggaaaagaga ccccgaggag      480
gatgaagaag gcgggggggct attcccgggg gaggacgcca ccctctaccg caaggacata      540
gcgggcctct ccaagagtgt gaatgagtta cagcacacgc tacaggccct cgcgcgggag      600
acgctgtcct acggccacac cggagtcgga tactgcccc agcagggccc ctgctacacc       660
cactcggggc cttacggatt tcagcctcat caaagctacg aagtgcccag atacgtccct      720
catccgcccc caccaccaac ttctcaccag gcagctcagg cgcagcctcc acccccgggc      780
acacaggccc ccgaagccca ctgtgtggcc gagtccacga tccctgaggc gggagcagcc      840
gggaactctg accccgggga ggacaccaac cctcagcagc ccaccaccga gggccaccac      900
cgcgggaaga aactggtgca ggcctctgcg tccggagtgg ctcagtctaa ggagcccacc      960
acccccaagg ccaagtctgt gtcagcccac ctcaagtcca tctttgcga ggaattgctg      1020

-continued aataaacgcg tggcttga                                                    1038

<210> SEQ ID NO 109
<211> LENGTH: 345
<212> TYPE: PRT
<213> ORGANISM: Artificial Sequence
<220> FEATURE:
<223> OTHER INFORMATION: Synthetic

<400> SEQUENCE: 109

Met Leu Ser Gly Asn Ala Gly Glu Gly Ala Thr Ala Cys Gly Gly Ser
1               5                   10                  15

Ala Ala Ala Gly Gln Asp Leu Ile Ser Val Pro Arg Asn Thr Phe Met
            20                  25                  30

Thr Leu Leu Gln Thr Asn Leu Asp Asn Lys Pro Pro Arg Gln Thr Pro
        35                  40                  45

Leu Pro Tyr Ala Ala Pro Leu Pro Pro Phe Ser His Gln Ala Ile Ala
    50                  55                  60

Thr Ala Pro Ser Tyr Gly Pro Gly Ala Gly Ala Val Ala Pro Ala Gly
65                  70                  75                  80

Gly Tyr Phe Thr Ser Pro Gly Gly Tyr Tyr Ala Gly Pro Ala Gly Gly
                85                  90                  95

Asp Pro Gly Ala Phe Leu Ala Met Asp Ala His Thr Tyr His Pro His
            100                 105                 110

Pro His Pro Pro Pro Ala Tyr Phe Gly Leu Pro Gly Leu Phe Gly Pro
        115                 120                 125

Pro Pro Pro Val Pro Pro Tyr Tyr Gly Ser His Leu Arg Ala Asp Tyr
    130                 135                 140

Val Pro Ala Pro Ser Arg Ser Asn Lys Arg Lys Arg Asp Pro Glu Glu
145                 150                 155                 160

Asp Glu Glu Gly Gly Gly Leu Phe Pro Gly Glu Asp Ala Thr Leu Tyr
                165                 170                 175

Arg Lys Asp Ile Ala Gly Leu Ser Lys Ser Val Asn Glu Leu Gln His
            180                 185                 190

Thr Leu Gln Ala Leu Arg Arg Glu Thr Leu Ser Tyr Gly His Thr Gly
        195                 200                 205

Val Gly Tyr Cys Pro Gln Gln Gly Pro Cys Tyr Thr His Ser Gly Pro
    210                 215                 220

Tyr Gly Phe Gln Pro His Gln Ser Tyr Glu Val Pro Arg Tyr Val Pro
225                 230                 235                 240

His Pro Pro Pro Pro Thr Ser His Gln Ala Ala Gln Ala Gln Pro
                245                 250                 255

Pro Pro Pro Gly Thr Gln Ala Pro Glu Ala His Cys Val Ala Glu Ser
            260                 265                 270

Thr Ile Pro Glu Ala Gly Ala Ala Gly Asn Ser Gly Pro Arg Glu Asp
        275                 280                 285

Thr Asn Pro Gln Gln Pro Thr Thr Glu Gly His His Arg Gly Lys Lys
    290                 295                 300

Leu Val Gln Ala Ser Ala Ser Gly Val Ala Gln Ser Lys Glu Pro Thr
305                 310                 315                 320

Thr Pro Lys Ala Lys Ser Val Ser Ala His Leu Lys Ser Ile Phe Cys
                325                 330                 335

Glu Glu Leu Leu Asn Lys Arg Val Ala
                340                 345

-continued

<210> SEQ ID NO 110
<211> LENGTH: 3000
<212> TYPE: DNA
<213> ORGANISM: Artificial Sequence
<220> FEATURE:
<223> OTHER INFORMATION: Synthetic

<400> SEQUENCE: 110
gtgcgcaggt gtacggcgga catcagggac aaggtggcct cggcggcctc cgattatctc      60
tcctaccttg aggacccaag cctcccaaca gtgatggatt ttgacgacct cctgacacac     120
ctgcggcaca catgccagat catcgcctcc ctgcctctcc taaacatccg gtacacgtcc     180
attgaatggg actatcgcga gctcctctac ctgggcaccg cccttagtga tatgagcggt     240
atcccctggc ccctggagcg agttgaggag gacgacccca gcattgcccc ccttccagag     300
tttgagacag tcgcgaaaaa acagaaggag ctcgagacca ccagagaaaa cgaaaagcgc     360
ctccgcacca tcctggacga catcgaggca atgttgggcc tggccggtgt ggcctcggcc     420
ccaggcgccc ccatctctcc cgcctctccc tctgcgacac ccgccaacca cgacaacccc     480
gaagccacgc caccgctggc cgacaccgcg gccctcacca tccccgtcat agaaaagtac     540
atcgcaaatg cagggtcgat agtcgggggc gcaaagaacc ccacgtacat ccgcctacgt     600
gacactatac agcagattgt tcgctccaaa aagtacctga tgaacatcct gaaatccatc     660
accttctaca ccatcgataa ctacattgcc tccttcgagg agagcataga ccacctctat     720
cgtgacttgc cggtccttga ccctgaggtg caggatggca ttgaccgcat cctggacccc     780
atggtctcag aggccctgca cacattcgag atgggcaacc ggctgacgct ggagccagcg     840
cgcctagtgg ccttgcagaa ttttgctact cacagcacct aaaggagac ggccgcggcg       900 gtgaatctgc tcccaggtct actggcggtc tatgatgcga cgatcacagg tcaggctcca     960
gaggatgccc tgagactact ctctgggctg cagaatcagc tctcccaaac gctcatccca    1020
gggaagctca agaaacgctt cctaagttac ctgcagaaat tgaagaataa caacaacgat    1080
cagctcagac agaaggaggt gcaggcctgg cgcctggagg ccgaaggctt taagcccgcc    1140
accgaggaac agctcgaggc ctttctggac actgcccca acaaagagct caagcgacag     1200
tatgagaaga gctgcggca gcttatggag accgggcgca aggaaaagga gaagctccga    1260
gaacaggaag acaaggagag gcaggagcgg cgagcgcgag aggcgaatga ggcctgggcc    1320
agaattagga aggcgctggg ggcacgccca gagcccgctc ccacttcgcc cgatgactgg    1380 aacacccctgc tggcctccct gctgccagac aatacggact cagccgcggc agcagcggcg    1440
gcagtagcca gaaacacgga catcttggac tccctcacac agatccttgc cgctatgcta    1500
ttgggaataa cgagggtgag gagggagaga ctgcgatccc tgctcgtgga cgatggtggt    1560
gcggcggaga gaatggaggc cgcggaaccc ggctggttca cggatatcga gaccggccct    1620
ctggccagac tggacgcttg gcccgccacc cccgcggcta ccgccaaaga aggaggagga    1680
gggcgaggag cggaggaagc ggccggggcc ctctttcgcg ccaggacggc ggccgatgcc    1740
atccgttcgg ccctcgcgca gacgcgccag gccctgcagt ccccggacat gaaatcagcg    1800
gtggtcaaca cggatctgga ggccccctac gcggagtacg agcgggggct ggccgggctt    1860
ctggaaaaaa gacgagcagc cgaggctgcc ctgacggcca tcgtgagcga gtacgtggat    1920
cggacgctac ccgaagccac taatgaccca ggccaggcta acctgcctcc tcctccaact    1980 atccccagg caaccgcccc gcccaggctg gcctcggact cggcgctctg gcctaagaag    2040
ccccagctgc tgacaaggcg agagcgggac gatctcctcc aggccacggg ggacttcttc    2100

-continued

```
tcggagctgc tgaccgaggc cgaggcggcc gaggtccggg cgctggaaga gcaggtccgg    2160
gagagccaga ccctgatggc gaaggcccac gagatggcgg caagcactcg gcggggcttt    2220
cacacggctc tggaggccgt cctctccagg tcacgcgacg aagcccccga cgatgaactc    2280
cggagcctgc ttccctcccc gcccaaagcc cctgtccagg ctcccctcga ggccgccctg    2340
gcccgggcag cggccgggaa cggctcatgg ccctaccgga aatccctggc agccgccaag    2400
tggatccggg gcatctgcga ggccgtgcgg ggtctttccg aaggagccct ggccttagct    2460
gggggcgcgg gtgcctggct gaacctagcc gctgcggctg acggtgaaat tcatgagcta    2520
acacggctcc tggaagtcga gggcatggcc cagaactcca tggatggcat ggaggagctg    2580
aggttggctc tggccacgtt ggaccccaag cgggtcgcgg ggggcaagga gaccgtcgca    2640
gactggaaaa ggcgcctctc ccgactggag gccatcatcc aggaggccca ggaagagtcc    2700
cagctgcagg gaacgctgca ggatctggtc acccaggcca ggggccacac cgacccgcgc    2760
cagctcaaga tcgtggtgga ggctgccagg ggcctggcgc ttggggcctc ggctggctcc    2820
cagtatgccc tcctcaagga caagctgctg cgctatgcct cggccaagca gagtttcctg    2880 gcttttttacg agaccgccca gcctaccgtt ttcgttaagc atcccttgac caacaacctg    2940
cccctcctca tcacgatttc ggcaccacca actggatggg gcaatggagc cccgacccgg    3000
```

<210> SEQ ID NO 111
<211> LENGTH: 1000
<212> TYPE: PRT
<213> ORGANISM: Artificial Sequence
<220> FEATURE:
<223> OTHER INFORMATION: Synthetic

<400> SEQUENCE: 111

```
Val Arg Arg Cys Thr Ala Asp Ile Arg Asp Lys Val Ala Ser Ala Ala
1               5                   10                  15

Ser Asp Tyr Leu Ser Tyr Leu Glu Asp Pro Ser Leu Pro Thr Val Met
            20                  25                  30

Asp Phe Asp Asp Leu Leu Thr His Leu Arg His Thr Cys Gln Ile Ile
        35                  40                  45

Ala Ser Leu Pro Leu Leu Asn Ile Arg Tyr Thr Ser Ile Glu Trp Asp
    50                  55                  60

Tyr Arg Glu Leu Leu Tyr Leu Gly Thr Ala Leu Ser Asp Met Ser Gly
65                  70                  75                  80

Ile Pro Trp Pro Leu Glu Arg Val Glu Glu Asp Asp Pro Ser Ile Ala
                85                  90                  95

Pro Leu Pro Glu Phe Glu Thr Val Ala Lys Lys Gln Lys Glu Leu Glu
            100                 105                 110

Thr Thr Arg Glu Asn Glu Lys Arg Leu Arg Thr Ile Leu Asp Asp Ile
            115                 120                 125

Glu Ala Met Leu Gly Leu Ala Gly Val Ala Ser Ala Pro Gly Ala Pro
    130                 135                 140

Ile Ser Pro Ala Ser Pro Ser Ala Thr Pro Ala Asn His Asp Asn Pro
145                 150                 155                 160

Glu Ala Thr Pro Pro Leu Ala Asp Thr Ala Ala Leu Thr Ile Pro Val
                165                 170                 175

Ile Glu Lys Tyr Ile Ala Asn Ala Gly Ser Ile Val Gly Ala Ala Lys
            180                 185                 190

Asn Pro Thr Tyr Ile Arg Leu Arg Asp Thr Ile Gln Gln Ile Val Arg
            195                 200                 205
```

-continued

```
Ser Lys Lys Tyr Leu Met Asn Ile Leu Lys Ser Ile Thr Phe Tyr Thr
    210             215             220

Ile Asp Asn Tyr Ile Ala Ser Phe Glu Glu Ser Ile Asp His Leu Tyr
225             230             235             240

Arg Asp Leu Pro Val Leu Asp Pro Glu Val Gln Asp Gly Ile Asp Arg
            245             250             255

Ile Leu Asp Pro Met Val Ser Glu Ala Leu His Thr Phe Glu Met Gly
            260             265             270

Asn Arg Leu Thr Leu Glu Pro Ala Arg Leu Val Ala Leu Gln Asn Phe
        275             280             285

Ala Thr His Ser Thr Leu Lys Glu Thr Ala Ala Ala Val Asn Leu Leu
    290             295             300

Pro Gly Leu Leu Ala Val Tyr Asp Ala Thr Ile Thr Gly Gln Ala Pro
305             310             315             320

Glu Asp Ala Leu Arg Leu Leu Ser Gly Leu Gln Asn Gln Leu Ser Gln
            325             330             335

Thr Leu Ile Pro Gly Lys Leu Lys Lys Arg Phe Leu Ser Tyr Leu Gln
            340             345             350

Lys Leu Lys Asn Asn Asn Asn Asp Gln Leu Arg Gln Lys Glu Val Gln
        355             360             365

Ala Trp Arg Leu Glu Ala Glu Gly Phe Lys Pro Ala Thr Glu Glu Gln
    370             375             380

Leu Glu Ala Phe Leu Asp Thr Ala Pro Asn Lys Glu Leu Lys Arg Gln
385             390             395             400

Tyr Glu Lys Lys Leu Arg Gln Leu Met Glu Thr Gly Arg Lys Glu Lys
            405             410             415

Glu Lys Leu Arg Glu Gln Glu Asp Lys Glu Arg Gln Glu Arg Arg Ala
            420             425             430

Arg Glu Ala Asn Glu Ala Trp Ala Arg Ile Arg Lys Ala Leu Gly Ala
        435             440             445

Arg Pro Glu Pro Ala Pro Thr Ser Pro Asp Asp Trp Asn Thr Leu Leu
    450             455             460

Ala Ser Leu Leu Pro Asp Asn Thr Asp Ser Ala Ala Ala Ala Ala Ala
465             470             475             480

Ala Val Ala Arg Asn Thr Asp Ile Leu Asp Ser Leu Thr Gln Ile Leu
            485             490             495

Ala Ala Met Leu Leu Gly Ile Thr Arg Val Arg Arg Glu Arg Leu Arg
            500             505             510

Ser Leu Leu Val Asp Asp Gly Gly Ala Ala Glu Arg Met Glu Ala Ala
        515             520             525

Glu Pro Gly Trp Phe Thr Asp Ile Glu Thr Gly Pro Leu Ala Arg Leu
    530             535             540

Asp Ala Trp Pro Ala Thr Pro Ala Ala Thr Ala Lys Glu Gly Gly Gly
545             550             555             560

Gly Arg Gly Ala Glu Glu Ala Ala Gly Ala Leu Phe Arg Ala Arg Thr
            565             570             575

Ala Ala Asp Ala Ile Arg Ser Ala Leu Ala Gln Thr Arg Gln Ala Leu
        580             585             590

Gln Ser Pro Asp Met Lys Ser Ala Val Val Asn Thr Asp Leu Glu Ala
    595             600             605

Pro Tyr Ala Glu Tyr Glu Arg Gly Leu Ala Gly Leu Leu Glu Lys Arg
    610             615             620
```

```
Arg Ala Ala Glu Ala Ala Leu Thr Ala Ile Val Ser Glu Tyr Val Asp
625             630                 635                 640

Arg Thr Leu Pro Glu Ala Thr Asn Asp Pro Gly Gln Ala Asn Leu Pro
                645                 650                 655

Pro Pro Pro Thr Ile Pro Gln Ala Thr Ala Pro Pro Arg Leu Ala Ser
            660                 665                 670

Asp Ser Ala Leu Trp Pro Lys Lys Pro Gln Leu Leu Thr Arg Arg Glu
        675                 680                 685

Arg Asp Asp Leu Leu Gln Ala Thr Gly Asp Phe Phe Ser Glu Leu Leu
    690                 695                 700

Thr Glu Ala Glu Ala Ala Glu Val Arg Ala Leu Glu Glu Gln Val Arg
705             710                 715                 720

Glu Ser Gln Thr Leu Met Ala Lys Ala His Glu Met Ala Ala Ser Thr
                725                 730                 735

Arg Arg Gly Phe His Thr Ala Leu Glu Ala Val Leu Ser Arg Ser Arg
            740                 745                 750

Asp Glu Ala Pro Asp Asp Glu Leu Arg Ser Leu Leu Pro Ser Pro Pro
        755                 760                 765

Lys Ala Pro Val Gln Ala Pro Leu Glu Ala Ala Leu Ala Arg Ala Ala
    770                 775                 780

Ala Gly Asn Gly Ser Trp Pro Tyr Arg Lys Ser Leu Ala Ala Ala Lys
785             790                 795                 800

Trp Ile Arg Gly Ile Cys Glu Ala Val Arg Gly Leu Ser Glu Gly Ala
            805                 810                 815

Leu Ala Leu Ala Gly Gly Ala Gly Ala Trp Leu Asn Leu Ala Ala Ala
        820                 825                 830

Ala Asp Gly Glu Ile His Glu Leu Thr Arg Leu Leu Glu Val Glu Gly
        835                 840                 845

Met Ala Gln Asn Ser Met Asp Gly Met Glu Glu Leu Arg Leu Ala Leu
    850                 855                 860

Ala Thr Leu Asp Pro Lys Arg Val Ala Gly Gly Lys Glu Thr Val Ala
865             870                 875                 880

Asp Trp Lys Arg Arg Leu Ser Arg Leu Glu Ala Ile Ile Gln Glu Ala
            885                 890                 895

Gln Glu Glu Ser Gln Leu Gln Gly Thr Leu Gln Asp Leu Val Thr Gln
            900                 905                 910

Ala Arg Gly His Thr Asp Pro Arg Gln Leu Lys Ile Val Val Glu Ala
        915                 920                 925

Ala Arg Gly Leu Ala Leu Gly Ala Ser Ala Gly Ser Gln Tyr Ala Leu
    930                 935                 940

Leu Lys Asp Lys Leu Leu Arg Tyr Ala Ser Ala Lys Gln Ser Phe Leu
945             950                 955                 960

Ala Phe Tyr Glu Thr Ala Gln Pro Thr Val Phe Val Lys His Pro Leu
            965                 970                 975

Thr Asn Asn Leu Pro Leu Leu Ile Thr Ile Ser Ala Pro Pro Thr Gly
            980                 985                 990

Trp Gly Asn Gly Ala Pro Thr Arg
        995                 1000
```

```
<210> SEQ ID NO 112
<211> LENGTH: 228
<212> TYPE: DNA
<213> ORGANISM: Artificial Sequence
<220> FEATURE:
<223> OTHER INFORMATION: Synthetic
```

-continued

<400> SEQUENCE: 112
atgggtgccc tctggtctct ttgccgacga cgagtcaact ccataggcga cgtggacggg      60
ggaataatca acctgtataa tgactatgag gagtttaacc tggagactac taagctaata     120
gcggccgaag aagggagggc ctgcggggaa accaacgagg ggctcgaata tgatgaggac     180
tctgaaaatg atgaattgct gttttttgcca aataaaaaac caaactaa                 228

<210> SEQ ID NO 113
<211> LENGTH: 75
<212> TYPE: PRT
<213> ORGANISM: Artificial Sequence
<220> FEATURE:
<223> OTHER INFORMATION: Synthetic

<400> SEQUENCE: 113

Met Gly Ala Leu Trp Ser Leu Cys Arg Arg Arg Val Asn Ser Ile Gly
1                5                   10                  15

Asp Val Asp Gly Gly Ile Ile Asn Leu Tyr Asn Asp Tyr Glu Glu Phe
            20                  25                  30

Asn Leu Glu Thr Thr Lys Leu Ile Ala Ala Glu Glu Gly Arg Ala Cys
        35                  40                  45

Gly Glu Thr Asn Glu Gly Leu Glu Tyr Asp Glu Asp Ser Glu Asn Asp
    50                  55                  60

Glu Leu Leu Phe Leu Pro Asn Lys Lys Pro Asn
65                  70                  75

<210> SEQ ID NO 114
<211> LENGTH: 1095
<212> TYPE: DNA
<213> ORGANISM: Artificial Sequence
<220> FEATURE:
<223> OTHER INFORMATION: Synthetic

<400> SEQUENCE: 114
atgaaggtcc aggggtccgt cgatcgccgc cgtctgcaac gccgaatcgc ggggctgctg      60 cccccctccgg cccggcgtct aaatatttcc cggggggtccg aattcacgcg ggacgttcgt     120
gggctggttg aggaacacgc gcaggcctcc tcgctgagtg cggcggccgt ctggcgcgca     180
gggctgctgg cccgggggga ggtggcggtc gccgggggtg gcagtggagg ggggagcttc     240
agctggtctg ggtggcggcc gccagtcttt ggggactttc tgatacacgc cagctccttc     300
aacaacgccg aggccactgg aacgcccctt ttccaattca agcagagtga cccgttctcg     360
ggcgtcgacg cggtattcac tcctctctcc ctgtttatcc taatgaatca cggccggggt     420
gtagccgccc gggtcgaggc aggtgggggc ctgacgcgga tggccaacct gctgtacgac     480
agccccgcaa ccctggctga cctggtcccg gactttgggc ggctggtggc cgaccgccgc     540
ttccacaact tcatcacccc tgtgggcccc ctggtggaga atataaagag cacctatctg     600
aataaaatca ccacggtggt ccacgggcct gtggtcagca aggccatccc tcgcagcacc     660
gtcaaggtga cggtgcccca ggaggccttt gtggatctgg acgcgtggct ctccggcggc     720 gccggggggtg gcggtggagt atgcttcgtc gggggggctgg gcctgcagcc gtgccccgcc     780
gatgcgcgcc tctatgtcgc tctgacctat gaggaagccg ggccgcggtt tacgtttttc     840
cagtcgtccc gcggccactg tcagatcatg aatatcttaa gaatttatta ctcaccatcc     900
atcatgcacc gctatgctgt ggtccagccc ctacatatag aggagctaac cttcggggcg     960
gttgcctgtc tggggacatt tagtgctact gacggttgga ggaggtctgc cttcaattac    1020
cgtggctcta gcctccccgt ggtggagatt gacagctttt attccaacgt ctctgactgg      1080
gaggtgattc tctag                                                       1095

<210> SEQ ID NO 115
<211> LENGTH: 364
<212> TYPE: PRT
<213> ORGANISM: Artificial Sequence
<220> FEATURE:
<223> OTHER INFORMATION: Synthetic

<400> SEQUENCE: 115

Met Lys Val Gln Gly Ser Val Asp Arg Arg Arg Leu Gln Arg Arg Ile
1               5                   10                  15

Ala Gly Leu Leu Pro Pro Ala Arg Arg Leu Asn Ile Ser Arg Gly
            20                  25                  30

Ser Glu Phe Thr Arg Asp Val Arg Gly Leu Val Glu Glu His Ala Gln
            35                  40                  45

Ala Ser Ser Leu Ser Ala Ala Ala Val Trp Arg Ala Gly Leu Leu Ala
        50                  55                  60

Pro Gly Glu Val Ala Val Ala Gly Gly Gly Ser Gly Gly Gly Ser Phe
65                  70                  75                  80

Ser Trp Ser Gly Trp Arg Pro Pro Val Phe Gly Asp Phe Leu Ile His
            85                  90                  95

Ala Ser Ser Phe Asn Asn Ala Glu Ala Thr Gly Thr Pro Leu Phe Gln
            100                 105                 110

Phe Lys Gln Ser Asp Pro Phe Ser Gly Val Asp Ala Val Phe Thr Pro
        115                 120                 125

Leu Ser Leu Phe Ile Leu Met Asn His Gly Arg Gly Val Ala Ala Arg
        130                 135                 140

Val Glu Ala Gly Gly Gly Leu Thr Arg Met Ala Asn Leu Leu Tyr Asp
145                 150                 155                 160

Ser Pro Ala Thr Leu Ala Asp Leu Val Pro Asp Phe Gly Arg Leu Val
            165                 170                 175

Ala Asp Arg Arg Phe His Asn Phe Ile Thr Pro Val Gly Pro Leu Val
            180                 185                 190

Glu Asn Ile Lys Ser Thr Tyr Leu Asn Lys Ile Thr Thr Val Val His
        195                 200                 205

Gly Pro Val Val Ser Lys Ala Ile Pro Arg Ser Thr Val Lys Val Thr
        210                 215                 220

Val Pro Gln Glu Ala Phe Val Asp Leu Asp Ala Trp Leu Ser Gly Gly
225                 230                 235                 240

Ala Gly Gly Gly Gly Gly Val Cys Phe Val Gly Gly Leu Gly Leu Gln
            245                 250                 255

Pro Cys Pro Ala Asp Ala Arg Leu Tyr Val Ala Leu Thr Tyr Glu Glu
            260                 265                 270

Ala Gly Pro Arg Phe Thr Phe Phe Gln Ser Ser Arg Gly His Cys Gln
        275                 280                 285

Ile Met Asn Ile Leu Arg Ile Tyr Tyr Ser Pro Ser Ile Met His Arg
        290                 295                 300

Tyr Ala Val Val Gln Pro Leu His Ile Glu Glu Leu Thr Phe Gly Ala
305                 310                 315                 320

Val Ala Cys Leu Gly Thr Phe Ser Ala Thr Asp Gly Trp Arg Arg Ser
            325                 330                 335

Ala Phe Asn Tyr Arg Gly Ser Ser Leu Pro Val Val Glu Ile Asp Ser

-continued

```
           340              345              350
Phe Tyr Ser Asn Val Ser Asp Trp Glu Val Ile Leu
        355              360
```

```
<210> SEQ ID NO 116
<211> LENGTH: 1137
<212> TYPE: DNA
<213> ORGANISM: Artificial Sequence
<220> FEATURE:
<223> OTHER INFORMATION: Synthetic

<400> SEQUENCE: 116
atgaatccag tatgcctgcc tgtaattgtt gcgccctacc tgttttggct ggcggctatt      60
gccgcctcgt gtttcacggc ctcagttagt accgttgtga ccgccaccgg cttggccctc     120
tcacttctac tcttggcagc agtggccagc tcatatgccg ctgcacaaag gaaactgctg     180
acaccggtga cagttcttac tgcggttgtc actttctttg caatttgcct aacatggagg     240
attgaggacc cacctttaa ttctcttctg tttgcattgc tggccgcagc tggcggacta      300
caaggcattt acgttctggt gatgcttgtg ctcctgatac tagcgtacag aaggagatgg     360
cgccgtttga ctgtttgtgg cggcatcatg tttttggcat gtgtacttgt cctcatcgtc     420
gacgctgttt tgcagctgag tcccctcctt ggagctgtaa ctgtggtttc catgacgctg     480
ctgctactgg ctttcgtcct ctggctctct tcgccagggg gcctaggtac tcttggtgca     540 gccctttaa cattggcagc agctctggca ctgctagcgt cactgatttt gggcacactt     600
aacttgacta caatgttcct tctcatgctc ctatggacac ttgtggttct cctgatttgc     660
tcttcgtgct cttcatgtcc actgaccaag atccttctgg cacgactgtt cctatatgct     720
ctcgcactct tgttgctagc ctccgcgcta atcgctggtg gcagtatttt gcaaacaaac     780
ttcaagagtt taagcagcac tgaatttata cccaatttgt tctgcatgtt attactgatt     840
gtcgctggca tactcttcat tcttgctatc ctgaccgaat ggggcagtgg aaatagaaca     900
tacggtccag ttttatgtg cctcggtggc ctgctcacca tggtagccgg cgctgtgtgg     960
ctgacggtga tgactaacac gcttttgtct gcctggattc ttacagcagg attcctgatt    1020
ttcctcattg gctttgccct ctttggggtc attagatgct gccgctactg ctgctactac    1080
tgccttacac tggaaagtga ggagcgccca ccgaccccat atcgcaacac tgtataa       1137
```

```
<210> SEQ ID NO 117
<211> LENGTH: 378
<212> TYPE: PRT
<213> ORGANISM: Artificial Sequence
<220> FEATURE:
<223> OTHER INFORMATION: Synthetic

<400> SEQUENCE: 117
```

```
Met Asn Pro Val Cys Leu Pro Val Ile Val Ala Pro Tyr Leu Phe Trp
1               5                   10                  15

Leu Ala Ala Ile Ala Ala Ser Cys Phe Thr Ala Ser Val Ser Thr Val
            20                  25                  30

Val Thr Ala Thr Gly Leu Ala Leu Ser Leu Leu Leu Ala Ala Val
        35                  40                  45

Ala Ser Ser Tyr Ala Ala Ala Gln Arg Lys Leu Leu Thr Pro Val Thr
    50                  55                  60

Val Leu Thr Ala Val Val Thr Phe Phe Ala Ile Cys Leu Thr Trp Arg
65                  70                  75                  80

Ile Glu Asp Pro Pro Phe Asn Ser Leu Leu Phe Ala Leu Leu Ala Ala
```

```
             85               90               95
Ala Gly Gly Leu Gln Gly Ile Tyr Val Leu Val Met Leu Val Leu Leu
                100               105               110

Ile Leu Ala Tyr Arg Arg Arg Trp Arg Arg Leu Thr Val Cys Gly Gly
            115               120               125

Ile Met Phe Leu Ala Cys Val Leu Val Leu Ile Val Asp Ala Val Leu
    130               135               140

Gln Leu Ser Pro Leu Leu Gly Ala Val Thr Val Val Ser Met Thr Leu
145               150               155               160

Leu Leu Leu Ala Phe Val Leu Trp Leu Ser Ser Pro Gly Gly Leu Gly
                165               170               175

Thr Leu Gly Ala Ala Leu Leu Thr Leu Ala Ala Ala Leu Ala Leu Leu
                180               185               190

Ala Ser Leu Ile Leu Gly Thr Leu Asn Leu Thr Thr Met Phe Leu Leu
    195               200               205

Met Leu Leu Trp Thr Leu Val Val Leu Leu Ile Cys Ser Ser Cys Ser
    210               215               220

Ser Cys Pro Leu Thr Lys Ile Leu Leu Ala Arg Leu Phe Leu Tyr Ala
225               230               235               240

Leu Ala Leu Leu Leu Leu Ala Ser Ala Leu Ile Ala Gly Gly Ser Ile
                245               250               255

Leu Gln Thr Asn Phe Lys Ser Leu Ser Ser Thr Glu Phe Ile Pro Asn
                260               265               270

Leu Phe Cys Met Leu Leu Leu Ile Val Ala Gly Ile Leu Phe Ile Leu
                275               280               285

Ala Ile Leu Thr Glu Trp Gly Ser Gly Asn Arg Thr Tyr Gly Pro Val
    290               295               300

Phe Met Cys Leu Gly Gly Leu Leu Thr Met Val Ala Gly Ala Val Trp
305               310               315               320

Leu Thr Val Met Thr Asn Thr Leu Leu Ser Ala Trp Ile Leu Thr Ala
                325               330               335

Gly Phe Leu Ile Phe Leu Ile Gly Phe Ala Leu Phe Gly Val Ile Arg
                340               345               350

Cys Cys Arg Tyr Cys Cys Tyr Tyr Cys Leu Thr Leu Glu Ser Glu Glu
                355               360               365

Arg Pro Pro Thr Pro Tyr Arg Asn Thr Val
    370               375
```

<210> SEQ ID NO 118
<211> LENGTH: 927
<212> TYPE: DNA
<213> ORGANISM: Artificial Sequence
<220> FEATURE:
<223> OTHER INFORMATION: Synthetic

<400> SEQUENCE: 118

```
atgggagacc gaagtgaagg ccctggacca acccggcccg ggcccccogg tatcgggcca      60 gagggtcccc tcggacagct cctaagaagg caccggtcgc ccagtcctac cagaggggc     120 caagaaccca gacgagtccg tagaagggtc ctcgtccagc aagaagagga ggtggtaagc     180
ggttcacctt cagggcctag gggagaccga agtgaaggcc ctggaccaac ccggcccggg     240
ccccccggta tcgggccaga gggtcccctc ggacagctcc taagaaggca ccggtcgccc     300
agtcctacca gaggggccaa gaacccagac gagtccgta gaagggtcct cgtccagcaa     360
gaagaggagg tggtaagcgg ttcaccttca gggcctaggg gagaccgaag tgaaggccct     420
```

```
ggaccaaccc ggcccgggcc ccccggtatc gggccagagg gtcccctcgg acagctccta      480
agaaggcacc ggtcgcccag tcctaccaga gggggccaag aacccagacg agtccgtaga      540
agggtcctcg tccagcaaga agaggaggtg gtaagcggtt caccttcagg gcctaggga      600 gaccgaagtg aaggccctgg accaacccgg cccgggcccc ccggtatcgg ccagagggt      660 cccctcggac agctcctaag aaggcaccgg tcgcccagtc ctaccagagg gggccaagaa      720
cccagacgag tccgtagaag ggtcctcgtc cagcaagaag aggaggtggt aagcggttca      780
ccttcagggc cactacggcc acgtccccgg cctcccgctc ggtctcttag agagtggctg      840
ctacgcatta gagaccactt tgagccaccc acagtaacca cccagcgcca atctgtctac      900
atagaagaag aagaggatga agactaa                                        927
```

<210> SEQ ID NO 119
<211> LENGTH: 308
<212> TYPE: PRT
<213> ORGANISM: Artificial Sequence
<220> FEATURE:
<223> OTHER INFORMATION: Synthetic

<400> SEQUENCE: 119

```
Met Gly Asp Arg Ser Glu Gly Pro Gly Pro Thr Arg Pro Gly Pro Pro
1               5                   10                  15

Gly Ile Gly Pro Glu Gly Pro Leu Gly Gln Leu Leu Arg Arg His Arg
            20                  25                  30

Ser Pro Ser Pro Thr Arg Gly Gly Gln Glu Pro Arg Arg Val Arg Arg
        35                  40                  45

Arg Val Leu Val Gln Gln Glu Glu Val Val Ser Gly Ser Pro Ser
    50                  55                  60

Gly Pro Arg Gly Asp Arg Ser Glu Gly Pro Gly Pro Thr Arg Pro Gly
65                  70                  75                  80

Pro Pro Gly Ile Gly Pro Glu Gly Pro Leu Gly Gln Leu Leu Arg Arg
                85                  90                  95

His Arg Ser Pro Ser Pro Thr Arg Gly Gly Gln Glu Pro Arg Arg Val
            100                 105                 110

Arg Arg Arg Val Leu Val Gln Gln Glu Glu Glu Val Val Ser Gly Ser
        115                 120                 125

Pro Ser Gly Pro Arg Gly Asp Arg Ser Glu Gly Pro Gly Pro Thr Arg
    130                 135                 140

Pro Gly Pro Pro Gly Ile Gly Pro Glu Gly Pro Leu Gly Gln Leu Leu
145                 150                 155                 160

Arg Arg His Arg Ser Pro Ser Pro Thr Arg Gly Gly Gln Glu Pro Arg
                165                 170                 175

Arg Val Arg Arg Arg Val Leu Val Gln Gln Glu Glu Val Val Ser
            180                 185                 190

Gly Ser Pro Ser Gly Pro Arg Gly Asp Arg Ser Glu Gly Pro Gly Pro
        195                 200                 205

Thr Arg Pro Gly Pro Pro Gly Ile Gly Pro Glu Gly Pro Leu Gly Gln
    210                 215                 220

Leu Leu Arg Arg His Arg Ser Pro Ser Pro Thr Arg Gly Gly Gln Glu
225                 230                 235                 240

Pro Arg Arg Val Arg Arg Arg Val Leu Val Gln Gln Glu Glu Glu Val
                245                 250                 255

Val Ser Gly Ser Pro Ser Gly Pro Leu Arg Pro Arg Pro Arg Pro Pro
            260                 265                 270
```

-continued

```
Ala Arg Ser Leu Arg Glu Trp Leu Leu Arg Ile Arg Asp His Phe Glu
        275                 280                 285

Pro Pro Thr Val Thr Thr Gln Arg Gln Ser Val Tyr Ile Glu Glu Glu
    290                 295                 300

Glu Asp Glu Asp
305

<210> SEQ ID NO 120
<211> LENGTH: 2979
<212> TYPE: DNA
<213> ORGANISM: Artificial Sequence
<220> FEATURE:
<223> OTHER INFORMATION: Synthetic

<400> SEQUENCE: 120
atggaatcat ttgaaggaca ggggggactct agacagtcac ccgacaatga gcggggagat        60
aatgtacaga ctaccggcga gcatgatcag daccctgggc cggggcctcc atccagtggg       120
gcttctgaga gattggtacc agaagagtca tactcaagag atcagcaacc ttgggggcaa       180 agcagggggtg atgaaaacag aggctggatg cagcgcatca ggcgaaggcg gagaagacgg       240
gctgccttgt ccggccatct tttagacacg gaagacaatg tgccgccatg gttgcctcca       300
cacgacatca caccatatac cgcaaggaat atcagggatg ctgcctgccg ggctgtcaag       360
caatcgcacc tgcaagcgct atcaaacctg tactcgata gtgggttaga cacacaacac       420
atcttgtgct tcgtgatggc agccaggcag cgtcttcagg acattcgacg tggacccttg       480
gttgcggagg cggtgtgggg ttggcgacat tggcttctaa catctcccag ccaatcctgg       540
cccatgggat atcgtacagc aacactacgc acattaactc ccgtgcctaa cagggttggg       600
gctgacagca tcatgttaac tgccacattt ggatgccaaa atgcggcacg aactctaaac       660
accttctctg ccaccgtgtg gacaccaccc catgctggac caagagagca agaaagatac       720
gctcgggaag ccgaggtacg cttccttcgt ggtaaatggc agaggcggta ccgaagaatc       780
tatgatttga tagaactgtg tggctctctg caccacatct ggcaaaactt gctccagacc       840
gaggagaacc ttttagattt cgtgcgtttc atgggtgtca tgtccagctg caataatcca       900
gctgtgaatt actggtttca caagacaatc ggaaacttta agccatatta cccgtggaat       960
gcaccaccta atgaaaatcc atatcacgcg cggagaggca taaagaaca cgtaatccag      1020 aacgcatttc gaaaggcaca aatacagggt ttatcaatgt tagcaacggg aggtgaaccc      1080
agaggtgatg ctactagtga aacgagcagt gatgaggaca ccggtagaca gggttcggac      1140
gtggagctag agtcctcgga cgatgagctg ccatatatcg atcccaatat ggagccggtt      1200
cagcagaggc ccgtcatgtt tgtgagccgt gtgcctgcaa agaaaccgag gaaactgcct      1260
tggcccacgc ccaagacgca cccagtgaag cgcacaaatg ttaagacctc tgatagatct      1320
gataaggcag aagcacaaag caccccctgaa aggccgggcc cttccgaaca atcatcagtg      1380
accgtggagc ccgccacccc gaccccggtg gagatgccaa tggtgattct ccatcaacca      1440
cctccagtgc ccaaaccggt tccagtcaag cctacgccac cgccttcccg taggagaagg      1500
ggagcgtgtg ttgtgtacga cgatgatgtc atagaggtga ttgatgttga aaccaccgaa      1560
gattcatcgt cagtgtcaca gccaaataag ccacatcgga acatcaaga cggctttcaa      1620 cgttcaggcc gacgtcaaaa acgagccgcg cctcccaccg tgagtccttc ggatactggg      1680
cctcctgccg tggggcctcc tgccgcgggg cctcctgccg cggggcctcc tgccgcgggg      1740
cctcctgccg cggggcctcc tgccgcgggg cctcctgccg cggggcctcg catactggcg      1800
```

-continued

```
cctctttccg ctgggcctcc tgccgcgggg cctcacatag tgacgcctcc ttccgcccgg    1860
cctcgtataa tggcgcctcc cgtcgtacgt atgtttatga gggagcgaca gctcccccag    1920
tccaccggcc gtaaacctca gtgcttctgg gaaatgcggg ctggtcgtga aattacacaa    1980
atgcaacaag aaccaagttc acacctgcag tccgccactc agcctacaac gcctcgccca    2040
tcatgggccc catcagtctg cgccctctcg gtgatggatg ctggtaaggc ccagcccata    2100
gaaagttcac acttgagttc catgtcgccc acacagccga tatcgcacga agaacaaccc    2160
cggtatgagg atcctgacgc tcctctggat ttaagtttac atccagacgt tgctgctcaa    2220
ccagctcccc aggctccata ccagggatac caggagccgc cggccccca ggctccatac     2280 cagggatacc aggagccgcc gccccccag gctccatacc agggatacca ggagccgccg     2340
gcccacgggc tccaatcatc ttcatatcca ggatatgcgg gtccctggac cccaaggtct     2400
caacatccat gttataggca cccctgggca ccatggtctc aagatcctgt gcatgggcac     2460
acccagggtc catgggatcc cagggcacca catctcccac ctcagtggga tggatctgca     2520
ggacatggcc aggatcaggt ctcccagttc ccacatctgc aatcggagac aggcccacca     2580
cgtcttcaac tttcattggt gccactggtc tcatcctctg caccatcatg gtcatctccc     2640
cagccccgag cccccatacg ccccattcca acaagattcc cccctccccc tatgccgtta     2700
caagatagca tggccgtggg gtgtgactca tcaggtacag catgcccaag catgcccttt     2760
gccagtgatt acagtcaagg tgcatttacc ccactggaca ttaatgccac cacgccaaaa    2820
aggcctcgag tagaagaaag ttctcacgga cctgcccggt gttcccaagc tactgctgaa     2880
gcacaggaga ttctcagtga caattctgag atctccgtgt tcccaaagga cgcgaagcag     2940
actgactacg atgcatccac tgaaagtgag ctagattaa                           2979
```

<210> SEQ ID NO 121
<211> LENGTH: 992
<212> TYPE: PRT
<213> ORGANISM: Artificial Sequence
<220> FEATURE:
<223> OTHER INFORMATION: Synthetic

<400> SEQUENCE: 121

```
Met Glu Ser Phe Glu Gly Gln Gly Asp Ser Arg Gln Ser Pro Asp Asn
1               5                   10                  15

Glu Arg Gly Asp Asn Val Gln Thr Thr Gly Glu His Asp Gln Asp Pro
            20                  25                  30

Gly Pro Gly Pro Pro Ser Ser Gly Ala Ser Glu Arg Leu Val Pro Glu
        35                  40                  45

Glu Ser Tyr Ser Arg Asp Gln Gln Pro Trp Gly Gln Ser Arg Gly Asp
    50                  55                  60

Glu Asn Arg Gly Trp Met Gln Arg Ile Arg Arg Arg Arg Arg Arg Arg
65                  70                  75                  80

Ala Ala Leu Ser Gly His Leu Leu Asp Thr Glu Asp Asn Val Pro Pro
                85                  90                  95

Trp Leu Pro Pro His Asp Ile Thr Pro Tyr Thr Ala Arg Asn Ile Arg
            100                 105                 110

Asp Ala Ala Cys Arg Ala Val Lys Gln Ser His Leu Gln Ala Leu Ser
        115                 120                 125

Asn Leu Ile Leu Asp Ser Gly Leu Asp Thr Gln His Ile Leu Cys Phe
    130                 135                 140

Val Met Ala Ala Arg Gln Arg Leu Gln Asp Ile Arg Arg Gly Pro Leu
```

-continued

```
145                 150                 155                 160

Val Ala Glu Gly Gly Val Gly Trp Arg His Trp Leu Leu Thr Ser Pro
                165                 170                 175

Ser Gln Ser Trp Pro Met Gly Tyr Arg Thr Ala Thr Leu Arg Thr Leu
                180                 185                 190

Thr Pro Val Pro Asn Arg Val Gly Ala Asp Ser Ile Met Leu Thr Ala
                195                 200                 205

Thr Phe Gly Cys Gln Asn Ala Ala Arg Thr Leu Asn Thr Phe Ser Ala
        210                 215                 220

Thr Val Trp Thr Pro Pro His Ala Gly Pro Arg Glu Gln Glu Arg Tyr
225                 230                 235                 240

Ala Arg Glu Ala Glu Val Arg Phe Leu Arg Gly Lys Trp Gln Arg Arg
                245                 250                 255

Tyr Arg Arg Ile Tyr Asp Leu Ile Glu Leu Cys Gly Ser Leu His His
                260                 265                 270

Ile Trp Gln Asn Leu Leu Gln Thr Glu Glu Asn Leu Leu Asp Phe Val
                275                 280                 285

Arg Phe Met Gly Val Met Ser Ser Cys Asn Asn Pro Ala Val Asn Tyr
        290                 295                 300

Trp Phe His Lys Thr Ile Gly Asn Phe Lys Pro Tyr Tyr Pro Trp Asn
305                 310                 315                 320

Ala Pro Pro Asn Glu Asn Pro Tyr His Ala Arg Arg Gly Ile Lys Glu
                325                 330                 335

His Val Ile Gln Asn Ala Phe Arg Lys Ala Gln Ile Gln Gly Leu Ser
                340                 345                 350

Met Leu Ala Thr Gly Gly Glu Pro Arg Gly Asp Ala Thr Ser Glu Thr
                355                 360                 365

Ser Ser Asp Glu Asp Thr Gly Arg Gln Gly Ser Asp Val Glu Leu Glu
        370                 375                 380

Ser Ser Asp Asp Glu Leu Pro Tyr Ile Asp Pro Asn Met Glu Pro Val
385                 390                 395                 400

Gln Gln Arg Pro Val Met Phe Val Ser Arg Val Pro Ala Lys Lys Pro
                405                 410                 415

Arg Lys Leu Pro Trp Pro Thr Pro Lys Thr His Pro Val Lys Arg Thr
                420                 425                 430

Asn Val Lys Thr Ser Asp Arg Ser Asp Lys Ala Glu Ala Gln Ser Thr
                435                 440                 445

Pro Glu Arg Pro Gly Pro Ser Glu Gln Ser Ser Val Thr Val Glu Pro
        450                 455                 460

Ala His Pro Thr Pro Val Glu Met Pro Met Val Ile Leu His Gln Pro
465                 470                 475                 480

Pro Pro Val Pro Lys Pro Val Pro Val Lys Pro Thr Pro Pro Pro Ser
                485                 490                 495

Arg Arg Arg Arg Gly Ala Cys Val Val Tyr Asp Asp Asp Val Ile Glu
                500                 505                 510

Val Ile Asp Val Glu Thr Thr Glu Asp Ser Ser Ser Val Ser Gln Pro
        515                 520                 525

Asn Lys Pro His Arg Lys His Gln Asp Gly Phe Gln Arg Ser Gly Arg
        530                 535                 540

Arg Gln Lys Arg Ala Ala Pro Pro Thr Val Ser Pro Ser Asp Thr Gly
545                 550                 555                 560

Pro Pro Ala Val Gly Pro Pro Ala Ala Gly Pro Pro Ala Ala Gly Pro
                565                 570                 575
```

-continued

```
Pro Ala Ala Gly Pro Pro Ala Ala Gly Pro Pro Ala Ala Gly Pro Pro
            580                 585                 590

Ala Ala Gly Pro Arg Ile Leu Ala Pro Leu Ser Ala Gly Pro Pro Ala
            595                 600                 605

Ala Gly Pro His Ile Val Thr Pro Pro Ser Ala Arg Pro Arg Ile Met
            610                 615                 620

Ala Pro Pro Val Val Arg Met Phe Met Arg Glu Arg Gln Leu Pro Gln
625                 630                 635                 640

Ser Thr Gly Arg Lys Pro Gln Cys Phe Trp Glu Met Arg Ala Gly Arg
                    645                 650                 655

Glu Ile Thr Gln Met Gln Gln Glu Pro Ser Ser His Leu Gln Ser Ala
                660                 665                 670

Thr Gln Pro Thr Thr Pro Arg Pro Ser Trp Ala Pro Ser Val Cys Ala
            675                 680                 685

Leu Ser Val Met Asp Ala Gly Lys Ala Gln Pro Ile Glu Ser Ser His
            690                 695                 700

Leu Ser Ser Met Ser Pro Thr Gln Pro Ile Ser His Glu Glu Gln Pro
705                 710                 715                 720

Arg Tyr Glu Asp Pro Asp Ala Pro Leu Asp Leu Ser Leu His Pro Asp
                    725                 730                 735

Val Ala Ala Gln Pro Ala Pro Gln Ala Pro Tyr Gln Gly Tyr Gln Glu
                740                 745                 750

Pro Pro Ala Pro Gln Ala Pro Tyr Gln Gly Tyr Gln Glu Pro Pro Pro
            755                 760                 765

Pro Gln Ala Pro Tyr Gln Gly Tyr Gln Glu Pro Pro Ala His Gly Leu
            770                 775                 780

Gln Ser Ser Ser Tyr Pro Gly Tyr Ala Gly Pro Trp Thr Pro Arg Ser
785                 790                 795                 800

Gln His Pro Cys Tyr Arg His Pro Trp Ala Pro Trp Ser Gln Asp Pro
                    805                 810                 815

Val His Gly His Thr Gln Gly Pro Trp Asp Pro Arg Ala Pro His Leu
                820                 825                 830

Pro Pro Gln Trp Asp Gly Ser Ala Gly His Gly Gln Asp Gln Val Ser
            835                 840                 845

Gln Phe Pro His Leu Gln Ser Glu Thr Gly Pro Pro Arg Leu Gln Leu
            850                 855                 860

Ser Leu Val Pro Leu Val Ser Ser Ser Ala Pro Ser Trp Ser Ser Pro
865                 870                 875                 880

Gln Pro Arg Ala Pro Ile Arg Pro Ile Pro Thr Arg Phe Pro Pro Pro
                    885                 890                 895

Pro Met Pro Leu Gln Asp Ser Met Ala Val Gly Cys Asp Ser Ser Gly
                900                 905                 910

Thr Ala Cys Pro Ser Met Pro Phe Ala Ser Asp Tyr Ser Gln Gly Ala
            915                 920                 925

Phe Thr Pro Leu Asp Ile Asn Ala Thr Thr Pro Lys Arg Pro Arg Val
            930                 935                 940

Glu Glu Ser Ser His Gly Pro Ala Arg Cys Ser Gln Ala Thr Ala Glu
945                 950                 955                 960

Ala Gln Glu Ile Leu Ser Asp Asn Ser Glu Ile Ser Val Phe Pro Lys
                    965                 970                 975

Asp Ala Lys Gln Thr Asp Tyr Asp Ala Ser Thr Glu Ser Glu Leu Asp
                980                 985                 990
```

<210> SEQ ID NO 122
<211> LENGTH: 1161
<212> TYPE: DNA
<213> ORGANISM: Artificial Sequence
<220> FEATURE:
<223> OTHER INFORMATION: Synthetic

<400> SEQUENCE: 122
atggaacacg accttgagag gggcccaccg ggcccgcgac ggcccctcg aggaccccc      60 ctctcctctt ccctaggcct tgctctcctt ctcctcctct tggcgctact gttttggctg    120
tacatcgtta tgagtgactg gactggagga gccctccttg tcctctattc ctttgctctc    180
atgcttataa ttataatttt gatcatcttt atcttcagaa gagaccttct ctgtccactt    240
ggagcccttt gtatactcct actgatgatc accctcctgc tcatcgctct ctggaatttg    300
cacggacagg cattgtacct tggaattgtg ctgttcatct tcgggtgctt acttgtctta    360
ggtctctgga tctacttatt ggagattctc tggcgacttg gtgccaccat ctggcagctt    420
ttggccttct tcctagcctt cttcctagac ctcatcctgc tcattattgc tctctatcta    480
caacaaaact ggtggactct attggttgat ctcctttggc tcctcctgtt tctggcgatt    540
ttaatctgga tgtattacca tggacaacga cacagtgatg aacaccacca cgatgactcc    600
ctcccgcacc ctcaacaagc taccgatgat tctggccatg aatctgactc taactccaac    660
gagggcagac accactgct cgtgagtgga gccggcgacg accccccact ctgctctcaa    720
aacctaggcg cacctggagg tggtcctgac aatggcccac aggaccctga caacactgat    780
gacaatggcc cacaggaccc tgacaacact gatgacaatg cccacatga cccgctgcct    840 caggaccctg acaacactga tgacaatggc ccacaggacc ctgacaacac tgatgacaat    900
ggcccacatg acccgctgcc tcatagccct agcgactctg ctggaaatga tggaggccct    960
ccacaattga cggaagaggt tgaaaacaaa ggaggtgacc agggcccgcc tttgatgaca   1020 gacgaggcg gcggtcatag tcatgattcc ggccatggcg gcggtgatcc acaccttcct   1080
acgctgcttt tgggttcttc tggttccggt ggagatgatg acgaccccca cggcccagtt   1140
cagctaagct actatgacta a                                            1161

<210> SEQ ID NO 123
<211> LENGTH: 386
<212> TYPE: PRT
<213> ORGANISM: Artificial Sequence
<220> FEATURE:
<223> OTHER INFORMATION: Synthetic

<400> SEQUENCE: 123

Met Glu His Asp Leu Glu Arg Gly Pro Pro Gly Pro Arg Arg Pro Pro
1               5                   10                  15

Arg Gly Pro Pro Leu Ser Ser Ser Leu Gly Leu Ala Leu Leu Leu Leu
            20                  25                  30

Leu Leu Ala Leu Leu Phe Trp Leu Tyr Ile Val Met Ser Asp Trp Thr
        35                  40                  45

Gly Gly Ala Leu Leu Val Leu Tyr Ser Phe Ala Leu Met Leu Ile Ile
    50                  55                  60

Ile Ile Leu Ile Ile Phe Ile Phe Arg Arg Asp Leu Leu Cys Pro Leu
65                  70                  75                  80

Gly Ala Leu Cys Ile Leu Leu Leu Met Ile Thr Leu Leu Leu Ile Ala
            85                  90                  95

Leu Trp Asn Leu His Gly Gln Ala Leu Tyr Leu Gly Ile Val Leu Phe

-continued

```
                100              105              110
Ile Phe Gly Cys Leu Leu Val Leu Gly Leu Trp Ile Tyr Leu Leu Glu
            115              120              125

Ile Leu Trp Arg Leu Gly Ala Thr Ile Trp Gln Leu Leu Ala Phe Phe
        130              135              140

Leu Ala Phe Phe Leu Asp Leu Ile Leu Leu Ile Ile Ala Leu Tyr Leu
145              150              155              160

Gln Gln Asn Trp Trp Thr Leu Leu Val Asp Leu Leu Trp Leu Leu Leu
                165              170              175

Phe Leu Ala Ile Leu Ile Trp Met Tyr Tyr His Gly Gln Arg His Ser
            180              185              190

Asp Glu His His His Asp Asp Ser Leu Pro His Pro Gln Gln Ala Thr
            195              200              205

Asp Asp Ser Gly His Glu Ser Asp Ser Asn Ser Asn Glu Gly Arg His
            210              215              220

His Leu Leu Val Ser Gly Ala Gly Asp Gly Pro Pro Leu Cys Ser Gln
225              230              235              240

Asn Leu Gly Ala Pro Gly Gly Gly Pro Asp Asn Gly Pro Gln Asp Pro
            245              250              255

Asp Asn Thr Asp Asp Asn Gly Pro Gln Asp Pro Asp Asn Thr Asp Asp
            260              265              270

Asn Gly Pro His Asp Pro Leu Pro Gln Asp Pro Asp Asn Thr Asp Asp
            275              280              285

Asn Gly Pro Gln Asp Pro Asp Asn Thr Asp Asp Asn Gly Pro His Asp
        290              295              300

Pro Leu Pro His Ser Pro Ser Asp Ser Ala Gly Asn Asp Gly Gly Pro
305              310              315              320

Pro Gln Leu Thr Glu Glu Val Glu Asn Lys Gly Gly Asp Gln Gly Pro
            325              330              335

Pro Leu Met Thr Asp Gly Gly Gly Gly His Ser His Asp Ser Gly His
            340              345              350

Gly Gly Gly Asp Pro His Leu Pro Thr Leu Leu Leu Gly Ser Ser Gly
            355              360              365

Ser Gly Gly Asp Asp Asp Asp Pro His Gly Pro Val Gln Leu Ser Tyr
        370              375              380

Tyr Asp
385
```

```
<210> SEQ ID NO 124
<211> LENGTH: 1419
<212> TYPE: DNA
<213> ORGANISM: Artificial Sequence
<220> FEATURE:
<223> OTHER INFORMATION: Synthetic

<400> SEQUENCE: 124
atggcccccg ggtacgctgt agaagctgtt gaaggaggtc tctatccagt cgctcggctc      60
gatgcctggc catatcaggg aagtcaggaa tgccttctgg tggggcagcg tacctgcggc     120
gtcacagcag cgagccaggg ccacgttgct gggtggggga agagcccgc tctcctccgc      180 caggggcccc gtgatgaagg tgtacaggct gtgcgtcagc gcgtgcaggt gctccgagct     240
cagggtctgg gtaaacaggt gtgttttgat gtacttggaa ttctcaaagg cggcaccctc     300
gccggcgcgc ctgtcctccc agggacccga gacgaaggcc cgtctgtaga ggaagtggtt     360
gcgcatgcgg gccagctccc agtagaccac gtcccccag acgcgcaggc acagggtctc       420
```

-continued

```
ggtcagggtc tcgctctgtt gcgccaggca ggactgcagc ttggccagac cctcggtggc    480
cacctggcgc aggtactgct ccttgcgctt gagcgcgtcc gagagggcgc cggacgggcc    540
gggctctcgt gccccagccg gccggggcac ctccgggctc tcccgggacg cctcctcctc    600
gcctcggccc aaccgctgca tggctcggtt gagccgcgtg tacagctcgt tcctcttttg    660
caggatggcc cggtactggg ggtgcgccgt gaaggcggcg gcgcagtccg ccttcagcgc    720
ctccaccgcg tcgcccgagg agctgtagac cccgccgcag aagagccgct ccgtggcccc    780
gggagccacg gcgtcaaaca ggtgagtcag ccttgccccc gccagcgcct cctcgcaggc    840
cccccgcacc agggccaggc gacgctcccg ggcaaacagg gcagagaggc gggaatggcc    900
gccaccctcc ccctgccccg ttgcaccgat agcatggccg ccagagttcc aatagaggag    960
ctccgagagc tccgccacct ccggggggcac tgtcgagaag acgttgtagg tgtccagcgc   1020
tctggtcgcc ccctctgcct ccggccgccc cgggcccggg accgcgccct cctctgggcc   1080
gcccggcctc gccttctcct cagcctccaa caggtgcccg agcccgcct ggcggacttc    1140 attctcaaac agtcccgaga ccggctccgg attcaccggc accgccaggt ggttacagga   1200
gacgtgggtc ccctctgccg tggaagggtt gccgtggttg ggcagaacca tcagctcgcc   1260
cacacagcgc cagcagggca cagaggtgat gtagaggcgc gggtctggga tgggacttac   1320
gccccgaaag cggcccagca gatccagggc ccgttccagg ctctccagcc ccatggtgtg   1380
agacatgcaa taaaacacgc tattgattct cttcattaa                          1419
```

<210> SEQ ID NO 125
<211> LENGTH: 472
<212> TYPE: PRT
<213> ORGANISM: Artificial Sequence
<220> FEATURE:
<223> OTHER INFORMATION: Synthetic

<400> SEQUENCE: 125

```
Met Ala Pro Gly Tyr Ala Val Glu Ala Val Glu Gly Gly Leu Tyr Pro
1               5                   10                  15

Val Ala Arg Leu Asp Ala Trp Pro Tyr Gln Gly Ser Gln Glu Cys Leu
            20                  25                  30

Leu Val Gly Gln Arg Thr Cys Gly Val Thr Ala Ala Ser Gln Gly His
        35                  40                  45

Val Ala Gly Trp Gly Lys Glu Pro Ala Leu Leu Arg Gln Gly Pro Arg
    50                  55                  60

Asp Glu Gly Val Gln Ala Val Arg Gln Arg Val Gln Val Leu Arg Ala
65                  70                  75                  80

Gln Gly Leu Gly Lys Gln Val Cys Phe Asp Val Leu Gly Ile Leu Lys
                85                  90                  95

Gly Gly Thr Leu Ala Gly Ala Pro Val Leu Pro Gly Thr Arg Asp Glu
            100                 105                 110

Gly Pro Ser Val Glu Glu Val Val Ala His Ala Gly Gln Leu Pro Val
        115                 120                 125

Asp His Val Pro Pro Asp Ala Gln Ala Gln Gly Leu Gly Gln Gly Leu
    130                 135                 140

Ala Leu Leu Arg Gln Ala Gly Leu Gln Leu Gly Gln Thr Leu Gly Gly
145                 150                 155                 160

His Leu Ala Gln Val Leu Leu Leu Ala Leu Glu Arg Val Arg Glu Gly
                165                 170                 175

Ala Gly Arg Ala Gly Leu Ser Cys Pro Ser Arg Pro Gly His Leu Arg
```

-continued

```
                180              185                190
Ala Leu Pro Gly Arg Leu Leu Leu Ala Ser Ala Gln Pro Leu His Gly
        195              200                205

Ser Val Glu Pro Arg Val Gln Leu Val Pro Leu Leu Gln Asp Gly Pro
    210              215                220

Val Leu Gly Val Arg Arg Glu Gly Gly Gly Ala Val Arg Leu Gln Arg
225              230                235                240

Leu His Arg Val Ala Arg Gly Ala Val Asp Pro Ala Ala Glu Glu Pro
            245              250                255

Leu Arg Gly Pro Gly Ser His Gly Val Lys Gln Val Ser Gln Pro Cys
            260              265                270

Pro Arg Gln Arg Leu Leu Ala Gly Pro Pro His Gln Gly Gln Ala Thr
            275              280                285

Leu Pro Gly Lys Gln Gly Arg Glu Ala Gly Met Ala Ala Thr Leu Pro
        290              295                300

Leu Pro Arg Cys Thr Asp Ser Met Ala Ala Arg Val Pro Ile Glu Glu
305              310                315                320

Leu Arg Glu Leu Arg His Leu Arg Gly His Cys Arg Glu Asp Val Val
            325              330                335

Gly Val Gln Arg Ser Gly Arg Pro Leu Cys Leu Arg Pro Pro Arg Ala
            340              345                350

Arg Asp Arg Ala Leu Leu Trp Ala Ala Arg Pro Arg Leu Leu Leu Ser
            355              360                365

Leu Gln Gln Val Pro Glu Pro Arg Leu Ala Asp Phe Ile Leu Lys Gln
        370              375                380

Ser Arg Asp Arg Leu Arg Ile His Arg His Arg Gln Val Val Thr Gly
385              390                395                400

Asp Val Gly Pro Leu Cys Arg Gly Arg Val Ala Val Val Gly Gln Asn
            405              410                415

His Gln Leu Ala His Thr Ala Pro Ala Gly His Arg Gly Asp Val Glu
            420              425                430

Ala Arg Val Trp Asp Gly Thr Tyr Ala Pro Lys Ala Ala Gln Gln Ile
            435              440                445

Gln Gly Pro Phe Gln Ala Leu Gln Pro His Gly Val Arg His Ala Ile
        450              455                460

Lys His Ala Ile Asp Ser Leu His
465              470
```

```
<210> SEQ ID NO 126
<211> LENGTH: 1464
<212> TYPE: DNA
<213> ORGANISM: Artificial Sequence
<220> FEATURE:
<223> OTHER INFORMATION: Synthetic

<400> SEQUENCE: 126
atgcctacat tctatcttgc gttacatggg ggacaaacat atcatctaat tgttgacacg      60
gatagtcttg gaaacccgtc actctcagta attccctcga atccctacca ggaacaactg     120
tcagacactc cattaattcc actaacaatc tttgttgggg aaaacacggg ggtgcccca      180 ccactcccac caccccccc accaccaccc ccaccaccc caccacccc accaccccca     240 ccacccccac cacctccacc accttcacca ccaccccgc ccccaccacc cccaccacct     300
cagcgcaggg atgcctggac acaagagcca tcacctcttg atagggatcc gctaggatat     360
gacgtcgggc atggacctct agcatctgct atgcgaatgc tttggatggc taattatatt     420
```

-continued

```
gtaagacaat cacggggtga ccggggcctt attttgccac aaggcccaca aacagccct      480 caggccaggt tggtccagcc acatgtcccc cctctacgcc cgacagcacc caccattttg      540
tcacctctgt cacaaccgag gcttacccct ccacaaccac tcatgatgcc accaaggcct      600 accctcta ccctctgcc acctgcaaca ctaacggtgc caccaaggcc tacccgtcct      660
accactctgc cacccacacc actactcacg gtactacaaa ggcctaccga acttcaaccc      720
acaccatcac caccacgcat gcatctccct gtcttgcatg tgccagacca atcaatgcac      780
cctcttactc atcaaagcac cccaaatgat ccagatagtc cagaaccacg gtccccgact      840
gtattttata acattccacc tatgccatta cccccctcac aattgccacc accagcagca      900
ccagcacagc cacctccagg ggtcatcaac gaccaacaat tacatcatct accctcgggg      960
ccaccatggt ggccacccat ctgcgacccc ccgcaaccct ctaagactca aggccagagc     1020
cggggacaga gcagggggag gggcagggc aggggcaggg gcagggcaa gggcaagtcc     1080 agggacaagc aacgcaagcc cggtggacct tggagaccag agccaaacac ctccagtcct     1140
agcatgcctg aactaagtcc agtcctcggt cttcatcagg acaaggggc tggggactca     1200 ccaactcctg gcccatccaa tgccgcccc gtttgtagaa attcacacac ggcaaccct     1260 aacgtttcac caatacatga accggagtcc cataatagcc cagaggctcc cattctcttc     1320
cccgatgatt ggtatcctcc atctatagac cccgcagact tagacgaaag ttgggattac     1380 attttgaga caacagaatc tcctagctca gatgaagatt atgtggaggg acccagtaaa     1440
agacctcgcc cctccatcca gtaa                                           1464
```

<210> SEQ ID NO 127
<211> LENGTH: 487
<212> TYPE: PRT
<213> ORGANISM: Artificial Sequence
<220> FEATURE:
<223> OTHER INFORMATION: Synthetic

<400> SEQUENCE: 127

```
Met Pro Thr Phe Tyr Leu Ala Leu His Gly Gly Gln Thr Tyr His Leu
1               5                   10                  15

Ile Val Asp Thr Asp Ser Leu Gly Asn Pro Ser Leu Ser Val Ile Pro
            20                  25                  30

Ser Asn Pro Tyr Gln Glu Gln Leu Ser Asp Thr Pro Leu Ile Pro Leu
        35                  40                  45

Thr Ile Phe Val Gly Glu Asn Thr Gly Val Pro Pro Pro Leu Pro Pro
    50                  55                  60

Pro Pro Pro Pro Pro Pro Pro Pro Pro Pro Pro Pro Pro Pro Pro Pro
65                  70                  75                  80

Pro Pro Pro Pro Pro Pro Pro Pro Ser Pro Pro Pro Pro Pro Pro Pro
                85                  90                  95

Pro Pro Pro Pro Gln Arg Arg Asp Ala Trp Thr Gln Glu Pro Ser Pro
            100                 105                 110

Leu Asp Arg Asp Pro Leu Gly Tyr Asp Val Gly His Gly Pro Leu Ala
        115                 120                 125

Ser Ala Met Arg Met Leu Trp Met Ala Asn Tyr Ile Val Arg Gln Ser
    130                 135                 140

Arg Gly Asp Arg Gly Leu Ile Leu Pro Gln Gly Pro Gln Thr Ala Pro
145                 150                 155                 160

Gln Ala Arg Leu Val Gln Pro His Val Pro Pro Leu Arg Pro Thr Ala
            165                 170                 175
```

```
Pro Thr Ile Leu Ser Pro Leu Ser Gln Pro Arg Leu Thr Pro Pro Gln
            180                 185                 190

Pro Leu Met Met Pro Pro Arg Pro Thr Pro Pro Thr Pro Leu Pro Pro
            195                 200                 205

Ala Thr Leu Thr Val Pro Pro Arg Pro Thr Arg Pro Thr Thr Leu Pro
            210                 215                 220

Pro Thr Pro Leu Leu Thr Val Leu Gln Arg Pro Thr Glu Leu Gln Pro
225                 230                 235                 240

Thr Pro Ser Pro Pro Arg Met His Leu Pro Val Leu His Val Pro Asp
                245                 250                 255

Gln Ser Met His Pro Leu Thr His Gln Ser Thr Pro Asn Asp Pro Asp
                260                 265                 270

Ser Pro Glu Pro Arg Ser Pro Thr Val Phe Tyr Asn Ile Pro Pro Met
            275                 280                 285

Pro Leu Pro Pro Ser Gln Leu Pro Pro Pro Ala Ala Pro Ala Gln Pro
            290                 295                 300

Pro Pro Gly Val Ile Asn Asp Gln Gln Leu His His Leu Pro Ser Gly
305                 310                 315                 320

Pro Pro Trp Trp Pro Pro Ile Cys Asp Pro Pro Gln Pro Ser Lys Thr
                325                 330                 335

Gln Gly Gln Ser Arg Gly Gln Ser Arg Gly Arg Gly Arg Gly Arg Gly
                340                 345                 350

Arg Gly Arg Gly Lys Gly Lys Ser Arg Asp Lys Gln Arg Lys Pro Gly
                355                 360                 365

Gly Pro Trp Arg Pro Glu Pro Asn Thr Ser Ser Pro Ser Met Pro Glu
            370                 375                 380

Leu Ser Pro Val Leu Gly Leu His Gln Gly Gln Gly Ala Gly Asp Ser
385                 390                 395                 400

Pro Thr Pro Gly Pro Ser Asn Ala Ala Pro Val Cys Arg Asn Ser His
                405                 410                 415

Thr Ala Thr Pro Asn Val Ser Pro Ile His Glu Pro Glu Ser His Asn
                420                 425                 430

Ser Pro Glu Ala Pro Ile Leu Phe Pro Asp Asp Trp Tyr Pro Pro Ser
            435                 440                 445

Ile Asp Pro Ala Asp Leu Asp Glu Ser Trp Asp Tyr Ile Phe Glu Thr
            450                 455                 460

Thr Glu Ser Pro Ser Ser Asp Glu Asp Tyr Val Glu Gly Pro Ser Lys
465                 470                 475                 480

Arg Pro Arg Pro Ser Ile Gln
                485
```

```
<210> SEQ ID NO 128
<211> LENGTH: 2724
<212> TYPE: DNA
<213> ORGANISM: Artificial Sequence
<220> FEATURE:
<223> OTHER INFORMATION: Synthetic

<400> SEQUENCE: 128
atggacaagg acaggccggg tcccccggcc ctggatgaca acatggaaga agaagtccca        60
tctacctcgg ttgtgcagga acaggtatcg gcgggagatt gggaaaatgt cctcatagag       120
ttatcagata gcagctcaga aaaggaagca gaagatgccc acctggagcc ggcccagaag       180
ggtacgaaga gaaagcgggt cgatcatgat gccggtgggt cagctccagc acgacccatg       240
```

-continued

```
ctcccacccc agccggatct ccctgggcga gaagccattc tccgcaggtt tccactagat      300 ctaagaaacac ttcttcaagc gattggagcc gcggctacgc gcatcgacac acgagccata     360
gaccagtttt tcggatccca gatttcaaat accgagatgt acataatgta tgccatggcc      420
attcgacagg ccattagaga tcgtcggaga aatccagctt ctcgtagaga tcaggccaaa      480
tggagactgc aaaccctggc cgccggatgg cctatgggtt accaggcata cagcagctgg      540
atgtacagct acaccgatca ccagacgact cccacattcg tacatctcca ggcgacactt      600
gggtgcacag gtggccgtag gtgtcacgtg accttttccg ccggcacctt taagctgccg      660
cgatgtaccc ccggggatcg ccagtggttg tatgttcaga gctccgtggg taacattgta      720
cagagctgta atcccttgca gagaacggat ttgtcctata tcaagagctt tgtcagcgat      780
gccctgggca ccactagtat ccaaacaccg tggatcgatg acaatcctag cacggagacg      840
gcacaggctt ggaatgccgg ctttctccgg ggtcgtgcgt atgggataga cttgcttaga      900
actgaagggg aacatgtcga aggtgctacc ggtgaaacgc gagaagaaag tgaggacacg      960
gagagcgatg gagatgatga agatcttcct tgtatagtgt ccagaggtgg acctaaggtc     1020
aaacgacccc ctatatttat aagacgtctg cacaggttgc tgctgatgag agcgggcaaa     1080
cgaacagaac agggcaagga ggtactggaa aaggcccgtg ggagcactta tggcacacct     1140
aggccgcctg ttccgaaacc aagaccagag gtcccacaaa gcgacgagac agctaccagt     1200
cacgggtcgg cgcaagtccc agaacccca accattcacc tagcagctca gggaatggca     1260
tacccattac atgaacaaca cggcatggcc ccgtgtccgg tagcacaggc cccacctacg     1320
cccttgcccc ctgtatctcc aggggatcaa ctcccaggtg tttttagcga cgggcgagtg     1380
gcgtgtgcac cagtacccgc cccggctggg cctattgtcc ggccctggga gccatccctg     1440
acacaggctg cggggcaggc ctttgcaccc gttagaccac aacacatgcc agtagaaccc     1500
gtccctgtcc cgacagtggc acttgagcga ccagtttacc ccaagccagt tcgtccggca     1560
cctcctaaga ttgctatgca gggccccggg gaaacttctg gcattagacg cgcgcgggag     1620
cgttggaggc ccgcaccttg gacgccaaat ccacccgtt ctcccagtca gatgtccgtg     1680
cgtgaccgtc tggctcgttt gcgtgctgag gcacaggtca aacaggctag tgttgaggtg     1740
cagccccccc agttgaccca agtatcccct cagcaaccaa tggaggggcc gttggtacca     1800
gagcagcaga tgtccctgg tgcccccttt agccaggttg ctgatgtggt ccgggcacct     1860
ggggtaccgg cgatgcagcc acagtacttt gacctcccct taattcaacc cattagccag     1920
ggggcacccg tggccccgtt gagggctagt atgggcccgg tacctccggt accggcaaca     1980
cagccacagt attttgacat cccccttaact gaacccatta accagggggc atccgcggcc     2040
cattttctcc ctcagcaacc gatggagggg ccgttggtac ctgagcagtg gatgttccca     2100
ggtgccgccc tgagccagag tgttaggcca ggggtagcgc agtcacaata ttttgacctc     2160
cccttaactc aacccattaa ccatggggca cccgcagccc atttcctcca tcagccacca     2220
atggaggggc cgtgggtacc cgagcagtgg atgttccaag tgccccccc tagccaaggc     2280 actgacgtgg tccaacatca gctggatgct ttggggtata cactccatgg tcttaaccat     2340 cccgggttc ccgtgtctcc tgccgttaac caatatcatc tcagccaggc tgcctttggg     2400
ttacctattg atgaggatga gagtggcgag gggtccgata cctccgagcc gtgtgaagct     2460
cttgatttgt caatccatgg caggccctgc cctcaggccc ccgagtggcc tgttcaagag     2520
gagggtggcc aggatgccac cgaggttctt gatttgtcaa tccatggcag gccccgccct     2580
cggacccccg agtggcctgt tcaaggggaa ggtggccaaa atgtcacagg ccctgaaact     2640
```

-continued

```
agaagggtgg tggtgtcagc tgttgttcac atgtgtcagg atgacgagtt tccggatcta      2700
caagatcctc cagatgaggc ctaa                                             2724

<210> SEQ ID NO 129
<211> LENGTH: 907
<212> TYPE: PRT
<213> ORGANISM: Artificial Sequence
<220> FEATURE:
<223> OTHER INFORMATION: Synthetic

<400> SEQUENCE: 129

Met Asp Lys Asp Arg Pro Gly Pro Pro Ala Leu Asp Asp Asn Met Glu
1               5                   10                  15

Glu Glu Val Pro Ser Thr Ser Val Val Gln Glu Gln Val Ser Ala Gly
                20                  25                  30

Asp Trp Glu Asn Val Leu Ile Glu Leu Ser Asp Ser Ser Ser Glu Lys
            35                  40                  45

Glu Ala Glu Asp Ala His Leu Glu Pro Ala Gln Lys Gly Thr Lys Arg
        50                  55                  60

Lys Arg Val Asp His Asp Ala Gly Gly Ser Ala Pro Ala Arg Pro Met
65                  70                  75                  80

Leu Pro Pro Gln Pro Asp Leu Pro Gly Arg Glu Ala Ile Leu Arg Arg
                85                  90                  95

Phe Pro Leu Asp Leu Arg Thr Leu Leu Gln Ala Ile Gly Ala Ala Ala
            100                 105                 110

Thr Arg Ile Asp Thr Arg Ala Ile Asp Gln Phe Phe Gly Ser Gln Ile
            115                 120                 125

Ser Asn Thr Glu Met Tyr Ile Met Tyr Ala Met Ala Ile Arg Gln Ala
        130                 135                 140

Ile Arg Asp Arg Arg Arg Asn Pro Ala Ser Arg Arg Asp Gln Ala Lys
145                 150                 155                 160

Trp Arg Leu Gln Thr Leu Ala Ala Gly Trp Pro Met Gly Tyr Gln Ala
                165                 170                 175

Tyr Ser Ser Trp Met Tyr Ser Tyr Thr Asp His Gln Thr Thr Pro Thr
            180                 185                 190

Phe Val His Leu Gln Ala Thr Leu Gly Cys Thr Gly Gly Arg Arg Cys
            195                 200                 205

His Val Thr Phe Ser Ala Gly Thr Phe Lys Leu Pro Arg Cys Thr Pro
        210                 215                 220

Gly Asp Arg Gln Trp Leu Tyr Val Gln Ser Ser Val Gly Asn Ile Val
225                 230                 235                 240

Gln Ser Cys Asn Pro Leu Gln Arg Thr Asp Leu Ser Tyr Ile Lys Ser
                245                 250                 255

Phe Val Ser Asp Ala Leu Gly Thr Thr Ser Ile Gln Thr Pro Trp Ile
            260                 265                 270

Asp Asp Asn Pro Ser Thr Glu Thr Ala Gln Ala Trp Asn Ala Gly Phe
            275                 280                 285

Leu Arg Gly Arg Ala Tyr Gly Ile Asp Leu Leu Arg Thr Glu Gly Glu
        290                 295                 300

His Val Glu Gly Ala Thr Gly Glu Thr Arg Glu Glu Ser Glu Asp Thr
305                 310                 315                 320

Glu Ser Asp Gly Asp Asp Glu Asp Leu Pro Cys Ile Val Ser Arg Gly
                325                 330                 335

Gly Pro Lys Val Lys Arg Pro Pro Ile Phe Ile Arg Arg Leu His Arg
```

-continued

```
                340                 345                 350

Leu Leu Leu Met Arg Ala Gly Lys Arg Thr Glu Gln Gly Lys Glu Val
        355                 360                 365

Leu Glu Lys Ala Arg Gly Ser Thr Tyr Gly Thr Pro Arg Pro Pro Val
        370                 375                 380

Pro Lys Pro Arg Pro Glu Val Pro Gln Ser Asp Glu Thr Ala Thr Ser
385                 390                 395                 400

His Gly Ser Ala Gln Val Pro Glu Pro Pro Thr Ile His Leu Ala Ala
                405                 410                 415

Gln Gly Met Ala Tyr Pro Leu His Glu Gln His Gly Met Ala Pro Cys
                420                 425                 430

Pro Val Ala Gln Ala Pro Pro Thr Pro Leu Pro Pro Val Ser Pro Gly
                435                 440                 445

Asp Gln Leu Pro Gly Val Phe Ser Asp Gly Arg Val Ala Cys Ala Pro
        450                 455                 460

Val Pro Ala Pro Ala Gly Pro Ile Val Arg Pro Trp Glu Pro Ser Leu
465                 470                 475                 480

Thr Gln Ala Ala Gly Gln Ala Phe Ala Pro Val Arg Pro Gln His Met
                485                 490                 495

Pro Val Glu Pro Val Pro Val Pro Thr Val Ala Leu Glu Arg Pro Val
                500                 505                 510

Tyr Pro Lys Pro Val Arg Pro Ala Pro Pro Lys Ile Ala Met Gln Gly
                515                 520                 525

Pro Gly Glu Thr Ser Gly Ile Arg Arg Ala Arg Glu Arg Trp Arg Pro
        530                 535                 540

Ala Pro Trp Thr Pro Asn Pro Pro Arg Ser Pro Ser Gln Met Ser Val
545                 550                 555                 560

Arg Asp Arg Leu Ala Arg Leu Arg Ala Glu Ala Gln Val Lys Gln Ala
                565                 570                 575

Ser Val Glu Val Gln Pro Pro Gln Leu Thr Gln Val Ser Pro Gln Gln
                580                 585                 590

Pro Met Glu Gly Pro Leu Val Pro Glu Gln Gln Met Phe Pro Gly Ala
                595                 600                 605

Pro Phe Ser Gln Val Ala Asp Val Val Arg Ala Pro Gly Val Pro Ala
        610                 615                 620

Met Gln Pro Gln Tyr Phe Asp Leu Pro Leu Ile Gln Pro Ile Ser Gln
625                 630                 635                 640

Gly Ala Pro Val Ala Pro Leu Arg Ala Ser Met Gly Pro Val Pro Pro
                645                 650                 655

Val Pro Ala Thr Gln Pro Gln Tyr Phe Asp Ile Pro Leu Thr Glu Pro
                660                 665                 670

Ile Asn Gln Gly Ala Ser Ala Ala His Phe Leu Pro Gln Gln Pro Met
                675                 680                 685

Glu Gly Pro Leu Val Pro Glu Gln Trp Met Phe Pro Gly Ala Ala Leu
        690                 695                 700

Ser Gln Ser Val Arg Pro Gly Val Ala Gln Ser Gln Tyr Phe Asp Leu
705                 710                 715                 720

Pro Leu Thr Gln Pro Ile Asn His Gly Ala Pro Ala Ala His Phe Leu
                725                 730                 735

His Gln Pro Pro Met Glu Gly Pro Trp Val Pro Glu Gln Trp Met Phe
                740                 745                 750

Gln Gly Ala Pro Pro Ser Gln Gly Thr Asp Val Val Gln His Gln Leu
        755                 760                 765
```

```
Asp Ala Leu Gly Tyr Thr Leu His Gly Leu Asn His Pro Gly Val Pro
    770             775             780

Val Ser Pro Ala Val Asn Gln Tyr His Leu Ser Gln Ala Ala Phe Gly
785             790             795             800

Leu Pro Ile Asp Glu Asp Glu Ser Gly Glu Gly Ser Asp Thr Ser Glu
            805             810             815

Pro Cys Glu Ala Leu Asp Leu Ser Ile His Gly Arg Pro Cys Pro Gln
            820             825             830

Ala Pro Glu Trp Pro Val Gln Glu Glu Gly Gly Gln Asp Ala Thr Glu
            835             840             845

Val Leu Asp Leu Ser Ile His Gly Arg Pro Arg Pro Arg Thr Pro Glu
    850             855             860

Trp Pro Val Gln Gly Glu Gly Gly Gln Asn Val Thr Gly Pro Glu Thr
865             870             875             880

Arg Arg Val Val Val Ser Ala Val Val His Met Cys Gln Asp Asp Glu
            885             890             895

Phe Pro Asp Leu Gln Asp Pro Pro Asp Glu Ala
            900             905
```

<210> SEQ ID NO 130
<211> LENGTH: 312
<212> TYPE: DNA
<213> ORGANISM: Artificial Sequence
<220> FEATURE:
<223> OTHER INFORMATION: Synthetic

<400> SEQUENCE: 130

```
atggccggag ctcgtcgacg ggcaaggtgc ccagcgtcag caggatgcgc ctatagcgcc      60
cggcctcctc ccctgtcgac cagaggacgc aggatatctg caggatcagg tcagcctcgt     120
tggtggccgt ggggaagccc tcctccccca gacactcgat atcgaaggcc agggcctggt     180
aggagggcca ggagctgtct tcacgccgga ccgagaggtc gcccacctca cagtcgtact     240
cgagctcggc gtacgagtcc cggtgctgga ggcgggggat ggcgcggcgg cagctgtacc     300
agccaaaggt ga                                                         312
```

<210> SEQ ID NO 131
<211> LENGTH: 103
<212> TYPE: PRT
<213> ORGANISM: Artificial Sequence
<220> FEATURE:
<223> OTHER INFORMATION: Synthetic

<400> SEQUENCE: 131

```
Met Ala Gly Ala Arg Arg Arg Ala Arg Cys Pro Ala Ser Ala Gly Cys
1               5                   10                  15

Ala Tyr Ser Ala Arg Pro Pro Pro Leu Ser Thr Arg Gly Arg Arg Ile
                20              25              30

Ser Ala Gly Ser Gly Gln Pro Arg Trp Trp Pro Trp Gly Ser Pro Pro
            35              40              45

Pro Pro Asp Thr Arg Tyr Arg Arg Pro Gly Pro Gly Arg Arg Ala Arg
    50              55              60

Ser Cys Leu His Ala Gly Pro Arg Gly Arg Pro Pro His Ser Arg Thr
65              70              75              80

Arg Ala Arg Arg Thr Ser Pro Gly Ala Gly Gly Gly Gly Trp Arg Gly
                85              90              95

Gly Ser Cys Thr Ser Gln Arg
```

```
        100
```

```
<210> SEQ ID NO 132
<211> LENGTH: 381
<212> TYPE: DNA
<213> ORGANISM: Artificial Sequence
<220> FEATURE:
<223> OTHER INFORMATION: Synthetic

<400> SEQUENCE: 132
atgagcatgc cgccgaaggg gttttttgaag aaggagatga aaccagagac caggctgcta       60
aacaaacccc ccaccgtgct gactaggccg gcgatgtttt gcgcctggaa gttgtactcc      120
cggaagatgc cctccaggtc aaagacgttg gaggcacgct gttcgtcccg ccctccgtgt      180
gattctcccg cgtgccaaac gagggacact ggatgtccga ggagaagcgg aacaggtcgc      240
cgtggctgga gagctcgcag actcggaaag gaaagctggt ttgctgacgc gtggcggatg      300
gcccggtact gggggtgcgc cgtgaaggcg gcggcgcagt ccgccttcag cgcctccacc      360
gcgtcgcccg aggagctgta g                                                381
```

```
<210> SEQ ID NO 133
<211> LENGTH: 126
<212> TYPE: PRT
<213> ORGANISM: Artificial Sequence
<220> FEATURE:
<223> OTHER INFORMATION: Synthetic

<400> SEQUENCE: 133

Met Ser Met Pro Pro Lys Gly Phe Leu Lys Lys Glu Met Lys Pro Glu
1               5                   10                  15

Thr Arg Leu Leu Asn Lys Pro Pro Thr Val Leu Thr Arg Pro Ala Met
            20                  25                  30

Phe Cys Ala Trp Lys Leu Tyr Ser Arg Lys Met Pro Ser Arg Ser Lys
        35                  40                  45

Thr Leu Glu Ala Arg Cys Ser Ser Arg Pro Pro Cys Asp Ser Pro Ala
    50                  55                  60

Cys Gln Thr Arg Asp Thr Gly Cys Pro Arg Arg Ser Gly Thr Gly Arg
65                  70                  75                  80

Arg Gly Trp Arg Ala Arg Arg Leu Gly Lys Glu Ser Trp Phe Ala Asp
                85                  90                  95

Ala Trp Arg Met Ala Arg Tyr Trp Gly Cys Ala Val Lys Ala Ala Ala
                100                 105                 110

Gln Ser Ala Phe Ser Ala Ser Thr Ala Ser Pro Glu Glu Leu
            115                 120                 125
```

```
<210> SEQ ID NO 134
<211> LENGTH: 408
<212> TYPE: DNA
<213> ORGANISM: Artificial Sequence
<220> FEATURE:
<223> OTHER INFORMATION: Synthetic

<400> SEQUENCE: 134
atgacacatc tgggtggcaa ggtgaggtct tctgggtttt taataccggg gtcggcacca       60
gtttctggga caccgccaca aggacaaggt gggctagcaa gttctcgagt ctacgaagac      120
tccgggggca gtcttttgag tttctcgcct atgatccacc ccaatctcgc cccctaatt       180 gcgccatctg cctacgcgag gctgaacctc ctgaatcact gcatctttct tgaggcgttt      240
aaagaagaga atagtggcca gggcctcggt ggggtccagc gtgaggtctt atttttgaaa      300
```

-continued

```
aggggatatta taaaacaggt cattgctcgg attgtggcag ccgatagcac cctagatcta      360
gtgaatcatg gcgagcccgg aagagaggct cctagacgag ctcaataa                    408
```

```
<210> SEQ ID NO 135
<211> LENGTH: 135
<212> TYPE: PRT
<213> ORGANISM: Artificial Sequence
<220> FEATURE:
<223> OTHER INFORMATION: Synthetic

<400> SEQUENCE: 135

Met Thr His Leu Gly Gly Lys Val Arg Ser Ser Gly Phe Leu Ile Pro
1               5                   10                  15

Gly Ser Ala Pro Val Ser Gly Thr Pro Pro Gln Gly Gln Gly Gly Leu
            20                  25                  30

Ala Ser Ser Arg Val Tyr Glu Asp Ser Gly Gly Ser Leu Leu Ser Phe
        35                  40                  45

Ser Pro Met Ile His Pro Asn Leu Ala Pro Leu Ile Ala Pro Ser Ala
    50                  55                  60

Tyr Ala Arg Leu Asn Leu Leu Asn His Cys Ile Phe Leu Glu Ala Phe
65                  70                  75                  80

Lys Glu Glu Asn Ser Gly Gln Gly Leu Gly Gly Val Gln Arg Glu Val
                85                  90                  95

Leu Phe Leu Lys Arg Asp Ile Ile Lys Gln Val Ile Ala Arg Ile Val
            100                 105                 110

Ala Ala Asp Ser Thr Leu Asp Leu Val Asn His Gly Glu Pro Gly Arg
        115                 120                 125

Glu Ala Pro Arg Arg Ala Gln
    130                 135
```

```
<210> SEQ ID NO 136
<211> LENGTH: 234
<212> TYPE: DNA
<213> ORGANISM: Artificial Sequence
<220> FEATURE:
<223> OTHER INFORMATION: Synthetic

<400> SEQUENCE: 136
atgtctgccc ccggatgctc tgaaagacag gataagaagc gaggcactat tggggagaga       60
gaatttggag aattgctgag ctgggacccc actgaccttc cccggacggt ggcccgcgtc      120
tacgtggcgg tggaggtct ctttgagcag gaggtctctg aggtgcagcg cctggagaat      180
atttgcaccc tcctggacct ggccgggtg gaatgtcaga ccaaggccga ttga            234
```

```
<210> SEQ ID NO 137
<211> LENGTH: 77
<212> TYPE: PRT
<213> ORGANISM: Artificial Sequence
<220> FEATURE:
<223> OTHER INFORMATION: Synthetic

<400> SEQUENCE: 137

Met Ser Ala Pro Gly Cys Ser Glu Arg Gln Asp Lys Lys Arg Gly Thr
1               5                   10                  15

Ile Gly Glu Arg Glu Phe Gly Glu Leu Leu Ser Trp Asp Pro Thr Asp
            20                  25                  30

Leu Pro Arg Thr Val Ala Arg Val Tyr Val Ala Val Gly Gly Leu Phe
        35                  40                  45
```

Glu Gln Glu Val Ser Glu Val Gln Arg Leu Glu Asn Ile Cys Thr Leu
    50                  55                  60

Leu Asp Leu Ala Gly Val Glu Cys Gln Thr Lys Ala Asp
65                  70                  75

<210> SEQ ID NO 138
<211> LENGTH: 1290
<212> TYPE: DNA
<213> ORGANISM: Artificial Sequence
<220> FEATURE:
<223> OTHER INFORMATION: Synthetic

<400> SEQUENCE: 138
atggccgaag cttaccccgg aggagcccat gcagcactag cgtcccggcg ctcgtcgttc        60
aggaacagcc tccgccgcct gcggcccact gaaaaaccag acacgtcgtt catgagaggc       120
gtgtggaagt acgagatctt cccctcatac gtccgcgtca ccaacaagca ggtattgcag       180
ctggacgcgc agtgccaaga gctgcctccc tgccctcgg tgggccagat actcagcttc        240
aagttacctt ctttctcctt caacacgacc acctacggca gccgctactt tacggtcgcg       300
tttttgttct ttggagcgga agacaacgag gtattcctca gcccttctt cgttatgcac        360 tctgaccagg acatcgtgct aagcgtcctg aatccgcgca gcctgttcat agagaaaggg       420
aagtttacct ggtacattgt gcccatcaga ttggtcaaga accccacct ctacctgcag        480 attctgcccg ggcagagcga cattcagctg acacgctcct gcaccagag cggggacaag        540 ctaaacacca gcgagcccca gatcttcctc agtggctctc ccgtcaccag ccaggacgag       600
tgcctgcctt acctgctggc gcagcacacg cccccatttc taaagtcata cgcccgtatt       660
cacacattcc cggggaaggt atgtccggtc aacgccatac gccgcggtaa gggctacgtc       720
cgagtctccg tggacacgcc ggacctgaaa cgagagggcc cgctgaacgt caaggtgggc       780 atgacccttat tggatgatgt gattattgcc ttccgttaca cccctaccc taagagccac       840 tggcgctggg acggggaatc cacagacatc cgctactttg ctcccctgt gattattcct        900 cctaatttca tcacggagct ggaatacaac aacacctacg aggcccccct gagctccaag       960
attacggcca ttgtcgtgtc ccactcctcc aacccggtct tctacgtcta cccgcaggag      1020
tggaagccgg gccagaccct caagctgacg gtccggaaca tttccaacaa ccccataacg      1080
atcgtgaccg gccagagcat ggcccaggcc tttttcatct acgccggaga cccctctatc      1140
agcaccatca tgagaagata catacaacgg cagggctgcg cgctcacgct gcccgggaac      1200
attgttgtgg agagctcctc cctccccacc tttgagagaa tcaacaagac atttaacggg      1260
aatatcgtag cctccgaggg cactctgtaa                                      1290

<210> SEQ ID NO 139
<211> LENGTH: 429
<212> TYPE: PRT
<213> ORGANISM: Artificial Sequence
<220> FEATURE:
<223> OTHER INFORMATION: Synthetic

<400> SEQUENCE: 139

Met Ala Glu Ala Tyr Pro Gly Gly Ala His Ala Ala Leu Ala Ser Arg
1                   5                   10                  15

Arg Ser Ser Phe Arg Asn Ser Leu Arg Arg Leu Arg Pro Thr Glu Lys
                20                  25                  30

Pro Asp Thr Ser Phe Met Arg Gly Val Trp Lys Tyr Glu Ile Phe Pro
            35                  40                  45

```
Ser Tyr Val Arg Val Thr Asn Lys Gln Val Leu Gln Leu Asp Ala Gln
    50                  55                  60

Cys Gln Glu Leu Pro Pro Cys Pro Ser Val Gly Gln Ile Leu Ser Phe
65                  70                  75                  80

Lys Leu Pro Ser Phe Ser Phe Asn Thr Thr Thr Tyr Gly Ser Arg Tyr
                85                  90                  95

Phe Thr Val Ala Phe Leu Phe Phe Gly Ala Glu Asp Asn Glu Val Phe
                100                 105                 110

Leu Lys Pro Phe Phe Val Met His Ser Asp Gln Asp Ile Val Leu Ser
                115                 120                 125

Val Leu Asn Pro Arg Ser Leu Phe Ile Glu Lys Gly Lys Phe Thr Trp
    130                 135                 140

Tyr Ile Val Pro Ile Arg Leu Val Lys Asn Pro Tyr Leu Tyr Leu Gln
145                 150                 155                 160

Ile Leu Pro Gly Gln Ser Asp Ile Gln Leu Thr Arg Ser Cys Thr Gln
                165                 170                 175

Ser Gly Asp Lys Leu Asn Thr Ser Glu Pro Gln Ile Phe Leu Ser Gly
                180                 185                 190

Ser Pro Val Thr Ser Gln Asp Glu Cys Leu Pro Tyr Leu Leu Ala Gln
                195                 200                 205

His Thr Pro Pro Phe Leu Lys Ser Tyr Ala Arg Ile His Thr Phe Pro
    210                 215                 220

Gly Lys Val Cys Pro Val Asn Ala Ile Arg Arg Gly Lys Gly Tyr Val
225                 230                 235                 240

Arg Val Ser Val Asp Thr Pro Asp Leu Lys Arg Glu Gly Pro Leu Asn
                245                 250                 255

Val Lys Val Gly Met Thr Leu Leu Asp Asp Val Ile Ile Ala Phe Arg
                260                 265                 270

Tyr Asn Pro Tyr Pro Lys Ser His Trp Arg Trp Asp Gly Glu Ser Thr
                275                 280                 285

Asp Ile Arg Tyr Phe Gly Ser Pro Val Ile Ile Pro Pro Asn Phe Ile
    290                 295                 300

Thr Glu Leu Glu Tyr Asn Asn Thr Tyr Glu Ala Pro Leu Ser Ser Lys
305                 310                 315                 320

Ile Thr Ala Ile Val Val Ser His Ser Ser Asn Pro Val Phe Tyr Val
                325                 330                 335

Tyr Pro Gln Glu Trp Lys Pro Gly Gln Thr Leu Lys Leu Thr Val Arg
                340                 345                 350

Asn Ile Ser Asn Asn Pro Ile Thr Ile Val Thr Gly Gln Ser Met Ala
                355                 360                 365

Gln Ala Phe Phe Ile Tyr Ala Gly Asp Pro Ser Ile Ser Thr Ile Met
    370                 375                 380

Arg Arg Tyr Ile Gln Arg Gln Gly Cys Ala Leu Thr Leu Pro Gly Asn
385                 390                 395                 400

Ile Val Val Glu Ser Ser Ser Leu Pro Thr Phe Glu Arg Ile Asn Lys
                405                 410                 415

Thr Phe Asn Gly Asn Ile Val Ala Ser Glu Gly Thr Leu
                420                 425
```

<210> SEQ ID NO 140
<211> LENGTH: 1410
<212> TYPE: DNA
<213> ORGANISM: Artificial Sequence
<220> FEATURE:
<223> OTHER INFORMATION: Synthetic -continued

<400> SEQUENCE: 140

```
atggccctgc aaactgacac acaggcctgg cgggtggaga tagggaccag aggactaatg    60
ttctctaact gtgtcccact ccacctgccg gagggacagt accacaagct ccggctgccc   120
gtctcggcct acgaggccct ggccgtggcc aggtacgggc tggtgggctc cctctgggag   180
gtgcccgccg tgaactctgc ccttcagtgt ctggcggctg ctgcgccctg taaagatgta   240
aagatctacc ccagctgcat cttccaggtg cacgctccca tgtttgtaac tataaagaca   300
agcctgcgtt gcctaaatcc tcatgacctg tgtctgtgtc tcatttgtgt aggtgcggct   360
atcctagata taccctcct atgcgccccc cgtgacggag ctggggcacg ggccgccgag   420
gggcaggctg cggccgccca gggggggcaaa ttgcgtgtct ggggccgcct gagcccatcc   480
tcgcccacat cgctctccct ggcttttccc tatgcgggcc cgcccccgt ggcgtggtac   540 cgacattcta tcaacctaac aaggagtgaa ggtgtgggga tcggcaaaga ttgcgcccag   600
gatcacgcct gccccgtccc accccaaggt catgcttcct ctgcggctga ccaggctggg   660
gtgccggaga gaggtagaaa gcgggcccat gaaggcccgg gggctggcga ggcggcgtcc   720
gcgggccgag gggatgtggc cctgagtcag tcccgggctt tgctctggcg cggcctcggc   780
tgggacacgg gacgtggtcg gctggcacca ggcctggcca tgtcacgaga cgcagcctcc   840
gggtccgtgc acctggacat acaggtggac agggccgagg agggctgggt ctgcgacgtt   900
ctgctggagc ccgggccgcc caccgcccgg gagggctgtt ttctaagcat ggaccccggt   960
ctcgtgaccc tgaaagatgc ctggacgcta ttcccctcc acccggagca cgacgccgtc  1020
gttccaccca aggaggaaat acatgtgatg gcacagggcc atctccaggg cggcacgccc  1080
tctctctggg ggtttacatt ccaggaggcg gcgtgcgacc aatgggtgct gcgcccgcgc  1140
gtgtggaccg cccactcgcc cataaaaatg acagtctaca actgcgggca caaaccgctg  1200
cacatcggcc ccagcaccag acttggactt gcgctcttct ggccggccga gcgaagtgac  1260
aacctagacg ccgggcggat attctaccag ctaacgagcg gagagttgta ttggggccgc  1320
accgtcgccc gccccccaac tctcaccttg cccgtcgacg agctccggcc atggccgaag  1380
cttaccccgg aggagcccat gcagcactag                                   1410
```

<210> SEQ ID NO 141
<211> LENGTH: 469
<212> TYPE: PRT
<213> ORGANISM: Artificial Sequence
<220> FEATURE:
<223> OTHER INFORMATION: Synthetic

<400> SEQUENCE: 141

```
Met Ala Leu Gln Thr Asp Thr Gln Ala Trp Arg Val Glu Ile Gly Thr
1               5                   10                  15

Arg Gly Leu Met Phe Ser Asn Cys Val Pro Leu His Leu Pro Glu Gly
            20                  25                  30

Gln Tyr His Lys Leu Arg Leu Pro Val Ser Ala Tyr Glu Ala Leu Ala
        35                  40                  45

Val Ala Arg Tyr Gly Leu Val Gly Ser Leu Trp Glu Val Pro Ala Val
    50                  55                  60

Asn Ser Ala Leu Gln Cys Leu Ala Ala Ala Ala Pro Cys Lys Asp Val
65                  70                  75                  80

Lys Ile Tyr Pro Ser Cys Ile Phe Gln Val His Ala Pro Met Phe Val
                85                  90                  95
```

-continued

```
Thr Ile Lys Thr Ser Leu Arg Cys Leu Asn Pro His Asp Leu Cys Leu
            100                 105                 110

Cys Leu Ile Cys Val Gly Ala Ala Ile Leu Asp Ile Pro Leu Leu Cys
            115                 120                 125

Ala Pro Arg Asp Gly Ala Gly Ala Arg Ala Ala Glu Gly Gln Ala Ala
        130                 135                 140

Ala Ala Gln Gly Gly Lys Leu Arg Val Trp Gly Arg Leu Ser Pro Ser
145                 150                 155                 160

Ser Pro Thr Ser Leu Ser Leu Ala Phe Pro Tyr Ala Gly Pro Pro Pro
                165                 170                 175

Val Ala Trp Tyr Arg His Ser Ile Asn Leu Thr Arg Ser Glu Gly Val
                180                 185                 190

Gly Ile Gly Lys Asp Cys Ala Gln Asp His Ala Cys Pro Val Pro Pro
                195                 200                 205

Gln Gly His Ala Ser Ser Ala Ala Asp Gln Ala Gly Val Pro Glu Arg
        210                 215                 220

Gly Arg Lys Arg Ala His Glu Gly Pro Gly Ala Gly Glu Ala Ala Ser
225                 230                 235                 240

Ala Gly Arg Gly Asp Val Ala Leu Ser Gln Ser Arg Ala Leu Leu Trp
                245                 250                 255

Arg Gly Leu Gly Trp Asp Thr Gly Arg Gly Arg Leu Ala Pro Gly Leu
                260                 265                 270

Ala Met Ser Arg Asp Ala Ala Ser Gly Ser Val His Leu Asp Ile Gln
                275                 280                 285

Val Asp Arg Ala Glu Glu Gly Trp Val Cys Asp Val Leu Leu Glu Pro
        290                 295                 300

Gly Pro Pro Thr Ala Arg Glu Gly Cys Phe Leu Ser Met Asp Pro Gly
305                 310                 315                 320

Leu Val Thr Leu Lys Asp Ala Trp Thr Leu Phe Pro Leu His Pro Glu
                325                 330                 335

His Asp Ala Val Val Pro Pro Lys Glu Glu Ile His Val Met Ala Gln
                340                 345                 350

Gly His Leu Gln Gly Gly Thr Pro Ser Leu Trp Gly Phe Thr Phe Gln
                355                 360                 365

Glu Ala Ala Cys Asp Gln Trp Val Leu Arg Pro Arg Val Trp Thr Ala
        370                 375                 380

His Ser Pro Ile Lys Met Thr Val Tyr Asn Cys Gly His Lys Pro Leu
385                 390                 395                 400

His Ile Gly Pro Ser Thr Arg Leu Gly Leu Ala Leu Phe Trp Pro Ala
                405                 410                 415

Glu Arg Ser Asp Asn Leu Asp Ala Gly Arg Ile Phe Tyr Gln Leu Thr
                420                 425                 430

Ser Gly Glu Leu Tyr Trp Gly Arg Thr Val Ala Arg Pro Pro Thr Leu
                435                 440                 445

Thr Leu Pro Val Asp Glu Leu Arg Pro Trp Pro Lys Leu Thr Pro Glu
        450                 455                 460

Glu Pro Met Gln His
465
```

<210> SEQ ID NO 142
<211> LENGTH: 939
<212> TYPE: DNA
<213> ORGANISM: Artificial Sequence
<220> FEATURE:
<223> OTHER INFORMATION: Synthetic

```
<400> SEQUENCE: 142
atgctctcca ccatggtccc cgggtccact gtggggaccc tggtggccaa catgacttcc        60
gtcaatgcaa cggaagatgc gtgcactaaa tcctacagcg ccttcctcag cggcatgaca       120
agcctgctgc tcgtcctgct gattctgcta acactggctg gcatcttgtt tatcatcttt       180
gtaagaaaat tggttcaccg aatggatgtc tggctgatag ctcttctcat agaactgctg       240
ctctgggtgc tgggaaaaat gattcaggag ttctcgtcta ccggtctctg ccttttgacc       300
cagaacatga tgttcttggg cctgatgtgc tccgtatgga ctcacttggg tatggcgttg       360
gagaagaccc tagcattgtt cagccgaacg cccaagcgaa cctcccacag aaatgtgtgc       420
ctgtacctga tgggcgtgtt ttgtctggta ctcctgctga ttatcatcct cctcattacc       480
atgggccccg acgccaatct caacagaggc cccaacatgt gcagggaagg ccccaccaaa       540
ggcatgcaca cggccgtcca aggactgaaa gccggctgct acctactggc ggcagtcctg       600
atcgtcctcc tcacagtcat catcatctgg aaacttttgc gcacaaaatt cggaaggaag       660
ccgcgcctga tatgcaacgt caccttcacc ggactcatct gcgccttctc ctggtttatg       720
ctgtccctgc cgctgctctt cctgggtgag gccgggagcc tggggtttga ttgcacagag       780
tctctcgttg cccgctacta cccaggcccc gccgcctgtc tggccctgtt gctcattata       840
ctatacgcct ggagcttcag ccattttatg gactctctca agaaccaggt gacagtcacc       900
gccagatact tcagaagggt gcctagccag tccacctga                              939
```

```
<210> SEQ ID NO 143
<211> LENGTH: 312
<212> TYPE: PRT
<213> ORGANISM: Artificial Sequence
<220> FEATURE:
<223> OTHER INFORMATION: Synthetic

<400> SEQUENCE: 143

Met Leu Ser Thr Met Val Pro Gly Ser Thr Val Gly Thr Leu Val Ala
1               5                   10                  15

Asn Met Thr Ser Val Asn Ala Thr Glu Asp Ala Cys Thr Lys Ser Tyr
            20                  25                  30

Ser Ala Phe Leu Ser Gly Met Thr Ser Leu Leu Leu Val Leu Leu Ile
        35                  40                  45

Leu Leu Thr Leu Ala Gly Ile Leu Phe Ile Ile Phe Val Arg Lys Leu
    50                  55                  60

Val His Arg Met Asp Val Trp Leu Ile Ala Leu Leu Ile Glu Leu Leu
65                  70                  75                  80

Leu Trp Val Leu Gly Lys Met Ile Gln Glu Phe Ser Ser Thr Gly Leu
                85                  90                  95

Cys Leu Leu Thr Gln Asn Met Met Phe Leu Gly Leu Met Cys Ser Val
            100                 105                 110

Trp Thr His Leu Gly Met Ala Leu Glu Lys Thr Leu Ala Leu Phe Ser
        115                 120                 125

Arg Thr Pro Lys Arg Thr Ser His Arg Asn Val Cys Leu Tyr Leu Met
    130                 135                 140

Gly Val Phe Cys Leu Val Leu Leu Leu Ile Ile Ile Leu Leu Ile Thr
145                 150                 155                 160

Met Gly Pro Asp Ala Asn Leu Asn Arg Gly Pro Asn Met Cys Arg Glu
                165                 170                 175

Gly Pro Thr Lys Gly Met His Thr Ala Val Gln Gly Leu Lys Ala Gly
```

-continued

```
                180              185               190
Cys Tyr Leu Leu Ala Ala Val Leu Ile Val Leu Leu Thr Val Ile Ile
        195              200               205
Ile Trp Lys Leu Leu Arg Thr Lys Phe Gly Arg Lys Pro Arg Leu Ile
    210              215               220
Cys Asn Val Thr Phe Thr Gly Leu Ile Cys Ala Phe Ser Trp Phe Met
225              230               235               240
Leu Ser Leu Pro Leu Leu Phe Leu Gly Glu Ala Gly Ser Leu Gly Phe
            245              250               255
Asp Cys Thr Glu Ser Leu Val Ala Arg Tyr Tyr Pro Gly Pro Ala Ala
            260              265               270
Cys Leu Ala Leu Leu Leu Ile Ile Leu Tyr Ala Trp Ser Phe Ser His
        275              280               285
Phe Met Asp Ser Leu Lys Asn Gln Val Thr Val Thr Ala Arg Tyr Phe
        290              295               300
Arg Arg Val Pro Ser Gln Ser Thr
305              310
```

```
<210> SEQ ID NO 144
<211> LENGTH: 768
<212> TYPE: DNA
<213> ORGANISM: Artificial Sequence
<220> FEATURE:
<223> OTHER INFORMATION: Synthetic

<400> SEQUENCE: 144
atggcatcgc gggggctaga cctctggctg gatgagcacg tgtggaagag gaaacaggag      60
attggtgtga aaggagaaaa tctgcttctc cccgacttat ggctagattt cctacaactc     120
agccccatct tccagcgcaa gcttgctgcc gttattgcct gtgtccgacg cctgcggact     180
caggccaccg tctacccaga ggaggacatg tgcatggcct gggcccgctt ttgcgacccc     240
tctgatatta aggtggttat tttgggccag gaccccctatc acggggggtca agcaaacggc     300 ctggcattca gcgtcgcata cggctttcca gttcccccca gcctgaggaa catctacgcg     360
gagctgcacc ggagcctgcc ggagtttcct ccccccagatc acggctgtct agacgcgtgg     420
gcctcccagg gggtgttgct actcaacacc atcctgaccg tgcaaaaggg caagcccggc     480
tcgcacgcag acattggctg ggcgtggttt actgaccacg taatttcatt gctctctgag     540
cggttaaaag cgtgcgtgtt tatgctgtgg ggtgcgaagg cgggagacaa agcttcacta     600
atcaactcca agaagcatct ggttctgacc tctcagcatc cctctccct ggcccagaac     660 agcacccgaa agagtgccca gcagaagttc ctgggcaaca accactttgt cctcgctaac     720
aactttttgc gtgagaaggg gctcggtgag atagattgga ggctgtag                  768
```

```
<210> SEQ ID NO 145
<211> LENGTH: 255
<212> TYPE: PRT
<213> ORGANISM: Artificial Sequence
<220> FEATURE:
<223> OTHER INFORMATION: Synthetic

<400> SEQUENCE: 145

Met Ala Ser Arg Gly Leu Asp Leu Trp Leu Asp Glu His Val Trp Lys
1               5                10                15
Arg Lys Gln Glu Ile Gly Val Lys Gly Glu Asn Leu Leu Leu Pro Asp
            20               25                30
Leu Trp Leu Asp Phe Leu Gln Leu Ser Pro Ile Phe Gln Arg Lys Leu
```

-continued

```
          35              40              45
Ala Ala Val Ile Ala Cys Val Arg Arg Leu Arg Thr Gln Ala Thr Val
      50              55              60

Tyr Pro Glu Glu Asp Met Cys Met Ala Trp Ala Arg Phe Cys Asp Pro
65              70              75              80

Ser Asp Ile Lys Val Val Ile Leu Gly Gln Asp Pro Tyr His Gly Gly
              85              90              95

Gln Ala Asn Gly Leu Ala Phe Ser Val Ala Tyr Gly Phe Pro Val Pro
          100             105             110

Pro Ser Leu Arg Asn Ile Tyr Ala Glu Leu His Arg Ser Leu Pro Glu
          115             120             125

Phe Ser Pro Pro Asp His Gly Cys Leu Asp Ala Trp Ala Ser Gln Gly
      130             135             140

Val Leu Leu Leu Asn Thr Ile Leu Thr Val Gln Lys Gly Lys Pro Gly
145             150             155             160

Ser His Ala Asp Ile Gly Trp Ala Trp Phe Thr Asp His Val Ile Ser
              165             170             175

Leu Leu Ser Glu Arg Leu Lys Ala Cys Val Phe Met Leu Trp Gly Ala
          180             185             190

Lys Ala Gly Asp Lys Ala Ser Leu Ile Asn Ser Lys Lys His Leu Val
          195             200             205

Leu Thr Ser Gln His Pro Ser Pro Leu Ala Gln Asn Ser Thr Arg Lys
      210             215             220

Ser Ala Gln Gln Lys Phe Leu Gly Asn Asn His Phe Val Leu Ala Asn
225             230             235             240

Asn Phe Leu Arg Glu Lys Gly Leu Gly Glu Ile Asp Trp Arg Leu
              245             250             255
```

<210> SEQ ID NO 146
<211> LENGTH: 1155
<212> TYPE: DNA
<213> ORGANISM: Artificial Sequence
<220> FEATURE:
<223> OTHER INFORMATION: Synthetic

<400> SEQUENCE: 146

```
atggtctggg aggcagaggg tcggcctagg cccgggaag tggaggggga tcgcccgggt       60
ctctgttggc agagtccggg cgatcctctg agaccctccg ggcccggacg gtcgccctca      120
gcccccagga cagaccccag ggtctccagg cagggtccgg catcttcagg ggcagcaggc      180
tcaccaccac aggccccca gacccgggtc tcggccagcc gagccgaccg gccccgcgcc       240
tggcgcctcc tcgggggccag ccgccggggt tggttctgcc cctctctctg tccttcagag      300
gaaccaggga cctcgggcac cccagagccc ctcgggcccg cctccaggcg ccctcctggt      360
ctccgctccc ctctgagccc cgttaaaccc aaagaatgtc tgaggggagc caccctcggg      420
gcccaggccc cagagtccag aggtcagggg cacctcaggg tgcctccccg ggtcccaggc      480
cagccggagg acccccggca gcccgggcgg ccccagaggc cggttcctcg cccccttcccc      540 gggcttcaga gcccaggatg tcccccagaa gggaccctag gcgtcccctc tcctcccctc      600
caggcccgag cctctccctc gcggagaggg gcctctttgg gccctcaagt ccagcccac      660 cgagacccga gtggcccgga tccccccacc ggcccttctc tctgtccccc tgctcctctc      720
caaccttcgc tccacccctag accccagctt ctggcctccc cgggtccacc aggccagccg      780
gagggacccc ggcagcccgg gcgagtcgcc ttccctctcc cctggcctct ccttcccgcc      840
```

-continued

```
tcccacccga gcccctcag cttgcctccc caccgggtcc atcaggccgg ccggagggac      900
cccggcggcc cggtgtcagt cccccctgca gccgcccagt ctctgcctcc aggcaagggc      960
gccagctttt ctcccccag cctgaggccc agtctcctgt gcactgtctg taaagtccag     1020
cctcccacgc ccgtccacgg ctcccggggc cagcctcgtc caccctccc acggtggac      1080 aggccctctg tccacccggg ccatcccgc ccccctgtgt ccacccagt cccgtccagg     1140 ggggacttta tgtga                                                     1155
```

```
<210> SEQ ID NO 147
<211> LENGTH: 384
<212> TYPE: PRT
<213> ORGANISM: Artificial Sequence
<220> FEATURE:
<223> OTHER INFORMATION: Synthetic

<400> SEQUENCE: 147

Met Val Trp Glu Ala Glu Gly Arg Pro Arg Pro Gly Glu Val Glu Gly
1               5                   10                  15

Asp Arg Pro Gly Leu Cys Trp Gln Ser Pro Gly Asp Pro Leu Arg Pro
                20                  25                  30

Ser Gly Pro Gly Arg Ser Pro Ser Ala Pro Gln Thr Asp Pro Arg Val
            35                  40                  45

Ser Arg Gln Gly Pro Ala Ser Ser Gly Ala Ala Gly Ser Pro Pro Gln
        50                  55                  60

Ala Pro Gln Thr Arg Val Ser Ala Ser Arg Ala Asp Arg Pro Arg Ala
65                  70                  75                  80

Trp Arg Leu Leu Gly Ala Ser Arg Arg Gly Trp Phe Cys Pro Ser Leu
                85                  90                  95

Cys Pro Ser Glu Glu Pro Gly Thr Ser Gly Thr Pro Glu Pro Leu Gly
                100                 105                 110

Pro Ala Ser Arg Arg Pro Pro Gly Leu Arg Ser Pro Leu Ser Pro Val
                115                 120                 125

Lys Pro Lys Glu Cys Leu Arg Gly Ala Thr Leu Gly Ala Gln Ala Pro
        130                 135                 140

Glu Ser Arg Gly Gln Gly His Leu Arg Val Pro Pro Arg Val Pro Gly
145                 150                 155                 160

Gln Pro Glu Gly Pro Arg Gln Pro Gly Arg Pro Gln Arg Pro Val Pro
                165                 170                 175

Arg Pro Phe Pro Gly Leu Gln Ser Pro Gly Cys Pro Pro Glu Gly Thr
                180                 185                 190

Leu Gly Val Pro Ser Pro Pro Leu Gln Ala Arg Ala Ser Pro Ser Arg
                195                 200                 205

Arg Gly Ala Ser Leu Gly Pro Gln Val Gln Pro His Arg Asp Pro Ser
        210                 215                 220

Gly Pro Asp Pro Pro Thr Gly Pro Ser Leu Cys Pro Pro Ala Pro Leu
225                 230                 235                 240

Gln Pro Ser Leu His Pro Arg Pro Gln Leu Leu Ala Ser Pro Gly Pro
                245                 250                 255

Pro Gly Gln Pro Glu Gly Pro Arg Gln Pro Gly Arg Val Ala Phe Pro
                260                 265                 270

Leu Pro Trp Pro Leu Leu Pro Ala Ser His Pro Ser Pro Leu Ser Leu
                275                 280                 285

Pro Pro His Arg Val His Gln Ala Gly Arg Arg Asp Pro Gly Gly Pro
        290                 295                 300
```

-continued

```
Val Ser Val Pro Pro Ala Ala Ala Gln Ser Leu Pro Pro Gly Lys Gly
305             310             315             320

Ala Ser Phe Ser Pro Pro Ser Leu Arg Pro Ser Leu Leu Cys Thr Val
                325             330             335

Cys Lys Val Gln Pro Pro Thr Pro Val His Gly Ser Arg Ala Gln Pro
            340             345             350

Arg Pro Pro Leu Pro Thr Val Asp Arg Pro Ser Val His Pro Gly His
        355             360             365

Pro Arg Pro Pro Val Ser Thr Pro Val Pro Ser Arg Gly Asp Phe Met
    370             375             380
```

```
<210> SEQ ID NO 148
<211> LENGTH: 3720
<212> TYPE: DNA
<213> ORGANISM: Artificial Sequence
<220> FEATURE:
<223> OTHER INFORMATION: Synthetic

<400> SEQUENCE: 148
atggcgtccg ctatggagag tgacagcagc ggcggtagcg gaggggcaga cgcccagcca        60
cccctggcag aggtggacgg ggggctcgcc cgcgtgacgc gtcagttgct gctgtctggg       120
gacgaccccg ctgcccgcct gcgcgcgctg atgcctctgg agctggggat ctttggactg       180
ggggatttgg cccagccggt gctggtgcgc gattttttaa atactctcac cctcatgagc       240
ggccacgctt acccggcggc ggtcctccgc caccacgcct actacctact ccgggcggcc       300
tccttttcca ggcgcagctt cggcctcggc catctggagg cggccctgga cgtgctggca       360
tcctcactgc cccccacgac agcctctccg gccaccgacg atccgctgga cggctctcgg       420
ctcatcgcag agacccgggc cctggcggcc gcgtaccggc gcatcatcga agagggcagc       480
ggggaggtgc tcgcggtctc tggcccaacg gccacctttg ccttcgtgga agagctggtg       540
gccgacactt atctggcccg gtgggacgcc ttcccgcggg aggggctgtc attctacgct       600
tttaacgcgg cgaaaacgac gctggggaga tggctggtca ccgtatacgc ggagaccaac       660 cgctaccct gggcggctgc agggcagggt cagcccacgg ccgcggacat caaggccatg       720
gccgtggagc tggtggagca cagtgggggc ggggccggcg ggggagaggg tgaagaaagc       780
ggtggtggtc tctttcaccg cccccgagtca ctttccagcg tggtggcctc gctgcccctg       840
gcccggcggg ggcggtaga gatcctgggc gtgtacgcgg aggccagcgg gggacaaacg       900
ccccccgtcg cggctgtgcc cgtcctggcc tttgacgccg cccggctccg gcttttggag       960
ccctcagggg ccctctttta cgactatgtg tacgaggccc tgctctggga ccagacttac      1020
ggcgtcccag actcggtcat cgaggccttc ctggccggga tggcggcaga gatggaggcc      1080
ctggccgctc gtgtgcagga ggcggcgggg agccgggcat ccttctctcc agccgccatc      1140
gagcaggtgg ccacggttct gctctcggcc gggctcaacg agaccgtggc gggggactac      1200
gccatgatgc tggcctctgt gccccgggtg tcccgctcgc ggtggaggtg gctcgaggcc      1260
accgccgccc tcctagagag tctatcgggc tttgccctgc actttttccg actgctgccc      1320
accgcgagcc ccacgagccg cttcgcccgt gtggcccggg cggcctacct gcgggcggag      1380
gccgaggccg tggacagacg agcccggcgc accagcggcc cctctacgcc cgccgccgcc      1440
cccgccgcga cggctgtggg tgtgggggcg cggcggacc cttgggacgc cgtaacccct      1500
ctgcgcatct tcatcgtccc ccctcccgcg gccgagtatg agcaggtggc gggggacctt      1560
tcatccgaac tcctcaggtc tctgctatgg gtccgctaca gccgcctgtg gcaggccccg      1620
```

-continued

```
gccccggctc cggccctccc ctgtaagccc ccctactcc ccggcgagca gggaagaagg        1680
cagtggacgg cagcggtggc ggcggccccg cggacagacg tcgaggcata ctgccggtcc        1740
ctgagggccg gccaaacggc gcgcgcggat ccggcctatg tccacagccc cttcttcccg        1800
gccgccttca tcgagttcca aatctggccc gcccttcgcc gggtcctctc caacgagctg        1860
cccaaaaccc gctctctggc cgccctgcgc tggctggtct ccttcggcag cgacctggcc        1920
ctcccttccc ccgagctgac ccgggcccgc cgtcctctcg agctcatata cgccaccgtc        1980
tgggagatct atgacggggc ccctccgatg cctggggagt ccccccaggc ggtcggactg        2040
cgccccctca acttagaggg ggaaggcaag gccggggacg caggagccga gggtgcagaa        2100
gacgaagagg gcgggggccc ctgggggctg tcgtcccacg acgcagtcct taggatcatg        2160
gacgccgtcc gagaggtctc aggcatcatc tccgagacta tctcagcttc agagcgggcg        2220
gcggaagcac caccgcttgc ctggcccacc tccctctttt cactcctctt caccctgaga        2280
tacagcacga cggcggagtc gttgggcctg gccacccgcc gctttctggt ctcgggtgag        2340
accctctcgg aggacatctc gcgcttgacg ggggcagctt ggaggctgtg ctcccgcccg        2400
ctcctgtacg acgcagagac cgggagggtg cagatccctc tggcgacgga agaggaggag        2460
gaggcggtgg tagcggtgaa ggaaaagagc gtttcatcct cccccgcca ctactccacg         2520 gacctccaga cgctaaagag cgtcgtggag ggcatccagg atgtgtgccg ggacgccgcc        2580
gccaggtggg ccctggccac ggccgacacg gccaccctca gaaggcgcct cctggtgccg        2640
gccctcaggg agagccgggg catcgcggat cacccctct gggcccacac cagcgagccc         2700
ctgcgtccgg atctcgagga gctcaacgag cgggtggagc acgccctgga gctgggatac        2760
agcctgacgg gcgccctcag gcgcagcgtc gcctaccggt tccgggatta cacattcgcc        2820
cgcctgttcc agccacccgc catcgacgcc gagcgtgccg aggccatagt ccggcgagac        2880
gcccgcccac cacctgtctt catccccgca cccaggcggc ttccgcaggg gggagcagac        2940
accccacctc ccctcagcat ggacgacatc ctgtatctag caagagcat ctgcaaggcc         3000 ctggtggacg tcctcgacca tcatcctgcc gcgccagaga ccacccctat taaaacatac        3060
acacccgcca tggacctaaa tccggaacag atcacagtca ccccccagaag cccctcggtt        3120 ctcgccgcct ttgctcgcac ggccccgggtc cagacccacc acctcgtgcc ggccctaacc        3180
gacgattccc cctcacccgt gggacaaacg ccccgccat tccgcatcct ccccgccaaa         3240
aaactcgcgg ccattctcct gggtaacggc aggaacgcga gcaagcgccg ggccagccgg        3300
gacctgtcac caccgcccca cggcaggtgg cgtgccgttt tggactcctc cccattctcc        3360
ttctcctcct cagactttc cgaccaggac gagggagagg gaggggaggc agatctcagg         3420
ggcgtgccgg gaggaggagg agaaggagca tacgaggaag acagggaaag gccatcggat        3480
atcgacaccg cggcccgagc ccagaaggtt gagacctcct gcccccgcag acgcagtccg        3540
cggactaccc cctctccttc aaggcgggca agcggcggcg gcggcccaga cagaggagag        3600
gcggaggcac acacgtaccc cccttatctc tcggcggctg ccgccgccag ccgcgtaaga        3660
ccccggacca gaaggggggc gacaaggcgt cctccccgcc ccaccgccga agatgagtaa        3720
```

```
<210> SEQ ID NO 149
<211> LENGTH: 1239
<212> TYPE: PRT
<213> ORGANISM: Artificial Sequence
<220> FEATURE:
<223> OTHER INFORMATION: Synthetic

<400> SEQUENCE: 149
```

-continued

```
Met Ala Ser Ala Met Glu Ser Asp Ser Ser Gly Gly Ser Gly Gly Ala
1               5                   10                  15

Asp Ala Gln Pro Pro Leu Ala Glu Val Asp Gly Gly Leu Ala Arg Val
                20                  25                  30

Thr Arg Gln Leu Leu Leu Ser Gly Asp Asp Pro Ala Ala Arg Leu Arg
            35                  40                  45

Ala Leu Met Pro Leu Glu Leu Gly Ile Phe Gly Leu Gly Asp Leu Ala
        50                  55                  60

Gln Pro Val Leu Val Arg Asp Phe Leu Asn Thr Leu Thr Leu Met Ser
65                  70                  75                  80

Gly His Ala Tyr Pro Ala Ala Val Leu Arg His His Ala Tyr Tyr Leu
                85                  90                  95

Leu Arg Ala Ala Ser Phe Ser Arg Arg Ser Phe Gly Leu Gly His Leu
            100                 105                 110

Glu Ala Ala Leu Asp Val Leu Ala Ser Ser Leu Pro Pro Thr Thr Ala
            115                 120                 125

Ser Pro Ala Thr Asp Asp Pro Leu Asp Gly Ser Arg Leu Ile Ala Glu
        130                 135                 140

Thr Arg Ala Leu Ala Ala Ala Tyr Arg Arg Ile Ile Glu Glu Gly Ser
145                 150                 155                 160

Gly Glu Val Leu Ala Val Ser Gly Pro Thr Ala Thr Phe Ala Phe Val
                165                 170                 175

Glu Glu Leu Val Ala Asp Thr Tyr Leu Ala Arg Trp Asp Ala Phe Pro
            180                 185                 190

Arg Glu Gly Leu Ser Phe Tyr Ala Phe Asn Ala Ala Lys Thr Thr Leu
            195                 200                 205

Gly Arg Trp Leu Val Thr Val Tyr Ala Glu Thr Asn Arg Tyr Pro Trp
        210                 215                 220

Ala Ala Ala Gly Gln Gly Gln Pro Thr Ala Ala Asp Ile Lys Ala Met
225                 230                 235                 240

Ala Val Glu Leu Val Glu His Ser Gly Gly Gly Ala Gly Gly Gly Glu
                245                 250                 255

Gly Glu Glu Ser Gly Gly Gly Leu Phe His Arg Pro Glu Ser Leu Ser
            260                 265                 270

Ser Val Val Ala Ser Leu Pro Leu Ala Arg Arg Arg Ala Val Glu Ile
        275                 280                 285

Leu Gly Val Tyr Ala Glu Ala Ser Gly Gly Gln Thr Pro Pro Val Ala
    290                 295                 300

Ala Val Pro Val Leu Ala Phe Asp Ala Ala Arg Leu Arg Leu Leu Glu
305                 310                 315                 320

Pro Ser Gly Ala Leu Phe Tyr Asp Tyr Val Tyr Glu Ala Leu Leu Trp
            325                 330                 335

Asp Gln Thr Tyr Gly Val Pro Asp Ser Val Ile Glu Ala Phe Leu Ala
            340                 345                 350

Gly Met Ala Ala Glu Met Glu Ala Leu Ala Ala Arg Val Gln Glu Ala
        355                 360                 365

Ala Gly Ser Arg Ala Ser Phe Ser Pro Ala Ala Ile Glu Gln Val Ala
    370                 375                 380

Thr Val Leu Leu Ser Ala Gly Leu Asn Glu Thr Val Ala Gly Asp Tyr
385                 390                 395                 400

Ala Met Met Leu Ala Ser Val Pro Arg Val Ser Arg Ser Arg Trp Arg
                405                 410                 415
```

-continued

```
Trp Leu Glu Ala Thr Ala Ala Leu Leu Glu Ser Leu Ser Gly Phe Ala
            420                 425                 430

Leu His Phe Phe Arg Leu Leu Pro Thr Ala Ser Pro Thr Ser Arg Phe
            435                 440                 445

Ala Arg Val Ala Arg Ala Ala Tyr Leu Arg Ala Glu Ala Glu Ala Val
            450                 455                 460

Asp Arg Arg Ala Arg Arg Thr Ser Gly Pro Ser Thr Pro Ala Ala Ala
465                 470                 475                 480

Pro Ala Ala Thr Ala Val Gly Val Gly Ala Ala Asp Pro Trp Asp
            485                 490                 495

Ala Val Thr Pro Leu Arg Ile Phe Ile Val Pro Pro Pro Ala Ala Glu
            500                 505                 510

Tyr Glu Gln Val Ala Gly Asp Leu Ser Ser Glu Leu Leu Arg Ser Leu
            515                 520                 525

Leu Trp Val Arg Tyr Ser Arg Leu Trp Gln Ala Pro Ala Pro Ala Pro
            530                 535                 540

Ala Leu Pro Cys Lys Pro Pro Leu Leu Pro Gly Glu Gln Gly Arg Arg
545                 550                 555                 560

Gln Trp Thr Ala Ala Val Ala Ala Ala Pro Arg Thr Asp Val Glu Ala
            565                 570                 575

Tyr Cys Arg Ser Leu Arg Ala Gly Gln Thr Ala Arg Ala Asp Pro Ala
            580                 585                 590

Tyr Val His Ser Pro Phe Phe Pro Ala Ala Phe Ile Glu Phe Gln Ile
            595                 600                 605

Trp Pro Ala Leu Arg Arg Val Leu Ser Asn Glu Leu Pro Lys Thr Arg
            610                 615                 620

Ser Leu Ala Ala Leu Arg Trp Leu Val Ser Phe Gly Ser Asp Leu Ala
625                 630                 635                 640

Leu Pro Ser Pro Glu Leu Thr Arg Ala Arg Arg Pro Leu Glu Leu Ile
            645                 650                 655

Tyr Ala Thr Val Trp Glu Ile Tyr Asp Gly Ala Pro Pro Met Pro Gly
            660                 665                 670

Glu Ser Pro Gln Ala Val Gly Leu Arg Pro Leu Asn Leu Glu Gly Glu
            675                 680                 685

Gly Lys Ala Gly Asp Ala Gly Ala Glu Gly Ala Glu Asp Glu Glu Gly
            690                 695                 700

Gly Gly Pro Trp Gly Leu Ser Ser His Asp Ala Val Leu Arg Ile Met
705                 710                 715                 720

Asp Ala Val Arg Glu Val Ser Gly Ile Ile Ser Glu Thr Ile Ser Ala
            725                 730                 735

Ser Glu Arg Ala Ala Glu Ala Pro Pro Leu Ala Trp Pro Thr Ser Leu
            740                 745                 750

Phe Ser Leu Leu Phe Thr Leu Arg Tyr Ser Thr Thr Ala Glu Ser Leu
            755                 760                 765

Gly Leu Ala Thr Arg Arg Phe Leu Val Ser Gly Glu Thr Leu Ser Glu
            770                 775                 780

Asp Ile Ser Arg Leu Thr Gly Ala Ala Trp Arg Leu Cys Ser Arg Pro
785                 790                 795                 800

Leu Leu Tyr Asp Ala Glu Thr Gly Arg Val Gln Ile Pro Leu Ala Thr
            805                 810                 815

Glu Glu Glu Glu Glu Ala Val Val Ala Val Lys Glu Lys Ser Val Ser
            820                 825                 830

Ser Ser Pro Arg His Tyr Ser Thr Asp Leu Gln Thr Leu Lys Ser Val
```

-continued

```
              835                840                845

Val Glu Gly Ile Gln Asp Val Cys Arg Asp Ala Ala Ala Arg Trp Ala
    850                 855                860

Leu Ala Thr Ala Asp Thr Ala Thr Leu Arg Arg Arg Leu Leu Val Pro
865                 870                875                880

Ala Leu Arg Glu Ser Arg Gly Ile Ala Asp His Pro Leu Trp Ala His
                885                890                895

Thr Ser Glu Pro Leu Arg Pro Asp Leu Glu Glu Leu Asn Glu Arg Val
            900                905                910

Glu His Ala Leu Glu Leu Gly Tyr Ser Leu Thr Gly Ala Leu Arg Arg
            915                920                925

Ser Val Ala Tyr Arg Phe Arg Asp Tyr Thr Phe Ala Arg Leu Phe Gln
    930                935                940

Pro Pro Ala Ile Asp Ala Glu Arg Ala Glu Ala Ile Val Arg Arg Asp
945                 950                955                960

Ala Arg Pro Pro Pro Val Phe Ile Pro Ala Pro Arg Arg Leu Pro Gln
                965                970                975

Gly Gly Ala Asp Thr Pro Pro Pro Leu Ser Met Asp Asp Ile Leu Tyr
                980                985                990

Leu Gly Lys Ser Ile Cys Lys Ala  Leu Val Asp Val Leu  Asp His His
            995                1000                1005

Pro Ala  Ala Pro Glu Thr Thr  Pro Ile Lys Thr Tyr  Thr Pro Ala
    1010                1015                1020

Met Asp  Leu Asn Pro Glu Gln  Ile Thr Val Thr Pro  Arg Ser Pro
    1025                1030                1035

Ser Val  Leu Ala Ala Phe Ala  Arg Thr Ala Arg Val  Gln Thr His
    1040                1045                1050

His Leu  Val Pro Ala Leu Thr  Asp Asp Ser Pro Ser  Pro Val Gly
    1055                1060                1065

Gln Thr  Pro Pro Pro Phe Arg  Ile Leu Pro Ala Lys  Lys Leu Ala
    1070                1075                1080

Ala Ile  Leu Leu Gly Asn Gly  Arg Asn Ala Ser Lys  Arg Arg Ala
    1085                1090                1095

Ser Arg  Asp Leu Ser Pro Pro  Pro His Gly Arg Trp  Arg Ala Val
    1100                1105                1110

Leu Asp  Ser Ser Pro Phe Ser  Phe Ser Ser Ser Asp  Phe Ser Asp
    1115                1120                1125

Gln Asp  Glu Gly Glu Gly Gly  Glu Ala Asp Leu Arg  Gly Val Pro
    1130                1135                1140

Gly Gly  Gly Gly Glu Gly Ala  Tyr Glu Glu Asp Arg  Glu Arg Pro
    1145                1150                1155

Ser Asp  Ile Asp Thr Ala Ala  Arg Ala Gln Lys Val  Glu Thr Ser
    1160                1165                1170

Cys Pro  Arg Arg Arg Ser Pro  Arg Thr Thr Pro Ser  Pro Ser Arg
    1175                1180                1185

Arg Ala  Ser Gly Gly Gly Gly  Pro Asp Arg Gly Glu  Ala Glu Ala
    1190                1195                1200

His Thr  Tyr Pro Pro Tyr Leu  Ser Ala Ala Ala Ala  Ala Ser Arg
    1205                1210                1215

Val Arg  Pro Arg Thr Arg Arg  Gly Ala Thr Arg Arg  Pro Pro Arg
    1220                1225                1230

Pro Thr  Ala Glu Asp Glu
    1235
```

<210> SEQ ID NO 150
<211> LENGTH: 1140
<212> TYPE: DNA
<213> ORGANISM: Artificial Sequence
<220> FEATURE:
<223> OTHER INFORMATION: Synthetic

<400> SEQUENCE: 150

```
atgagcatcc gggggcagac atttcacctc ttgtttgtgg acgaggctaa ctttatcaag        60
aaggaggccc tgccggcgat cctgggcttt atgcttcaga aggatgccaa gattatcttc       120
atctcgtctg tgaactcggc tgaccaggcc accagctttc tttataagct gaaggatgct       180
caggagcggc tgctgaacgt ggtaagttat gtgtgtcagg agcatcggca agattttgac       240
atgcaggaca gcatggtctc atgcccctgc tttcgcctgc acatcccgtc ctacatcacc       300
atggacagca acatccgagc aaccaccaac ctctttctgg acggggcctt tagcaccgag       360
ctgatgggtg acacctcctc gctgagccag ggtagcctga ccgcactgt gcgtgacgat       420 gccatcaacc agctggagct ctgccgggtt gacaccctca accccgagt agccggacgc       480 ctagcctcct ccctctacgt gtacgttgat ccggcctata ccaacaacac atccgcatca       540
ggcaccggaa tcgccgccgt gactcacgac agggcggacc ctaacagggt catcgtcctg       600
ggcctggaac acttcttcct caaggaccta acaggggacg ctgccctcca gatcgccacc       660
tgcgtcgtgg ccctcgtctc ctcgatcgtc accctgcacc cccacttgga ggaggtgaag       720
gtagccgtgg agggcaacag cagtcaggac tctgcggtgg ccattgcctc aatcattggg       780
gaatcctgcc ccctcccctg cgccttcgtg cacaccaagg acaagacgtc cagcctgcag       840
tggcccatgt acctcctgac taatgagaag tccaaggcct ttgagaggct catctacgca       900
gtgaacacgg ccagcctttc tgccagtcag gtcaccgtct ccaacaccat ccagctctcc       960
ttcgatccgg tcctctatct catctcccag atcagggcca tcaagcccat ccctctccgc      1020
gacggtacct acacctacac cggcaagcag cgcaacctct ctgacgacgt gctggttgcg      1080
ctagtcatgg ctcattttct cgcaacaaca cagaagcaca cgttcaagaa agttcattaa      1140
```

<210> SEQ ID NO 151
<211> LENGTH: 379
<212> TYPE: PRT
<213> ORGANISM: Artificial Sequence
<220> FEATURE:
<223> OTHER INFORMATION: Synthetic

<400> SEQUENCE: 151

```
Met Ser Ile Arg Gly Gln Thr Phe His Leu Leu Phe Val Asp Glu Ala
1               5                   10                  15

Asn Phe Ile Lys Lys Glu Ala Leu Pro Ala Ile Leu Gly Phe Met Leu
            20                  25                  30

Gln Lys Asp Ala Lys Ile Ile Phe Ile Ser Ser Val Asn Ser Ala Asp
        35                  40                  45

Gln Ala Thr Ser Phe Leu Tyr Lys Leu Lys Asp Ala Gln Glu Arg Leu
    50                  55                  60

Leu Asn Val Val Ser Tyr Val Cys Gln Glu His Arg Gln Asp Phe Asp
65                  70                  75                  80

Met Gln Asp Ser Met Val Ser Cys Pro Cys Phe Arg Leu His Ile Pro
                85                  90                  95

Ser Tyr Ile Thr Met Asp Ser Asn Ile Arg Ala Thr Thr Asn Leu Phe
            100                 105                 110
```

-continued

```
Leu Asp Gly Ala Phe Ser Thr Glu Leu Met Gly Asp Thr Ser Ser Leu
        115                 120                 125

Ser Gln Gly Ser Leu Ser Arg Thr Val Arg Asp Asp Ala Ile Asn Gln
        130                 135                 140

Leu Glu Leu Cys Arg Val Asp Thr Leu Asn Pro Arg Val Ala Gly Arg
145                 150                 155                 160

Leu Ala Ser Ser Leu Tyr Val Tyr Val Asp Pro Ala Tyr Thr Asn Asn
                165                 170                 175

Thr Ser Ala Ser Gly Thr Gly Ile Ala Ala Val Thr His Asp Arg Ala
                180                 185                 190

Asp Pro Asn Arg Val Ile Val Leu Gly Leu Glu His Phe Phe Leu Lys
        195                 200                 205

Asp Leu Thr Gly Asp Ala Ala Leu Gln Ile Ala Thr Cys Val Val Ala
        210                 215                 220

Leu Val Ser Ser Ile Val Thr Leu His Pro His Leu Glu Glu Val Lys
225                 230                 235                 240

Val Ala Val Glu Gly Asn Ser Ser Gln Asp Ser Ala Val Ala Ile Ala
                245                 250                 255

Ser Ile Ile Gly Glu Ser Cys Pro Leu Pro Cys Ala Phe Val His Thr
                260                 265                 270

Lys Asp Lys Thr Ser Ser Leu Gln Trp Pro Met Tyr Leu Leu Thr Asn
        275                 280                 285

Glu Lys Ser Lys Ala Phe Glu Arg Leu Ile Tyr Ala Val Asn Thr Ala
        290                 295                 300

Ser Leu Ser Ala Ser Gln Val Thr Val Ser Asn Thr Ile Gln Leu Ser
305                 310                 315                 320

Phe Asp Pro Val Leu Tyr Leu Ile Ser Gln Ile Arg Ala Ile Lys Pro
                325                 330                 335

Ile Pro Leu Arg Asp Gly Thr Tyr Thr Tyr Thr Gly Lys Gln Arg Asn
                340                 345                 350

Leu Ser Asp Asp Val Leu Val Ala Leu Val Met Ala His Phe Leu Ala
        355                 360                 365

Thr Thr Gln Lys His Thr Phe Lys Lys Val His
        370                 375
```

ANTIBODIES FOR DETECTING EPSTEIN BARR VIRUS-POSITIVE GASTRIC CANCER

CROSS-REFERENCE TO RELATED APPLICATIONS

This application is a national stage application filed under 35 U.S.C. § 371 of International Application No. PCT/US2020/057010, filed Oct. 23, 2020, which claims priority to U.S. Provisional Application No. 62/925,584, filed Oct. 24, 2019, which is hereby incorporated by reference herein in its entirety.

STATEMENT REGARDING FEDERALLY SPONSORED RESEARCH

This invention was made with government support under R01 CA199948 and U01 CA214201 awarded by the National Institutes of Health. The government has certain rights in the invention.

In accordance with 37 C.F.R. § 1.821(c), the present specification makes reference to a Sequence Listing submitted electronically in the form of an ASCII text file (named "112624.01327_ST25.txt", 448,936 bytes in size, created on Nov. 6, 2025). The sequence listing is electronically submitted via Patent Center with the application and is incorporated herein by reference in its entirety, with the intention that, upon publication (including issuance), this incorporated Sequence Listing will be inserted in the published document immediately before the claims.

BACKGROUND

Gastric cancer (GC) is a major public health problem. GC represents the third leading cause of cancer mortality in the world, with approximately 1,000,000 new diagnoses and over 783,000 deaths in 2018 (equal to 1 in every 12 deaths globally). Besides gastric cancer induced by *Helicobacter pylori* (*H. pylori*) infection, around 10% of gastric cancer present the evidence of Epstein Barr Virus (EBV) involvement. As a ubiquitous virus that infects over 90% of adults, the association of EBV infection and gastric cancer is still unclear.

Like other cancers associated with EBV (e.g., nasopharyngeal carcinoma (NPC), Burkitt lymphoma (BL), Hodgkin lymphoma (HL), and non-Hodgkin lymphoma (NHL)), EBV-associated gastric cancer (EBV⁺ GC) is conventionally detected by in situ hybridization of EBV-encoded small RNA (EBER), a specific marker for EBV presence. EBV⁺ GC is a distinct subtype of gastric cancer classified by The Cancer Genome Atlas (TCGA) with overall lower mortality, occurs more frequently in male than female, is non-cardiac gastric carcinoma type with 90% prevalence of lymphoepithelioma-like gastric carcinoma, and displays significant intra- or peritumoral immune cell infiltration compared to EBV⁻ GC. Current knowledge of EBV⁺ GC has been focused on epigenetic and genetic aberrance. EBV⁺ GC displays unique molecular characteristics, recurrent PIK3CA mutations, extreme DNA hypermethylation, and amplification of JAK2, PD-L1 and PD-L2.

Consideration of its unique molecular characterization and distinct gastric cancer subtype, distinguishing EBV⁺ GC from EBV⁻ GC would benefit a following targeted therapy and precision medicine. Previously, anti-VCAp18 IgG/IgA, anti-EBNA1 IgG/IgA, and anti-Early protein (EA) IgG/IgA, which were used to detect EBV induced cancers, NPC, BL, and HL, as serological biomarkers, had been applied for EBV⁺ GC detection. However, their presence in EBV⁺ GC has been controversial. Some groups reported elevated anti-VCA IgA and anti-EA IgG in EBV⁺ GC as compared to EBV– GC or healthy controls. Other groups have studied these antibodies but did not find a significant association between them and EBV⁺ GC. Other than anti-EBV antibodies, Chung et al. had reported the present of circulating EBER in serum for limited EBV⁺ GC cases (n=5) but not in controls (n=197). However, to date, none of these proposed markers have demonstrated enough discriminative power to be used for EBV⁺ GC diagnosis. Accordingly, there remains a need in the art for improved reagents and methods for detecting EBV-associated gastric cancer, assessing risk of developing EBV⁺ gastric cancer, and identifying subjects in need of treatment for this is unique subtype of gastric cancer, meaning reagents and methods that are more reliable and have sufficient discriminatory power for risk stratification and for early detection in asymptomatic individuals.

SUMMARY

In a first aspect, provided herein is a method for identifying a subject having increased risk of developing EBV-positive gastric cancer (EBV⁺ GC). The method can comprise or consist essentially of (a) reacting a biological sample obtained from a subject with a reagent composition that comprises components for detecting in the biological sample the presence of one or more antibodies selected from anti-BORF2, anti-LF2, anti-BDLF2, anti-BXLF1, anti-BRLF1, anti-BaRF1, anti-BGLF5, anti-BRRF1, anti-BALF2, anti-BLLF3, and anti-BSLF2; and (b) detecting the presence of the antibodies in the sample, wherein increased seroreactivity relative to a control for one or more of the antibodies is indicative of at least a four-fold increased risk of EBV⁺ GC. The detected antibodies can comprise anti-BALF2, anti-BORF2, and anti-BRRF1. The biological sample can be one or more of a whole blood sample, a serum sample, and a plasma sample. The method can detect EBV⁺ GC gastric cancer prior to symptom onset. The determining step can be carried out using an ELISA assay or a Western Blot assay. The method can further comprise administering a vaccine-based gastric cancer treatment to the subject if identified as having an increased risk of EBV⁺ GC gastric cancer.

In another aspect, provided herein is a method to detect EBV-positive gastric cancer (EBV⁺ GC) in a subject at risk of having EBV⁺ GC, the method comprising: (a) contacting a biological sample obtained from the subject with a set of reagents, wherein the set of reagents specifically binds to at least three biomarkers in the biological sample, wherein the biomarkers are selected from the group consisting of BORF2, LF2, BDLF2, BXLF1, BRLF1, BaRF1, BGLF5, BRRF1, BALF2, BLLF3, and BSLF2; (b) measuring the level of the at least three biomarkers in the biological sample; and (c) detecting that the level of the at least three biomarkers is increased in the biological sample relative to a control sample from a subject without EBV⁺ GC, thereby detecting the presence of EBV⁺ GC in the subject. The at least three biomarkers can comprise anti-BALF2, anti-BORF2, and anti-BRRF1. The method can further comprise (d) administering an EBV⁺ gastric cancer therapy to the subject, wherein the EBV⁺ gastric cancer therapy is selected from the group consisting of chemotherapy, hormonal therapy, radiotherapy, immunotherapy, and surgical removal of stomach tissue. The biological sample can be one or more of a whole blood sample, a serum sample, and a plasma sample. The determining step can be carried out using an immunoassay.

In another aspect, provided herein is a method of determining an Epstein Barr Virus (EBV) gastric cancer antibody signature comprising antibodies, contained in a biological sample from an individual, that specifically bind to immobilized EBV antigens, the method comprising: (a) contacting the sample to a panel of immobilized EBV antigens under conditions that promote formation of antigen-antibody complexes; and (b) identifying complexes formed by immobilized EBV antigens and antibody in the sample, to determine an EBV antibody signature. The antibody signature can be expressed as a level of antibody specifically binding to each immobilized antigen. The method can further comprise comparing an antibody signature from one individual to the antibody signature from another individual. In some cases, one individual has a disease process, and one individual is a healthy individual and the method allows comparison of the antibody signature in the healthy individual and the individual with a disease. The disease process can comprise EBV+ gastric cancer. The immobilized EBV antigens comprise one or more of BORF2, LF2, BDLF2, BXLF1, BRLF1, BaRF1, BGLF5, BOLF1, BRRF1, BALF2, BLLF3, and BSLF2.

In a further aspect, provided herein is a kit for determining and/or detecting at least one biomarker associated with EBV$^+$ gastric cancer, the kit comprising a reagent composition that comprises components for detecting in a biological sample the presence of one or more antibodies selected from anti-BORF2, anti-LF2, anti-BDLF2, anti-BXLF1, anti-BRLF1, anti-BaRF1, anti-BGLF5, anti-BOLF1, anti-BRRF1, anti-BALF2, anti-BLLF3, and anti-BSLF2.

In another aspect, provided herein is a kit for diagnosing a EBV$^+$ gastric cancer in a subject, the kit comprising a reagent composition that comprises components for detecting in a biological sample obtained from the subject presence of one or more antibodies selected from anti-BORF2, anti-LF2, anti-BDLF2, anti-BXLF1, anti-BRLF1, anti-BaRF1, anti-BGLF5, anti-BOLF1, anti-BRRF1, anti-BALF2, anti-BLLF3, and anti-BSLF2.

BRIEF DESCRIPTION OF THE DRAWINGS

The present invention will be better understood and features, aspects, and advantages other than those set forth above will become apparent when consideration is given to the following detailed description thereof. Such detailed description makes reference to the following drawings, wherein.

Figure 1:
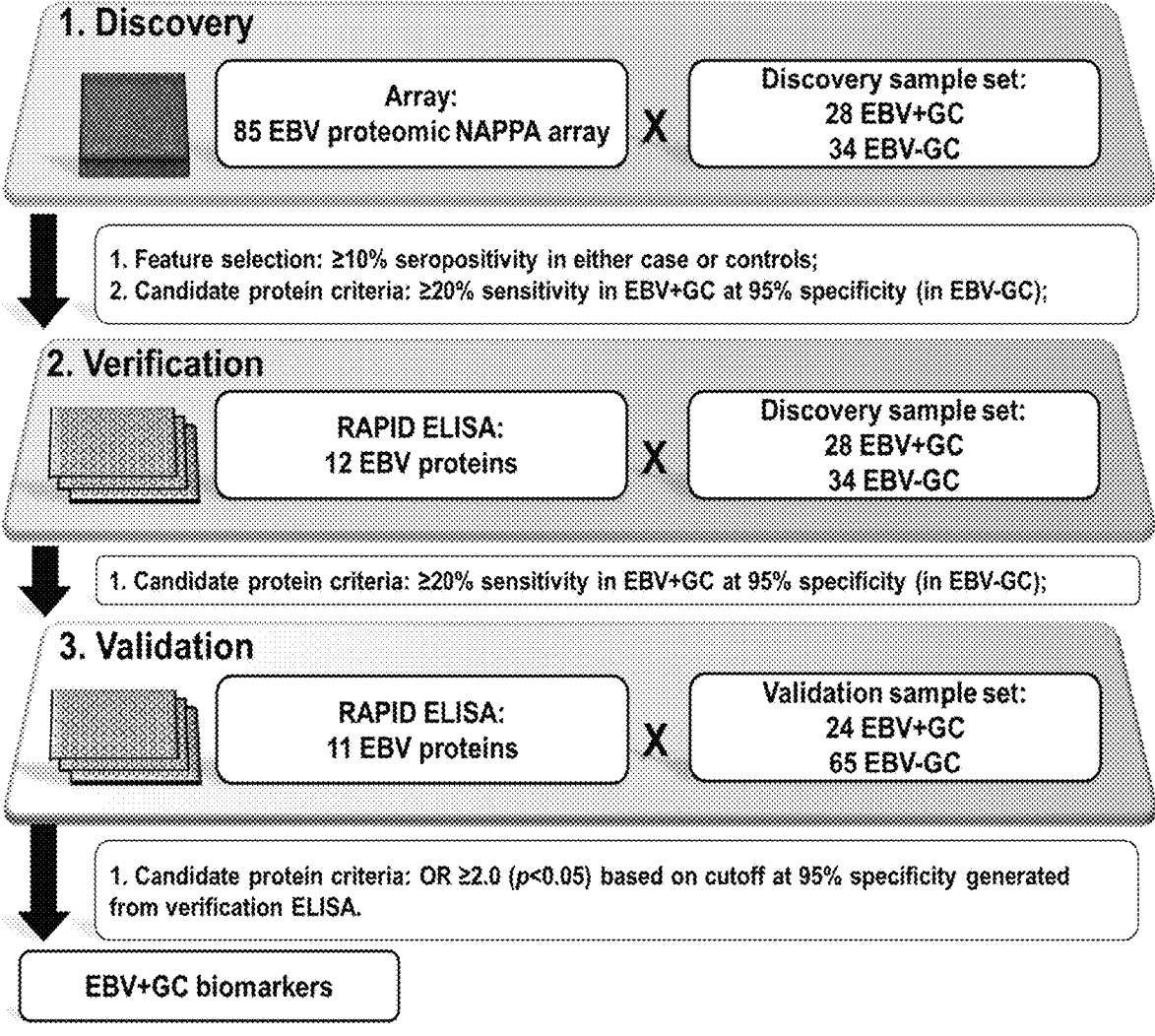
FIG. 1 is a schematic flow-chart of EBV$^+$ GC biomarker discovery on NAPPA array, and verification and validation by ELISA.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION OF THE DISCLOSURE

All publications, including but not limited to patents and patent applications, cited in this specification are herein incorporated by reference as though set forth in their entirety in the present application.

With few biomarkers for non-invasive diagnostic testing, conventional methods of gastric cancer detection were based on endoscopy, which is a highly invasive technique, and histology to verify disease. Unfortunately, endoscopy is often performed after the patient has exhibited symptoms associated with gastric cancer, and the cancer is already in late stages, which lowers overall survival rate. The methods, devices, combinations, kits, and systems for diagnosing, predicting the risk of, and treating gastric cancer provided herein are based at least in part on the inventors' comprehensive anti-EBV protein immune profiling of EBV$^+$ GC and EBV$^-$ GC patients and their development and validation of a panel of protein biomarkers useful for non-invasive identification of Epstein Barr Virus-associated gastric cancer patients from healthy controls in discovery samples and validation samples. In particular, this disclosure relates to the development and validation of unique EBV immunoproteomic profiles useful for identifying subjects having an increased risk of EBV-associated gastric cancer relative to subject-matched controls. An interesting and unexpected finding of this investigation was that, while EBV infections are quite ubiquitous among adult humans, certain EBV antibodies possess high discriminatory power to distinguish EBV$^+$ GC and EBV$^-$ GC samples. A three-antibody panel provides discriminatory power of AUC=0.87 with 79.2% sensitivity at 95% specificity, making non-invasive diagnosis of EBV$^+$ GC possible. Interestingly, the target proteins of these EBV antibodies are primarily expressed in during the early lytic stages of the EBV life cycle. Without being bound to any particular mechanism or mode of action, the early lytic stage proteins may be involved in cancer development or progression and, thus provide new targets for precision medicine and targeted therapies.

Accordingly, in a first aspect, this disclosure provides methods for identifying a subject as having increased risk of developing EBV-associated gastric cancer ("EBV$^+$ GC"). In some cases, the method comprises (a) reacting a biological sample obtained from a subject with a reagent composition that comprises components for detecting in the serum sample the presence of antibodies specific to EBV proteins; and detecting the presence of the antibodies in the sample. As used herein, the term "EBV-positive gastric cancer" or "EBV$^+$ GC" (also known as "EBV+ stomach cancer") refers to a type of cancer of the stomach or of stomach cells. EBV$^+$ GC is a distinct subtype of gastric cancer classified by The Cancer Genome Atlas (TCGA) with overall lower mortality, occurs more frequently in male than female, is non-cardiac gastric carcinoma type with 90% prevalence of lymphoepithelioma-like gastric carcinoma, and displays significant intra- or peritumoral immune cell infiltration compared to EBV$^-$ GC. Previous studies of EBV$^+$ GC focused on epigenetic and genetic aberrance. EBV$^+$ GC displays unique molecular characteristics, recurrent PIK3CA mutations, extreme DNA hypermethylation, and amplification of JAK2, PD-L1 and PD-L2, but the utility of detecting circulating nucleic acids (e.g., by EBER) for reliable, reproducible diagnostic purposes has not been established.

In preferred embodiments, the method comprises detecting and/or measuring a level of a biomarker such as, for example, an IgG or IgA antibody having specificity for Epstein Barr Virus (EBV) proteins. As used herein, the term "biomarker" means a distinctive biological or biologically derived indicator of a process, event, or condition. Protein or antibody biomarkers can be used in methods of diagnosis, e.g. clinical screening, and prognosis assessment and in monitoring the results of therapy. In some cases, biomarkers are useful for identifying patients most likely to respond to a particular therapeutic treatment and for drug screening and development. In some cases, biomarkers include IgG specific antibodies having specificity for EBV proteins that show a statistically significant difference in EBV$^+$ GC diagnosis. In some cases, therefore, the methods comprise detecting IgG and IgA antibodies having specificity for EBV proteins in a sample obtained from a subject. Data is provided herein which demonstrates that specific panels of biomarkers described herein, contains statistically significant biomarkers for the diagnosis of EBV$^+$ GC. For example, data provided herein demonstrates that increase seroreactivity for antibodies specific to particular EBV proteins is associated with increased risk of EBV-positive gastric cancer relative to a reference sample (e.g., in some cases obtained from healthy (e.g., free of EBV$^+$ GC) subject or pool of subjects; in other cases obtained from a EBV$^-$ GC subject or pool of subjects). The antibodies include those listed in Table 1. Preferably, the antibodies are anti-BORF2, anti-LF2, anti-BDLF2, anti-BXLF1, anti-BRLF1, anti-BaRF1, anti-BGLF5, anti-BOLF1, anti-BRRF1, anti-BALF2, anti-BLLF3, and anti-BSLF2 antibodies. Increased seroreactivity for these antibodies, relative to the reference sample, is associated with increased risk of EBV$^+$ GC. As shown in Table 1 and FIG. 3, the following ten antibodies were validated (provided here with odds ratio (OR) and p-value): anti-LF2 (110.0, p<0.01), anti-BORF2 (54.2, p<0.01), anti-BALF2 (44.1, p<0.01), anti-BaRF1 (26.7, p<0.01), anti-BGLF5 (16.8, p<0.01), anti-BXLF1 (12.8, p=0.01), anti-BRRF1 (10.2, p<0.01), anti-BRLF1 (8.3, p<0.01), anti-BLLF3 (5.4, p=0.02), and anti-BSLF2 (4.0, p=0.04). In various embodiments, diagnostic tests that use these biomarkers alone or in combination show a sensitivity and specificity of at least 85%, at least 90%, at least 95%, at least 98% and at least 99%.

As used herein, the term "seroreactivity" refers to a level and/or presence of reactivity to specific antibodies in a sample (e.g., biological sample of a subject or a pooled sample from multiple subjects) as determined using with techniques known in the art, such as ELISA. As described in this disclosure, it was determined that increased seroreactivity to particular antigen-specific antibodies relative to a control (e.g., in some cases, a control sample obtained from a subject that does not have gastric cancer) is indicative of an increased risk of EBV$^+$ GC. The increased level of seroreactivity may be at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, at least or about a 95% increase, at least or about at 100% increase, at least or about at 200% increase, or more.

As used herein, the terms "seropositivity" and "seropositive" refer to a positive result (or a subject having a positive result) in a test of blood serum, e.g., obtaining a positive result for the presence of an antigen-specific antibody. The term seropositive can encompass patients for whom blood tests reveal the presence of particular antibodies. As used herein, the terms "seronegativity" and "seronegative" refer to a reduced or a negative result (or a subject having a negative result) in a test of blood serum, e.g., obtaining a negative result for the presence of an antigen-specific antibody. The term seronegative can encompass patients for whom blood tests do not reveal the presence of particular antibodies, which can mean the patient does not possess the antibodies, or the patient possesses low levels of the antibodies that cannot be detected by a particular assay.

In some cases, the levels of one or more EBV$^+$ GC biomarkers or the levels of a specific panel of EBV$^+$ GC biomarkers in a sample are compared to a reference standard ("reference standard" or "reference level") in order to direct treatment decisions. The reference standard used for any embodiment disclosed herein may comprise average, mean, or median levels of the one or more EBV$^+$ GC biomarkers or the levels of the specific panel of EBV$^+$ GC biomarkers in a control population. The reference standard may additionally comprise cutoff values or any other statistical attribute of the control population, such as a standard deviation from the mean levels of the one or more EBV$^+$ GC biomarkers or the levels of the specific panel of EBV$^+$ GC biomarkers.

In some embodiments, comparing the level of the one or more EBV$^+$ GC biomarkers is performed using a cutoff value. In related embodiments, if the level of the one or more EBV$^+$ GC biomarkers is greater than the cutoff value, the individual may be diagnosed as having, or being at risk of developing EBV$^+$ GC. In other distinct embodiments, if the level of the one or more EBV$^+$ GC biomarkers is less than the cutoff value, the individual may be diagnosed as having, or being at risk of developing EBV$^+$ GC. Cutoff values may be determined by statistical analysis of the control population to determine which levels represent a high likelihood that an individual does or does not belong to the control population. In some embodiments, comparing the level of the one or more EBV$^+$ GC biomarkers is performed using other statistical methods. In related embodiments, comparing comprises logistic or linear regression. In other embodiments, comparing comprises computing an odds ratio.

In a further aspect, provided herein are methods for detecting Epstein Barr Virus-associated gastric cancer in a subject. In some cases, the method comprises (a) reacting a biological sample obtained from a subject with a reagent composition that comprises components for determining a level of antibodies to one or more of the EBV proteins listed in Table 2 are present in the sample; (b) determining levels of the antibodies in the biological sample; and (c) comparing the levels to predetermined values indicative of EBV$^+$ GC, wherein if the level of antibodies in the biological sample falls within the predetermined values indicative of EBV$^+$ GC, the level in the biological sample indicates that the subject has EBV$^+$ GC. The predetermined values can be obtained from a reference sample obtained from an individual or a group of individuals (e.g., a cohort) having EBV$^+$ GC.

In preferred embodiments, the antibodies comprise one or more of anti-BORF2, anti-LF2, anti-BDLF2, anti-BXLF1, anti-BRLF1, anti-BaRF1, anti-BGLF5, anti-BOLF1, anti-BRRF1, anti-BALF2, anti-BLLF3, and anti-BSLF2. In some cases, the antibodies are a panel that comprises or consists essentially of anti-BALF2, anti-BORF2, and anti-BRRF1 antibodies.

In another aspect, provided herein are methods to determine risk of EBV$^+$ GC. In some cases, the method comprises (a) reacting a biological sample obtained from a subject with a reagent composition that comprises components for determining the level of antibodies to one or more EBV proteins present in the sample; (b) determining levels of the antibodies in the sample; and (c) comparing the levels of antibodies to predetermined values indicative of high risk of EBV$^+$ GC, wherein if the level of antibodies in the sample falls within the levels antibodies of a subject with high risk of EBV$^+$ GC, the level in the sample of the subject is predictive for the risk of EBV$^+$ GC in the subject. Preferably, the EBV proteins are selected from those listed in Table 1.

In another aspect, provided herein is a method to detect EBV-positive gastric cancer (EBV$^+$ GC) in a subject at risk of having EBV$^+$ GC, where the method comprises: (a) contacting a biological sample obtained from the subject with a set of reagents, wherein the set of reagents specifically binds to at least three biomarkers in the biological sample, wherein the biomarkers are selected from the group consisting of BORF2, LF2, BDLF2, BXLF1, BRLF1, BaRF1, BGLF5, BOLF1, BRRF1, BALF2, BLLF3, and BSLF2; (b) measuring the level of the at least three biomarkers in the biological sample; and (c) detecting that the level of the at least three biomarkers is increased in the biological sample relative to a control sample from a subject without EBV$^+$ GC, thereby detecting the presence of EBV$^+$ GC in the subject. In some cases, the at least three biomarkers comprise anti-BALF2, anti-BORF2, and anti-BRRF1.

In some cases, the method further comprises (d) administering an EBV$^+$ GC therapy to the subject, wherein the EBV$^+$ GC therapy is selected from the group consisting of chemotherapy, hormonal therapy, radiotherapy, immunotherapy, and surgical removal of stomach tissue.

In some cases, the method further comprises administering an effective amount of a treatment regimen to treat EBV$^+$ GC. In some cases, the treatment regimen comprises one or more of a vaccine-based therapy, chemotherapy, hormonal therapy, radiotherapy, surgery, and immunotherapy.

As used herein, the term "individual," which may be used interchangeably with the terms "patient" or "subject," refers to one who receives medical care, attention or treatment and may encompass a human patient. As used herein, the term "individual" is meant to encompass a person who has EBV$^+$ GC, is suspected of having EBV$^+$ GC, or is at risk of EBV$^+$ GC. As used herein, "at risk of gastric cancer" means that the subject may be asymptomatic or suffering from one or more symptoms of gastric cancer such as discomfort in the upper abdomen, a feeling of fullness, and the like, but has not been diagnosed with EBV$^+$ GC.

In preferred embodiments, the biological sample is a blood sample. Any suitable blood sample obtained from the subject may be used, including but not limited to whole blood, serum, and blood plasma. In a preferred embodiment, a blood plasma sample is used. Methods for obtaining and preparing blood samples are well known in the art; such methods include those described herein. In one embodiment, plasma is prepared by centrifuging a blood sample under conditions suitable for pelleting of the cellular component of the blood.

The methods for detecting gastric cancer of this disclosure can be used as methods for diagnosing gastric cancer, and are effective for detecting EBV$^+$ GC at an early stage and/or prior to symptom onset. As used herein, the term "symptom onset" refers to the time point where the subject presents one or more symptoms characteristic of gastric cancer. Exemplary symptoms of gastric cancer include but are not limited to stomach pain, fatigue, feeling bloated after eating, feeling full after eating small amounts of food, severe persistent heartburn, severe indigestion, unexplained persistent nausea, persistent vomiting, and unintentional weight loss. In another aspect, provided herein is a method for assessing the risk for gastric cancer in a subject, i.e., the likelihood of gastric cancer being present in the subject and/or the likelihood of the subject developing the disease at a later time.

As used herein, the terms "detect" and "detection" refer to identifying the presence, absence, or amount of the object to be detected. Standard detection methods include, for example, radioisotope immunoassay, an enzyme-linked immunosorbent assay (ELISA), SISCAPA (Stable Isotope Standards and Capture by Anti-Peptide Antibodies, mass spectrometry, immunofluorescence assays, Western blot, affinity chromatography (affinity ligand bound to a solid phase), fluorescent antibody assays, immunochromatography, and in situ detection with labeled antibodies. Although any appropriate method can be selected, taking various factors into consideration, ELISA methods are particularly sensitive.

The terms "biomolecular marker," "biomarker," or "marker" (also sometimes referred to herein as a "target analyte") are used interchangeably and refer to a molecule whose measurement provides information as to the state of a subject. In various exemplary embodiments, the biomarker is used to assess a pathological state. Measurements of the biomarker may be used alone or combined with other data obtained regarding a subject in order to determine the state of the subject. In one embodiment, the biomarker is "differentially present" in a sample taken from a subject of one phenotypic status (e.g., having EBV⁺ GC) as compared with another phenotypic status (e.g., not having EBV⁺ GC). In one embodiment, the biomarker is "differentially present" in a sample taken from a subject undergoing no therapy or one type of therapy as compared with another type of therapy. Alternatively, the biomarker may be "differentially present" even if there is no phenotypic difference, e.g. the biomarkers may allow the detection of asymptomatic risk. A biomarker may be determined to be "differentially present" in a variety of ways, for example, between different phenotypic statuses if the mean or median level (particularly the expression level of antibodies specific to the EBV proteins described herein) of the biomarker in the different groups is calculated to be statistically significant. Common tests for statistical significance include, among others, t-test, ANOVA, Kruskal-Wallis, Wilcoxon, Mann-Whitney and odds ratio.

The actual measurement of levels of a target analyte can be determined (for example, at the protein level) using any method(s) known in the art. A molecule or analyte such as a protein, polypeptide or peptide, or a group of two or more molecules or analytes such as two or more proteins, polypeptides or peptides, is "measured" in a sample when the presence or absence and/or quantity of said molecule or analyte or of said group of molecules or analytes is detected or determined in the sample, preferably substantially to the exclusion of other molecules and analytes. The terms "quantity," "amount," and "level" are synonymous and generally well-understood in the art. The terms as used herein may particularly refer to an absolute quantification of a molecule or an analyte in a sample, or to a relative quantification of a molecule or analyte in a sample, i.e., relative to another value such as relative to a reference value as taught herein, or to a range of values indicating a base-line expression of the molecule or analyte in a sample obtained from a healthy subject or, as appropriate, a sample obtained from a subject known to have EBV⁺ GC and/or a particular type or stage of EBV⁺ GC. These values or ranges can be obtained from a single patient or from a group of patients.

A target analyte is differentially present between the two samples if the amount of the target analyte in one sample is statistically significantly different from the amount of the target analyte in the other sample. As used herein, the phrase "differentially expressed" refers to differences in the quantity and/or the frequency of a target analyte present in a sample taken from patients having, for example, a particular disease as compared to a control subject.

For example, without limitation, a target analyte can be a polypeptide that is present at an elevated level or at a decreased level in samples of patients having a particular condition as compared to samples of control subjects. A target analyte can be differentially present in terms of quantity, frequency or both. In some cases, a target analyte is differentially present between the two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively (or additionally), a target analyte is differentially present between the two sets of samples if the frequency of detecting the target analyte in samples of patients suffering from a particular disease or condition is statistically significantly higher or lower than in the control samples. For example, a target analyte is differentially present between the two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

Articles of Manufacture

In another aspect, provided herein is a kit for determining and/or detecting at least one biomarker associated with EBV⁺ GC. In some cases, the kit comprises a reagent composition that comprises components for detecting in a biological sample the presence of one or more biomarkers of EBV⁺ GC. In some cases, the biomarkers of EBV⁺ GC are antibodies selected from of anti-BORF2, anti-LF2, anti-BDLF2, anti-BXLF1, anti-BRLF1, anti-BaRF1, anti-BGLF5, anti-BOLF1, anti-BRRF1, anti-BALF2, anti-BLLF3, and anti-BSLF2. In some cases, the kit may further comprise instructions for detecting EBV⁺ GC or identifying a subject has having increased risk of EBV⁺ GC according to the methods provided herein. In some cases, the kit further comprises materials for obtaining and preserving a biological sample, for example, from an individual.

In another aspect, provided herein is a kit for diagnosing a EBV⁺ GC in a subject. In some cases, the kit comprises a reagent composition that comprises components for detecting in a biological sample obtained from the subject the presence of one or more biomarkers diagnostic of EBV⁺ GC. In some cases, the biomarkers diagnostic of gastric cancer are antibodies selected from anti-BORF2, anti-LF2, anti-BDLF2, anti-BXLF1, anti-BRLF1, anti-BaRF1, anti-BGLF5, anti-BOLF1, anti-BRRF1, anti-BALF2, anti-BLLF3, and anti-BSLF2. In some cases, the kit may further comprise instructions for detecting EBV+gastric cancer or identifying a subject has having increased risk of EBV⁺ GC according to the methods provided herein. In some cases, the kit further comprises materials for obtaining, retaining, and/or preserving a biological sample, for example, obtained from an individual.

In some cases, provided herein is a kit for the detection of EBV-specific antibodies in a subject comprising: a container for retaining a tissue sample; one or more antibodies selected from anti-BORF2, anti-LF2, anti-BDLF2, anti-BXLF1, anti-BRLF1, anti-BaRF1, anti-BGLF5, anti-BOLF1, anti-BRRF1, anti-BALF2, anti-BLLF3, and anti-BSLF2; and a reagent for detection of the one or more antibodies bound to the corresponding antigen in the tissue sample. Preferably, the reagent is the reagent is capable of determining the level of an antibody against a gastric cancer-associated EBV protein by immunologic assay. In this manner, the kit is a diagnostic kit for detection of EBV⁺ GC in the subject from whom the tissue sample is obtained. In other cases, the kit is a diagnostic kit for detection or quantification of gastric cancer-associated EBV antibodies in a biological sample. In some cases, the kits of this disclosure are used in tests such as, for example, immunoenzymatic tests, preferably ELISA, immunofluorescent, immunochemiluminescent, radioimmunological, immuno-chromatographic, immunodiffusion, and immunoprecipitation tests.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

The terms "comprising", "comprises" and "comprised of" as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of" when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

It should also be understood that, unless clearly indicated to the contrary, in any methods claimed herein that include more than one step or act, the order of the steps or acts of the method is not necessarily limited to the order in which the steps or acts of the method are recited.

The present invention has been described in terms of one or more preferred embodiments, and it should be appreciated that many equivalents, alternatives, variations, and modifications, aside from those expressly stated, are possible and within the scope of the invention. The invention will be more fully understood upon consideration of the following non-limiting Examples. The invention will be described in greater detail by way of specific examples. The following examples are offered for illustrative purposes, and are not intended to limit the invention in any manner.

EXAMPLES

Example 1—Epstein Barr Virus Immunoproteomic
Profiles in EBV-Associated Gastric Cancer This example describes characterization of gastric cancer (GC)-specific antibody responses to Epstein Barr Virus (EBV) to assess the virus' contribution to gastric carcinogenesis and to develop a non-invasive method for detecting EBV$^+$ GC. As described herein, despite the ubiquity of EBV infection in adults, ten novel anti-EBV IgG antibodies elevated in EBV$^+$ GC were discovered and blindly validated in an independent sample set. Characterization of these ten antibodies demonstrates that a humoral response to EBV can distinguish EBV involvement in gastric cancer, and that anti-EBV antibodies can be used in clinical diagnosis of EBV$^+$ GC, for epidemiologic studies, and for development of treatment guidelines for EBV$^+$ GC. The GC-specific antibody response to this common infection, which may provide a noninvasive method to detect EBV$^+$ GC and elucidate its contribution to carcinogenesis.

Materials and Methods

Abbreviations

AUC—area under the curve
CI—confidence intervals
EBER—Epstein-Barr encoded small RNA
EBV—Epstein-Barr virus
EDTA—ethylenediaminetetraacetic acid
ELISA—enzyme-linked immunosorbent assay
GC—gastric cancer
HL—Hodgkin lymphoma
IgA—immunoglobulin A
IgG—immunoglobulin G
MNI—median normalized intensity
NAPPA—Nuclear Acid Programmable Protein Array
NPC—nasopharyngeal carcinoma
OD—optical density at 450 nm
OR—odds ratio
ORF—open reading frame
ROC—receiver operating characteristics
Subjects: EBV$^+$ GC and EBV$^-$ GC patients were identified from three participating centers in Latvia, Korea, and Poland. For all three series, in situ EBER hybridization testing of GC tissue was utilized to distinguish EBV tumor status. Ethylenediaminetetraacetic acid (EDTA)-plasma samples for marker discovery were obtained from 28 Latvian EBV-positive GC patients frequency-matched to 34 with EBV-negative tumors by age at diagnosis (overall mean, 63 years), sex (89% males), Lauren histological type (24% diffuse, 61% intestinal, 15% mixed/unspecified) and anatomical subsite (5% cardiac, 95% non-cardiac). Blood samples for marker validation were collected from 24 EBV-positive and 65 EBV-negative GC patients from Korea (plasma) and Poland (serum) with comparable clinical characteristics (mean age 57 years, 78% males, 56% diffuse-type, 26% intestinal-type and 54% noncardiac; Table 2). Laboratory personnel performing biospecimen assays were blinded to patient characteristics and tumor EBV status. All subjects provided informed consent and the original studies were approved by Institutional Review Boards in Latvia, Korea, Poland, and NCI (Bethesda, MD, USA).

TABLE 1

Identification of EBV-positive GC discriminatory IgG antibodies.

| Antibody | EBV protein or activity | Stage of EBV life cycle | Discovery Sample NAPPA | | |
| --- | --- | --- | --- | --- | --- |
| | | | Se (%) at MNI ≥2.0 | Sp (%) at MNI ≥2.0 | Se (%) at 95% Sp |
| anti-BALF2 | single-stranded DNA binding protein | Early lytic | 89 | 32 | 21 |
| anti-LF2 | protein that binds Rta | Unknown | 43 | 94 | 36 |
| anti-BORF2 | ribonucleotide reductase, large subunit | Early lytic | 68 | 59 | 36 |
| anti-BaRF1 | ribonucleotide reductase, small subunit | Early lytic | 21 | 100 | 21[e] |
| anti-BRLF1 | encodes lytic genes transactivator Rta | Immediate-early lytic | 32 | 97 | 32[e] |
| anti-BLLF3 | dUTPase | Early lytic | 36 | 88 | 21 |
| anti-BXLF1 | thymidine kinase | Early lytic | 32 | 91 | 32 |
| anti-BDLF2 | glycoprotein that binds BMRF2, an important factor for EBV attachment to epithelial cells | Late lytic | 29 | 97 | 29[e] |
| anti-BOLF1 | tegument protein binding phosphoprotein | Unknown | 32 | 79 | 25 |

| Antibody | Discovery Sample ELISA | | Validation Sample ELISA | | | | |
| --- | --- | --- | --- | --- | --- | --- | --- |
| | Se (%) at 95% Sp | Verified[a] | Se (%) at discovery cutoff[b] | Sp (%) at discovery cutoff[b] | p-value[c] | Validated[d] | AUC |
| anti-BALF2 | 43 | yes | 58 | 97 | <0.001 | yes | 0.85 |
| anti-LF2 | 43 | yes | 46 | 100 | <0.001 | yes | 0.81 |
| anti-BORF2 | 39 | yes | 46 | 99 | <0.001 | yes | 0.84 |
| anti-BaRF1 | 39 | yes | 46 | 97 | <0.001 | yes | 0.79 |
| anti-BRLF1 | 25 | yes | 21 | 97 | 0.006 | yes | 0.58 |
| anti-BLLF3 | 39 | yes | 21 | 95 | 0.018 | yes | 0.71 |
| anti-BXLF1 | 25 | yes | 17 | 99 | 0.006 | yes | 0.72 |
| anti-BDLF2 | 32 | yes | 13 | 94 | 0.324 | no | |
| anti-BOLF1 | 7 | no | (not tested) | | | | |

Abbreviations:

AUC = area under curve;

EBV = Epstein-Barr virus;

ELISA = enzyme-linked immunosorbent assay;

GC = gastric cancer;

IgG = immunoglobulin G;

Se = sensitivity;

Sp = specificity;

MNI = median normalized intensity;

NAPPA = Nucleic Acid-Programmable Protein Array

[a]Defined as sensitivity ≥20%

[b]Using OD450 cutoff for 95% specificity in discovery samples

[c]p-value calculated by chi-square test

[d]Defined as p-value < 0.05, chi-square test

[e]Based on minimum MNI cutoff 2.0 instead of 95% specificity

TABLE 2

| | | Discovery sample set | | Validation sample set | |
|---|---|---|---|---|---|
Selected demographic and histologic characteristics of EBV-positive and EBV-negative GC in discovery and validation sample sets.

| | | EBV-positive GC (28) | EBV-negative GC (34) | EBV-positive GC (24) | EBV-negative GC (65) |
|---|---|---|---|---|---|
| | Age, median (range) | 64 (35 to 86) | 63.5 (47 to 78) | 56 (25 to 73) | 59 (28 to 77) |
| | Male sex, n (%) | 24 (86) | 31 (91) | 19 (79) | 43 (66) |
| Lauren | Intestinal, n (%) | 15 (54) | 23 (68) | 7 (29) | 13 (20) |
| classification | Diffuse, n (%) | 8 (29) | 5 (15) | 15 (63) | 31 (48) |
| | Mixed, n (%) | 4 (14) | 5 (15) | 0 (0) | 0 (0) |
| | Undifferentiated, n (%) | 1 (4) | 1 (3) | 2 (8) | 13 (20) |

Selection of EBV genes and EBV NAPPA array fabrication: The NAPPA was fabricated with the same procedure as previously reported. 89 EBV open reading frames (ORFs) from 85 total unique proteins for Type-1 EBV (B95-8) were included as part of a multi-microbe array, along with 1631 ORFs from *H. pylori* and several other microbes. By stage of expression in the EBV replication cycle, there were 2 ORFs from immediate-early lytic phase, 31 from early lytic phase, 32 from late lytic phase, 12 from latent phase and 12 of unknown phase (Table 3). All clones were obtained from DNASU (available at dnasu.org/DNASU/Home.do on the World Wide Web; Tempe, AZ, USA) in a NAPPA compatible pANT7-cGST expression vector.

TABLE 3

Replication cycle stage for expression of 89 EBV open reading frames.

| Protein | Clone ID in DNASU | DNA SEQ ID NO | PROTEIN SEQ ID NO | VECTOR SEQ ID NO | Stage of EBV life cycle |
|---|---|---|---|---|---|
| BHRF1 | HhCD00595127 | 1 | 2 | 3 | Early lytic |
| BaRF1 | HhCD00595137 | 4 | 5 | 3 | Early lytic |
| BMRF2 | HhCD00595138 | | | | Early lytic |
| BSLF1 | HhCD00595139 | 6 | 7 | 3 | Early lytic |
| BLLF3 | HhCD00595141 | 8 | 9 | 3 | Early lytic |
| BLLF2 | HhCD00595145 | 10 | 11 | 3 | Early lytic |
| BZLF2 | HhCD00595148 | 12 | 13 | 3 | Early lytic |
| BRRF1 | HhCD00595149 | 14 | 15 | 3 | Early lytic |
| BBLF4 | HhCD00595153 | 16 | 17 | 3 | Early lytic |
| BBLF2/BBLF3 | HhCD00595156 | 18 | 19 | 3 | Early lytic |
| BGLF5 | HhCD00595158 | 20 | 21 | 3 | Early lytic |
| BGLF4 | HhCD00595159 | 22 | 23 | 3 | Early lytic |
| BDLF4 | HhCD00595165 | 24 | 25 | 3 | Early lytic |
| BcRF1 | HhCD00595171 | | | | Early lytic |
| BXLF1 | HhCD00595174 | 26 | 27 | 3 | Early lytic |
| BVLF1 | HhCD00595177 | 28 | 29 | 3 | Early lytic |
| BALF2 | HhCD00595185 | 30 | 31 | 3 | Early lytic |
| BALF1 | HhCD00595186 | 32 | 33 | 3 | Early lytic |
| BARF1 | HhCD00595187 | 34 | 35 | 3 | Early lytic |
| BSLF2/BMLF1 | HhCD00595190 | 36 | 37 | 3 | Early lytic |
| BALF5 | HhCD00595193 | 38 | 39 | 3 | Early lytic |
| BHLF1 | HhCD00595200 | 40 | 41 | 3 | Early lytic |
| BORF2 | HhCD00595201 | 42 | 43 | 3 | Early lytic |
| BMRF1 | HhCD00595202 | 44 | 45 | 3 | Early lytic |
| BFLF2 | HhCD00595128 | 46 | 47 | 3 | Early lytic |
| BFLF1 | HhCD00595129 | | | | Early lytic |
| BFRF1 | HhCD00595131 | 48 | 49 | 3 | Early lytic |
| BFRF2 | HhCD00595132 | 50 | 51 | 3 | Early lytic |
| BVRF1 | HhCD00595176 | 52 | 53 | 3 | Early lytic |
| BNLF2b | HhCD00595194 | 54 | 55 | 3 | Early lytic |
| BNLF2a | HhCD00595206 | 56 | 57 | 3 | Early lytic |
| BZLF1 | HhCD00595191 | 58 | 59 | 3 | Immediate-early lytic |
| BRLF1 | HhCD00595192 | 60 | 61 | 3 | Immediate-early lytic |
| BNRF1 | HhCD00595124 | | | | Late lytic |
| BCRF1 | HhCD00595125 | 62 | 63 | 3 | Late lytic |
| BSRF1 | HhCD00595140 | | | | Late lytic |
| BLRF1 | HhCD00595142 | 64 | 65 | 3 | Late lytic |
| BLRF2 | HhCD00595143 | 66 | 67 | 3 | Late lytic |
| BLLF1 | HhCD00595144 | | | | Late lytic |
| BBRF3 | HhCD00595157 | 68 | 69 | 3 | Late lytic |
| BGLF2 | HhCD00595163 | 70 | 71 | 3 | Late lytic |
| BGLF1 | HhCD00595164 | 72 | 73 | 3 | Late lytic |
| BDLF3 | HhCD00595167 | 74 | 75 | 3 | Late lytic |
| BDLF2 | HhCD00595168 | 76 | 77 | 3 | Late lytic |
| BTRF1 | HhCD00595172 | 78 | 79 | 3 | Late lytic |

TABLE 3-continued

Replication cycle stage for expression of 89 EBV open reading frames.

| Protein | Clone ID in DNASU | DNA SEQ ID NO | PROTEIN SEQ ID NO | VECTOR SEQ ID NO | Stage of EBV life cycle |
|---|---|---|---|---|---|
| BXLF2 | HhCD00595173 | 80 | 81 | 3 | Late lytic |
| BXRF1 | HhCD00595175 | | | | Late lytic |
| BILF2 | HhCD00595180 | | | | Late lytic |
| BALF4 | HhCD00595184 | 82 | 83 | 3 | Late lytic |
| BKRF2 | HhCD00595195 | 84 | 85 | 3 | Late lytic |
| BXLF2 | HhCD00595203 | 86 | 87 | 3 | Late lytic |
| BILF2 | HhCD00595204 | 88 | 89 | 3 | Late lytic |
| BFRF3 | HhCD00595133 | 90 | 91 | 3 | Late lytic |
| BPLF1 | HhCD00595134 | 92 | 93 | 3 | Late lytic |
| BRRF2 | HhCD00595150 | 94 | 95 | 3 | Late lytic |
| BKRF4 | HhCD00595152 | 96 | 97 | 3 | Late lytic |
| BBRF1 | HhCD00595154 | 98 | 99 | 3 | Late lytic |
| BBRF2 | HhCD00595155 | 100 | 101 | 3 | Late lytic |
| BDLF1 | HhCD00595169 | 102 | 103 | 3 | Late lytic |
| BcLF1 | HhCD00595170 | 104 | 105 | 3 | Late lytic |
| BVRF2 | HhCD00595178 | 106 | 107 | 3 | Late lytic |
| BdRF1 | HhCD00595179 | 108 | 109 | 3 | Late lytic |
| BPLF1 | HhCD00595189 | 110 | 111 | 3 | Late lytic |
| BBLF1 | HhCD00595197 | 112 | 113 | 3 | Late lytic |
| BORF1 | HhCD00595198 | 114 | 115 | 3 | Late lytic |
| LMP-2A | HhCD00595122 | | | | Latent |
| LMP-2B | HhCD00595123 | 116 | 117 | 3 | Latent |
| EBNA-LP | HhCD00595126 | 118 | 119 | 3 | Latent |
| EBNA-3B | HhCD00595146 | | | | Latent |
| EBNA-3C | HhCD00595147 | 120 | 121 | 3 | Latent |
| EBNA-1 | HhCD00595151 | | | | Latent |
| LMP-1 | HhCD00595188 | 122 | 123 | 3 | Latent |
| BARF0 | HhCD00595205 | 124 | 125 | 3 | Latent |
| EBNA2 | HhCD00595207 | 126 | 127 | 3 | Latent |
| EBNA3A | HhCD00595208 | 128 | 129 | 3 | Latent |
| RPMS1 | HhCD00595209 | 130 | 131 | 3 | Latent |
| A73 | HhCD00595210 | 132 | 133 | 3 | Latent |
| BFRF1A | HhCD00595130 | 134 | 135 | 3 | Unknown |
| BGLF3.5 | HhCD00595160 | | | | Unknown |
| BGLF3 | HhCD00595161 | | | | Unknown |
| BDLF3.5 | HhCD00595166 | 136 | 137 | 3 | Unknown |
| LF2 | HhCD00595181 | 138 | 139 | 3 | Unknown |
| LF1 | HhCD00595182 | 140 | 141 | 3 | Unknown |
| BILF1 | HhCD00595183 | 142 | 143 | 3 | Unknown |
| BKRF3 | HhCD00595196 | 144 | 145 | 3 | Unknown |
| BWRF1.1 | HhCD00595199 | 146 | 147 | 3 | Unknown |
| BPLF1 | HhCD00595135 | | | | Unknown |
| BOLF1 | HhCD00595136 | 148 | 149 | 3 | Unknown |
| BGRF1/BDRF1 | HhCD00595162 | 150 | 151 | 3 | Unknown |

Figure 7A:
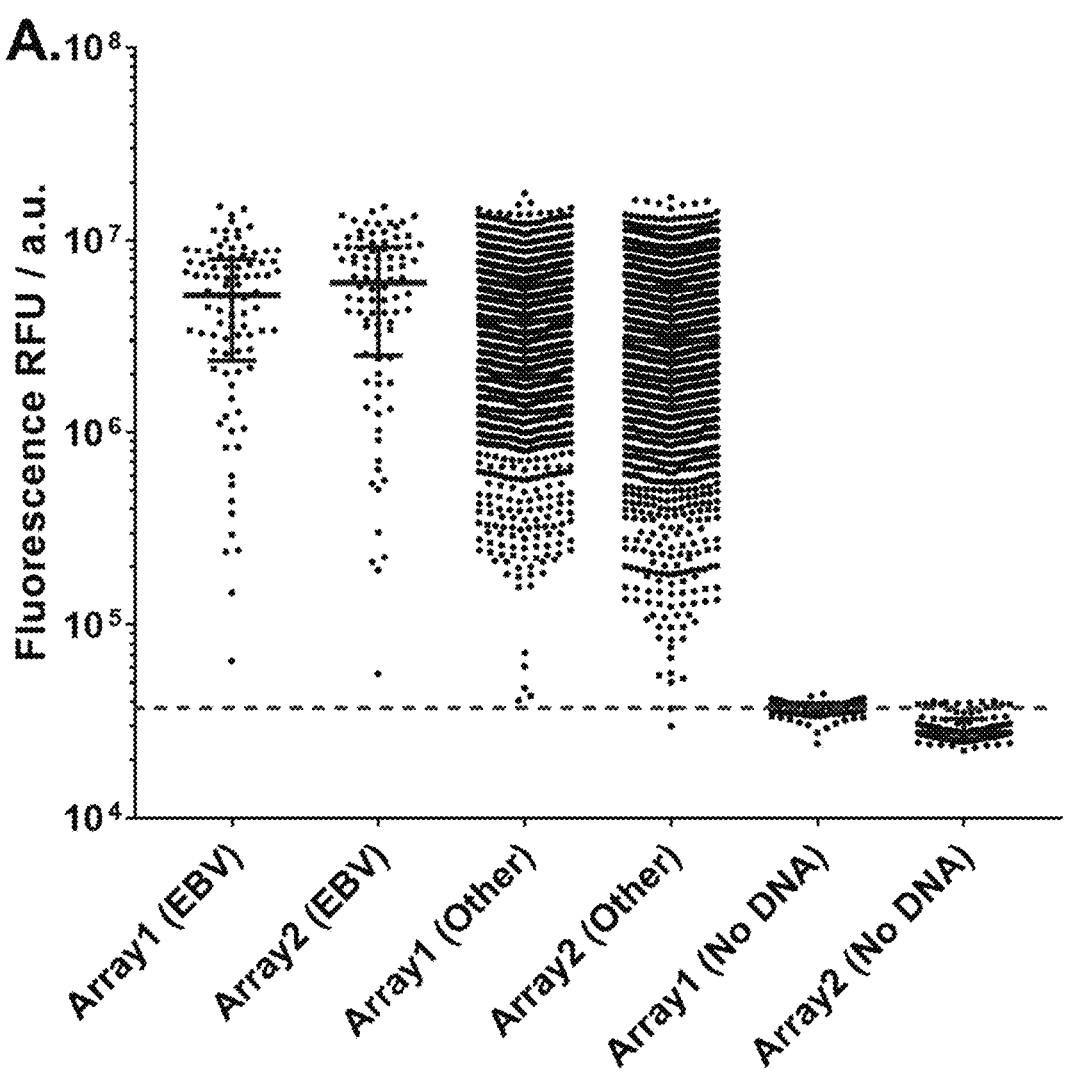
FIGS. 7A-7B. (A) Expression of EBV and other microbial proteins on multi-microbial NAPPA array compared to no DNA negative control spots. The dotted line indicates cutoff based on no DNA sample spots from array 1 (mean+3 standard deviations). (B) Inter-array reproducibility (R=0.95) of median normalized intensities (MNI) for a pooled plasma sample. MNI=median normalized intensities; RFU=relative fluorescence units.
Figure 7B:
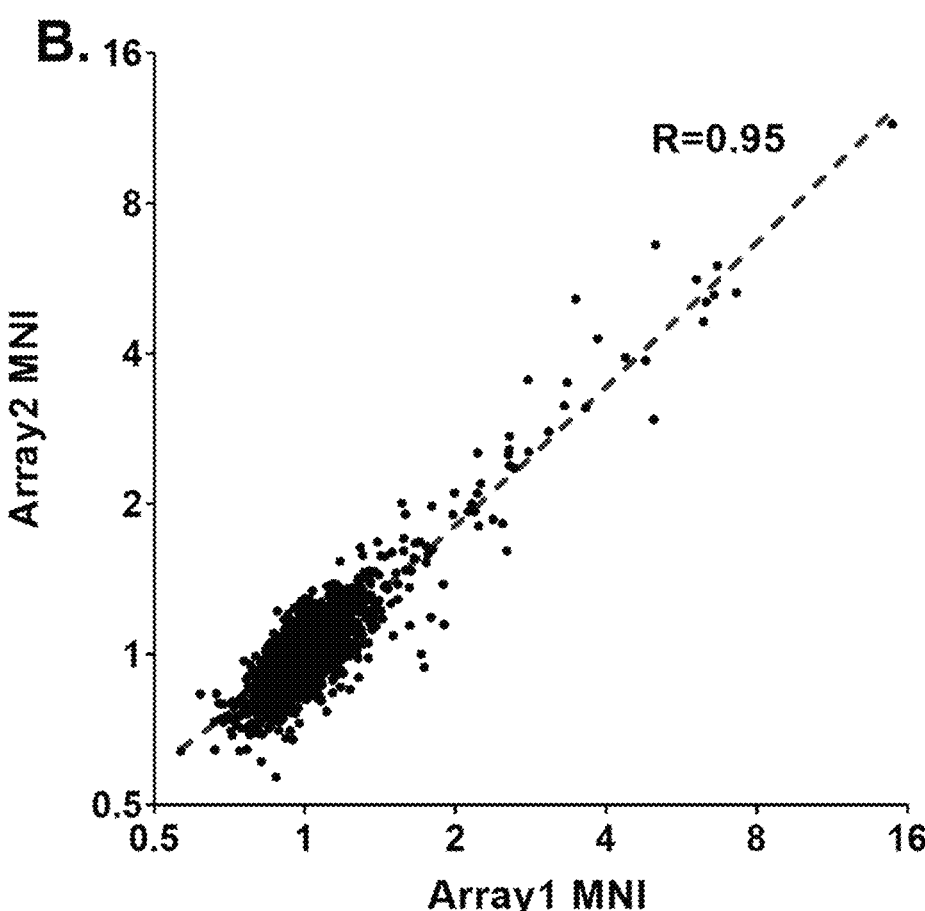

EBV+GC associated antibody discovery on EBV NAPPA array: Proteins were expressed by in vitro transcription and translation. Expression levels of all microbial proteins exceeded no DNA wells (mean+3 standard deviations), as confirmed by a monoclonal mouse anti-GST antibody (FIG. 7A). Arrays were probed with 1:100 diluted plasma from the discovery sample set, followed by incubation with 1:200 diluted Alex647 labeled Goat anti-human IgG (H+L) and 1:200 diluted Cy3 labeled Goat anti-human IgA (Jackson ImmunoResearch Labs, PA, USA), to evaluate specific anti-EBV IgG and IgA antibodies. IgG and IgA antibody binding signals were detected with a bi-color Tecan PowerScanner (Tecan Group Ltd., Mannedorf, Switzerland) at 635 nm and 532 nm as two separate images, which were further analyzed with ArrayPro Analyzer Software (Media Cybernetics, Inc., MD, USA) to generate raw fluorescence intensity data. A pooled plasma that combined all samples was probed along with individual samples on each run day to determine array reproducibility. The inter-slide correlation coefficient r for pooled samples was 0.95 (FIG. 7B).

Figure 2:
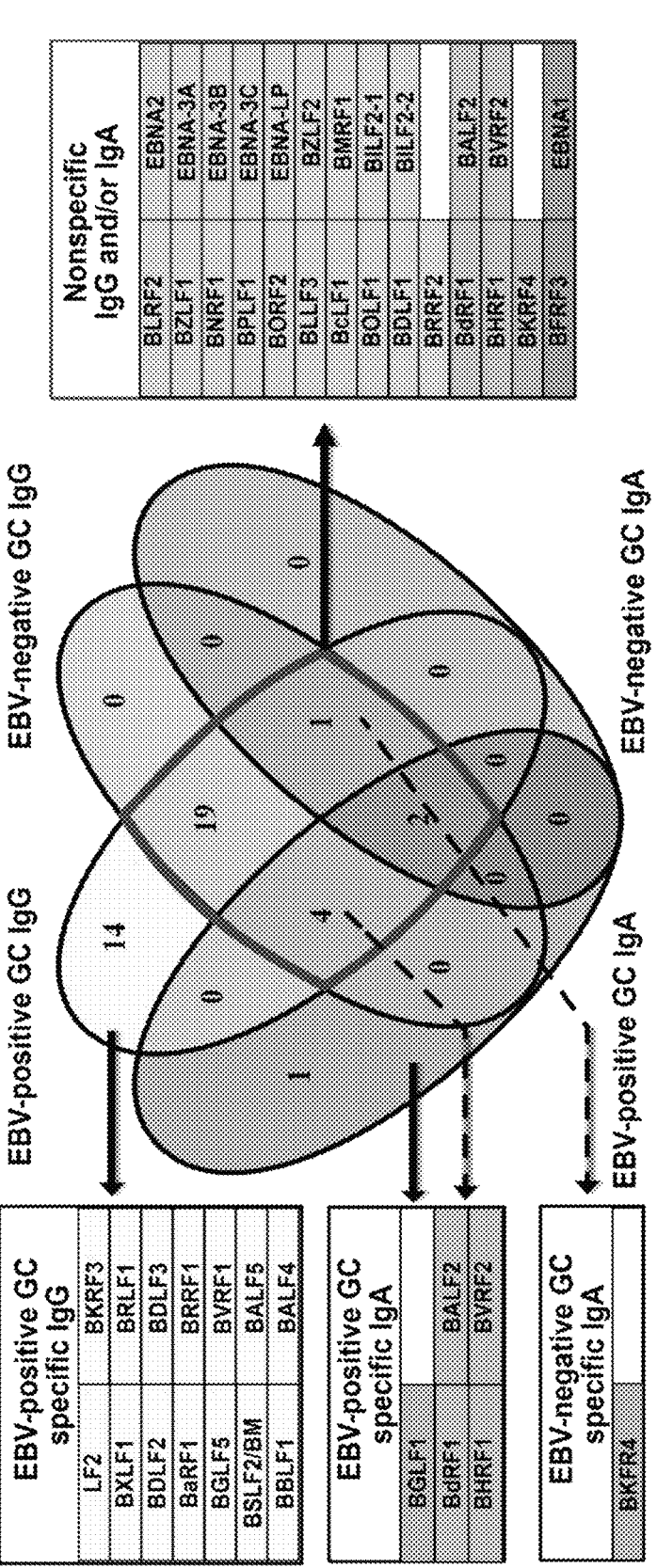
FIG. 2 demonstrates anti-EBV IgG and IgA antibodies with >10% seropositivity by NAPPA in either EBV-positive or EBV-negative GC ("EBV$^-$ GC"). Antibodies specific for either EBV-positive (n=19) or EBV-negative GC (n=1) antibodies are listed on the left and nonspecific antibodies (n=26) are listed on the right. Table colors correspond to groups in the Venn diagram. Abbreviations: EBV=Epstein-Barr virus; GC=gastric cancer; IgA=immunoglobulin A; IgG=immunoglobulin G; NAPPA=Nucleic Acid-Programmable Protein Array.

Antibody responses on NAPPA were analyzed as Median Normalized Intensity (MNI) via dividing by the median signal intensity of all proteins within each array. Seropositive responses were defined as MNI≥2.0. Antibodies that showed more than 10% seropositivity in either EBV-positive or EBV-negative GC were assessed for discrimination between these groups (FIG. 2). Using an MNI cutoff at 95% specificity for EBV-negative GC with minimum cutoff 2.0, anti-EBV antibodies with more than 20% sensitivity for EBV-positive GC on NAPPA were selected as candidates for further evaluation.

RAPID ELISA verification and validation: Candidate biomarkers were verified in the discovery sample set by Rapid Antigenic Protein In Situ Display (RAPID) ELISA following a previously reported protocol. In brief, 96-well ELISA plates (Corning, NY, USA) were first coated with goat anti-GST antibody (GE Healthcare Bio-Sciences, PA, USA) and incubated with candidate GST tag fusion antigen expressed with IVTT. After washing, 1:500 diluted plasma/serum samples were added, followed by incubation with HRP-conjugated goat anti-human IgG (Jackson ImmunoResearch Labs, PA, USA). Plates were developed using TMB substrate (Thermo Fisher Scientific, MA, USA), and optical density at 450 nm (OD450) was measured on a PerkinElmer Envision plate reader (Waltham, MA, USA). GST tag alone was set as a blank control, and ELISA readings were normalized by subtracting the OD450 of GST alone from OD450 of the target protein. Using an OD cutoff at 95% specificity for EBV-negative GC with minimum cutoff 0.1, markers verified as more than 20% sensitive were further evaluated in the validation sample set. Sensitivity and specificity in the validation sample ELISAs were calculated using the same cutoffs that were generated with the discovery sample set. P-values were calculated based on chi-square tests and antibodies with p<0.05 were designated to be validated.

Statistical analyses: The difference in quantitative antibody response on NAPPA and differences between numbers of seropositive antibodies in EBV-positive and EBV-negative GC were assessed by the Mann-Whitney U (MW) test. Odds ratios (OR) were analyzed for statistical significance by chi-square tests to select and validate markers in discovery and validation sample sets, respectively. The discriminatory power of selected markers was further evaluated in the validation sample set by area under the receiver operating characteristics (ROC) curve (AUC). Lasso logistic regression model was used to construct antibody panel models using the validation data set, and classification performance was evaluated by AUC 95% confidence intervals (95% Cl). Pearson correlation coefficients were used to assess pair-wise correlations between antibody responses in the validation sample set. All statistical tests were two-sided and p-values<0.05 were considered statistically significant. The significance level was corrected for the number of examined markers with the Bonferroni procedure. Statistical analyses were conducted with Stata version 15 (Stata Corp, College Station, TX, USA), GraphPad Prism 8.0.2 (GraphPad Software, Inc., CA, USA) and R version 3.6 (R Core Team, R Foundation for Statistical Computing, Vienna, Austria).

Results

Antibody selection by NAPPA: Immunoprofiling of discovery samples by NAPPA identified a total of 41 antibodies seropositive in at least 10% of either $EBV^+$ GC or $EBV^-$ GC patients, including 7 with both IgG and IgA, 33 with IgG only, and 1 with IgA only antibody (FIG. 2). Twenty-six of the 40 IgG antibodies and 2 of the 8 IgA antibodies were common to both $EBV^+$ GC and $EBV^-$ GC. Anti-EBNA1 and anti-BFRF3 were the most prevalent IgG antibodies, present in more than 90% of both EBV-positive GC and EBV-negative GC. Fourteen IgG and 5 IgA antibodies were only present in EBV-positive GC, whereas one IgA antibody but no IgG antibody was found only in $EBV^-$ GC.

Figure 3:
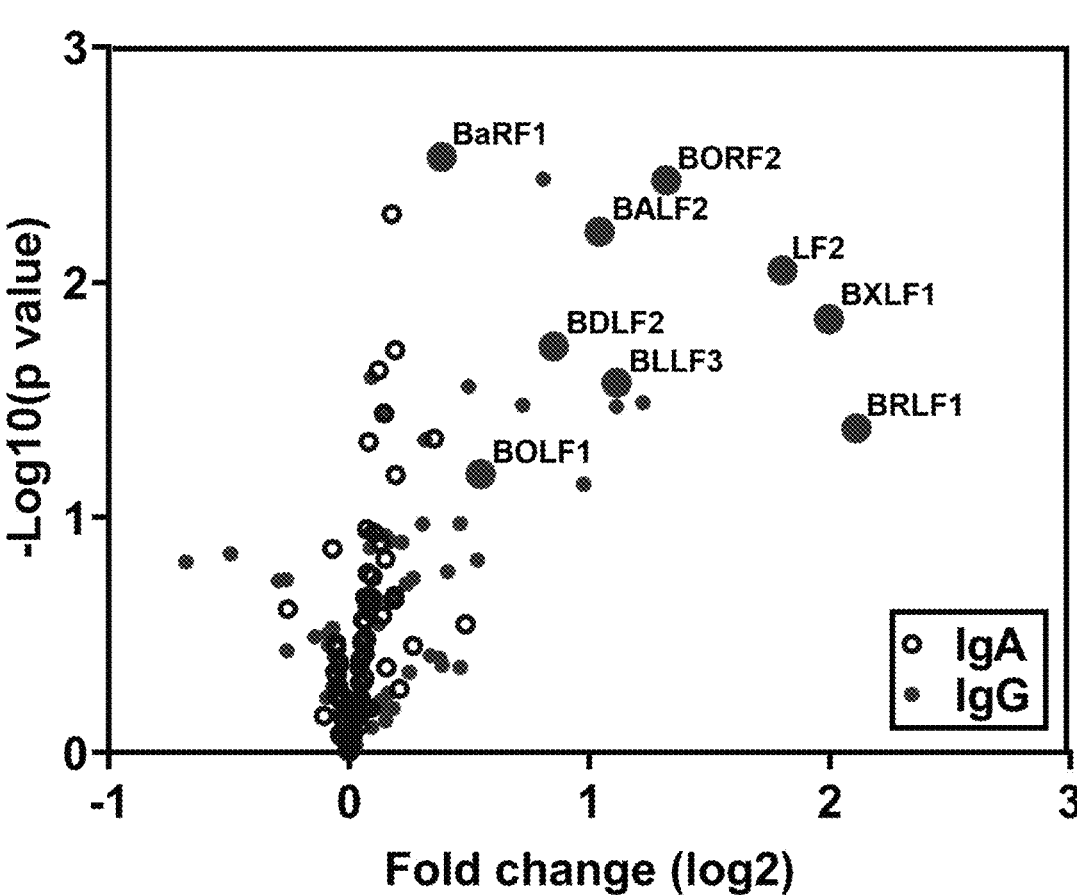
FIG. 3 demonstrates magnitude and statistical significance of differential antibody responses by NAPPA between EBV$^+$ GC and EBV$^-$ GC. Labels indicate viral antibodies that have >20% sensitivity at 95% specificity for EBV$^+$ GC.

Median signal intensity for individual antibodies ranged up to 4.3-fold higher in EBV-positive as compared to $EBV^-$ GC (FIG. 3). Notably, there was no difference in signal intensity between EBV-positive and $EBV^-$ GC for anti-EBNA1 (median MNIs of 4.2 vs. 4.7, respectively, p=0.348) or anti-BFRF3 (25.0 vs. 27.1, p=0.850) by Mann-Whitney tests.

Figure 4:
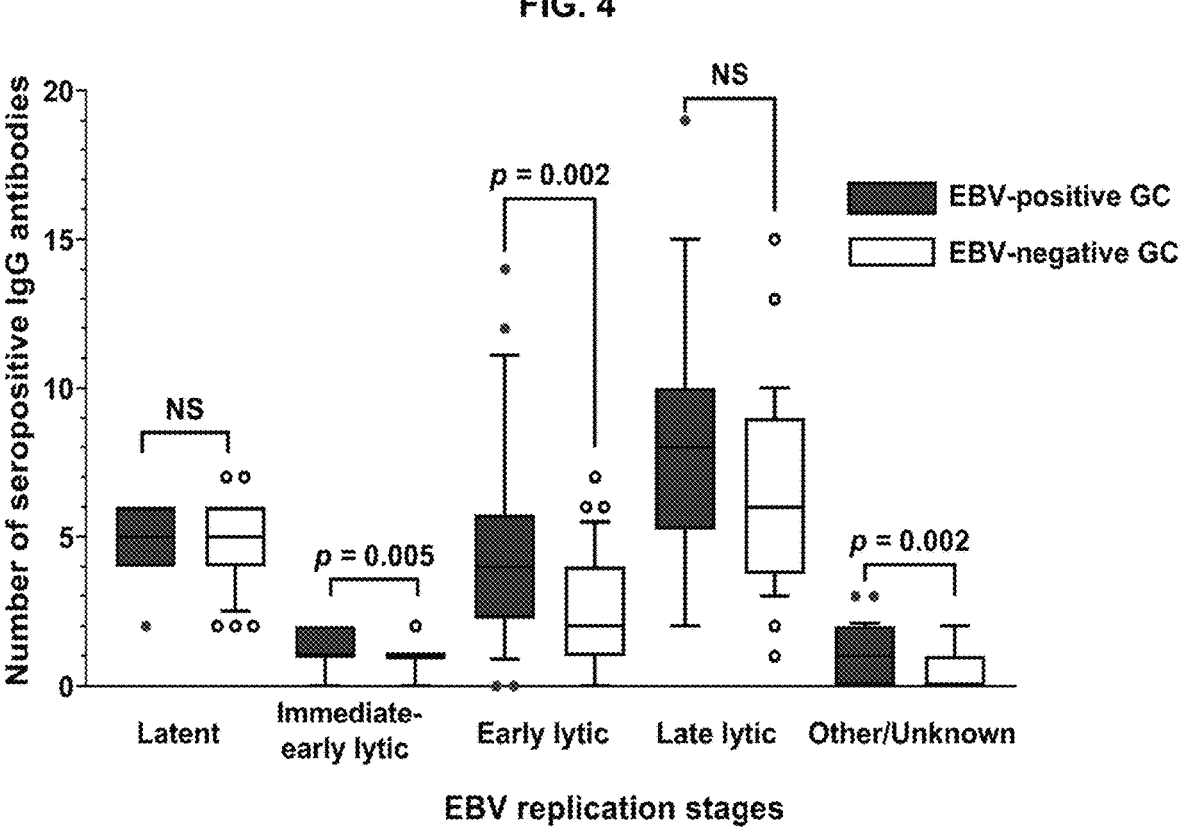
FIG. 4 demonstrates numbers of positive IgG NAPPA antibody responses of EBV-positive and EBV$^-$ GC to EBV proteins expressed at different stages of the viral replication cycle, classified as latent (n=12), immediate-early lytic (n=2), early lytic (n=31), late lytic (n=32), and other/unknown (n=11). p-values represent differences between patient groups with p>0.05 not statistically significant. NS=not statistically significant.

Out of the 85 EBV proteins displayed on NAPPA, the EBV-positive GC samples had a median of 20 seropositive IgG antibodies while the $EBV^-$ GC samples had a median of 14 (MW=284.5, p=0.006). $EBV^+$ GC had significantly more IgG antibodies than $EBV^-$ GC to immediate-early lytic, early lytic, and unknown phase proteins (FIG. 4). Both sample groups had medians of 1.0 seropositive IgA antibody (p=0.737).

Nine IgG antibodies were elevated in EBV-positive GC with greater than 20% sensitivity at 95% specificity: anti-BALF2, anti-LF2, anti-BORF2, anti-BaRF1, anti-BRLF1, anti-BLLF3, anti-BXLF1, anti-BDLF2 and anti-BOLF1 (Table 1). None of the IgA antibodies were 20% sensitive and 95% specific for EBV-positive GC, and no IgG or IgA antibodies met these criteria for $EBV^-$ GC.

Verification and validation by RAPID ELISA: Using the same discovery sample set (Table 2), 8 of the 9 differential IgG antibodies by NAPPA were verified to have greater than 20% sensitivity at 95% specificity by RAPID ELISA, except for anti-BOLF1 (Table 1). Seven of these 8 antibodies were blindly validated to differ at p<0.05 between $EBV^+$ GC and $EBV^-$ GC in an independent validation sample set, except anti-BDLF2. These seven markers were either early lytic or immediate-early lytic phase in EBV life cycle, except anti-LF2 of which the cycle is unknown. Six of the 7 validated markers still showed significant differences after Bonferroni correction, satisfying our alternative significance level of 0.05/8=0.00625, except for anti-BLLF3 (p=0.018).

Figure 5A:
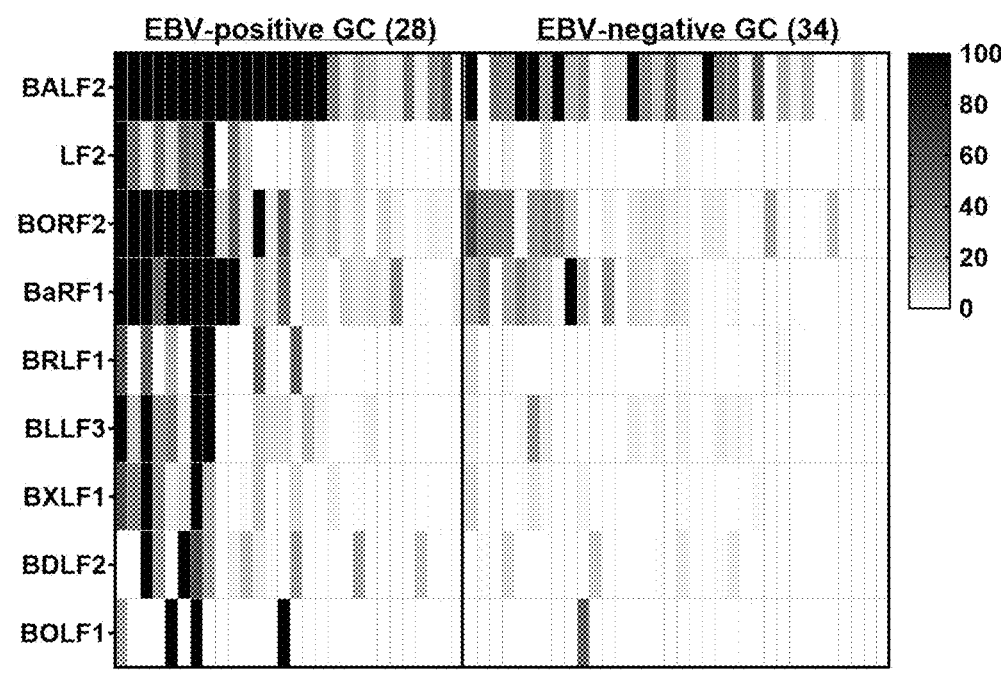
FIGS. 5A-5B. (A) Heatmaps of IgG antibody responses by ELISA in discovery (top) and validation (bottom) sample sets of EBV$^+$ GC and EBV$^-$ GC. Optical density measurements were normalized according to the highest value for each antibody across all samples. Each vertical bar represents a different serum. (B) Odds ratio (OR) and 95% confidence intervals (CI) for discovery (top) and validation (bottom) samples based on cutoffs at 95% specificity for EBV-negative GC in the discovery samples. ELISA=enzyme-linked immunosorbent assay.
Figure 5A:
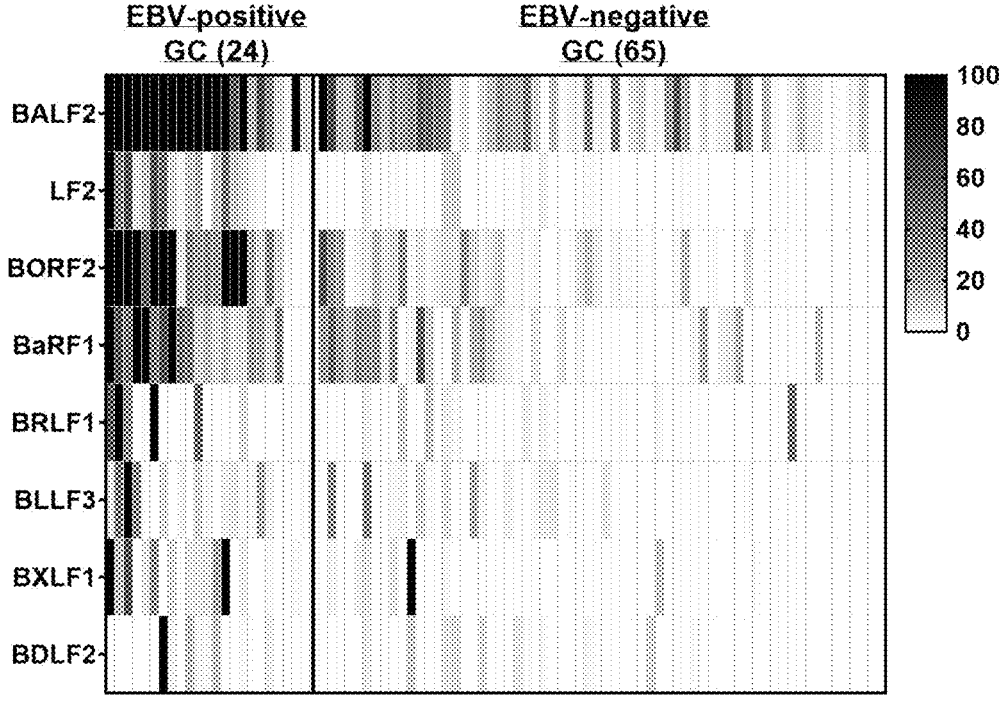
Figure 5B:
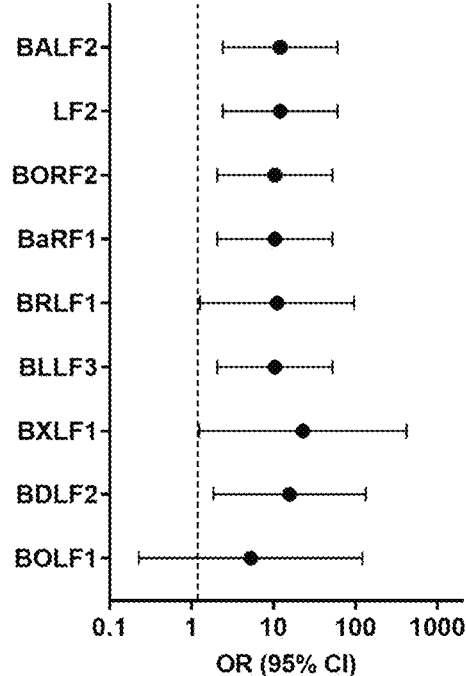
Figure 5B:
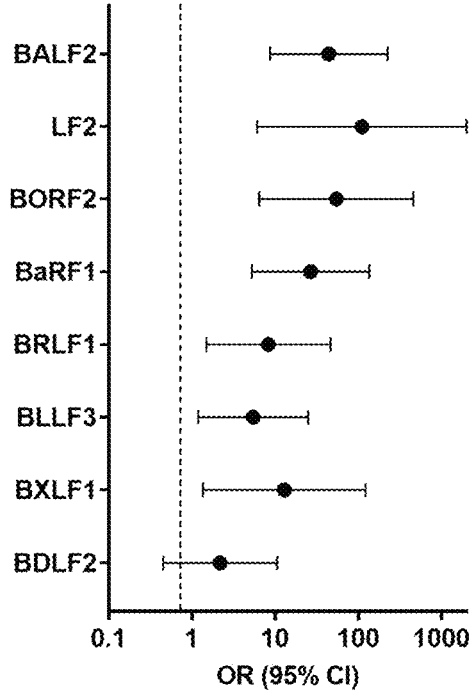

ELISA reactivity was markedly stronger for $EBV^+$ GC than $EBV^-$ GC (FIG. 5A). Using the cutoffs for 95% specificity of $EBV^-$ GC in the discovery samples, the 7 validated markers all had ORs exceeding 5.0 for distinguishing EBV status in the validation samples, ranging up to 111 for anti-LF2 (FIG. 5B).

Figure 6:
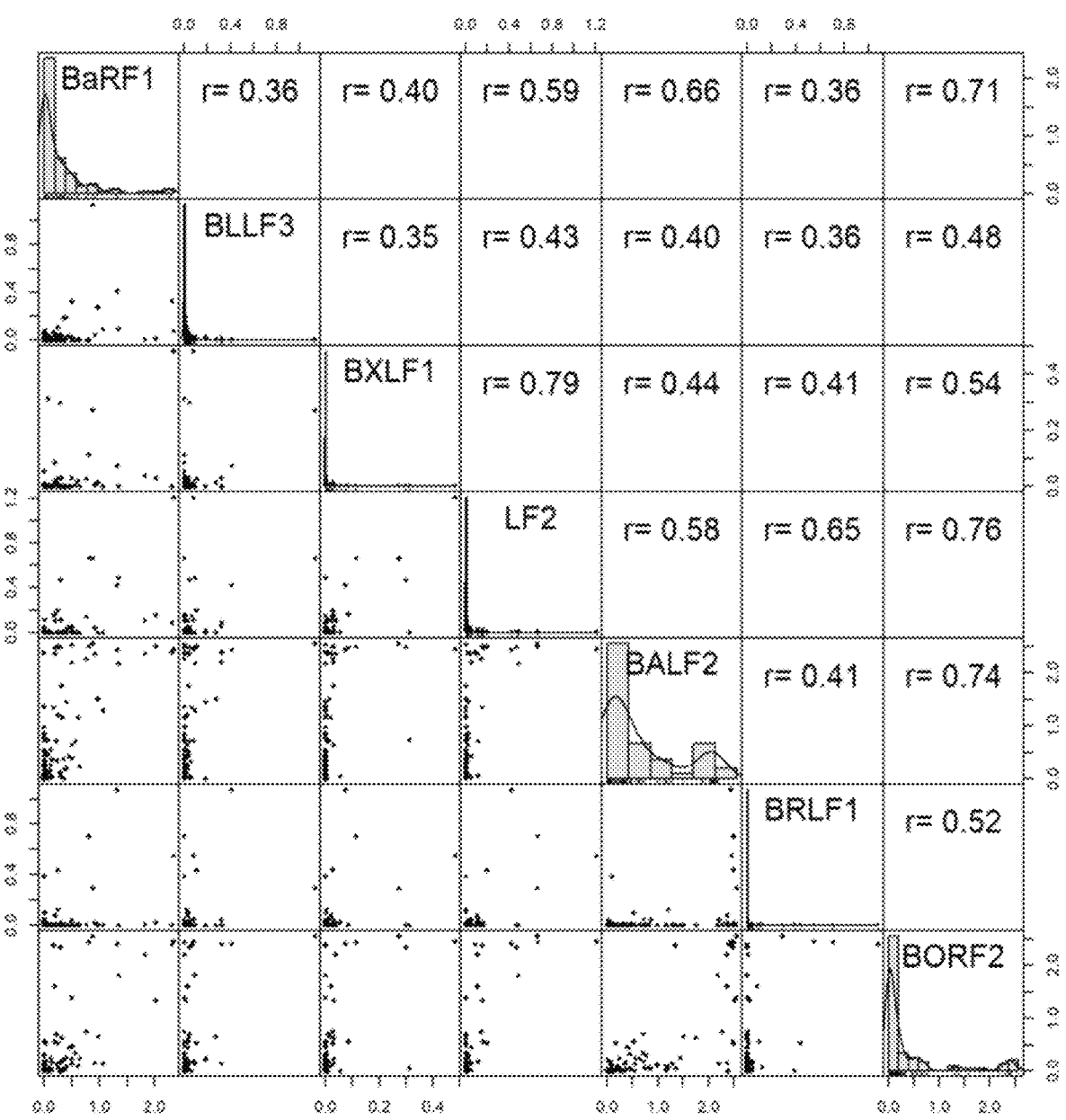
FIG. 6 presents two-way scatterplots and pair-wise Pearson correlations among IgG antibody responses by ELISA for all validation samples. Four coefficients of correlation were high (>0.7), 6 were moderate (0.5-0.7) and 11 were low (<0.5); all correlations were statistically significant with p-values<0.01. Frequency histograms and density plots on diagonal represent individual antibody responses. Abbreviation: OD450=optical density 450.

All pair-wise correlations among the 9 anti-EBV antibodies were statistically significant with p-values <0.01 in the validation samples (FIG. 6). For $EBV^+$ GC and $EBV^-$ GC groups combined, correlation coefficients ranged from 0.35 (anti-BLLF3 vs. anti-BXLF1) to 0.79 (anti-BXLF1 vs. anti-LF2).

Anti-BALF2 had the greatest discriminatory power among individual antibodies with an AUC of 0.85 (95% Cl, 0.75-0.96). AUCs of the other validated antibodies ranged from 0.58 to 0.84 (Table 1). LASSO logistic regression identified a maximal AUC of 0.88 (95% CI, 0.78-0.98) for the 3-marker combination of anti-BALF2, anti-BORF2, and anti-LF2.

Discussion

In summary, this example describes the first comprehensive proteome-level study to identify anti-EBV antibodies for $EBV^+$ GC, identifying 7 highly discriminatory IgG biomarkers. Our findings indicate that the EBV-positive GC-specific humoral response is primarily restricted to the lytic cycle immediate-early and early antigens. The functions of the seven proteins targeted by the identified antibodies include roles in DNA replication, virus maturation, gene transcription, and protein-protein interaction. The discriminatory biomarkers were identified by comparing individuals having gastric cancer: comparing $EBV^+$ GC to $EBV^-$ GC. As described herein, these biomarkers are useful to distinguish between these types of gastric cancer, but also be used to distinguish $EBV^+$ GC and healthy (non-GC) persons.

Of note, antibodies to BRLF1, BALF2 and BXLF1 were also increased in patients with the epithelial cell tumor NPC, but not in those with lymphoma. BRLF1, also known as Rta, encodes one of the two immediate-early EBV lytic proteins that control the initiation of viral lytic gene expression and viral reactivation from latency. BRLF1 expression is specific for viral reactivation in epithelial cells, while the other immediate-early EBV lytic protein is needed in B cells. BALF2 is the major single-stranded DNA binding protein and is required for viral DNA replication. BXLF1 encodes the viral thymidine kinase that catalyzes the phosphorylation of deoxythymidine to deoxythymidine monophosphate, which is important for viral DNA replication. BaRF1 and BORF2 are the ribonucleoside-diphosphate reductase small subunit and large subunit, respectively, and provide precursors necessary for viral DNA synthesis. Their presence enhances virus replication and assists in reactivation of virus from latency in NPC and BL. BORF2 can induce p53 expression to regulate G1/S transition arrest in the cell cycle. This protein also binds with the cellular apolipoprotein B messenger RNA editing enzyme catalytic polypeptide-like protein APOBEC3B, inhibiting its DNA cytosine deaminase activity to preserve viral genome integrity. LF2 is a type I interferon antagonist that prevents establishment of an antiviral response by blocking cellular IRF7-mediated innate immunity. It also inhibits viral replication by modulating BRLF1 (Rta) activity. BLLF3 is the viral deoxyuridine 5'-triphosphate nucleotidohydrolase which modulates innate and adaptive immune responses by engaging toll-like receptor 2 to activate NF-κB and proinflammatory cytokines.

EBV has a life cycle alternating between latency and lytic replication. Latency is manifested by persistence in host cells maintained with cell division, while lytic replication results in cell death and virus dissemination. With respect to timing of expression in the EBV replication cycle, 1 of our EBV-positive GC-specific target antigens is present in immediate-early lytic phase (BRLF1) and 5 in early lytic phase (BALF2, BXLF1, BLLF3, BaRF1, BORF2). The stage for LF2 expression is unknown. While EBV+ GC cells are known to express latency proteins with transforming activities, there is increasing evidence suggesting that lytic replication proteins also have an important role in tumor development and progression. Our discovery that antibodies to immediate-early and early lytic proteins are elevated in EBV+ GC vs. EBV− GC is consistent with these concepts. An abortive lytic cycle, where full virus replication does not occur, may result in limited expression of lytic genes that promote tumorigenesis without complete lytic replication that would lead to cell death; co-expression of these genes along with EBV latency proteins may together be important for induction of EBV-positive GC and may provide new targets for treatment of the disease.

EBV is also implicated in the etiologies of NPC, Burkitt lymphoma, HL, and non-Hodgkin lymphoma. Anti-EBV antibodies in these epithelial and non-epithelial tumors have been assessed by multiplex platforms similar to the current study. In contrast to our findings for EBV-positive GC, the serologic response characterizing other EBV-associated tumors often includes proteins expressed in late lytic and latent phases of viral replication. Furthermore, unlike NPC's where IgA antibodies are frequently expressed, EBV+ GCs largely were IgG responses.

Given the limited diagnostic options for EBV+ GC, apart from humoral profiles, other blood markers of the virus itself and/or host response warrant consideration as biomarkers. Conceivably, multiple markers in combination could be pathognomonic for EBV+ GC.

The serology study described herein has several strengths. Covering 85 full length EBV proteins, it is believed to be the most comprehensive evaluation of EBV+ GC immunoproteomics. This approach provided for evaluation of more viral proteins and the interplay among them, extending previous targeted studies. Second, the findings were consistent across two different assay platforms, increasing the technical validity of the markers. Third, results were replicated in two independent populations of different racial backgrounds. However, this study used post-diagnosis samples that may be reflective of the disease status, limiting interpretation regarding etiologic significance. To investigate causal pathways, prospective studies are needed. In addition, our sample size would not have had enough statistical power for detecting associations with small effects, warranting a larger-scale study in the future.

Despite the near universal infection of adults with EBV, seven novel IgG antibodies were identified to discriminate EBV+ GC from EBV− GC. Unlike nasopharyngeal carcinoma, EBV-specific IgA response does not seem to play an important role in GC. A noninvasive blood test for EBV+ GC based on the IgG antibodies could have potential translation to noninvasive detection, preventive screening, precision therapy and etiologic understanding. Furthermore, the proteins bound by these antibodies, primarily expressed during the early lytic stage of virus replication, may be important for development, maintenance, or progression of EBV-positive malignancies and represent potential new targets for precision therapeutics.

We claim:

1. A method for identifying a subject having increased risk of developing Epstein-Barr Virus-positive gastric cancer (EBV$^+$ GC), the method comprising:
   (a) reacting a biological sample obtained from the subject with a reagent composition that comprises components for detecting in the biological sample the presence of one or more IgG antibodies selected from anti-BORF2, anti-LF2, anti-BDLF2, anti-BXLF1, anti-BRLF1, anti-BaRF1, anti-BGLF5, anti-BOLF1, anti-BRRF1, anti-BALF2, anti-BLLF3, and anti-BSLF2;
   wherein the components comprise a panel of EBV antigens that bind to the anti-BORF2, anti-LF2, anti-BDLF2, anti-BXLF1, anti-BRLF1, anti-BaRF1, anti-BGLF5, anti-BOLF1, anti-BRRF1, anti-BALF2, anti-BLLF3, and anti-BSLF2 antibodies;
   (b) contacting the biological sample and reagent composition with an anti-IgG antibody comprising a label; and
   (c) detecting the presence of the one or more IgG antibodies in the sample, wherein increased seroreactivity of the one or more IgG antibodies relative to the seroreactivity of the one or more IgG antibodies in a control sample obtained from a subject that does not have EBV$^+$ GC is indicative of increased risk of EBV$^+$ GC.

2. The method of claim 1, wherein the detected antibodies comprise anti-BALF2, anti-BORF2, and anti-BRRF1.

3. The method of claim 1, wherein the biological sample is one or more of a whole blood sample, a serum sample, and a plasma sample.

4. The method of claim 1, wherein the EBV antigens are encoded by SEQ ID NOs: 42, 138, 76, 26, 60, 4, 34, 20, 148, 14, 30, 8, and 36.

5. The method of claim 1, wherein the detection step is carried out using an ELISA assay or a Western Blot assay.

6. The method of claim 1, further comprising administering a vaccine-based gastric cancer treatment to the subject if identified as having an increased risk of EBV$^+$ GC gastric cancer.

7. A method to detect EBV$^+$ GC in a subject at risk of having EBV$^+$ GC, the method comprising:

(a) contacting a biological sample obtained from the subject with a set of reagents, wherein the set of reagents binds to at least three biomarkers in the biological sample, wherein the biomarkers are IgG antibodies selected from the group consisting of anti-BORF2, anti-LF2, anti-BDLF2, anti-BXLF1, anti-BRLF1, anti-BaRF1, anti-BGLF5, anti-BOLF1, anti-BRRF1, anti-BALF2, anti-BLLF3, and anti-BSLF2;

wherein the set of reagents comprises a panel of EBV antigens that bind to the anti-BORF2, anti-LF2, anti-BDLF2, anti-BXLF1, anti-BRLF1, anti-BaRF1, anti-BGLF5, anti-BOLF1, anti-BRRF1, anti-BALF2, anti-BLLF3, and anti-BSLF2 antibodies;

(b) measuring the level of the at least three biomarkers in the biological sample; and (c) detecting that the level of the at least three biomarkers is increased in the biological sample relative to a level of the at least three biomarkers in a control sample from a subject without EBV$^+$ GC, thereby detecting the presence of EBV$^+$ GC in the subject.

8. The method according to claim 7, wherein the at least three biomarkers comprise anti-BALF2, anti-BORF2, and anti-BRRF1.

9. The method of claim 7, further comprising (d) administering an EBV+ gastric cancer therapy to the subject, wherein the EBV$^+$ GC therapy is selected from the group consisting of chemotherapy, hormonal therapy, radiotherapy, immunotherapy, and surgical removal of stomach tissue.

10. The method of claim 7, wherein the biological sample is one or more of a whole blood sample, a serum sample, and a plasma sample.

11. The method of claim 7, wherein the detection step is carried out using an immunoassay.

12. A method of determining an Epstein Barr Virus (EBV) gastric cancer antibody signature comprising IgG antibodies, contained in a biological sample from an individual, that bind to immobilized EBV antigens, the method comprising:

(a) contacting the sample to a panel of immobilized EBV antigens under conditions that promote formation of antigen-antibody complexes, wherein the immobilized EBV antigens comprise one or more of BORF2, LF2, BDLF2, BXLF1, BRLF1, BaRF1, BGLF5, BOLF1, BRRF1, BALF2, BLLF3, and BSLF2; and (b) identifying complexes formed by immobilized EBV antigens and antibody in the sample, to determine an EBV antibody signature.

13. The method of claim 12, wherein the antibody signature is expressed as a level of antibody binding to each immobilized antigen.

14. The method of claim 12, further comprising comparing an antibody signature from one individual to the antibody signature from another individual.

15. The method of claim 12, wherein one individual has a disease process, and one individual is a healthy individual and the method allows comparison of the antibody signature in the healthy individual and the individual with a disease.

16. The method of claim 15, wherein the disease process comprises EBV$^+$ GC.

17. The method of claim 12, wherein the immobilized EBV antigens are encoded by SEQ ID NOs: 42, 138, 76, 26, 60, 4, 34, 20, 148, 14, 30, 8, and 36.

18. A kit for performing the method of claim 1, the kit comprising a panel of EBV antigens comprising at least three of BORF2, LF2, BDLF2, BXLF1, BRLF1, BaRF1, BGLF5, BOLF1, BRRF1, BALF2, BLLF3, and BSLF2.

19. The kit of claim 18, wherein the EBV antigens are encoded by SEQ ID NOs: 42, 138, 76, 26, 60, 4, 34, 20, 148, 14, 30, 8, and 36.

20. The method of claim 7, wherein the EBV antigens are encoded by SEQ ID NOs: 42, 138, 76, 26, 60, 4, 34, 20, 148, 14, 30, 8, and 36.

\* \* \* \* \*